United States Patent
Tuerdi et al.

(10) Patent No.: US 7,550,499 B2
(45) Date of Patent: Jun. 23, 2009

(54) UREA ANTAGONISTS OF $P2Y_1$ RECEPTOR USEFUL IN THE TREATMENT OF THROMBOTIC CONDITIONS

(75) Inventors: Huji Tuerdi, Yardley, PA (US); Hannguang J. Chao, Lawrenceville, NJ (US); Jennifer X. Qiao, Princeton, NJ (US); Tammy C. Wang, Lawrenceville, NJ (US); Timur Gungor, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 251 days.

(21) Appl. No.: 11/126,567

(22) Filed: May 10, 2005

(65) Prior Publication Data

US 2005/0261244 A1 Nov. 24, 2005

Related U.S. Application Data

(60) Provisional application No. 60/570,288, filed on May 12, 2004, provisional application No. 60/665,735, filed on Mar. 28, 2005.

(51) Int. Cl.
| | |
|---|---|
| A01N 43/38 | (2006.01) |
| A61K 31/40 | (2006.01) |
| A61K 31/405 | (2006.01) |
| C07D 207/00 | (2006.01) |
| C07D 209/00 | (2006.01) |
| C07D 295/00 | (2006.01) |

(52) U.S. Cl. .................. 514/409; 514/415; 548/400; 548/452

(58) Field of Classification Search .............. 514/409, 514/415; 548/400, 452
See application file for complete search history.

(56) References Cited

U.S. PATENT DOCUMENTS

| | | | |
|---|---|---|---|
| 3,118,888 A | 1/1964 | Giraldi et al. | |
| 3,162,644 A | 12/1964 | Englisch et al. | |
| 4,179,563 A | 12/1979 | Butler | |
| 4,186,199 A | 1/1980 | Glamkowski et al. | |
| 4,435,391 A | 3/1984 | Sasahara et al. | |
| 4,663,453 A | 5/1987 | Glamkowski et al. | |
| 4,840,947 A | 6/1989 | Glamkowski et al. | |
| 4,886,822 A | 12/1989 | Shibuya et al. | |
| 5,500,424 A | 3/1996 | Nagamine et al. | |
| 5,547,966 A | 8/1996 | Atwal et al. | |
| 5,612,359 A | 3/1997 | Murugesan | |
| 5,708,008 A | 1/1998 | Audia et al. | |
| 5,886,004 A | 3/1999 | Audia et al. | |
| 6,020,357 A | 2/2000 | Pinto et al. | |
| 6,043,265 A | 3/2000 | Murugesan et al. | |
| 6,143,764 A | 11/2000 | Kubo et al. | |
| 6,180,675 B1 | 1/2001 | Widdowson et al. | |
| 6,187,797 B1 | 2/2001 | Pruitt et al. | |
| 6,329,395 B1 | 12/2001 | Dugar et al. | |
| 6,410,529 B1* | 6/2002 | Chan et al. | 514/233.5 |
| 6,586,453 B2 | 7/2003 | Dhanoa et al. | |
| 6,596,746 B1 | 7/2003 | Das et al. | |
| 6,656,933 B2 | 12/2003 | Hickey | |
| 6,825,355 B2 | 11/2004 | Das et al. | |
| 6,863,647 B2 | 3/2005 | Pevarello et al. | |
| 6,906,063 B2* | 6/2005 | Scarborough et al. | 514/222.8 |
| 2002/0077486 A1 | 6/2002 | Scarborough et al. | |
| 2003/0061667 A1 | 4/2003 | Lim et al. | |
| 2003/0065176 A1 | 4/2003 | Kang et al. | |
| 2003/0153568 A1 | 8/2003 | Cusack et al. | |
| 2003/0195232 A1 | 10/2003 | Kawasaki et al. | |
| 2003/0207870 A1 | 11/2003 | Dumas et al. | |
| 2003/0216396 A1 | 11/2003 | Dumas et al. | |
| 2004/0023961 A1 | 2/2004 | Dumas et al. | |
| 2004/0038992 A1 | 2/2004 | Bemis et al. | |
| 2004/0102636 A1 | 5/2004 | Miller et al. | |
| 2004/0209930 A1 | 10/2004 | Carboni et al. | |
| 2004/0259875 A1 | 12/2004 | Yura et al. | |
| 2005/0009815 A1 | 1/2005 | DeVita et al. | |
| 2005/0012254 A1 | 1/2005 | Hsu | |
| 2005/0119304 A1 | 6/2005 | Yura et al. | |
| 2005/0203146 A1 | 9/2005 | Herpin et al. | |
| 2005/0256161 A1 | 11/2005 | Tempest et al. | |
| 2005/0267119 A1 | 12/2005 | Chao et al. | |
| 2006/0173002 A1 | 8/2006 | Sutton et al. | |
| 2006/0293281 A1 | 12/2006 | Qiao et al. | |

(Continued)

FOREIGN PATENT DOCUMENTS

EP 0 028 489 5/1981

(Continued)

OTHER PUBLICATIONS

Okino, et al., Enantioselective Michael Reaction of Malonates to Nitroolefins Catalyzed by Bifunctional Organocatalysts, J. Am. Chem. Soc., 125, 12672-12673 (2003).*

(Continued)

Primary Examiner—James O Wilson
Assistant Examiner—Erich A Leeser
(74) Attorney, Agent, or Firm—Jing G. Sun

(57) ABSTRACT

The present invention provides novel ureas containing N-aryl or N-heteroaryl substituted heterocycles and analogues thereof, which are selective inhibitors of the human $P2Y_1$ receptor. The invention also provides for various pharmaceutical compositions of the same and methods for treating diseases responsive to modulation of $P2Y_1$ receptor activity.

20 Claims, No Drawings

U.S. PATENT DOCUMENTS

| | | |
|---|---|---|
| 2006/0293336 A1 | 12/2006 | Sutton et al. |
| 2006/0293522 A1 | 12/2006 | Sutton |
| 2007/0004677 A1 | 1/2007 | Chao et al. |

FOREIGN PATENT DOCUMENTS

| | | |
|---|---|---|
| EP | 0 129 692 | 1/1985 |
| EP | 0 265 734 | 5/1988 |
| EP | 0 286 979 | 10/1988 |
| EP | 0 638 557 | 2/1995 |
| EP | 1 120 409 | 8/2001 |
| EP | 1123918 | 8/2001 |
| EP | 1 402 888 | 3/2004 |
| EP | 1 661 879 | 5/2006 |
| EP | 1 712 242 | 10/2006 |
| FR | 1 342 550 | 12/1962 |
| JP | 56-167649 | 12/1981 |
| JP | 58072562 | * 4/1983 |
| JP | 62280847 | 12/1987 |
| JP | 03039740 | 2/1991 |
| JP | 4-319958 | 11/1992 |
| JP | 1995101153 | 4/1995 |
| JP | 2001089412 | 4/2001 |
| WO | WO9617825 | 6/1996 |
| WO | WO 97/29743 | 8/1997 |
| WO | WO98/18430 | 5/1998 |
| WO | WO9818430 | 5/1998 |
| WO | WO 98/37035 | 8/1998 |
| WO | WO 98/57951 | 12/1998 |
| WO | WO 99/31086 | 6/1999 |
| WO | WO 99/32463 | 7/1999 |
| WO | WO 00/01389 | 1/2000 |
| WO | WO 00/59506 | 10/2000 |
| WO | WO 00/76495 | 12/2000 |
| WO | WO 00/76970 | 12/2000 |
| WO | WO0123358 | 4/2001 |
| WO | WO 01/40231 | 6/2001 |
| WO | WO 01/47919 | 7/2001 |
| WO | WO0151490 | 7/2001 |
| WO | WO 01/55146 | 8/2001 |
| WO | WO 01/57008 | 8/2001 |
| WO | WO 01/72751 | 10/2001 |
| WO | WO 02/44145 | 6/2002 |
| WO | WO 02/064211 | 8/2002 |
| WO | WO 02/090352 | 11/2002 |
| WO | WO02088090 | 11/2002 |
| WO | WO03007955 | 1/2003 |
| WO | WO 03/014064 | 2/2003 |
| WO | WO03013517 | 2/2003 |
| WO | WO 03/026652 | 4/2003 |
| WO | WO 03/045920 | 6/2003 |
| WO | WO 03/055484 | 7/2003 |
| WO | WO 03/055848 | 7/2003 |
| WO | WO 03/080553 | 10/2003 |
| WO | WO2004/002481 | 1/2004 |
| WO | WO2004002481 | 1/2004 |
| WO | WO 2004/012733 | 2/2004 |
| WO | WO 2004/022529 | 3/2004 |
| WO | WO 2004/046090 | 6/2004 |
| WO | WO 2004/060907 | 7/2004 |
| WO | WO 2004/085433 | 10/2004 |
| WO | WO 2004/110374 | 12/2004 |
| WO | WO 2005/080330 | * 1/2005 |
| WO | WO 2005/113511 | * 1/2005 |
| WO | WO 2005/037763 | 4/2005 |
| WO | WO 2005/042488 | 5/2005 |
| WO | WO 2005/063293 | 7/2005 |
| WO | WO2005070920 | 8/2005 |
| WO | WO 2006/091963 | 8/2006 |

OTHER PUBLICATIONS

Tasler, et al., Non-competitive Inhibitors of Metabotropic Glutamate Receptor 5 (mGluR5), Bioorganic & Medicinal Chemistry Letters 15, 2876-2880 (2005).*

West, Anthony R., Solid State Chemistry and Its Applications, Wiley, New York, 1988, 365.*

U.S. Appl. No. 11/126,915, filed May 10, 2005, Chao et al.

U.S. Appl. No. 11/038,862, filed Jan. 19, 2005, Herpin et al.

Hamada et al., "The antimicrobial activity and syntheses of carbanilide derivatives," Yakugaku Zasshi, vol. 96 (5), pp. 663-668, 1976, Abstract only, Journal written in Japanese.

Takeuchi et al., "On the antimicrobial activity and syntheses of carbanilide and salicylanilide derivatives," Yakugaku Zasshi, vol. 102(11), pp. 1023-1030, 1982.

Abbracchio et al., "Purinoceptors: Are there families of P2X and P2Y Purinoceptors?" Pharmac. Ther. vol. 64, pp. 445-475, 1994.

Abbracchio et al., "Characterization of the UDP-glucose receptor (re-named here the $P2Y_{14}$ receptor) adds diversity to the P2Y receptor family", Trends in Pharmacological Sciences, vol. 24, No. 2, Feb. 2003.

Baurand et al., "The $P2Y_1$ Receptor as a Target for the New Antithrombotic Drugs: A Review of the $P2Y_1$ Antagonist MRS-2179", Cardiovascular Drug Reviews, vol. 21, No. 1, pp. 67-76, 2003.

Boeynaems et al., "Overview of the P2Y Receptors as Therapeutic Targets", Drug Development Research, vol. 52, pp. 187-189, 2001.

Burnstock et al., "P2 Purinergic Receptors: Modulation of Cell Function and Therapeutic Potential", The Journal of Pharmacology and Experimental Therapeutics, vol. 295, No. 3, pp. 862-869, 2000.

Cobern et al., "Some New-p-Chlorophenoxycarbanilides and Their Bacteriostatic Activities", Notes, Unilever Research Laboratory, Colworth House, Sharnbrook, Bedford, England.

Daniel et al., "Molecular Basis for ADP-induced Platelet Activation", The Journal of Bilogical Chemistry, vol. 273, No. 4, pp. 2024-2029, 1998.

Fabre et al., "Decreased platelet aggregation, increased bleeding time and resistance to thromboembolism in $P2Y_1$-deficient mice", Nature Medicine, vol. 5, No. 10, Oct. 1999.

Gramatica et al., "QSAR approach for the selection of congeneric compounds with a similar toxicological mode of action", Chemosphere, vol. 42, pp. 873-883, 2001.

Gschwend et al., "Specificity in Structure-Based Drug Design: Identification of a Novel, Selective Inhibitor of Pneumocystis carinii Dihydrofolate Reductase", Proteins: Structure, Function and Genetics, vol. 29, pp. 59-67, 1997.

Hechler et al., "The $P2Y_1$ receptor, necessary but not sufficient to support full ADP-induced platelet aggregation, is not the target of the drug clopidogrel", British Journal of Haematology, vol. 103, pp. 858-866, 1998.

Janssens et al., "Cloning and Tissue Distribution of the Human $P2Y_1$ Receptor", Biochemical and Biophysical Research Communications, vol. 221, pp. 588-593, 1996.

Jin et al., "Coactivation of two different G protein-coupled receptors is essential for ADP-induced platelet aggregation", Proc. Natl. Acad. Sci., vol. 95, pp. 8070-8074, 1998.

Lenain, et al., "Inhibition of localized thrombosis in $P2Y_1$-deficient mice and rodents treated with MRS2179, A $P2Y_1$ receptor antagonist".

Leon et al., "Key Role of the $P2Y_1$ Receptor in Tissue Factor-Induced Thrombin-Dependent Acute Thromboembolism Studies in $P2Y_1$-Knockout Mice and Mice Treated with a $P2Y_1$ Antagonist", Circulation, pp. 718-723, 2000.

Norenberg, et al., "Characterization and possible function of adenosine 5'-triphosphate receptors in activated rat microglia", Br. J. Pharmacol., vol. 111, pp. 942-950, 1994.

Phillips et al, "Design, Synthesis, and Activity of 2,6-Diphenoxypyridine-Derived Factor Xa Inhibitors", J. Med. Chem., vol. 42, pp. 1749-1756, 1999.

Salter et al., "ATP Causes Release of Intracellular Ca$^{2+}$ via the Phospholipase Cβ/IP$_3$ Pathway in Astrocytes from the Dorsal Spinal Cord", The Journal of Neuroscience, vol. 15(4), pp. 2961-2971, 1995.

Savi et al., "Role of P2Y1 purinoceptor in ADP-induced platelet activation", FEBS Letters, vol. 422, pp. 291-295, 1998.

Taylor, E.C. et al., "Pteridines XIV", J. Am. Chem. Soc., vol. 78, pp. 210-213.

Wisterowicz, K. et al., "Badania Nad Pochodnymi Pyrazyny", Acta Poloniae Pharmaceutica, vol. 46, No. 2, 1989, pp. 101-113.

Rajanarendar, et al., "Synthesis of isoxazolylpyrazolo'3,4-dithiazoles and isoxazolylthiazoles and their antibacterial and antifungal activity" Indian Journal of Chemistry, Section B: Organic Chemistry Including Medicinal Chemistry, 43B(1), 168-173.

U.S. Appl. No. 11/872,816, filed Oct. 16, 2007, Lam et al.

Atwal, K.S. et al., "Cardioselective Antiischemic ATP-Sensitive Potassium Channel Openers. 4. Stucture-Activity Studies on Benzopyranylcyanoguanidines: Replacement of the Benzopyran Portion", Journal of Medicinal Chemistry, vol. 39, No. 1, pp. 304-313 (1996).

Bareich, D.C. et al., "Simultaneous In Vitro Assay of the First Four Enzymes in the Fungal Aspartate Pathway Identifies a New Class of Aspartate Kinase Inhibitor", Chemistry & Biology, vol. 10, pp. 967-973 (2003).

Beaver, D.J. et al., "The Preparation and Bacteriostatic Activity of Substituted Ureas", J. Am. Chem. Soc., vol. 79, pp. 1236-1245 (1957).

Bensemann, I. et al., "Creation of hydrogen bonded 1D networks by co-crystallization of N,N'-bis(2-pyridyl)aryldiamines with dicarboxylic acids", Org. Biomol. Chem., vol. 1, pp. 1425-1434 (2003).

Bundgaard, H., Chapter 5: "Design and Application of Prodrugs", A Textbook of Drug Design and Development, Harwood Academic Publishers, publ., Krogsgaard-Larsen, P. et al., eds., pp. 113-191 (1991).

Bundgaard, H., "Prodrugs as a means to improve the delivery of peptide drugs", Advanced Drug Delivery Reviews, vol. 8, pp. 1-38 (1992).

Chan, D.M.T. et al., Chapter 5: "Recent Advances in Copper-promoted C-Heteroatom Bond Cross-coupling Reactions with Boronic Acids and Derivatives", Boronic Acids: Preparation and Applications in Organic Synthesis and Medicine, Wiley-VCH Verlag GmbH & Co., publ., Hall, D.G., ed., pp. 205-240 (2005).

Chou, T.-C. et al., "Quantitative Analysis of Dose-Effect Relationships: The Combined Effects of Multiple Drugs or Enzyme Inhibitors", Adv. Enzyme Regul., vol. 22, pp. 27-55 (1984).

Duncan, Jr., R.L. et al., "Synthesis of Indolo- and Benzimidazoquinazolines and Benzodiazepines", Journal of Heterocyclic Chemistry, vol. 10, pp. 65-70 (1973).

Gachet, C. et al., "The platelet P2 receptors in arterial thrombosis", Blood Cells, Molecules, and Diseases, vol. 36, pp. 223-227 (2006).

Gallou, I. et al., "Practical Synthesis of Unsymmetrical Ureas from Isopropenyl Carbamates", J. Org. Chem., vol. 70, No. 17, pp. 6960-6963 (2005).

Glamkowski, E.J. et al., "Synthesis of 1,2-Dihydroindolo[1,7-ab][1,5]benzodiazepines and Related Structures (1). A New Heterocyclic Ring System", J. Heterocyclic Chem., vol. 16, pp. 865-869 (1979).

Glamkowski, E.J. et al., "Tetracyclic Benzodiazepines. 3. Synthesis of the 2,3-Dihydro-1H-quino[1,8-ab][1,5]benzodiazepine Ring System, and Derivatives of Potential Biological Interest", J. Heterocyclic Chem., vol. 24, pp. 733-737.

Hai, P.V. et al., "p-Cyclopentylacetophenone and Its Derivatives", J. Org. Chem., vol. 23, pp. 39-42 (1958).

Hechler, B. et al., "MRS2500 [2-Iodo-N$^6$-methyl-(N)-methanocarba-2'-deoxyadenosine-3',5'-bisphosphate], a Potent, Selective, and Stable Antagonist of the Platelet P2Y$_1$ Receptor with Strong Antithrombotic Activity in Mice", The Journal of Pharmacology and Experimental Therapeutics, vol. 316, No. 2, pp. 556-563 (2006).

Herr, R.J., "Product Class 5: Seven-Membered Hetarenes with Two or More Heteroatoms", Science of Synthesis, vol. 17, pp. 929-977 (2004).

Ito, Y. et al., "Syntheses of Nitrogen-containing Heterocyclic Compounds. XXIX. An Improved Method for the Preparation of 10H-Pyrido[3,2-b][1,4]benzoxazine (1-Azaphenoxazine)", Chem. Pharm. Bull., vol. 26, No. 5, pp. 1375-1383 (1978).

Jin, J. et al., "Molecular Basis for ADP-induced Platelet Activation", The Journal of Biological Chemistry, vol. 273, No. 4, pp. 2030-2034 (1998).

Kakeya, N. et al., "Studies on Prodrugs of Cephalosporins. I. Synthesis and Biological Properties of Glycyloxybenzoyloxymethyl and Glycylaminobenzoyloxymethyl Esters of 7β-[2-(2-Aminothiazol-4-yl)-(Z)-2-methoxyiminoacetamido]-3-methyl-3-cephem-4-carboxylic Acid", Chem. Pharm. Bull., vol. 32, No. 2, pp. 692-698 (1984).

Kane, Jr., J.L. et al., "Ureas of 5-Aminopyrazole and 2-Aminothiazole Inhibit Growth of Gram-Positive Bacteria", Bioorganic & Medicinal Chemistry Letters, vol. 13, pp. 4463-4466 (2003).

Lane, B.S. et al., "Direct Palladium-Catalyzed C-2 and C-3 Arylation of Indoles: A Mechanistic Rationale for Regioselectivity", J. Am. Chem. Soc., vol. 127, No. 22, pp. 8050-8057 (2005).

Ley, S.V. et al., "Modern Synthetic Methods for Copper-Mediated C(aryl)-O, C(aryl)-N, and C(aryl)-S Bond Formation", Angewandte Chemie Int. Ed., vol. 42, pp. 5400-5449 (2003).

Marcincal-Lefebvre, A. et al., "2-[2-(Phenylthio)phenylamino]nicotinic acids and 2-[4-(phenylthio)phenylamino]nicotinic acids. Synthesis and antiinflammatory activity", Annales Pharmaceutiques Francaises, vol. 38, No. 3, pp. 243-252 (1980) (English abstract).

Matsuo, M. et al., "New 2-Aryliminoimidazolidines. I. Synthesis and Antihypertensive Properties of 2-(2-Phenoxyphenylimino)imidazolidines and Related Compounds", Chem. Pharm. Bull., vol. 33, No. 10, pp. 4409-4421 (1985).

Nielsen, N.M. et al., "Glycolamide Esters as Biolabile Prodrugs of Carboxylic Acid Agents: Synthesis, Stability, Bioconversion, and Physicochemical Properties", Journal of Pharmaceutical Sciences, vol. 77, No. 4, pp. 285-298 (1988).

Peng, C.-T. et al., "The Synthesis of Some 6-N-Substituted Amido Derivatives of 4,6-Diaminoquinaldine and a Study of their in vitro Antibacterial Activity", J. Am. Chem. Soc., vol. 78, pp. 3703-3708 (1956).

Roberts, M.E. et al., "On the Alkyl Derivatives of the Isomeric Ortho and Para-phenoxyphenyl Thiazolidones", The University of Kansas Science Bulletin, vol. 25, No. 11, pp. 213-227 (1938).

Rodig, O.R. et al., "Pyridine Chemistry. II. Further Studies on the Smiles Rearrangement of the 3-Amino-2,2'-dipyridyl Sulfide System. The Synthesis of Some 1,6-Diazaphenothiazines", Journal of Medicinal Chemistry, vol. 9, pp. 116-120 (1966).

Still, W.C. et al., "Rapid Chromatographic Technique for Preparative Separations with Moderate Resolution", J. Org. Chem., vol. 43, No. 14, pp. 2923-2925 (1978).

Tomita, M. et al., "Synthesis of thiazole derivatives containing diphenyl ether nucleus", Yakugaku Zasshi, vol. 75, pp. 1077-1081 (1955) (English abstract).

Widder, K.J. et al., eds., Section III: "Prodrugs", Methods in Enzymology, vol. 112, Academic Press, Inc., publ., pp. 309-396 (1985).

Wong, P.C. et al., "Nonpeptide Factor Xa Inhibitors: I. Studies with SF303 and SK549, a New Class of Potent Antithrombotics", The Journal of Pharmacology and Experimental Therapeutics, vol. 292, No. 1, pp. 351-357 (2000).

Wong, P.C. et al., "Nonpeptide Factor Xa Inhibitors II. Antithrombotic Evaluation in a Rabbit Model of Electrically Induced Carotid Artery Thrombosis", The Journal of Pharmacology and Experimental Therapeutics, vol. 295, No. 1, pp. 212-218 (2000).

Woźniak, K. et al., "Structural Similarities and Differences between N-Phenylureas and N-Phenylthioureas", J. Phys. Chem., vol. 99, No. 21, pp. 8888-8895 (1995).

Beilstein Registry No. 235048.
Beilstein Registry No. 835983.
Beilstein Registry No. 8980514.
CAS Registry No. 50829-71-5.
CAS Registry No. 55007-82-4.
CAS Registry No. 72114-14-8.
CAS Registry No. 96014-78-7.

CAS Registry No. 102595-49-3.
CAS Registry No. 104272-83-5.
CAS Registry No. 112631-42-2.
CAS Registry No. 325821-30-5.
CAS Registry No. 433947-53-6.
CAS Registry No. 500114-29-4.
CAS Registry No. 518348-64-6.
CAS Registry No. 518348-65-7.
CAS Registry No. 518348-70-4.
CAS Registry No. 683783-31-5.
CAS Registry No. 728878-33-9.
CAS Registry No. 858362-22-8.
Rajanarendar, E. et al., "Synthesis of isoxazolylpyrazolo[3,4-*d*] thiazoles and isoxazolylthiazoles and their antibacterial and antifungal activity", Indian Journal of Chemistry, vol. 43B, pp. 168-173 (2004).
Taylor, Jr. E.C., "Pteridines. XIV. Further Studies on a New Approach to Pteridine Synthesis", Journal of the American Chemical Society, vol. 78, pp. 210-213 (1956).

* cited by examiner

UREA ANTAGONISTS OF P2Y$_1$ RECEPTOR USEFUL IN THE TREATMENT OF THROMBOTIC CONDITIONS

CROSS-REFERENCE TO RELATED APPLICATIONS

The present application claims the priority benefit of U.S. Provisional Application No. 60/570,288, filed May 12, 2004 and the priority benefit of U.S. Provisional Application No. 60/665,735, filed Mar. 28, 2005, all of which are expressly incorporated fully herein by reference.

FIELD OF THE INVENTION

The present invention provides novel ureas containing N-aryl or N-heteroaryl substituted heterocycles and analogues thereof, which are selective inhibitors of the human P2Y$_1$ receptor. The invention also provides for various pharmaceutical compositions of the same and methods for treating diseases responsive to modulation of P2Y$_1$ receptor activity.

BACKGROUND OF THE INVENTION

Purinoreceptors bind to and are activated by a variety of both ribosylated (nucleotide) and non-ribosylated (nucleoside) purines. This distinction has been used to classify these receptors into two broad groups: the P1 receptors (A1, A2a, A2b and A3), which bind to and are activated by the nucleoside adenosine, and the P2 receptors, which comprise a second, more diverse class of receptors which are activated by a wide variety of nucleotides including ATP, ADP, UTP and UDP. The P2 receptors can be further subdivided into two distinct types of receptors; the ionotropic P2X receptors that mediate cation flux across cellular membranes in response to ATP and the metabotropic P2Y family of receptors which are G-protein coupled receptors. In humans, the P2Y family of receptors is generally considered to consist of seven distantly related members; P2Y$_1$, P2Y$_2$, P2Y$_4$, P2Y$_6$, P2Y$_{11}$, P2Y$_{12}$, and P2Y$_{13}$ (Boeynaems, J. M. et al. *Drug Development Research* 2000, 52, 187-9). In addition, an eighth receptor, P2Y$_{14}$, has been considered by some to be a member of this class although it does not respond to ribosylated nucleotides and is activated by UDP-glucose (Abbracchio, M. P. et al. *Trends Pharmacol. Sci.* 2003, 24, 52-5).

Several studies have suggested that modulators of specific members of the P2Y family of receptors could have therapeutic potential for the treatment of a variety of disorders (for review see Burnstock, G. and Williams, M. *J. Pharm. Exp Ther.* 2000, 295, 862-9), including diabetes, cancer, CF, and treatment of ischemia-reperfusion injury (Abbracchio M. P., Burnstock G. *Pharmacol. Ther.* 1994, 64, 445-475). P2Y1 receptors, almost ubiquitous among human organs (Jassens R; Communi D.; Pirotton S. et al. *Biochem. Biophys. Res. Comm.* 1996, 221, 588-593) have been identified on microglia (Norenberg W. et al; Br. *J. Pharmacol.* 1994, 111, 942-950) and on astrocytes (Salter M. W. and Hicks J. L. *J. Neurosc.* 1995, 15, 2961-2971). Extracellular ATP activates microglial and/or astrocytes via P2Y receptors and leads directly to the release of inflammatory mediators. Microglia and astrocytes are believed to play a role in the progression of Alzheimer's disease and other CNS inflammatory disorders such as stroke and multiple sclerosis.

Two members of the P2Y family, P2Y$_1$ and P2Y$_{12}$, are of particular interest as they have now both been shown to act as important receptors for ADP in platelets (Jin, J. et al. *Proc. Natl. Acad. Sci.* 1998, 95, 8070). ADP is a key activator of platelets and platelet activation is known to play a pivotal role in thrombus formation under conditions of high shear stress such as those found in the arterial circulation. In addition, more recent data has suggested that platelet activation may also play a role in mediating thrombus formation under lower shear stress such as that found in the venous circulation. ADP activates platelets by simultaneously interacting with both P2Y$_1$ and P2Y$_{12}$ to produce two separate intracellular signals which synergize together to produce complete platelet activation. The first signal arises from ADP driven activation of the P2Y$_1$ receptor and can most easily be tracked by measuring the transitory increase in intracellular free $Ca^{+2}$. This signal appears to mediate the initial shape change reaction and to initiate the process of platelet activation. The second signal appears to be derived from ADP activation of the P2Y$_{12}$ receptor and serves to consolidate the process and produce an irreversible platelet aggregate. Using three structurally related but distinct inhibitors of P2Y$_1$ (A3P5P, A3P5PS and A2P5P), Daniel, J. L. et al. (*J. Biol. Chem.* 1998, 273, 2024-9), Savi, P. et al. (*FEBS Letters* 1998, 422, 291-5), and Hechler, B. et al. (*Br. J. Haematol.* 1998, 103, 858-66) were the first to publish the observation that the inhibition of P2Y$_1$ activity alone could block ADP-driven aggregation independently of the P2Y$_{12}$ receptor. Although inhibition of platelet reactivity is often thought of as firm evidence of an anti-thrombotic activity, these antagonists lacked the necessary pharmacological properties for in vivo study. The first direct demonstration that inhibition of P2Y$_1$ activity could lead to an anti-thrombotic effect in vivo was reported by Leon, C. et al. *Circulation* 2001, 103, 718-23, in a model of thromboplastin induced thromboembolism using both a P2Y$_1$ knock-out mouse and the P2Y$_1$ antagonist MRS-2 179 (Baurand, A. and Gachet, C. *Cardiovascular Drug Reviews* 2003, 21, 67-76). These results were subsequently extended to include the inhibition of both venous and arterial thrombosis in the rat (Lenain, N. et al. *J. Thromb. Haemost.* 2003, 1, 1144-9) and confirmed by a second laboratory using an independently derived P2Y$_1$ knock-out mouse (Fabre, J-E. et al. *Nature Medicine* 1999, 5, 1199-1202). Taken together, these data suggest that the discovery of novel P2Y$_1$ antagonists with improved pharmaceutical characteristics could have significant utility in the treatment of a variety of thromboembolic disorders.

SUMMARY OF THE INVENTION

Accordingly, the present invention provides novel ureas containing N-aryl or N-heteroaryl substituted heterocycles, which are useful as selective inhibitors of the P2Y$_1$ receptor including stereoisomers, pharmaceutically acceptable salts, solvates, or prodrugs thereof.

The present invention also provides processes and intermediates for making the compounds of the present invention or a stereoisomer or a pharmaceutically acceptable salt, solvate, or prodrug form thereof.

The present invention also provides pharmaceutical compositions comprising a pharmaceutically acceptable carrier and a therapeutically effective amount of at least one of the compounds of the present invention or a pharmaceutically acceptable salt, solvate, or prodrug form thereof.

The present invention also provides a method for modulation of platelet reactivity comprising administering to a host in need of such treatment a therapeutically effective amount of at least one of the compounds of the present invention or a pharmaceutically acceptable salt, solvate, or prodrug form thereof.

The present invention also provides a method for treating thromboembolic disorders comprising administering to a host in need of such treatment a therapeutically effective amount of at least one of the compounds of the present invention or a pharmaceutically acceptable salt, solvate, or prodrug form thereof.

The present invention also provides novel pyridyl ureas for use in therapy for other disease states which are responsive to modulation of P2Y$_1$ activity.

The present invention also provides the use of novel pyridyl ureas for the manufacture of a medicament for the treatment of a thromboembolic or other disorders.

These and other embodiments, which will become apparent during the following detailed description, have been achieved by the inventors' discovery that the presently claimed novel compounds of the present invention, or pharmaceutically acceptable salt or prodrug forms thereof, are effective P2Y$_1$ inhibitors.

DETAILED DESCRIPTION OF PREFERRED EMBODIMENTS

In a first embodiment, the present invention provides, inter alia, a compound of Formula (I):

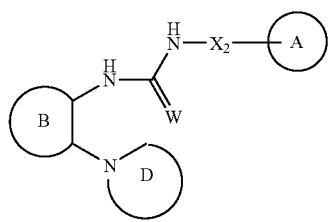

(I)

or a stereoisomer or pharmaceutically acceptable salt, solvate, or prodrug thereof, wherein:

ring A is C$_{6-10}$ aryl substituted with 0-5 R$^1$, or a 5- to 10-membered heterocycle comprising: carbon atoms and 1-4 heteroatoms selected from N, NR$^{11}$, O, and S(O)$_p$, wherein said heterocycle is substituted with 0-5 R$^1$;

ring B is phenyl or naphthyl substituted with 0-4 R$^7$, or a 5- to 10-membered heteroaryl comprising: carbon atoms and 1-4 ring heteroatoms selected from N, NR$^{11}$, S(O)$_p$, and O, wherein said heteroaryl is substituted with 0-4 R$^7$;

ring D is substituted with 0-5 R$^{6a}$ and selected from:

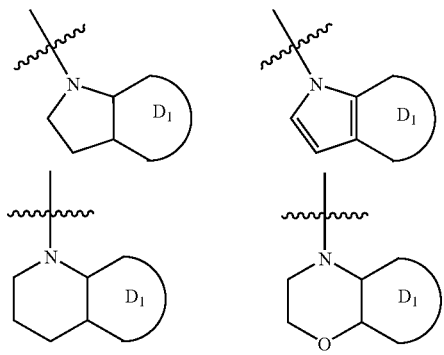

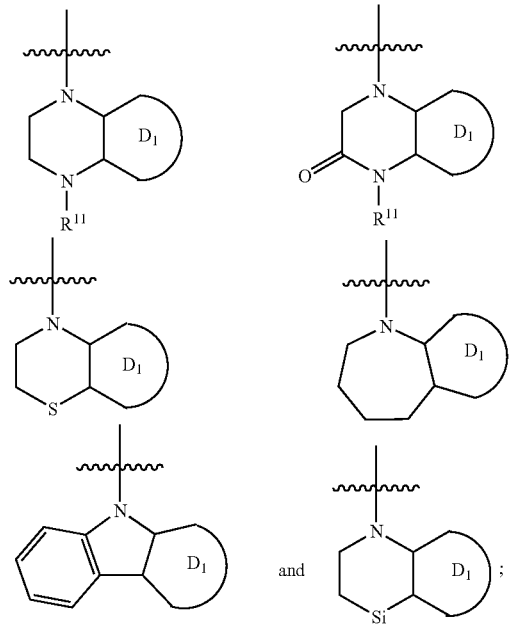

wherein D$_1$ is a 5- to 7-membered carbocycle or a 5-6-membered heterocycle comprising: carbon atoms and 0-3 ring heteroatoms selected from N, NR$^{11}$, O, and S(O)$_p$, and 0-2 carbonyl groups, and 0-3 double bonds;

W is O or S;

X$_2$ is —(CR$^{16}$R$^{17}$)$_s$—, or —(CR$^{16}$R$^{17}$)$_t$C(O)(CR$^{16}$R$^{17}$)$_r$—;

R$^1$ is, independently at each occurrence, H, =O, F, Cl, Br, I, CF$_3$, —CF$_2$CF$_3$, OCF$_3$, —OCF$_2$CF$_2$H, —OCF$_2$CF$_3$, SiMe$_3$, —(CR$^f$R$^f$)$_r$—OR$^c$, SR$^c$, CN, NO$_2$, —(CR$^f$R$^f$)$_r$—NR$^{12}$R$^{13}$, —(CR$^f$R$^f$)$_r$—C(O)R$^c$, —(CR$^f$R$^f$)$_r$—CO$_2$R$^c$, —(CR$^f$R$^f$)$_r$—C(O)NR$^{12}$R$^{13}$, —C(O)NR$^{14}$(CR$^f$R$^f$)$_t$N$^{12}$R$^{13}$, —(CR$^f$R$^f$)$_r$—OC(O)NR$^{12}$R$^{13}$, —(CR$^f$R$^f$)$_r$—NR$^{14}$C(O)NR$^{12}$R$^{13}$, —(CR$^f$R$^f$)$_r$—NR$^{14}$C(O)R$^d$, —(CR$^f$R$^f$)$_r$—NR$^{14}$C(O)OR$^h$, —NR$^{14}$(CR$^f$R$^f$)$_n$C(O)R$^d$, —NR$^{14}$CO(CR$^f$R$^f$)$_n$OR$^c$, —(CH$_2$)$_r$—CR$^{13}$ (—NOR$^c$), —S(O)$_p$NR$^{12}$R$^{13}$, —(CR$^f$R$^f$)$_r$—NR$^{14}$S(O)$_p$NR$^{12}$R$^{13}$, —NR$^{14}$SO$_2$CF$_3$, —NR$^{14}$S(O)$_2$R$^d$, —S(O)$_2$CF$_3$, —S(O)R$^d$, —S(O)$_2$R$^d$, —OP(O)(OEt)$_2$, —O(CH$_2$)$_2$OP(O)(OEt)$_2$, 4,4,5,5-tetramethyl-1,3,2-dioxaborolanyl, C$_{1-8}$ alkyl substituted with 0-2 R$^a$, C$_{2-8}$ alkenyl substituted with 0-2 R$^a$, C$_{2-8}$ alkynyl substituted with 0-2 R$^a$, (CR$^f$R$^f$)$_r$—C$_{3-13}$ carbocycle substituted with 0-5 R$^b$, or —(CR$^f$R$^f$)$_r$-5- to 10-membered heterocycle comprising: carbon atoms and 1-4 heteroatoms selected from N, NR$^{11}$, O, and S(O)$_p$, wherein said heterocycle is substituted with 0-5 R$^b$;

alternatively, two R$^1$s on two adjacent carbon atoms are combined with the carbon atoms to which they are attached, form a 5- to 10-membered carbocycle or heterocycle comprising: carbon atoms and 0-3 additional heteroatoms selected from N, NR$^{11}$, O, and S(O)$_p$, and 0-2 carbonyl groups, wherein said carbocycle or heterocycle is substituted with 0-4 R$^b$;

R$^{6a}$ is, independently at each occurrence, =O, F, Cl, Br, I, —(CR$^i$R$^i$)$_r$—OR$^c$, SR$^c$, CN, NO$_2$, CF$_3$, OCF$_3$, —CF$_2$CF$_3$, —OCF$_2$CF$_2$H, —OCF$_2$CF$_3$, —(CR$^f$R$^f$)$_r$—NR$^{12}$R$^{13}$, —C(O)R$^c$, —(CR$^f$R$^f$)$_r$—C(O)OR$^c$, —(CR$^f$R$^f$)$_r$—C(O)NR$^{12}$R$^{13}$, —(CR$^f$R$^f$)$_r$—NR$^{14}$C(O)R$^d$, —S(O)$_p$NR$^{12}$R$^{13}$, —S(O)R$^d$, —S(O)$_2$R$^d$, Si(Me)$_3$, Si(C$_{1-4}$ alkyl)$_3$, C$_{1-4}$ haloalkyl, C$_{1-4}$ haloalkyloxy-, C$_{1-4}$ alkyloxy-, C$_{1-4}$ alkylthio-, C$_1$-C$_4$ alkyl-C(O)—, C$_{1-4}$ alkyl-O—C(O)—, C$_{1-4}$ alkyl-C(O)NH—, C$_{1-8}$ alkyl substituted with 0-1 R$^a$, C$_{2-8}$ alkenyl substituted with 0-1 R$^a$, C$_{2-8}$ alkynyl substituted with 0-1 R$^a$, —(CR$^f$R$^f$)$_r$—C$_{3-10}$ carbocycle substituted with 0-2 R$^e$, or —(CR$^f$R$^f$)$_r$-5- to 10-membered heterocycle comprising: carbon atoms and 1-4 heteroatoms selected from N, NR$^{11}$, O, and S(O)$_p$, wherein said heterocycle is substituted with 0-2 R$^e$;

alternatively, when two R$^{6a}$ groups are attached to the same carbon atom or silicon atom, together with the carbon atom or silicon atom to which they are attached, they form a 3- to 7-membered carbocyclic or heterocyclic ring comprising: carbon atoms and 0-3 heteroatoms selected from N, NR$^{11}$, O, Si, and S(O)$_p$, 0-1 carbonyl and 0-3 ring double bonds, wherein said carbocyclic or heterocyclic ring is substituted with 0-3 R$^b$;

alternatively, when two R$^{6a}$ groups are attached to adjacent atoms, together with the atoms to which they are attached they form a 5- to 7-membered carbocyclic or heterocyclic ring comprising: carbon atoms and 0-2 heteroatoms selected from N, NR$^{11}$, O, Si, and S(O)$_p$, 0-1 carbonyl and 0-3 ring double bonds, wherein said carbocyclic or heterocyclic ring is substituted with 0-3 R$^b$;

R$^7$ is, independently at each occurrence, H, =O, F, Cl, Br, I, OCF$_3$, CF$_3$, OR$^c$, SR$^c$, CN, NO$_2$, —NR$^{12}$R$^{13}$, —C(O)R$^c$, —C(O)OR$^c$, —C(O)NR$^{12}$R$^{13}$, —NR$^{14}$C(O)R$^d$, —S(O)$_p$NR$^{12}$R$^{13}$, —S(O)R$^d$, —S(O)$_2$R$^d$, C$_{1-8}$ alkyl substituted with 0-2 R$^a$, C$_{2-8}$ alkenyl substituted with 0-2 R$^a$, C$_{2-8}$ alkynyl substituted with 0-2 R$^a$, —(CR$^f$R$^f$)$_r$—C$_{3-10}$ carbocycle substituted with 0-3 R$^b$, or —(CR$^f$R$^f$)$_r$-5- to 10-membered heterocycle comprising: carbon atoms and 1-4 heteroatoms selected from N, NR$^{7b}$, O, and S(O)$_p$, wherein said heterocycle is substituted with 0-3 R$^b$;

alternatively, two R$^7$s on two adjacent carbon atoms form a 5- to 7-membered carbocyclic or heterocyclic ring comprising: carbon atoms and 0-3 ring heteroatoms selected from O, N, NR$^{7b}$, and S(O)$_p$, wherein said carbocyclic or heterocyclic ring is substituted with 0-2 R$^{7c}$;

R$^{7b}$ is H, C$_{1-4}$ alkyl, —C(O)(C$_{1-4}$ alkyl), —C(O)phenyl, —C(O)benzyl, or benzyl;

R$^{7c}$ is, independently at each occurrence, H, F, Cl, Br, I, OCF$_3$, CF$_3$, OR$^c$, SR$^c$, CN, NO$_2$, —NR$^{12}$R$^{13}$, —C(O)R$^c$, —C(O)OR$^c$, —C(O)NR$^{12}$R$^{13}$, —NR$^{14}$C(O)R$^d$, —S(O)$_p$NR$^{12}$R$^{13}$, —S(O)R$^d$, —S(O)$_2$R$^d$, C$_{1-4}$ alkyl, phenyl substituted with 0-3 R$^b$, or benzyl substituted with 0-3 R$^b$;

R$^{11}$ is, independently at each occurrence, H, C$_{1-4}$ alkoxy, C$_{1-8}$ alkyl substituted with 0-2 R$^a$, C$_{2-4}$ alkenyl substituted with 0-1 R$^a$, C$_{2-4}$ alkynyl substituted with 0-1 R$^a$, —C(O)(C$_{1-6}$ alkyl), —C(O)(CH$_2$)$_n$(C$_{3-6}$ cycloalkyl), —C(O)(CH$_2$)$_n$(C$_{6-10}$ aryl), —C(O)(CH$_2$)$_n$(5- to 10-membered heteroaryl), —C(O)O(C$_{1-8}$ alkyl), —C(O)O(CH$_2$)$_n$(C$_{3-6}$ cycloalkyl), —C(O)O(CH$_2$)$_n$(C$_{6-10}$ aryl), —C(O)O(CH$_2$)$_n$(5- to 10-membered heteroaryl), —C(O)O(CH$_2$)$_{2-4}$(C$_{1-4}$ alkyl), —C(O)NH(C$_{1-8}$ alkyl), —C(O)NH(CH$_2$)$_n$(C$_{3-6}$ cycloalkyl), —C(O)NH(CH$_2$)$_n$(C$_{6-10}$ aryl), —C(O)NH(CH$_2$)$_n$(5- to 10-membered heteroaryl), —S(O)$_2$(C$_{1-8}$ alkyl), —S(O)$_2$(CH$_2$)$_n$(C$_{3-6}$ cycloalkyl), —S(O)$_2$(CH$_2$)$_n$(C$_{6-10}$ aryl), —S(O)$_2$(CH$_2$)$_n$(5- to 10-membered heteroaryl), —(CR$^f$R$^f$)$_r$—C$_{3-10}$ carbocycle, or —(CR$^f$R$^f$)$_r$-5- to 10-membered heterocycle; wherein said alkyl, cycloalkyl, phenyl, aryl, and carbocycle are substituted with 0-2 R$^b$, and said heteroaryl and heterocycle are substituted with 0-2 R$^b$ and comprise: carbon atoms and 1-4 heteroatoms selected from N, NR$^f$, O, and S(O)$_p$;

R$^{12}$ is, independently at each occurrence, H, C$_{1-6}$ alkyl, —C(O)(C$_{1-6}$ alkyl), —C(O)(CH$_2$)$_n$(C$_{6-10}$ aryl), —C(O)(CH$_2$)$_n$(5- to 10-membered heteroaryl), —C(O)O(C$_{1-4}$ alkyl), —C(O)OCH$_2$(C$_{6-10}$ aryl), —(CH$_2$)$_n$C(O)OCH$_2$(5- to 10-membered heteroaryl), —(CH$_2$)$_n$OC(O)(C$_{1-4}$ alkyl), —(CH$_2$)$_n$OC(O)(C$_{6-10}$ aryl), —(CH$_2$)$_n$OC(O)(5- to 10-membered heteroaryl), —(CH$_2$)$_n$C(O)O(C$_{1-4}$ alkyl), —(CH$_2$)$_n$C(O)O(C$_{6-10}$ aryl), —(CH$_2$)$_n$C(O)O(5- to 10-membered heteroaryl), —(CH$_2$)$_n$C(O)NH(C$_{1-6}$ alkyl), —(CH$_2$)$_n$C(O)NH(C$_{6-10}$ aryl), —(CH$_2$)$_n$C(O)NH(5- to 10-membered heteroaryl), —(CH$_2$)$_t$OC(O)NH(C$_{1-6}$ alkyl), —(CH$_2$)$_t$OC(O)NH(C$_{6-10}$ aryl), —(CH$_2$)$_t$OC(O)NH(5- to 10-membered heteroaryl), —S(O)$_2$(C$_{1-6}$ alkyl), —S(O)$_2$(CH$_2$)$_n$(C$_{6-10}$ aryl), —S(O)$_2$(CH$_2$)$_n$(5- to 10-membered heteroaryl), —(CR$^f$R$^f$)$_n$—(C$_{6-10}$ aryl), or —(CR$^f$R$^f$)$_n$-5- to 10-membered heteroaryl; wherein said alkyl, and aryl are substituted with 0-2 R$^g$; and said heteroaryl is substituted with 0-2 R$^g$ and comprises: carbon atoms and 1-4 heteroatoms selected from N, NR$^{11}$, O, and S(O)$_p$;

R$^{13}$ is, independently at each occurrence, H, C$_{1-6}$ alkyl, or —(CH$_2$)$_n$-phenyl;

alternatively, R$^{12}$ and R$^{13}$, when attached to the same nitrogen, combine to form a 5- to 10-membered heterocyclic ring comprising: carbon atoms and 1-2 additional heteroatoms selected from N, NR$^{11}$, O, and S(O)$_p$;

R$^{14}$ is, independently at each occurrence, H, C$_{1-6}$ alkyl substituted with 0-2 R$^{14a}$, C$_{2-6}$ alkenyl substituted with 0-2 R$^{14a}$, C$_{2-6}$ alkynyl substituted with 0-2 R$^{14a}$, —(CH$_2$)$_r$—C$_{3-10}$ carbocycle substituted with 0-3 R$^g$, or —(CH$_2$)$_r$-5- to 10-membered heterocycle comprising: carbon atoms and 1-4 heteroatoms selected from N, NR$^{11}$, O, and S(O)$_p$, wherein said heterocycle is substituted with 0-3 R$^g$;

R$^{14a}$ is, independently at each occurrence, H, C$_{1-4}$ alkyl, OR$^f$, Cl, F, Br, I, =O, CF$_3$, CN, NO$_2$, —C(O)R$^f$, —C(O)OR$^f$, —C(O)NR$^{12}$R$^{13}$, or —S(O)$_p$R$^f$;

R$^{16}$ is, independently at each occurrence, H, F, C$_{1-6}$ alkyl substituted with 0-2 R$^a$, C$_{2-6}$ alkenyl substituted with 0-2 R$^a$, C$_{2-6}$ alkynyl substituted with 0-2 R$^a$, or —(CH$_2$)$_r$-phenyl substituted with 0-2 R$^b$;

R$^{17}$ is, independently at each occurrence, H, OH, C$_{1-6}$ alkyl, or —(CH$_2$)$_n$-phenyl;

alternatively, R$^{16}$ and R$^{17}$ on the same carbon atom combine to form a 3- to 7-membered carbocyclic or heterocyclic ring comprising: carbon atoms and 0-2 heteroatoms selected from N, NR$^{11}$, O, and S(O)$_p$, 0-1 carbonyl, and 0-3 double bonds, wherein said carbocyclic or heterocyclic ring is substituted with 0-2 R$^b$;

alternatively, two R$^{16}$ groups on adjacent atoms combine to form a 3- to 7-membered carbocyclic or heterocyclic ring comprising: carbon atoms and 0-2 heteroatoms selected from N, NR$^{11}$, O, and S(O)$_p$, 0-1 carbonyl, and 0-3 double bonds, wherein said carbocyclic or heterocyclic ring is substituted with 0-2 R$^b$;

R$^a$ is, independently at each occurrence, H, =O, F, OCF$_3$, CF$_3$, OR$^c$, SR$^c$, CN, —NR$^{12}$R$^{13}$, —C(O)R$^c$, —C(O)OR$^c$, —C(O)NR$^{12}$R$^{13}$, —NR$^{14}$C(O)R$^d$, —S(O)$_p$NR$^{12}$R$^{13}$, —S(O)R$^d$, —S(O)$_2$R$^d$, —(CH$_2$)$_r$—C$_{3-10}$ carbocycle substituted with 0-3 R$^e$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-3 R$^e$;

$R^b$ is, independently at each occurrence, H, =O, F, Cl, Br, I, $(CH_2)_r$—$OR^c$, $SR^c$, CN, $NO_2$, $CF_3$, $OCF_3$, —$(CH_2)_r$—$NR^{12}R^{13}$, —$C(O)R^c$, —$(CH_2)_r$—$C(O)OR^c$, —$(CH_2)_r$—$C(O)NR^{12}R^{13}$, —$NR^{14}C(O)R^d$, —$S(O)_pNR^{12}R^{13}$, —$S(O)R^d$, —$S(O)_2R^d$, $C_{1-4}$ haloalkyl, $C_{1-4}$ haloalkyloxy-, $C_{1-4}$ alkyloxy-, $C_{1-4}$ alkylthio-, $C_{1-4}$ alkyl-C(O)—, $C_{1-4}$ alkyl-O—C(O)—, $C_{1-4}$ alkyl-C(O)NH—, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, $(CH_2)_r$—$C_{3-10}$ carbocycle substituted with 0-3 $R^e$, or —$(CH_2)_r$-5- to 10-membered heterocycle comprising: carbon atoms and 1-4 heteroatoms selected from N, $NR^f$, O, and $S(O)_p$, wherein said heterocycle is substituted with 0-3 $R^e$;

$R^c$ is, independently at each occurrence, H, —OP(O)(OEt)$_2$, $C_{1-8}$ alkyl substituted with 0-2 $R^e$, $C_{2-8}$ alkenyl substituted with 0-2 $R^e$, $C_{2-8}$ alkynyl substituted with 0-2 $R^e$, —$(CR^fR^f)_r$—$C_{3-8}$ cycloalkyl substituted with 0-2 $R^e$, —$(CR^fR^f)_r$—$C_{6-10}$ aryl substituted with 0-2 $R^e$, or —$(CR^fR^f)_r$-5- to 10-membered heterocycle comprising: carbon atoms and 1-4 heteroatoms selected from N, $NR^f$, O, and $S(O)_p$, wherein said heterocycle is substituted with 0-2 $R^e$;

$R^d$ is, independently at each occurrence, $CF_3$, OH, $C_{1-4}$ alkoxy, $C_{1-6}$ alkyl, —$(CH_2)_r$—$C_{3-10}$ carbocycle substituted with 0-2 $R^e$, or —$(CH_2)_r$-5- to 10-membered heterocycle comprising: carbon atoms and 1-4 heteroatoms selected from N, $NR^f$, O, and $S(O)_p$, wherein said heterocycle is substituted with 0-2 $R^e$;

$R^e$ is, independently at each occurrence, H, =O, —$(CH_2)_r$—$OR^f$, F, Cl, Br, I, CN, $NO_2$, —$(CH_2)_r$—$NR^{12}R^{13}$, —$C(O)R^f$, —$(CH_2)_r$—$C(O)OR^f$, —$NR^{14}C(O)R^f$, —$(CH_2)_r$—$C(O)NR^{12}R^{13}$, —$SO_2NR^{12}R^{13}$, —$NR^{14}SO_2NR^{12}R^{13}$, —$NR^{14}SO_2$—$C_{1-4}$ alkyl, —$NR^{14}SO_2CF_3$, —$NR^{14}SO_2$-phenyl, —$S(O)_2CF_3$, —$S(O)_p$—$OR^h$, —$(CF_2)_rCF_3$, $Si(Me)_3$, $Si(Me)_2$(t-Bu), $Si(C_{1-4}$ alkyl)$_3$, $C_{1-8}$ alkyl substituted with 0-2 $R^g$, $C_{2-8}$ alkenyl substituted with 0-2 $R^g$, $C_{2-8}$ alkynyl substituted with 0-2 $R^g$, —$(CH_2)_r$—$C_{3-8}$ cycloalkyl substituted with 0-2 $R^g$, —$(CH_2)_r$—$C_{6-10}$ aryl substituted with 0-2 $R^g$, or —$(CH_2)_r$-5- to 10-membered heterocycle comprising: carbon atoms and 1-4 heteroatoms selected from N, $NR^f$, O, and $S(O)_p$, wherein said heterocycle is substituted with 0-2 $R^g$;

$R^f$ is, independently at each occurrence, H, $C_{1-6}$ alkyl, or —$(CH_2)_n$-phenyl;

$R^g$ is, independently at each occurrence, H, =O, $OR^f$, F, Cl, Br, I, CN, $NO_2$, —$NR^fR^f$, —$C(O)R^f$, —$C(O)OR^f$, —$NR^fC(O)R^f$, —$C(O)NR^fR^f$, —$SO_2NR^fR^f$, —$NR^fSO_2NR^fR^f$, —$NR^fSO_2$—$C_{1-4}$ alkyl, —$NR^fSO_2CF_3$, —$NR^fSO_2$-phenyl, —$S(O)_2CF_3$, —$S(O)_p$—$C_{1-4}$ alkyl, —$S(O)_p$-phenyl, —$(CF_2)_rCF_3$, $C_{1-6}$ alkyl, $C_{2-6}$ alkenyl, or $C_{2-6}$ alkynyl;

$R^h$ is, independently at each occurrence, $C_{1-6}$ alkyl substituted with 0-2 $R^g$, —$(CH_2)_n$-phenyl substituted with 0-2 $R^g$, or —$(CH_2)_n$-5- to 10-membered heterocycle comprising: carbon atoms and 1-4 heteroatoms selected from N, $NR^f$, O, and $S(O)_p$, wherein said heterocycle is substituted with 0-2 $R^g$;

$R^i$ is, independently at each occurrence, H, $C_{1-6}$ alkyl substituted with 0-2 $R^g$, —$(CH_2)_n$-phenyl substituted with 0-2 $R^g$, or —$(CH_2)_n$-5- to 10-membered heterocycle comprising: carbon atoms and 1-4 heteroatoms selected from N, $NR^f$, O, and $S(O)_p$, wherein said heterocycle is substituted with 0-2 $R^g$;

n, at each occurrence, is selected from 0, 1, 2, 3, and 4;

p, at each occurrence, is selected from 0, 1, and 2;

r, at each occurrence, is selected from 0, 1, 2, 3, and 4;

s, at each occurrence, is selected from 0, 1, 2, and 3; and t, at each occurrence, is selected from 1, 2, 3, and 4;

provided that when ring D is dihydroindolyl, ring A is other than thiazolyl.

In a second embodiment, the present invention provides a compound of Formula (I), within the scope of the first aspect wherein:

W is O; and $X_2$ is a bond, —$CH_2$—, —$CH_2CH_2$—, —$CH_2CHMe$—, —$CH_2CO$—, or

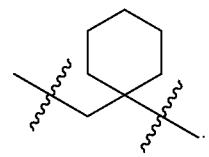

In a third embodiment, the present invention provides a compound of Formula (I), within the scope of the first aspect wherein:

ring B is substituted with 0-3 $R^7$ and selected from:

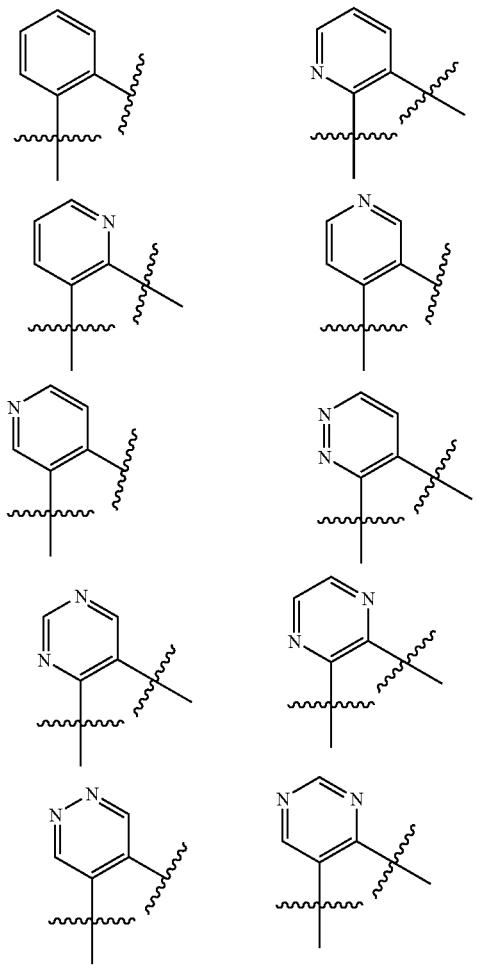

-continued
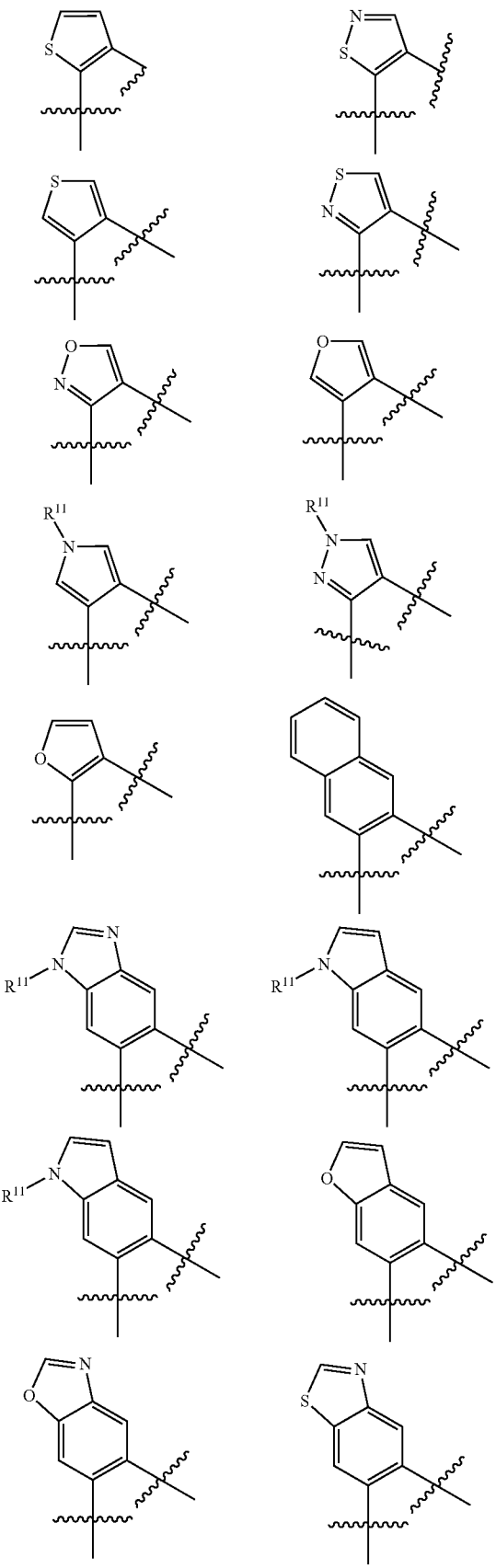
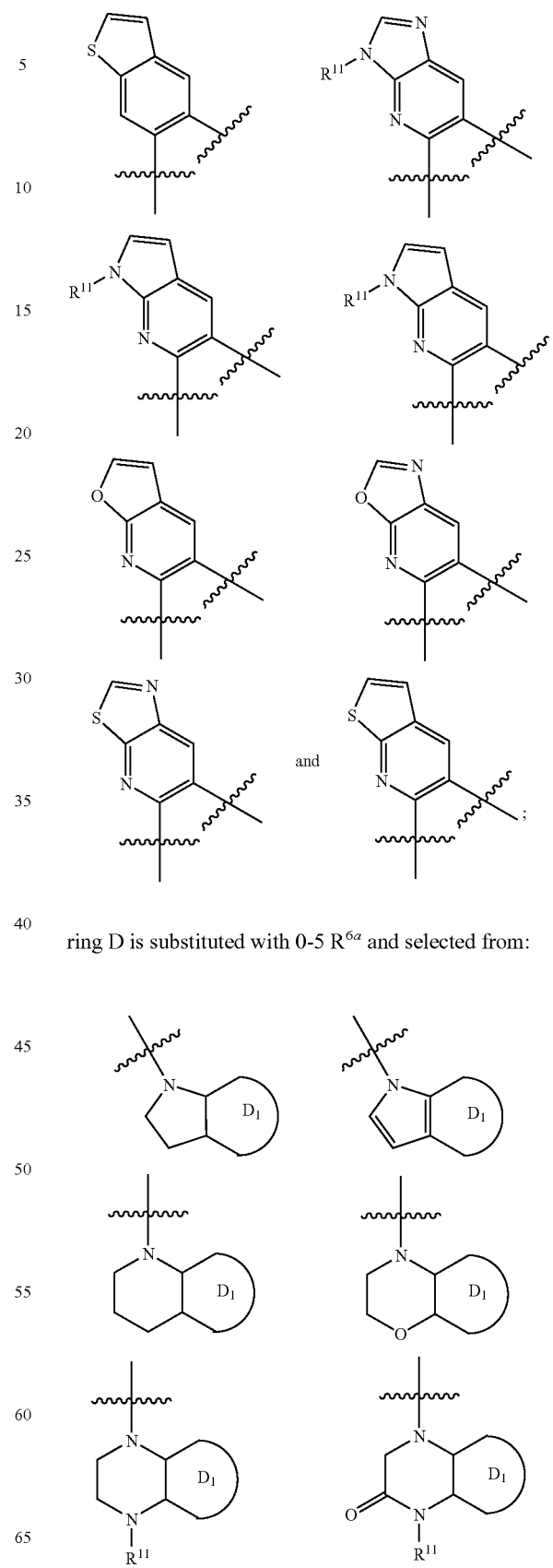
ring D is substituted with 0-5 $R^{6a}$ and selected from:

-continued

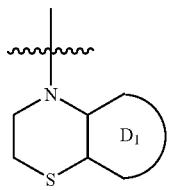 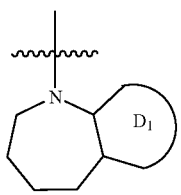

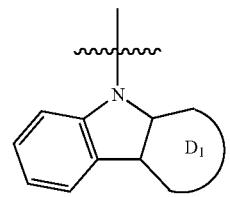 and 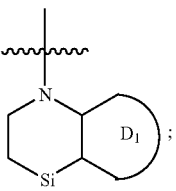 ;

wherein $D_1$ is selected from: cyclopentyl, cylohexyl, piperidinyl, tetrahydropyranyl, phenyl, pyridinyl, pyrimidinyl, thiophenyl, pyrrolyl, furanyl and thiazolyl;

W is O; and $X_2$ is a bond.

In a fourth embodiment, the present invention provides a compound of Formula (I), within the scope of the first embodiment wherein:

ring A is substituted with 0-5 $R^1$ and selected from: phenyl, pyridinyl, pyrimidinyl, furanyl, isoxazolyl, thiazolyl, thiadiazolyl, benzothiazolyl, indolyl, and benzimidazolyl.

In a fifth embodiment, the present invention provides a compound of Formula (I), within the scope of the first aspect wherein:

ring A is substituted with 0-4 $R^1$ and selected from: phenyl, pyridyl, isoxazolyl, furanyl, thienyl, thiazolyl, and benzothiazolyl; and ring B is substituted with 0-3 $R^7$ and selected from:

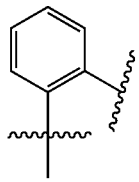 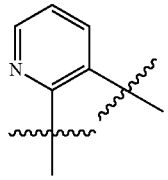

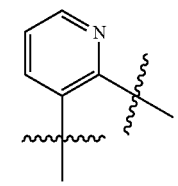 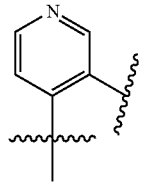

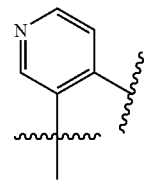 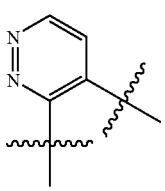

-continued

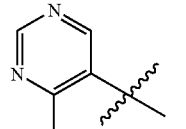 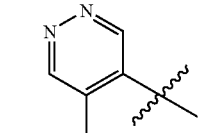

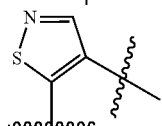 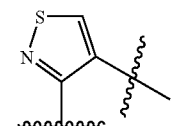

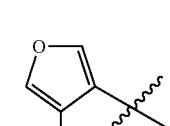 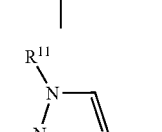

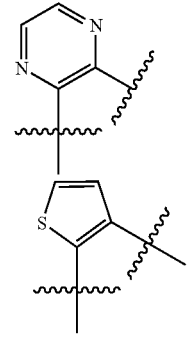 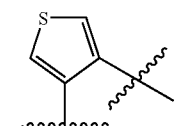

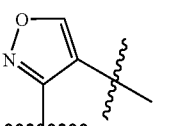 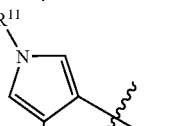 and

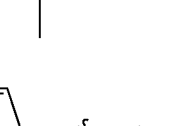

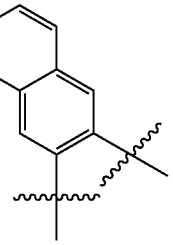 .

In a sixth embodiment, the present invention provides a compound of Formula (I), within the scope of the first embodiment wherein:

$R^1$ is, independently at each occurrence, F, Cl, Br, I, $CF_3$, —$CF_2CF_3$, $OCF_3$, —$OCF_2CF_2H$, —$OCF_2CF_3$, $SiMe_3$, —$(CR^fR^f)_r$—$OR^c$, $SR^c$, CN, $NO_2$, —$(CR^fR^f)_r$—$NR^{12}R^{13}$, —$(CR^fR^f)_r$—$C(O)R^c$, —$(CR^fR^f)_r$—$CO_2R^c$, —$(CR^fR^f)_r$—$C(O)NR^{12}R^{13}$, —$OP(O)(OEt)_2$, 4,4,5,5-tetramethyl-1,3,2-dioxaborolanyl, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, —$(CR^fR^f)_r$—$C_{3-13}$ carbocycle substituted with 0-5 $R^b$, or —$(CR^fR^f)_r$-5- to 10-membered heterocycle comprising: carbon atoms and 1-4 heteroatoms selected from N, $NR^{11}$, O, and $S(O)_p$, wherein said heterocycle is substituted with 0-5 $R^b$;

alternatively, two $R^1$s on two adjacent carbon atoms are combined with 10 the carbon atoms to which they attached, form a 5- to 7-membered carbocycle or heterocycle comprising: carbon atoms and 0-3 additional heteroatoms selected from N, $NR^{11}$, O, and $S(O)_p$, and 0-2 carbonyl groups, wherein said carbocycle or heterocycle is substituted with 0-4 $R^b$.

In a seventh embodiment, the present invention provides a compound of Formula (I), within the scope of the first embodiment wherein:

$R^{6a}$ is, independently at each occurrence, F, Cl, Br, I, —$(CR^iR^i)_r$—$OR^e$, $SR^e$, CN, $CF_3$, $OCF_3$, —$CF_2CF_3$, —$OCF_2CF_2H$, —$OCF_2CF_3$, —$NR^{12}R^{13}$, —$C(O)R^e$, —$(CR^fR^f)_r$—$C(O)OR^e$, —$Si(Me)_3$, $C_{1-4}$ haloalkyl, $C_{1-4}$ haloalkyloxy-, $C_{1-4}$ alkyloxy-, $C_{1-4}$ alkylthio-, $C_1$-$C_4$ alkyl-C(O)—, $C_{1-4}$ alkyl-O—C(O)—, $C_{1-4}$ alkyl-C(O)NH—, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, —$(CR^fR^f)_r$—$C_{3-10}$ carbocycle substituted with 0-2 $R^e$, or —$(CR^fR^f)_r$-5- to 10-membered heterocycle comprising: carbon atoms and 1-4 heteroatoms selected from N, $NR^{11}$, O, and $S(O)_p$, wherein said heterocycle is substituted with 0-2 $R^e$; and alternatively, when two $R^{6a}$ groups are attached to the same carbon atom or silicon atom, together with the carbon atom or silicon atom to which they are attached, they form a 3- to 7-membered carbocyclic or heterocyclic ring comprising: carbon atoms and 0-3 heteroatoms selected from N, $NR^{11}$, O, Si, and $S(O)_p$, 0-1 carbonyl and 0-3 ring double bonds, wherein said carbocyclic or heterocyclic ring is substituted with 0-3 $R^b$;

alternatively, when two $R^{6a}$ groups are attached to adjacent atoms, together with the atoms to which they are attached they form a 5- to 7-membered carbocyclic or heterocyclic ring comprising: carbon atoms and 0-2 heteroatoms selected from N, $NR^{11}$, O, Si, and $S(O)_p$, 0-1 carbonyl and 0-3 ring double bonds, wherein said carbocyclic or heterocyclic ring is substituted with 0-3 $R^b$.

In an eighth embodiment, the present invention provides a compound of Formula (I), within the scope of the first embodiment wherein:

$R^{11}$ is, independently at each occurrence, H, $C_{1-8}$ alkyl substituted with 0-2 $R^a$, —$C(O)(CH_2)_n(C_{3-6}$ cycloalkyl), —$C(O)(CH_2)_n$phenyl, —$C(O)O(C_{1-8}$ alkyl), —$C(O)O(CH_2)_n(C_{3-6}$ cycloalkyl), —$C(O)O(CH_2)_n$phenyl, —$C(O)O(CH_2)_{2-4}(C_{1-4}$ alkyl), —$C(O)NH(C_{1-6}$ alkyl), —$S(O)_2(C_{1-6}$ alkyl), —$S(O)_2(CH_2)_n$phenyl, —$(CR^fR^f)_r$—$C_{3-7}$ cycloalkyl, —$(CR^fR^f)_r$-phenyl, or —$(CR^fR^f)_r$-5- to 6-membered heterocycle; wherein said alkyl, cycloalkyl, phenyl, and aryl are substituted with 0-2 $R^b$, and said heteroaryl and heterocycle are substituted with 0-2 $R^b$ and comprise: carbon atoms and 1-4 heteroatoms selected from N, $NR^f$, O, and $S(O)_p$.

In a ninth embodiment, the present invention provides a compound of Formula (I), within the scope of the first embodiment wherein:

ring A is substituted with 0-4 $R^1$ and selected from: phenyl, pyridyl, isoxazolyl, furanyl, thienyl, thiazolyl, and benzothiazolyl;

ring B is substited with 0-3 $R^7$ and selected from:

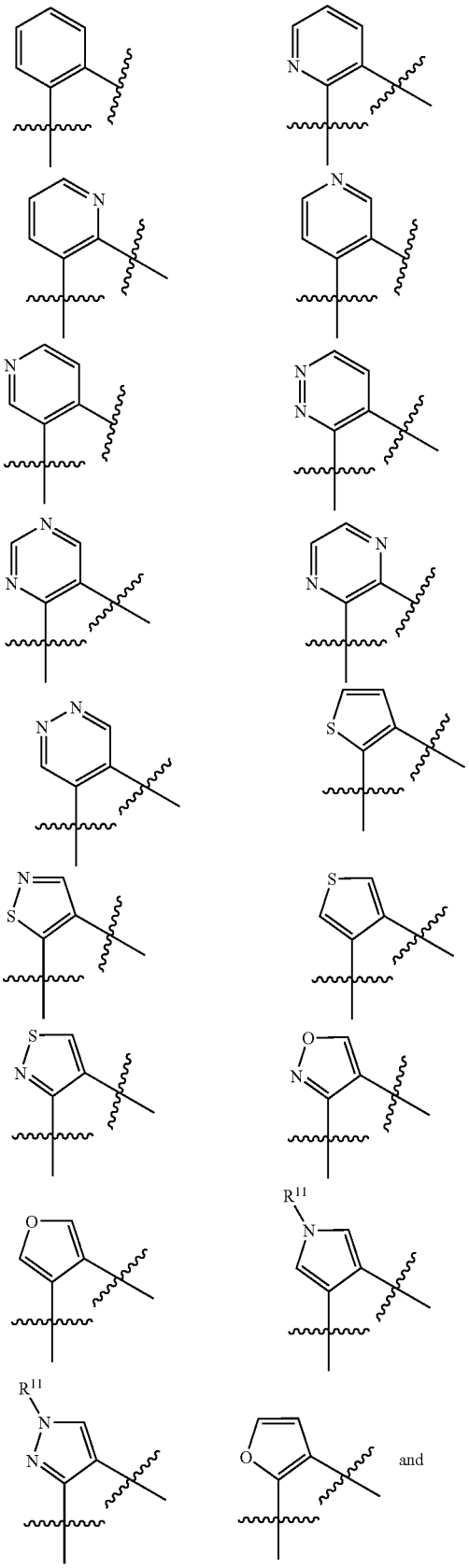

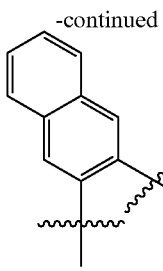

ring D is substituted with 0-5 $R^{6a}$ and selected from:

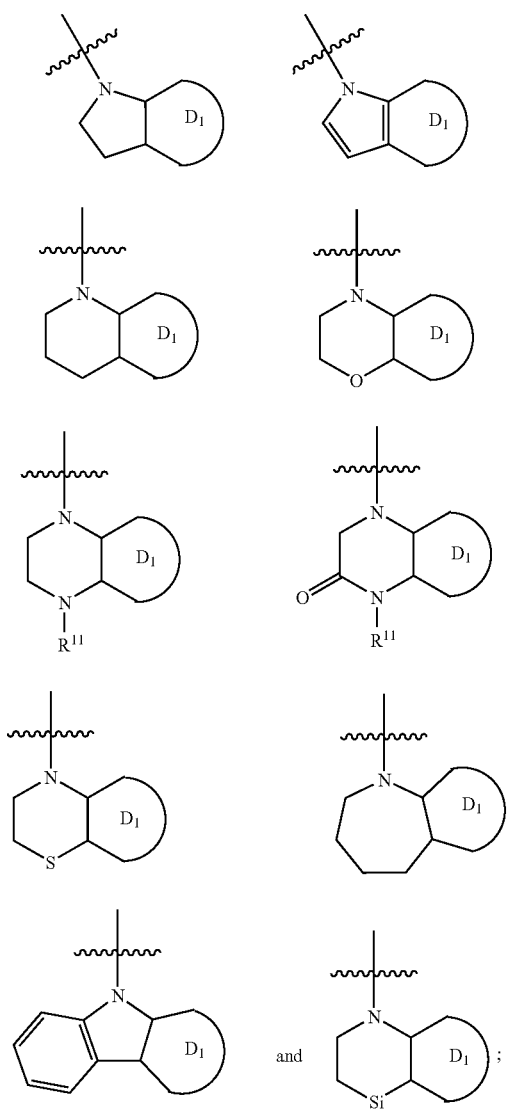

wherein $D_1$ is selected from: cyclopentyl, cylohexyl, piperidinyl, tetrahydropyranyl, phenyl, pyridinyl, pyrimidinyl, thiophenyl, pyrrolyl, furanyl and thiazolyl;

W is 0;

$X_2$ is a bond;

$R^1$ is, independently at each occurrence, F, Cl, Br, I, $CF_3$, —$CF_2CF_3$, $OCF_3$, —$OCF_2CF_2H$, —$OCF_2CF_3$, $SiMe_3$, —$(CR^fR^f)_r$—$OR^c$, $SR^c$, CN, $NO_2$, —$(CR^fR^f)_r$—$NR^{12}R^{13}$, —$(CR^fR^f)_r$—$C(O)R^c$, —$(CR^fR^f)_r$—$CO_2R^c$, —$(CR^fR^f)_r$—$C(O)NR^{12}R^{13}$, —$OP(O)(OEt)_2$, 4,4,5,5-tetramethyl-1,3,2-dioxaborolanyl, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, —$(CR^fR^f)_r$—$C_{3-13}$ carbocycle substituted with 0-5 $R^b$, or —$(CR^fR^f)_r$-5- to 10-membered heterocycle comprising: carbon atoms and 1-4 heteroatoms selected from N, $NR^{11}$, O, and $S(O)_p$, wherein said heterocycle is substituted with 0-5 $R^b$;

alternatively, two $R^1$s on two adjacent carbon atoms are combined with the carbon atoms to which they attached, form a 5- to 7-membered carbocycle or heterocycle comprising: carbon atoms and 0-3 additional heteroatoms selected from N, $NR^{11}$, O, and $S(O)_p$, and 0-2 carbonyl groups, wherein said carbocycle or heterocycle is substituted with 0-4 $R^b$;

$R^{6a}$ is, independently at each occurrence, F, Cl, Br, I, —$(CR^iR^i)_r$—$OR^c$, $SR^c$, CN, $CF_3$, $OCF_3$, —$CF_2CF_3$, —$OCF_2CF_2H$, —$OCF_2CF_3$, —$NR^{12}R^{13}$, —$C(O)R^c$, —$(CR^fR^f)_r$—$C(O)OR^c$, —$Si(Me)_3$, $C_{1-4}$ haloalkyl, $C_{1-4}$ haloalkyloxy-, $C_{1-4}$ alkyloxy-, $C_{1-4}$ alkylthio-, $C_1$-$C_4$ alkyl-C(O)—, $C_{1-4}$ alkyl-O—C(O)—, $C_{1-4}$ alkyl-C(O)NH—, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, —$(CR^fR^f)_r$—$C_{3-10}$ carbocycle substituted with 0-2 $R^e$, or —$(CR^fR^f)_r$-5- to 10-membered heterocycle comprising: carbon atoms and 1-4 heteroatoms selected from N, $NR^{11}$, O, and $S(O)_p$, wherein said heterocycle is substituted with 0-2 $R^e$;

alternatively, when two $R^{6a}$ groups are attached to the same carbon atom or silicon atom, together with the carbon atom or silicon atom to which they are attached, they form a 3- to 7-membered carbocyclic or heterocyclic ring comprising: carbon atoms and 0-3 heteroatoms selected from N, $NR^{11}$, O, Si, and $S(O)_p$, 0-1 carbonyl and 0-3 ring double bonds, wherein said carbocyclic or heterocyclic ring is substituted with 0-3 $R^b$;

alternatively, when two $R^{6a}$ groups are attached to adjacent atoms, together with the atoms to which they are attached they form a 5- to 7-membered carbocyclic or heterocyclic ring comprising: carbon atoms and 0-2 heteroatoms selected from N, $NR^{11}$, O, Si, and $S(O)_p$, 0-1 carbonyl and 0-3 ring double bonds, wherein said carbocyclic or heterocyclic ring is substituted with 0-3 $R^b$; and $R^{11}$ is, independently at each occurrence, H, $C_{1-8}$ alkyl substituted with 0-2 $R^a$, —$C(O)(CH_2)_n(C_{3-6}$ cycloalkyl), —$C(O)(CH_2)_n$phenyl, —$C(O)O(C_{1-8}$ alkyl), —$C(O)O(CH_2)_n(C_{3-6}$ cycloalkyl), —$C(O)O(CH_2)_n$phenyl, —$C(O)O(CH_2)_{2-4}(C_{1-4}$ alkyl), —$C(O)NH(C_{1-6}$ alkyl), —$S(O)_2(C_{1-6}$ alkyl), —$S(O)_2(CH_2)_n$phenyl, —$(CR^fR^f)_r$—$C_{3-7}$ cycloalkyl, —$(CR^fR^f)_r$-phenyl, or —$(CR^fR^f)_r$-5- to 6-membered heterocycle; wherein said alkyl, cycloalkyl, phenyl, and aryl are substituted with 0-2 $R^b$, and said heteroaryl and heterocycle are substituted with 0-2 $R^b$ and comprise: carbon atoms and 1-4 heteroatoms selected from N, $NR^f$, O, and $S(O)_p$.

In a tenth embodiment, the present invention provides a compound of Formnula (Ia):
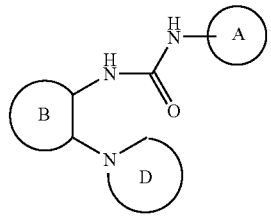
or a stereoisomer or pharmaceutically acceptable salt, solvate, or prodrug thereof, wherein:
ring A is
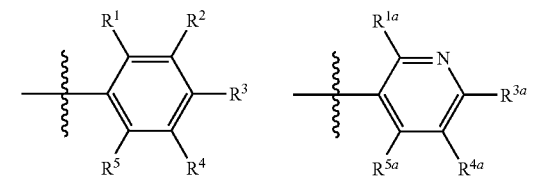
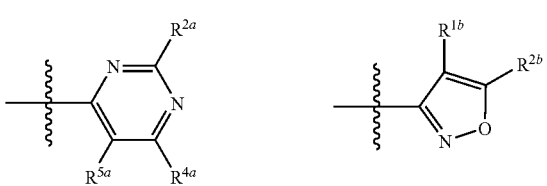
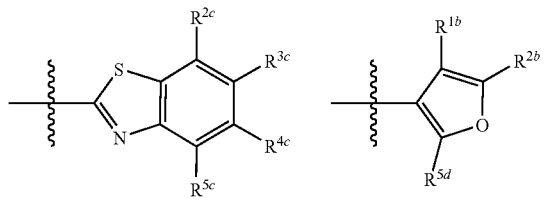
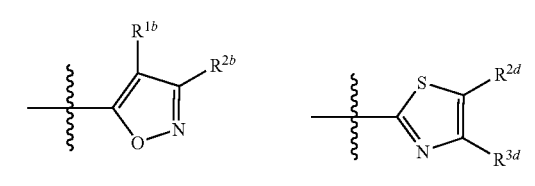
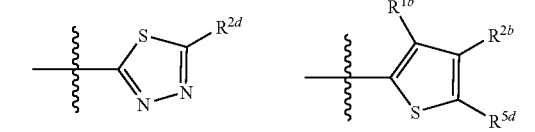
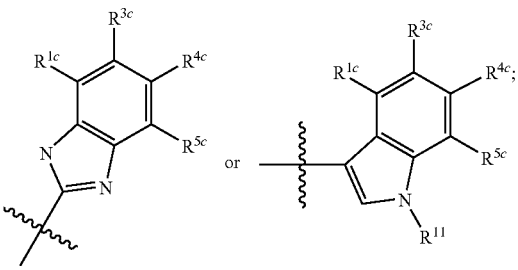
ring B is substituted with 0-3 $R^7$ and selected from:
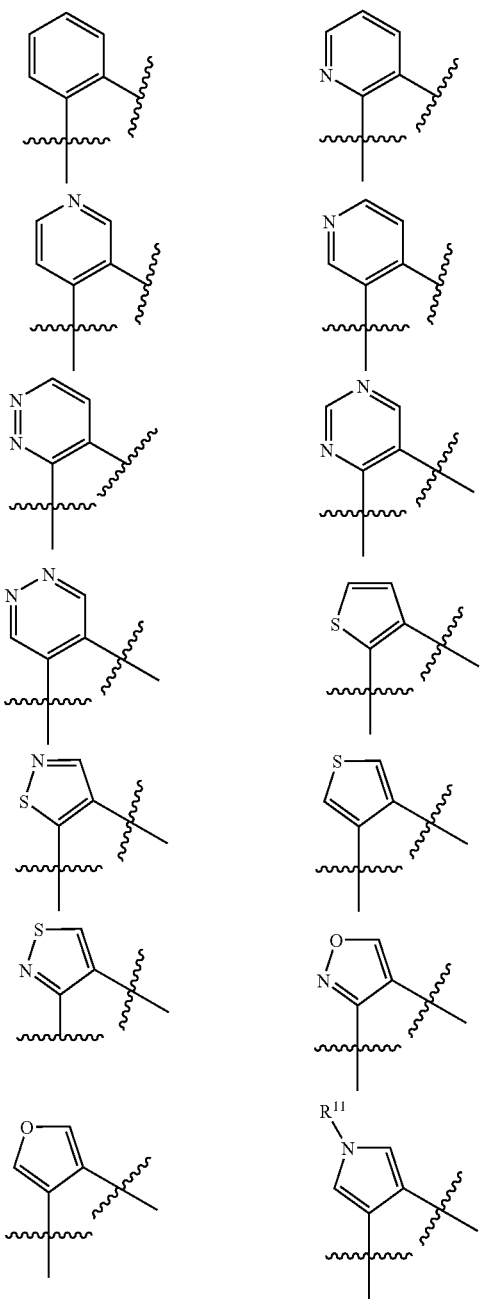

-continued

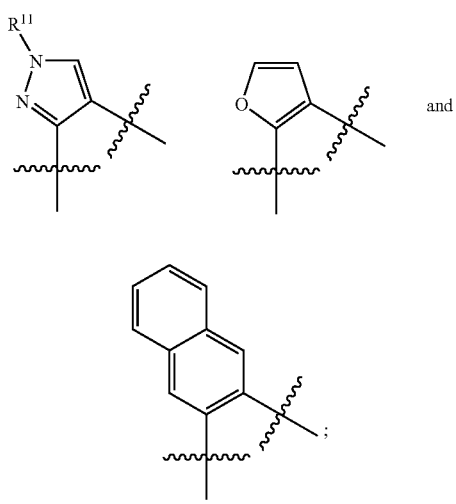

ring D is substituted with 0-5 $R^{6a}$ and selected from:

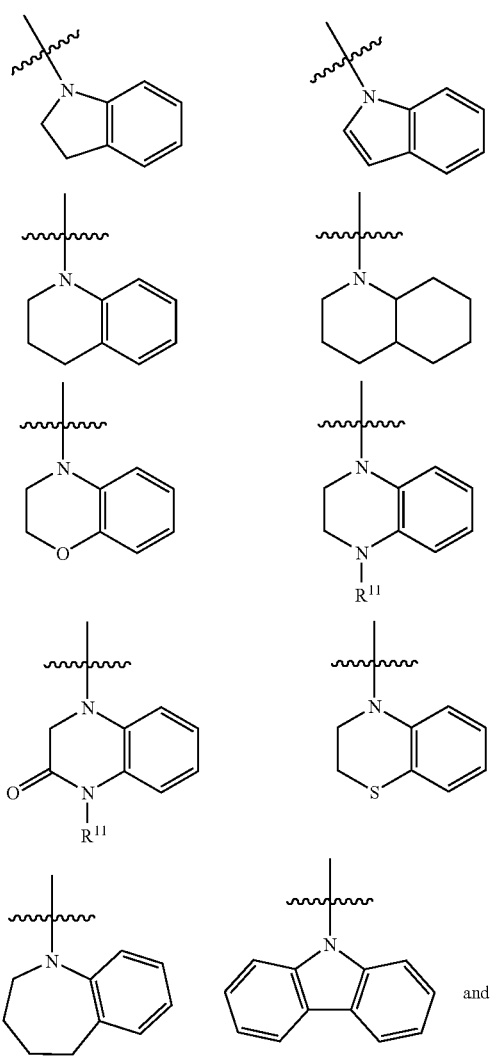

-continued

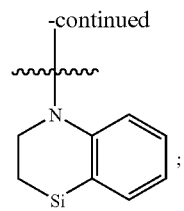

$R^1$, $R^{1a}$, $R^{1b}$, and $R^{1c}$ are, independently at each occurrence, H, F, Cl, Me, $NH_2$, or OH;

$R^2$, $R^{2a}$, $R^{2b}$, $R^{2c}$, $R^{2d}$, $R^3$, $R^{3a}$, $R^{3c}$, $R^{3d}$, $R^4$, $R^{4a}$, $R^{4c}$, $R^5$, $R^{5a}$, $R^{5c}$, and $R^{5d}$, are, independently at each occurrence, H, F, Cl, Br, I, $CF_3$, —$CF_2CF_3$, $OCF_3$, —$OCF_2CF_2H$, —$OCF_2CF_3$, $SiMe_3$, —$(CR^fR^f)_r$—$OR^c$, $SR^c$, CN, $NO_2$, —$(CR^fR^f)_r$—$NR^{12}R^{13}$, —$(CR^fR^f)_u$—C(O)$R^c$, —$(CR^fR^f)_r$—$CO_2R^c$, —$(CR^fR^f)_u$—C(O)$NR^{12}R^{13}$, —OP(O)(OEt)$_2$, 4,4,5,5-tetramethyl-1,3,2-dioxaborolanyl, $C_{1-8}$ alkyl substituted with 0-2 $R^a$, —$(CR^fR^f)_u$—$C_{3-6}$ carbocycle substituted with 0-2 $R^b$, or —$(CR^fR^f)_u$-5- to 6-membered heterocycle comprising: carbon atoms and 1-4 heteroatoms selected from N, $NR^{11}$, O, and S(O)$_p$, wherein said heterocycle is substituted with 0-2 $R^b$;

alternatively, $R^1+R^2$, $R^2+R^3$, $R^3+R^4$, $R^4+R^5$, $R^{1a}+R^{2a}$, $R^{2a}+R^{3a}$, $R^{3a}+R^{4a}$, $R^{4a}+R^{5a}$, $R^{1b}+R^{2b}$, $R^{2b}+R^{5d}$, $R^{1c}+R^{3c}$, $R^{2c}+R^{3c}$, $R^{2d}+R^{3d}$, $R^{3c}+R^{4c}$, or $R^{4c}+R^{5c}$, combine with the carbon atoms to which they are attached, form 5- to 10-membered carbocyclic or heterocyclic ring comprising: carbon atoms and 0-3 heteroatoms selected from N, $NR^{11}$, O, and S(O)$_p$, 0-1 carbonyl group, and additional 0-2 double bonds, wherein said carbocyclic or heterocyclic ring is substituted with 0-2 $R^b$;

$R^{6a}$ is, independently at each occurrence, F, Cl, Br, I, —$(CR^fR^f)_r$—$OR^c$, $SR^c$, CN, $CF_3$, $OCF_3$, —$CF_2CF_3$, —$OCF_2CF_2H$, —$OCF_2CF_3$, —$NR^{12}R^{13}$, —C(O)$R^c$, —$(CR^fR^f)_r$—C(O)$OR^c$, —Si(Me)$_3$, $C_{1-4}$ haloalkyl, $C_{1-4}$ haloalkyloxy-, $C_{1-4}$ alkyloxy-, $C_{1-4}$ alkylthio-, $C_1$-$C_4$ alkyl-C(O)—, $C_{1-4}$ alkyl-O—C(O)—, $C_{1-4}$ alkyl-C(O)NH—, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, —$(CR^fR^f)_r$—$C_{3-10}$ carbocycle substituted with 0-2 $R^e$, or —$(CR^fR^f)_r$-5- to 10-membered heterocycle comprising: carbon atoms and 1-4 heteroatoms selected from N, $NR^{11}$, O, and S(O)$_p$, wherein said heterocycle is substituted with 0-2 $R^e$;

alternatively, when two $R^{6a}$ groups are attached to the same carbon atom or silicon atom, together with the carbon atom or silicon atom to which they are attached, they form a 3- to 7-membered carbocyclic or heterocyclic ring comprising: carbon atoms and 0-3 heteroatoms selected from N, $NR^{11}$, O, Si, and S(O)$_p$, 0-1 carbonyl and 0-3 ring double bonds, wherein said carbocyclic or heterocyclic ring is substituted with 0-3 $R^b$;

alternatively, when two $R^{6a}$ groups are attached to adjacent atoms, together with the atoms to which they are attached they form a 5- to 7-membered carbocyclic or heterocyclic ring comprising: carbon atoms and 0-2 heteroatoms selected from N, $NR^{11}$, O, Si, and S(O)$_p$, 0-1 carbonyl and 0-3 ring double bonds, wherein said carbocyclic or heterocyclic ring is substituted with 0-3 $R^b$;

$R^7$ is, independently at each occurrence, H, =O, F, Cl, Br, I, $OCF_3$, $CF_3$, $OR^c$, $SR^c$, CN, $NO_2$, —$NR^{12}R^{13}$, —C(O)$R^c$, —C(O)O$R^c$, —C(O)$NR^{12}R^{13}$, —$NR^{14}$C(O)$R^d$, —S(O)$_p$$NR^{12}R^{13}$, —S(O)$R^d$, —S(O)$_2R^d$, $C_{1-6}$ alkyl substituted with 0-2 $R^a$, —$(CH_2)_u$—$C_{3-10}$ carbocycle substituted with 0-3 $R^b$, or —$(CH_2)_u$-5- to 10-membered heterocycle comprising: carbon atoms and 1-4 heteroatoms selected from N, $NR^{7b}$, O, and $S(O)_p$, wherein said heterocycle is substituted with 0-3 $R^b$;

$R^{7b}$ is H, $C_{1-4}$ alkyl, —$C(O)(C_{1-4}$ alkyl), —$C(O)$phenyl, —$C(O)$benzyl, or benzyl;

$R^{11}$ is, independently at each occurrence, H, $C_{1-8}$ alkyl substituted with 0-2 $R^a$, —$C(O)(CH_2)_n(C_{3-6}$ cycloalkyl), —$C(O)(CH_2)_n$phenyl, —$C(O)O(C_{1-8}$ alkyl), —$C(O)O(CH_2)_n(C_{3-6}$ cycloalkyl), —$C(O)O(CH_2)_n$phenyl, —$C(O)O(CH_2)_{2-4}(C_{1-4}$ alkyl), —$C(O)NH(C_{1-6}$ alkyl), —$S(O)_2(C_{1-6}$ alkyl), —$S(O)_2(CH_2)_n$phenyl, —$(CR^fR^f)_r$—$C_{3-7}$ cycloalkyl, —$(CR^fR^f)_r$-phenyl, or —$(CR^fR^f)_r$-5- to 6-membered heterocycle; wherein said alkyl, cycloalkyl, phenyl, and aryl are substituted with 0-2 $R^b$, and said heteroaryl and heterocycle are substituted with 0-2 $R^b$ and comprise: carbon atoms and 1-4 heteroatoms selected from N, $NR^f$, O, and $S(O)_p$;

$R^{12}$ is, independently at each occurrence, H, $C_{1-6}$ alkyl, —$C(O)(C_{1-6}$ alkyl), —$C(O)(CH_2)_n$phenyl, —$C(O)(CH_2)_n$(5- to 6-membered heteroaryl), —$C(O)O(C_{1-4}$ alkyl), —$C(O)OCH_2$phenyl, —$(CH_2)_nOC(O)OCH_2$(5- to 6-membered heteroaryl), —$(CH_2)_nOC(O)(C_{1-4}$ alkyl), —$(CH_2)_nOC(O)$phenyl, —$(CH_2)_nOC(O)$(5- to 6-membered heteroaryl), —$(CH_2)_nC(O)O(C_{1-4}$ alkyl), —$(CH_2)_nC(O)O$phenyl, —$(CH_2)_nC(O)O$(5- to 6-membered heteroaryl), —$(CH_2)_nC(O)NH(C_{1-6}$ alkyl), —$(CH_2)_nC(O)NH$phenyl, —$(CH_2)_nC(O)NH$(5- to 6-membered heteroaryl), —$(CH_2)_tOC(O)NH(C_{1-6}$ alkyl), —$(CH_2)_tOC(O)NH$phenyl, —$(CH_2)_tOC(O)NH$(5- to 6-membered heteroaryl), —$S(O)_2(C_{1-6}$ alkyl), —$S(O)_2(CH_2)_n$phenyl, —$S(O)_2(CH_2)_n$(5- to 6-membered heteroaryl), —$(CR^fR^f)_n$-phenyl, or —$(CR^fR^f)_n$-5- to 6-membered heteroaryl; wherein said alkyl, and aryl are substituted with 0-2 $R^g$; and said heteroaryl is substituted with 0-2 $R^g$ and comprises: carbon atoms and 1-4 heteroatoms selected from N, $NR^{11}$, O, and $S(O)_p$, $R^{13}$ is, independently at each occurrence, H, $C_{1-6}$ alkyl, or —$(CH_2)_n$-phenyl;

alternatively, $R^{12}$ and $R^{13}$, when attached to the same nitrogen, combine to form a 5- to 10-membered heterocyclic ring comprising: carbon atoms and 1-2 additional heteroatoms selected from N, $NR^{11}$, O, and $S(O)_p$;

$R^{14}$ is, independently at each occurrence, H, $C_{1-6}$ alkyl substituted with 0-2 $R^{14a}$, $C_{2-6}$ alkenyl substituted with 0-2 $R^{14a}$, $C_{2-6}$ alkynyl substituted with 0-2 $R^{14a}$, —$(CH_2)_u$—$C_{3-6}$ cycloalkyl substituted with 0-3 $R^g$, —$(CH_2)_u$-phenyl substituted with 0-3 $R^g$, or —$(CH_2)_u$-5- to 6-membered heterocycle comprising: carbon atoms and 1-4 heteroatoms selected from N, $NR^{11}$, O, and $S(O)_p$, wherein said heterocycle is substituted with 0-3 $R^g$;

$R^{14a}$ is, independently at each occurrence, H, $C_{1-4}$ alkyl, $OR^f$, Cl, F, Br, I, =O, $CF_3$, CN, $NO_2$, —$C(O)R^f$, —$C(O)OR^f$, —$C(O)NR^{12}R^{13}$, or —$S(O)_pR^f$;

$R^a$ is, independently at each occurrence, H, =O, F, $OCF_3$, $CF_3$, $OR^c$, $SR^c$, CN, —$NR^{12}R^{13}$, —$C(O)R^c$, —$C(O)OR^c$, —$C(O)NR^{12}R^{13}$, —$NR^{14}C(O)R^d$, —$S(O)_pNR^{12}R^{13}$, —$S(O)R^d$, —$S(O)_2R^d$, —$(CH_2)_u$—$C_3$-10 carbocycle substituted with 0-3 $R^e$, or —$(CH_2)_u$-5- to 10-membered heterocycle comprising: carbon atoms and 1-4 heteroatoms selected from N, $NR^f$, O, and $S(O)_p$, wherein said heterocycle is substituted with 0-3 $R^e$;

$R^b$ is, independently at each occurrence, H, =O, F, Cl, Br, I, —$(CH_2)_r$—$OR^c$, $SR^c$, CN, $NO_2$, $CF_3$, $OCF_3$, —$(CH_2)_r$—$NR^{12}R^{13}$, —$C(O)R^c$, —$(CH_2)_r$—$C(O)OR^c$, —$(CH_2)_r$—$C(O)NR^{12}R^{13}$, —$NR^{14}C(O)R^d$, —$S(O)_pNR^{12}R^{13}$, —$S(O)R^d$, —$S(O)_2R^d$, $C_{1-4}$ haloalkyl, $C_{1-4}$ haloalkyloxy-, $C_{1-4}$ alkyloxy-, $C_{1-4}$ alkylthio-, $C_{1-4}$ alkyl-C(O)—, $C_{1-4}$ alkyl-O—C(O)—, $C_{1-4}$ alkyl-C(O)NH—, $C_{1-6}$ alkyl substituted with 0-2 $R^a$, $C_{2-4}$ alkenyl substituted with 0-2 $R^a$, $C_{2-4}$ alkynyl substituted with 0-2 $R^a$, —$(CH_2)_u$—$C_{3-10}$ carbocycle substituted with 0-3 $R^e$, or —$(CH_2)_u$-5- to 10-membered heterocycle comprising: carbon atoms and 1-4 heteroatoms selected from N, $NR^f$, O, and $S(O)_p$, wherein said heterocycle is substituted with 0-3 $R^e$;

$R^c$ is, independently at each occurrence, H, —$OP(O)(OEt)_2$, $C_{1-8}$ alkyl substituted with 0-2 $R^e$, $C_{2-4}$ alkenyl substituted with 0-2 $R^e$, $C_{2-4}$ alkynyl substituted with 0-2 $R^e$, —$(CH_2)_u$—$C_{3-8}$ cycloalkyl substituted with 0-2 $R^e$, —$(CH_2)_u$—$C_{6-10}$ aryl substituted with 0-2 $R^e$, or —$(CH_2)_u$-5- to 10-membered heterocycle comprising: carbon atoms and 1-4 heteroatoms selected from N, $NR^f$, O, and $S(O)_p$, wherein said heterocycle is substituted with 0-2 $R^e$;

$R^d$ is, independently at each occurrence, $CF_3$, OH, $C_{1-4}$ alkoxy, $C_{1-6}$ alkyl, —$(CH_2)_u$—$C_{3-10}$ carbocycle substituted with 0-2 $R^e$, or —$(CH_2)_u$-5- to 10-membered heterocycle comprising: carbon atoms and 1-4 heteroatoms selected from N, $NR^f$, O, and $S(O)_p$, wherein said heterocycle is substituted with 0-2 $R^e$;

$R^e$ is, independently at each occurrence, H, =O, —$(CH_2)_r$—$OR^f$, F, Cl, Br, I, CN, $NO_2$, —$(CH_2)_u$—$NR^{12}R^{13}$, —$C(O)R^f$, —$(CH_2)_r$—$C(O)OR^f$, —$NR^{14}C(O)R^f$, —$(CH_2)_r$—$C(O)NR^{12}R^{13}$, —$SO_2NR^{12}R^{13}$, —$NR^{14}SO_2NR^{12}R^{13}$, —$NR^{14}SO_2$—$C_{1-4}$ alkyl, —$NR^{14}SO_2CF_3$, —$NR^{14}SO_2$-phenyl, —$S(O)_2CF_3$, —$S(O)_p$—$C_{1-4}$ alkyl, —$S(O)_p$-phenyl, —$(CF_2)_uCF_3$, $C_{1-6}$ alkyl substituted with 0-2 $R^g$, $C_{2-4}$ alkenyl substituted with 0-2 $R^g$, $C_{2-4}$ akynyl substituted with 0-2 $R^g$, —$(CH_2)_u$—$C_{3-8}$ cycloalkyl substituted with 0-2 $R^g$, —$(CH_2)_u$—$C_{6-10}$ aryl substituted with 0-2 $R^g$, or —$(CH_2)_u$-5- to 10-membered heterocycle comprising: carbon atoms and 1-4 heteroatoms selected from N, $NR^f$, O, and $S(O)_p$, wherein said heterocycle is substituted with 0-2 $R^g$;

$R^f$ is, independently at each occurrence, H, or $C_{1-4}$ alkyl;

$R^g$ is, independently at each occurrence, H, =O, $OR^f$, F, Cl, Br, I, CN, $NO_2$, —$NR^fR^f$, —$C(O)R^f$, —$C(O)OR^f$, —$NR^fC(O)R^f$, —$C(O)NR^fR^f$, —$SO_2NR^fR^f$, —$NR^fSO_2NR^fR^f$, —$NR^fSO_2$—$C_{1-4}$ alkyl, —$NR^fSO_2CF_3$, —$NR^fSO_2$-phenyl, —$S(O)_2CF_3$, —$S(O)_p$—$C_{1-4}$ alkyl, —$S(O)_p$-phenyl, —$(CF_2)_uCF_3$, $C_{1-6}$ alkyl, $C_{2-4}$ alkenyl, or $C_{2-4}$ alkynyl;

$R^h$ is, independently at each occurrence, $C_{1-6}$ alkyl substituted with 0-2 $R^g$, or —$(CH_2)_n$-phenyl substituted with 0-2 $R^g$;

n, at each occurrence, is selected from 0, 1, and 2;

p, at each occurrence, is selected from 0, 1, and 2;

r, at each occurrence, is selected from 0, 1, 2, 3, and 4;

s, at each occurrence, is selected from 0, 1, 2, and 3;

t, at each occurrence, is selected from 1 and 2; and u, at each occurrence, is selected from 0, 1, and 2;

provided that when ring D is dihydroindolyl, ring A is other than thiazolyl.

In an eleventh embodiment, the present invention provides a compound of Formula (Ia):
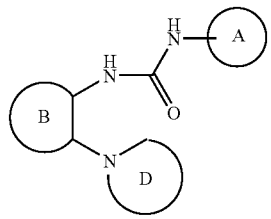
(Ia)
or a stereoisomer or pharmaceutically acceptable salt, solvate, or prodrug thereof, wherein:
ring A is
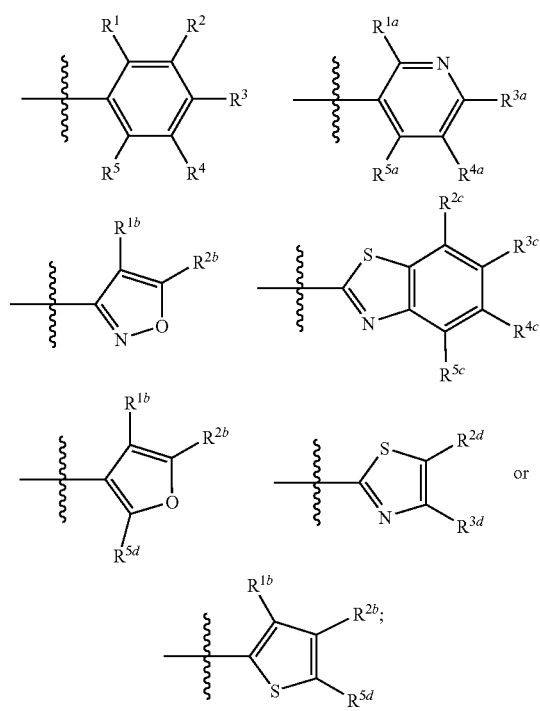
ring B is
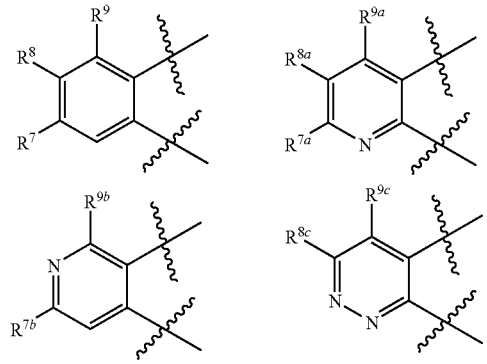
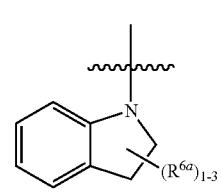 or 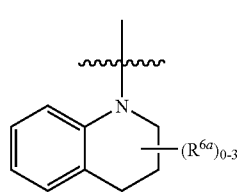;
ring D is selected from:
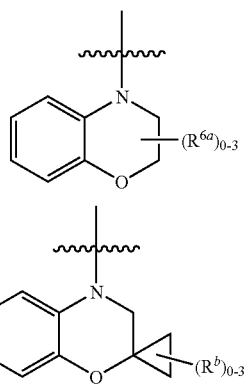 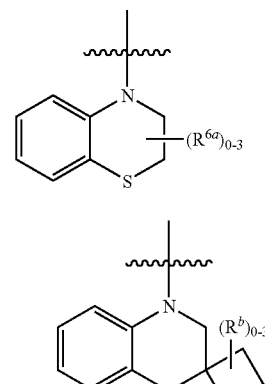
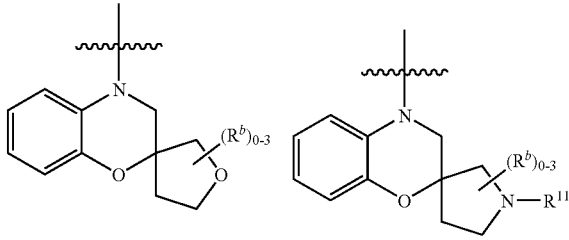
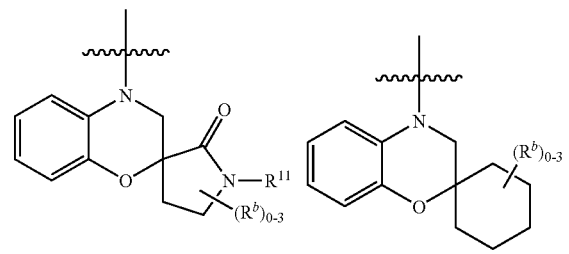
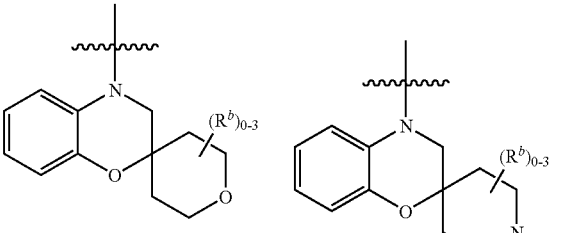

-continued
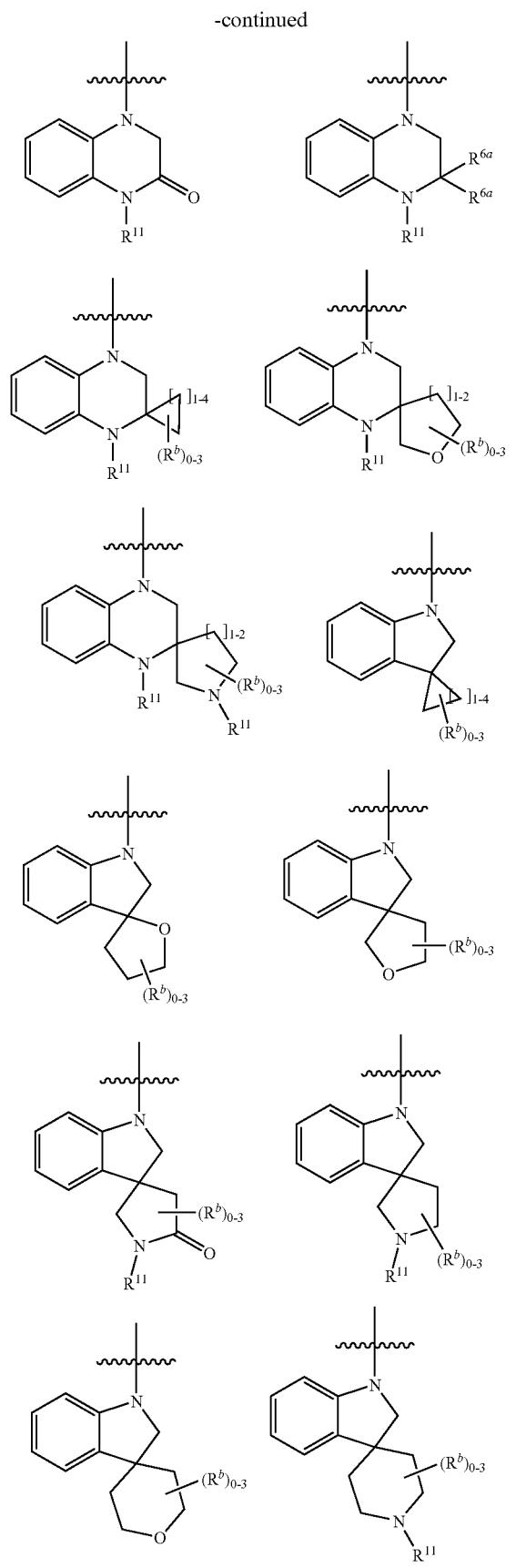
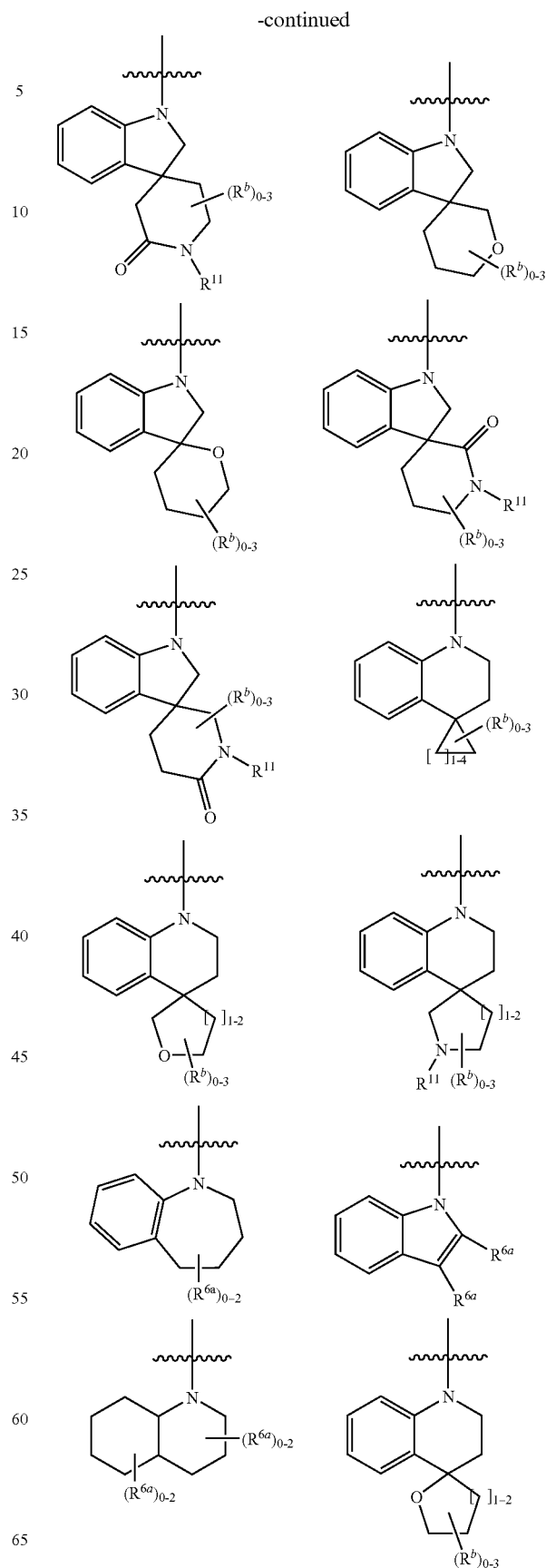

-continued

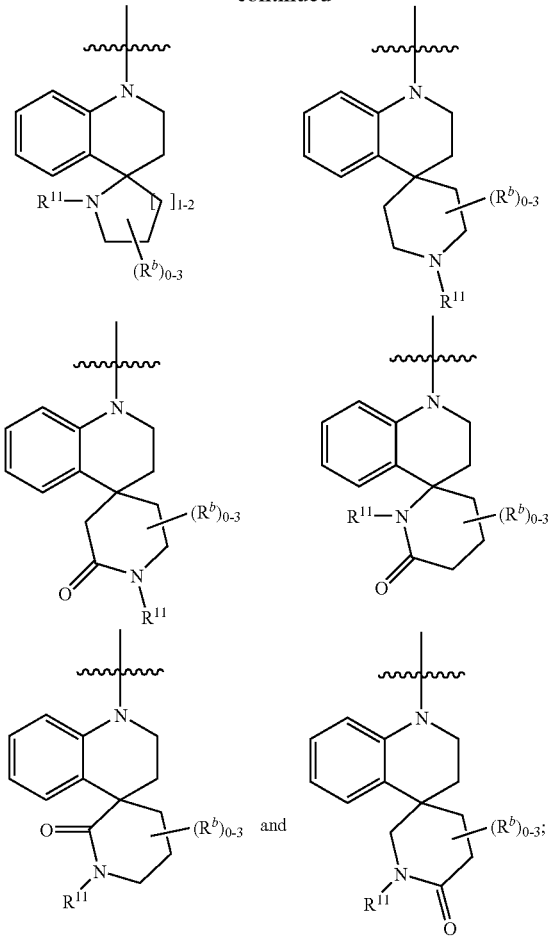

wherein the phenyl ring in each of the structures is substituted with 0-2 $R^{6a}$;

$R^1$, $R^{1a}$, and $R^{1b}$ are, independently at each occurrence, H, F, Cl, Me, $NH_2$, OH,

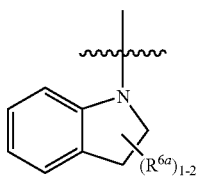

or phenoxy substituted with 0-2 $R^e$;

$R^2$, $R^{2b}$, $R^{2c}$, and $R^{2d}$ are, independently at each occurrence, H, F, Cl, Br, $C_{1-6}$ alkyl, $C_{1-6}$ alkoxy, —O($CH_2$)$_8$ $CO_2$Me, —O($CH_2$)$_2$C(Me)$_2$OMe, —O($CH_2$)$_2$OCOMe, $NO_2$, $CF_3$, $CF_2CF_3$, 2-$CH_2$N(Me)$_2$-Ph, Ph, cyclohexoxy, 4-Me-cyclohexoxy, cyclohexylmethoxy, (1-Bn-pyrrolidin-3-yl)oxy, (1-Bn-pyrrolidin-3-yl)methoxy, (1H-pyrrol-1-yl)ethoxy, (2-Bu-1H-imidazol-4-yl)methoxy, (1-Ph-1H-1,2,3-triazol-4-yl)methoxy, 1-Bn-piperidin-3-oxy, 1-Bn-piperidin-4-oxy, 4-Bn-morpholin-2-yl-methoxy, benzoxy, 4-$CO_2$Me-benzoxy or $SiMe_3$;

$R^3$, $R^{3a}$, $R^{3c}$, and $R^{3d}$ are, independently at each occurrence, H, F, Cl, Br, $C_{1-6}$ alkyl, $C_{1-6}$ alkoxy, —OCH(Me) $CH_2$O-t-Bu, $CF_3$, $OCF_3$, —$OCF_2CF_2H$, —$OCF_2CF_3$, $SiMe_3$, $NH_2$, $NMe_2$, —$CH_2NMe_2$, $NEt_2$, —NHPh, —N(Me)Ph, —NH(4-OMe-Ph), —NH(2-$CF_3$-Ph), -NH(2-t-Bu-Ph), —CH(Me)N(Me)(3-$CF_3$-Bn), —CH(Me)N(Me)(4-$CF_3$-Bn), —CH(Me)N(Me)(furan-2-ylmethyl), —CH(Me)N(Me)(thien-2-ylmethyl), —CH(Me)NHCH(Me)Ph, —CH(Me)OH, —CH(Me)O(i-Pr), —CH(Me)O(i-Bu), —CH(Me)O(3-$CF_3$-Bn), —CH(Me)O(4-$CF_3$-Bn), —CH(Me)O(1-Bn-pyrrolidin-3-ylmethyl), —CH(Me)OCH$_2$C(Me)$_2$CH$_2$NMe$_2$, —CH(Me)OBn, —CH(Me)O(4-i-Pr-Bn), —CH(Me)O (4-OPh-Bn), —CH(Me)O(3,5-diCl-Bn), —CH(Me) OCH$_2$(1-Bn-piperidin-4-yl), —CH$_2$NHBn, —CH$_2$NH (4-CF$_3$-Bn), —CH$_2$N(Me)Bn, —CH(Me)NHCH$_2$-pyridin-2-yl, —CH(Me)NHCH$_2$-pyridin-4-yl, —CH (Me)NHCH$_2$(6-Cl-pyridin-3-yl), —CH(Me)N(Me)(i-Bu), —CH(Me)N(Me)Bn, —CH(Me)N(Me)(4-OMe-Bn), —CH(Me)N(Me)(4-F-Bn), —CH(Me)N(Me)(3-Cl-Bn), —CH(Me)N(Me)(4-Cl-Bn), —CH(Me)N(Me) (3,4-diCl-Bn), —CH(Me)N(Me)CH$_2$CH$_2$Ph, —CH (Me)N(Me)CH$_2$-pyridin-2-yl, —CH(Me)N(Me)CH$_2$-pyridin-3-yl, —CH(Me)N(Me)CH$_2$-pyridin-4-yl, —CH(Me)N(Me)CH$_2$-furan-2-yl, —CH(Me)N(Me) CH$_2$-thien-2-yl, —CH(Me)N(Me)CH$_2$-(5-Me-thien-2-yl), —CH(Me)N(Me)CH$_2$-(5-Cl-thien-2-yl), —CH (Me)N(Et)Bn, —CH(Me)N(Et)(4-Me-Bn), —CH(Me) N(Et)(2-Cl-Bn), —CH(Me)N(Bn)CH$_2$CN, —CH(Me) N(Bn)CH$_2$CH$_2$OH, —CH(Me)N(Bn)CH$_2$CO$_2$Me, —CH(Me)N(Bn)CH$_2$CONMe$_2$, —CH(Me)N(Bn) CH$_2$CON(Me)(Bn), —CH(Me)-isoindolin-2-yl, —CH (Me)-(1,2,3,4-tetrahydroisoquinolin-2-yl), —CH(Me) (4-Bn-piperazin-1-yl), COMe, CO$_2$Me, CO$_2$Et, —CH$_2$CO$_2$Me, —C(Me)$_2$CO$_2$Me, —O(CH$_2$)$_5$CO$_2$Et, —O(CH$_2$)$_8$CO$_2$Me, —O(CH$_2$)$_2$C(Me)$_2$OMe, —O(CH$_2$)$_2$OCOMe, —OCH$_2$C(Me)$_2$CH$_2$NMe$_2$, Ph, 2-CH$_2$OH-Ph, 2-CH$_2$N(Me)$_2$-Ph, 3-CH$_2$N(Me)$_2$-Ph, 4-CH$_2$N(Me)$_2$-Ph, 2-((3-OH-pyrrolidin-1-yl)methyl)-Ph, phenoxy, 2-t-Bu-phenoxy, 2-CF$_3$-phenoxy, Bn, benzoxy, 3-OMe-benzoxy, 4-CO$_2$Me-benzoxy, 4-OCF$_3$-benzoxy, 2,4-diF-benzoxy, cyclohexylmethoxy, cyclohexylethoxy, cyclopentoxy, 3-Me-cyclopentoxy, cyclohexoxy, 4-Me-cyclohexoxy, 4-CO$_2$Et-cyclohexoxy, 1-Bn-pyrrolidin-3-oxy, (1-Bn-pyrrolidin-3-yl)methoxy, 1H-pyrazol-1-yl, 3-CO$_2$Et-5-Me-1H-pyrazol-1-yl, 4-CO$_2$Et-5-Me-1H-pyrazol-1-yl, 5-CO$_2$Et-3-Me-1H-pyrazol-1-yl, (2-Bu-1H-imidazol-4-yl)methoxy, 1H-1,2,4-triazol-1-yl, (1-Ph-1H-1,2,3-triazol-4-yl) methoxy, 2-(1H-pyrrol-1-yl)ethoxy, 1-piperidinyl, 1-Bn-piperazin-4-yl, (2,2-dimethyl-1,3-dioxolan-4-yl) methoxy, 1-Bn-piperidin-3-oxy, 1-Bn-piperidin-4-oxy, (1-(i-Bu)-piperidin-4-yl)methoxy, (1-isopentyl-piperidin-4-yl)methoxy, (1-CO$_2$(t-Bu)-piperidin-4-yl)methoxy, (1-CO$_2$Bn-piperidin-4-yl)methoxy, (1-Bn-piperidin-4-yl)methoxy, (1-phenethyl-piperidin-4-yl) methoxy, (1-(4-phenylbutyl)-piperidin-4-yl)methoxy, (1-cyclohexylmethyl-piperidin-4-yl-methoxy, (1-((pyridin-2-yl)methyl)-piperdin-4-yl)methoxy, (1-((pyridin-4-yl)methyl)-piperidin-4-yl)methoxy, (1-((1,3-dioxolan-2-yl)methyl)piperidin-4-yl)methoxy, N-morpholinyl, 4-Bn-morpholin-2-yl-methoxy, $C_{3-6}$ cycloalkyl substituted with —CO$_2$Me, —CH$_2$OH, or —CH$_2$OMe, 4,4,5,5-tetramethyl-1,3,2-dioxaborolanyl, or —OP(O)(OEt)$_2$;

$R^4$, $R^{4a}$, and $R^{4c}$ are H;

$R^5$, $R^{5a}$, $R^{5c}$, and $R^{5d}$ are, independently at each occurrence, H, Me, F or Cl;

alteratively, $R^1+R^2$, $R^2+R^3$, $R^3+R^4$, $R^4+R^5$, $R^{3a}+R^{4a}$, $R^{4a}+R^{5a}$, $R^{1b}+R^{2b}$, $R^{2c}+R^{3c}$, $R^{3c}+R^{4c}$, $R^{4c}+R^{5c}$, $R^{1b}+R^{2b}$, $R^{2d}+R^{3d}$, or $R^{2b}+R^{5d}$, combine with the carbon atoms to which they attached, form 5- to 10-membered carbocyclic or heterocyclic ring comprising: carbon atoms and 0-3 heteroatoms selected from N, $NR^{11}$, O, and $S(O)_p$, 0-1 carbonyl group, and additional 0-2 double bonds, wherein said carbocyclic or heterocyclic ring is substituted with 0-2 $R^b$;

$R^{6a}$ is, independently at each occurrence, H, F, Cl, Br, I, CN, —C(Me)$_2$CN, C$_{1-8}$ alkyl, C$_{2-8}$ alkenyl, OH, SMe, S(i-Pr), —C(Me)$_2$OMe, —C(Me)$_2$OEt, —C(Me)$_2$OPr, —CHMeO(CH$_2$)$_2$OMe, —C(Me)$_2$O(CH$_2$)$_2$OMe, —C(Et)$_2$OMe, —C(Et)$_2$OEt, COPh, —CH=CHCO$_2$(t-Bu), CF$_3$, OCF$_3$, C$_{1-4}$ alkyloxy, CO$_2$Me, —CH$_2$CO$_2$Me, C$_{3-7}$ cycloalkyl, Ph, Bn, 1-pyrrolidinyl, 5-isoxazolyl, N-morpholinyl, 4-Bn-piperazinyl, 1-piperidinyl, 1-Bn-piperidin-4-yl, or —Si(Me)$_3$;

alternatively, when two $R^{6a}$ groups are attached to the same carbon atom, together with the carbon atom to which they are attached, they form a 3- to 7-membered carbocyclic or heterocyclic ring comprising: carbon atoms and 0-2 heteroatoms selected from N, $NR^{11}$, O, and $S(O)_p$, 0-1 carbonyl and 0-3 ring double bonds, wherein said carbocyclic or heterocyclic ring is substituted with 0-2 $R^b$;

alternatively, when two $R^{6a}$ groups are attached to adjacent atoms, together with the atoms to which they are attached they form a 5- to 7-membered carbocyclic or heterocyclic ring comprising: carbon atoms and 0-2 heteroatoms selected from N, $NR^{11}$, O, and $S(O)_p$, 0-1 carbonyl and 0-3 ring double bonds, wherein said carbocyclic or heterocyclic ring is substituted with 0-2 $R^b$;

$R^7$, $R^{7a}$, $R^{7b}$, and $R^{7d}$, independently at each occurrence, H, Me, Cl, Br, CN, OMe, SMe, or NHMe;

$R^8$, $R^{8a}$, $R^{8b}$ and $R^{8e}$ are, independently at each occurrence, H, Me, Cl, or CN;

$R^{11}$ is, independently at each occurrence, C$_{1-6}$ alkyl, —CH$_2$CH$_2$OH, —CH$_2$CH$_2$OMe, —C(O)(C$_{1-6}$ alkyl), —C(O)phenyl, —C(O)benzyl, —C(O)O(C$_{1-6}$ alkyl), —C(O)Obenzyl, —CH$_2$CO$_2$H, —CH$_2$CO$_2$(C$_{1-6}$ alkyl), —C(O)NH(C$_{1-6}$ alkyl), —C(O)NHbenzyl, —S(O)$_2$(C$_{1-6}$ alkyl), —S(O)$_2$phenyl, -S(O)2benzyl, phenyl, or benzyl;

Y is O, S, or NH;

$R^b$ is, independently at each occurrence, H, F, Cl, Br, C$_{1-4}$ alkyl, OH, CO$_2$H, NH$_2$, CF$_3$, OCF$_3$, C$_{1-4}$ alkyloxy, C$_{3-7}$ cycloalkyl, phenyl, or benzyl;

$R^e$ is, independently at each occurrence, H, F, Cl, C$_{1-4}$ alkyl, OH, CO$_2$H, NH$_2$, CF$_3$, OCF$_3$, or C$_{1-4}$ alkyloxy; and p, at each occurrence, is selected from 0, 1, and 2;

provided that when ring D is dihydroindolyl, ring A is other than thiazolyl.

In a twelfth embodiment, the present invention includes compounds of Formula (Ia), within the scope of the eleventh embodiment wherein:

ring A is

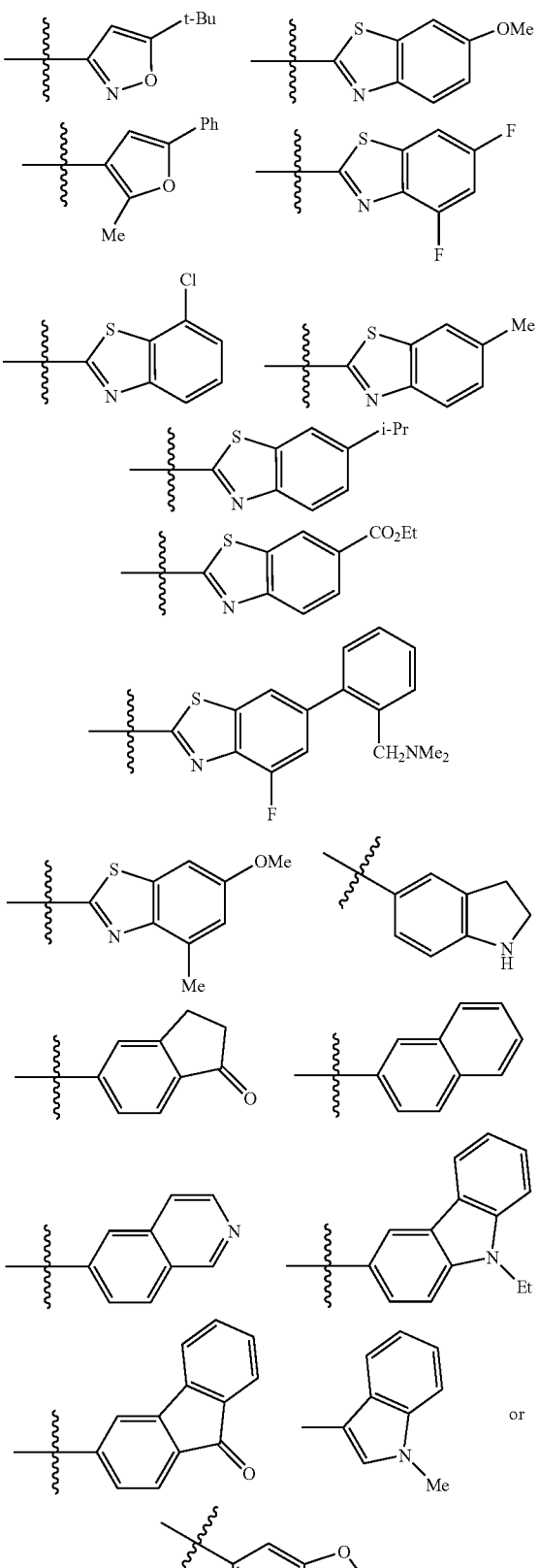

$R^1$ is H or F;
$R^{1a}$ is

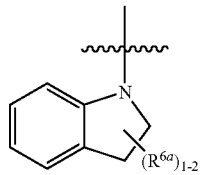

or phenoxy substituted with 0-2 $R^e$;

$R^2$ is H, F, Cl, Br, Me, t-Bu, isopentoxy, —O(CH$_2$)$_8$CO$_2$Me, —O(CH$_2$)$_2$C(Me)$_2$OMe, —O(CH$_2$)$_2$OCOMe, NO$_2$, CF$_3$, 2-CH$_2$N(Me)$_2$-Ph, cyclohexoxy, 4-Me-cyclohexoxy, cyclohexylmethoxy, (1-Bn-pyrrolidin-3-yl)oxy, (1-Bn-pyrrolidin-3-yl)methoxy, (1H-pyrrol-1-yl)ethoxy, (2-Bu-1H-imidazol-4-yl)methoxy, (1-Ph-1H-1,2,3-triazol-4-yl)methoxy, 1-Bn-piperidin-3-oxy, 1-Bn-piperidin-4-oxy, 4-Bn-morpholin-2-yl-methoxy, benzoxy, or 4-CO$_2$Me-benzoxy;

$R^3$ is H, F, Cl, Br, Me, Et, Pr, Bu, t-Bu, OMe, OEt, OPr, O-i-Pr, OBu, O-t-Bu, isopentoxy, neohexoxy, —OCH(Me)CH$_2$O-t-Bu, CF$_3$, OCF$_3$, NH$_2$, NMe$_2$, NEt$_2$, —NHPh, —N(Me)Ph, —NH(4-OMe-Ph), —NH(2-CF$_3$-Ph), —CH$_2$NMe$_2$, —CH(Me)N(Me)(3-CF$_3$-Bn), —CH(Me)N(Me)(4-CF$_3$-Bn), —CH(Me)N(Me)(furan-2-ylmethyl), —CH(Me)NHCH(Me)Ph, —CH(Me)N(Me)(thien-2-ylmethyl), —CH(Me)OH, —CH(Me)O(i-Pr), —CH(Me)O(i-Bu), —CH(Me)O(3-CF$_3$-Bn), —CH(Me)O(4-CF$_3$-Bn), —CH(Me)O(1-Bn-pyrrolidin-3-ylmethyl), COMe, CO$_2$Et, —CH$_2$CO$_2$Me, —C(Me)$_2$CO$_2$Me, —O(CH$_2$)$_5$CO$_2$Et, —O(CH$_2$)$_8$CO$_2$Me, —O(CH$_2$)$_2$C(Me)$_2$OMe, —O(CH$_2$)$_2$OCOMe, —OCH$_2$C(Me)$_2$CH$_2$NMe$_2$, Ph, 2-CH$_2$OH-Ph, 2-CH$_2$N(Me)$_2$-Ph, 3-CH$_2$N(Me)$_2$-Ph, 4-CH$_2$N(Me)$_2$-Ph, 2-((3-OH-pyrrolidin-1-yl)methyl)-Ph, phenoxy, Bn, benzoxy, 3-OMe-benzoxy, 4-CO$_2$Me-benzoxy, 4-OCF$_3$-benzoxy, 2,4-diF-benzoxy, cyclohexylmethoxy, cyclohexylethoxy, cyclopentoxy, 3-Me-cyclopentoxy, cyclohexoxy, 4-Me-cyclohexoxy, 4-CO$_2$Et-cyclohexoxy, 1-Bn-pyrrolidin-3-oxy, (1-Bn-pyrrolidin-3-yl)methoxy, 1H-pyrazol-1-yl, 3-CO$_2$Et-5-Me-1H-pyrazol-1-yl, 4-CO$_2$Et-5-Me-1H-pyrazol-1-yl, 5-CO$_2$Et-3-Me-1H-pyrazol-1-yl, (2-Bu-1H-imidazol-4-yl)methoxy, 1H-1,2,4-triazol-1-yl, (1-Ph-1H-1,2,3-triazol-4-yl)methoxy, 2-(1H-pyrrol-1-yl)-ethoxy, 1-piperidinyl, 1-Bn-piperazin-4-yl, (2,2-dimethyl-1,3-dioxolan-4-yl)-methoxy, 1-Bn-piperidin-3-oxy, 1-Bn-piperidin-4-oxy, (1-(i-Bu)-piperidin-4-yl)methoxy, (1-isopentyl-piperidin-4-yl)methoxy, (1-CO$_2$(t-Bu)-piperidin-4-yl)methoxy, (1-CO$_2$Bn-piperidin-4-yl)methoxy, (1-Bn-piperidin-4-yl)methoxy, (1-phenethyl-piperidin-4-yl)methoxy, (1-(4-phenylbutyl)-piperidin-4-yl)methoxy, (1-cyclohexylmethyl-piperidin-4-yl)methoxy, (1-((pyridin-2-yl)methyl)-piperidin-4-yl)methoxy, (1-((pyridin-4-yl)methyl)-piperidin-4-yl)methoxy, (1-((1,3-dioxolan-2-yl)methyl)piperidin-4-yl)methoxy, N-morpholinyl, (4-Bn-morpholin-2-yl)methoxy, 1-CH$_2$OH-cyclopropyl, 1-CH$_2$OMe-cyclopropyl, 1-CO$_2$Me-cyclopropyl, 1-CO$_2$Me-cyclobutyl, 1-CO$_2$Me-cyclopentyl, cyclohexyl, 1-CO$_2$Me-cyclohexyl, 4,4,5,5-tetramethyl-1,3,2-dioxaborolanyl, or —OP(O)(OEt)$_2$; and $R^{3a}$ is CF$_3$, —NHPh, —NH(2-CF$_3$-Ph), —NH(2-t-Bu-Ph), 2-t-Bu-phenoxy, or 2-CF$_3$-phenoxy.

In a thirteenth embodiment, the present invention provides a compound of Formula (Ia):

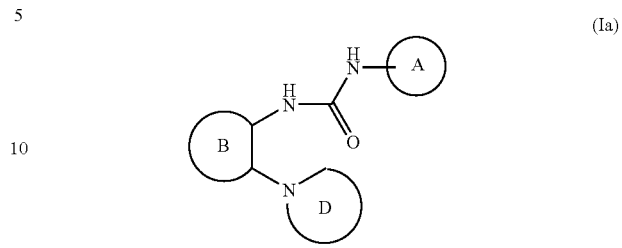

or a stereoisomer or pharmaceutically acceptable salt, solvate, or prodrug thereof, wherein:

ring A is

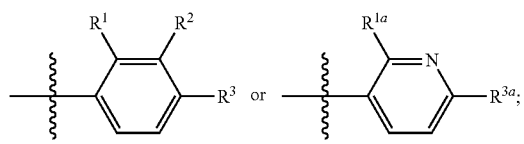

ring B is

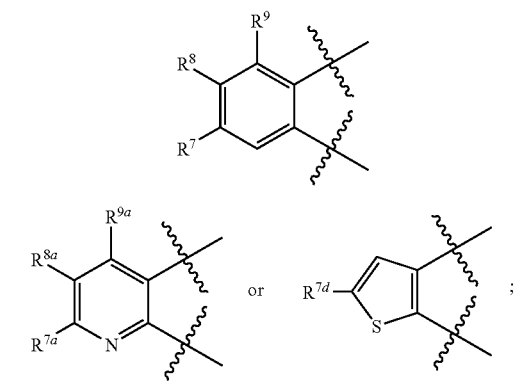

ring D is selected from:

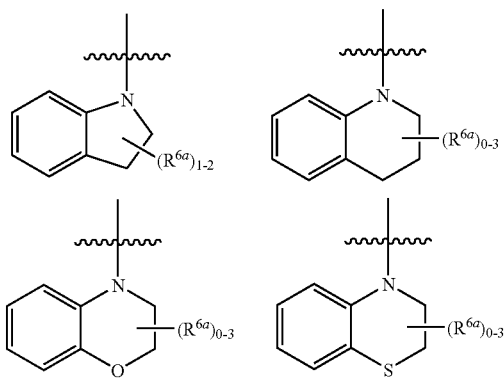

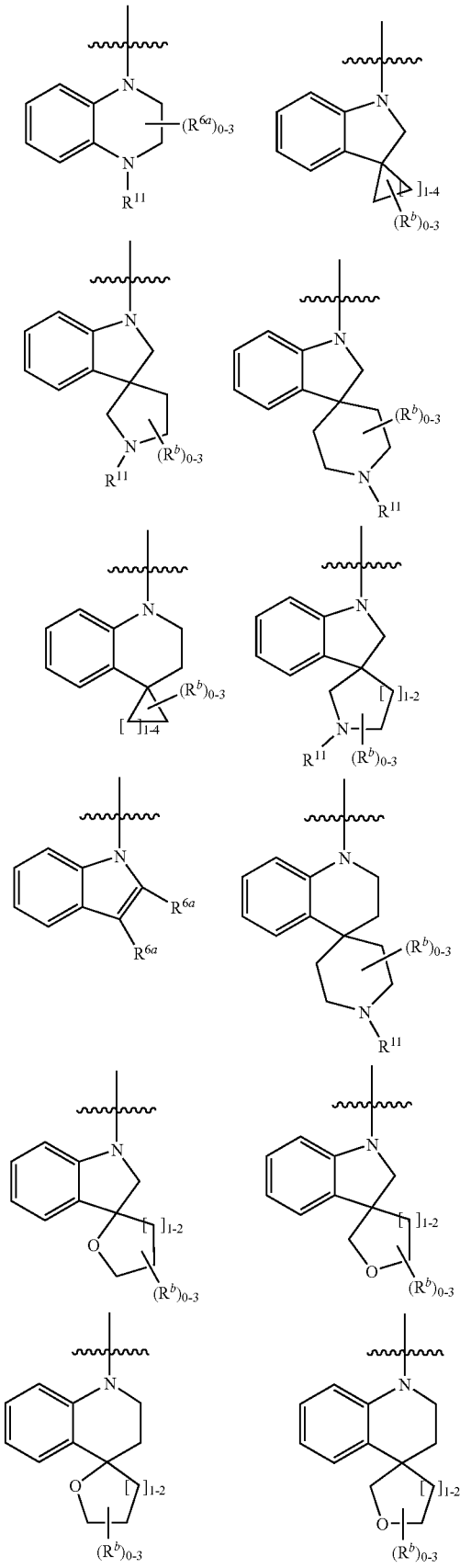

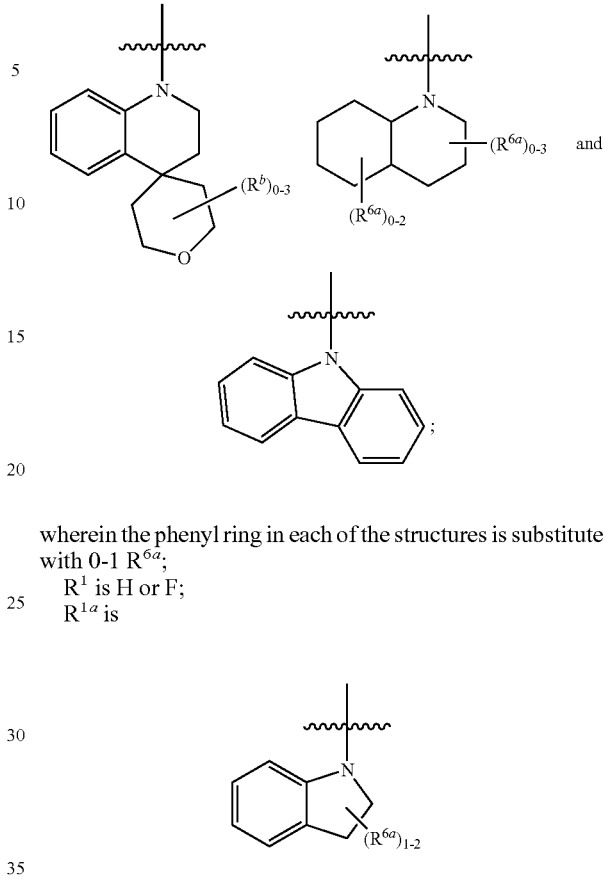

wherein the phenyl ring in each of the structures is substituted with 0-1 $R^{6a}$;

$R^1$ is H or F;

$R^{1a}$ is or phenoxy substituted with 0-2 $R^e$;

$R^2$ is H, F, Cl, Br, Me, t-Bu, isopentoxy, —O(CH$_2$)$_8$CO$_2$Me, —O(CH$_2$)$_2$C(Me)$_2$OMe, —O(CH$_2$)$_2$OCOMe, NO$_2$, CF$_3$, cyclohexoxy, 4-Me-cyclohexoxy, cyclohexylmethoxy, (1-Bn-pyrrolidin-3-yl)oxy, (1-Bn-pyrrolidin-3-yl)methoxy, (1H-pyrrol-1-yl)ethoxy, (2-Bu-1H-imidazol-4-yl)methoxy, (1-Ph-1H-1,2,3-triazol-4-yl)methoxy, 1-Bn-piperidin-3-oxy, 1-Bn-piperidin-4-oxy, 4-Bn-morpholin-2-yl-methoxy, or 4-CO$_2$Me-benzoxy;

$R^3$ is H, F, Cl, Br, Me, Et, Pr, Bu, t-Bu, OMe, OEt, OPr, O-i-Pr, OBu, O-t-Bu, isopentoxy, neohexoxy, —OCH(Me)CH$_2$O-t-Bu, CF$_3$, OCF$_3$, NH$_2$, NMe$_2$, NEt$_2$, —NHPh, —N(Me)Ph, —NH(4-OMe-Ph), —NH(2-CF$_3$-Ph), —CH$_2$NMe$_2$, —CH(Me)OH, —CH(Me)O(i-Bu), —CH(Me)O(4-CF$_3$-Bn), —CH(Me)N(Me)(3-CF$_3$-Bn), —CH(Me)N(Me)(4-CF$_3$-Bn), —CH(Me)N(Me)(furan-2-ylmethyl), —CH(Me)N(Me)(thien-2-ylmethyl), —CH(Me)NHCH(Me)Ph, COMe, CO$_2$Et, —CH$_2$CO$_2$Me, —C(Me)$_2$CO$_2$Me, —O(CH$_2$)$_5$CO$_2$Et, —O(CH$_2$)$_8$CO$_2$Me, —O(CH$_2$)$_2$C(Me)$_2$OMe, —O(CH$_2$)$_2$OCOMe, —OCH$_2$C(Me)$_2$CH$_2$NMe$_2$, 1-CH$_2$OH-cyclopropyl, cyclohexyl, Ph, 2-CH$_2$OH-phenyl, 2-CH$_2$N(Me)$_2$-phenyl, 3-CH$_2$N(Me)$_2$-phenyl, 4-CH$_2$N(Me)$_2$-phenyl, 2-((3-OH-pyrrolidin-1-yl)methyl)-phenyl, phenoxy, Bn, 3-OMe-benzoxy, 4-CO$_2$Me-benzoxy, 4-OCF$_3$-benzoxy, 2,4-diF-benzoxy, cyclohexylmethoxy, cyclohexylethoxy, cyclopentoxy, 3-Me-cyclopentoxy, cyclohexoxy, 4-Me-cyclohexoxy, 4-CO$_2$Et-cyclohekoxy, 1-Bn-pyrrolidin-3-oxy, (1-Bn-pyrrolidin-3-yl)methoxy, 1H-pyrazol-1-yl, 3-CO$_2$Et-5-Me-1H-pyrazol-1-yl, 4-CO$_2$Et-5-Me-1H-pyrazol-1-yl, 5-CO₂Et-3-Me-1H-pyrazol-1-yl, (2-Bu-1H-imidazol-4-yl)methoxy, 1H-1,2,4-triazol-1-yl, (1-Ph-1H-1,2,3-triazol-4-yl)methoxy, 2-(1H-pyrrol-1-yl)-ethoxy, 1-piperidinyl, 1-Bn-piperazin-4-yl, (2,2-dimethyl-1,3-dioxolan-4-yl)-methoxy, 1-Bn-piperidin-3-oxy, 1-Bn-piperidin-4-oxy, (1-(i-Bu)-piperidin-4-yl)methoxy, (1-isopentyl-piperidin-4-yl)methoxy, (1-CO₂(t-Bu)-piperidin-4-yl)methoxy, (1-CO₂Bn-piperidin-4-yl)methoxy, (1-Bn-piperidin-4-yl)methoxy, (1-phenethyl-piperidin-4-yl)methoxy, (1-(4-phenylbutyl)-piperidin-4-yl)methoxy, (1-cyclohexylmethyl-piperidin-4-yl)methoxy, (1-((pyridin-2-yl)methyl)-piperidin-4-yl)methoxy, (1-((pyridin-4-yl)methyl)-piperidin-4-yl)methoxy, (1-((1,3-dioxolan-2-yl)methyl)piperidin-4-yl)methoxy, N-morpholinyl, (4-Bn-morpholin-2-yl)methoxy, 1-CO₂Me-cyclopropyl, 1-CH₂OMe-cyclopropyl, 1-CO₂Me-cyclobutyl, 1-CO₂Me-cyclopentyl, 1-CO₂Me-cyclohexyl, 4,4,5,5-tetramethyl-1,3,2-dioxaborolanyl, or —OP(O)(OEt)₂;

$R^3$ is H, F, Cl, Br, $C_{1-4}$ alkyl, or $C_{1-4}$ alkoxy;

$R^{6a}$ is, independently at each occurrence, H, F, Cl, Br, I, CN, —C(Me)₂CN, $C_{1-8}$ alkyl, $C_{2-8}$ alkenyl, OH, SMe, S(i-Pr), —C(Me)₂OMe, —C(Me)₂OEt, —C(Me)₂OPr, —CHMeO(CH₂)₂OMe, —C(Me)₂O(CH₂)₂OMe, —C(Et)₂OMe, —C(Et)₂OEt, COPh, CO₂Me, CO₂Bn, —CH₂CO₂Me, —CH=CHCO₂(t-Bu), CF₃, OCF₃, $C_{1-4}$ alkyloxy, $C_{3-7}$ cycloalkyl, Ph, Bn, 1-pyrrolidinyl, 5-isoxazolyl, N-morpholinyl, 4-Bn-piperazinyl, 1-piperidinyl, 1-Bn-piperidin-4-yl, or -Si(Me)₃;

$R^7$, $R^{7a}$, and $R^{7d}$ are, independently at each occurrence, H, Me, Cl, Br, CN, OMe, SMe, or NHMe;

$R^8$ and $R^{8a}$ are, independently at each occurrence, H, Me, F, Cl, or CN;

$R^9$ and $R^{9a}$ are, independently at each occurrence, H, Me, F, Cl, or CN;

$R^{11}$ is, independently at each occurrence, Me, i-Pr, i-Bu, t-Bu, Bn, —CH₂CH₂OH, —CH₂CH₂OMe, —CO(i-Pr), CO₂Me, CO₂Et, CO₂Bn, —CH₂CO₂H, —CH₂CO₂Me, —CONH(i-Pr), or SO₂(i-Pr);

$R^b$ is, independently at each occurrence, H, F, Cl, $C_{1-4}$ alkyl, OH, CO₂H, NH₂, CF₃, OCF₃, or $C_{1-4}$ alkyloxy; and $R^e$ is, independently at each occurrence, H, F, Cl, $C_{1-4}$ alkyl, OH, CO₂H, NH₂, CF₃, OCF₃, or $C_{1-4}$ alkyloxy.

In a fourteenth embodiment, the present invention includes compounds of Formula (Ia), within the scope of the thirteenth embodiment wherein:

ring A is 3-Me-Ph, 4-Me-Ph, 4-t-Bu-Ph, 4-OCF₃-Ph, 4-NMe₂-Ph, 4-COMe-Ph, 4-CH(OH)Me-Ph,

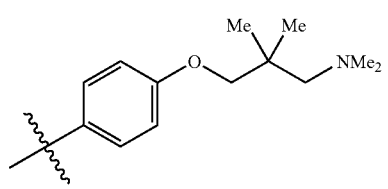

-continued

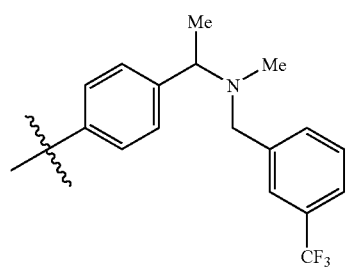

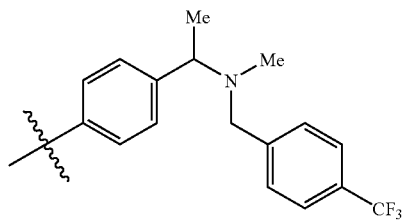

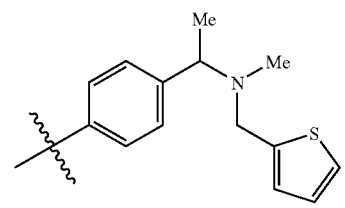

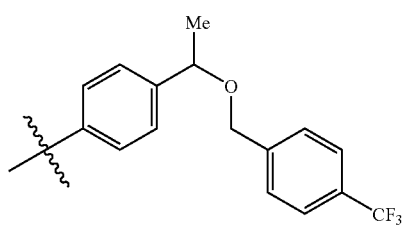

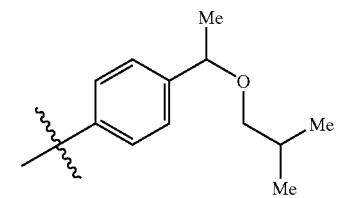

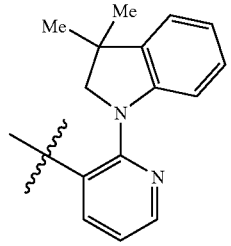

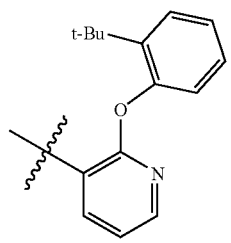

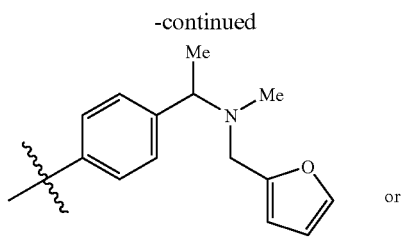
or
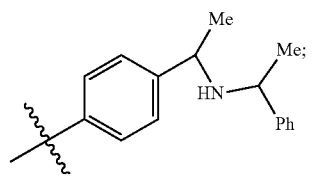
ring B is
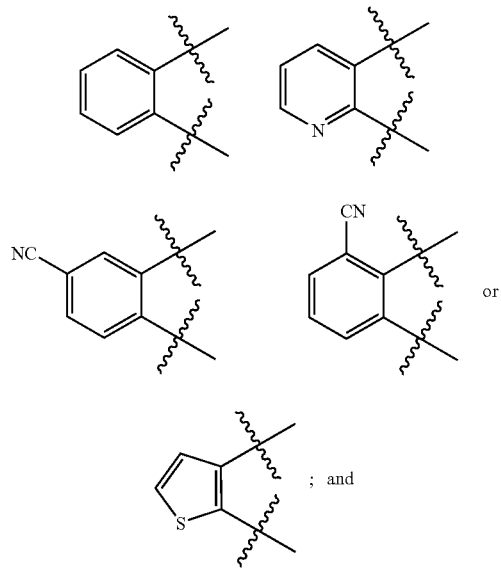
; and
ring D is selected from:
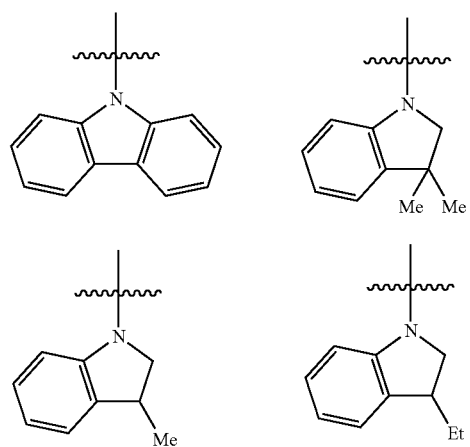
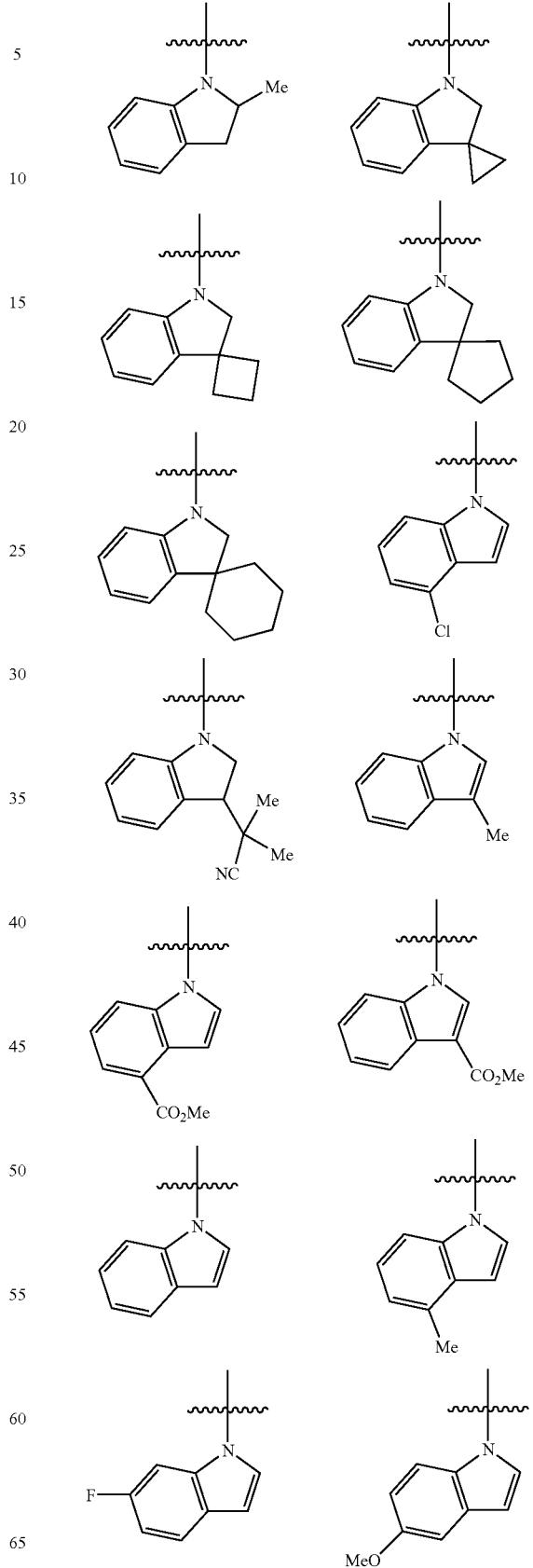

-continued
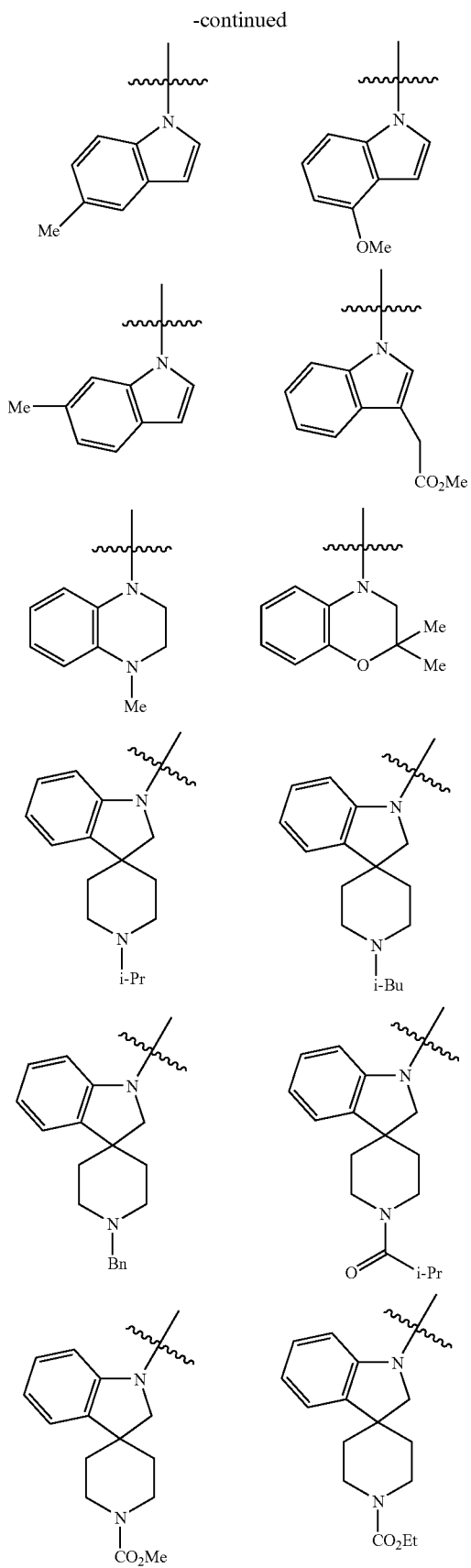
-continued
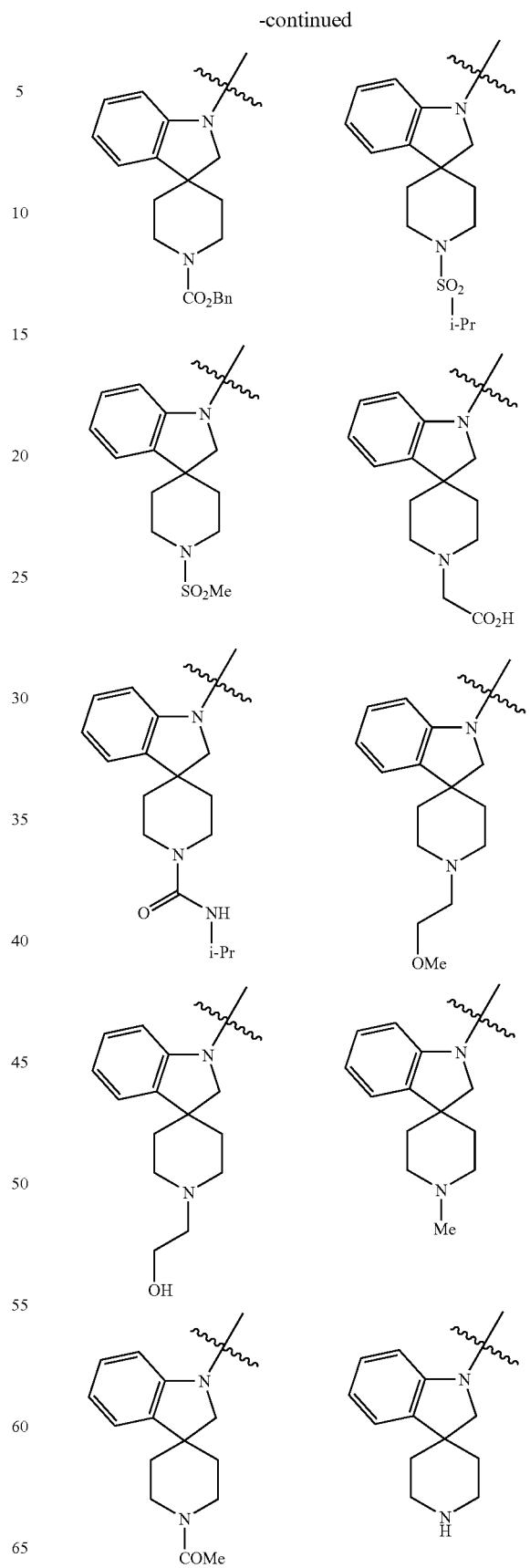

-continued
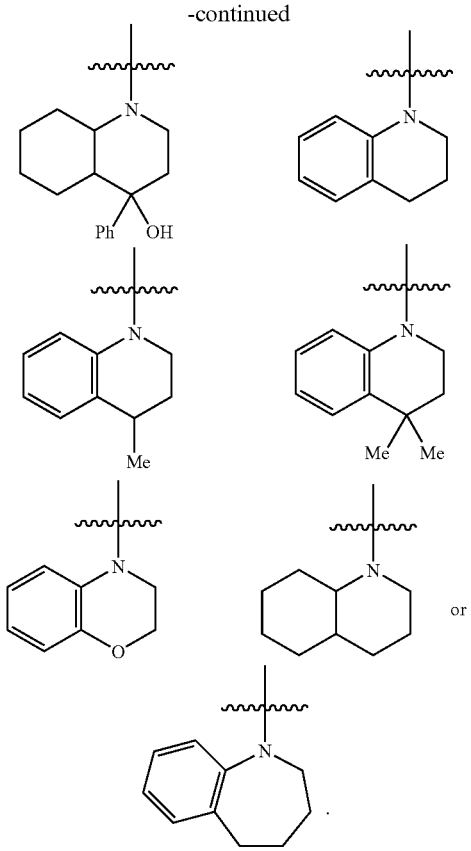
In a fifteenth embodiment, the present invention includes compounds of Formula (Ia), within the scope of the thirteenth embodiment wherein:
ring A is 4-Me-Ph, 4-t-Bu-Ph, 4-OCF$_3$-Ph, 4-NMe$_2$-Ph, 4-COMe-Ph,
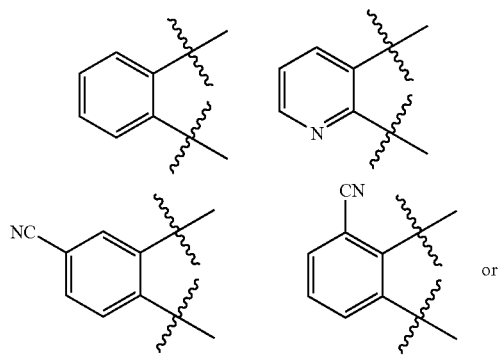
ring B is
-continued
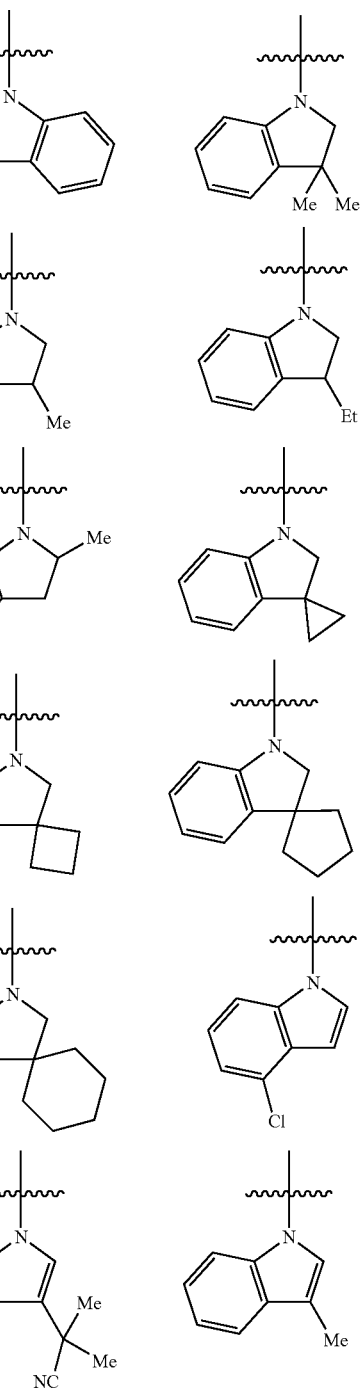
ring D is selected from:

-continued
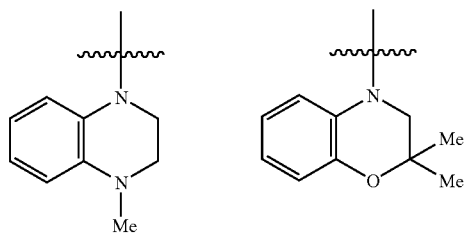
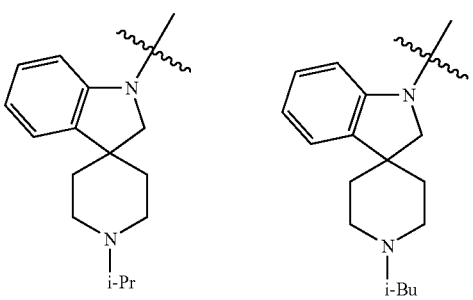
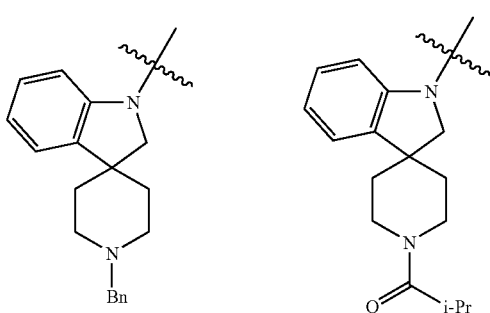
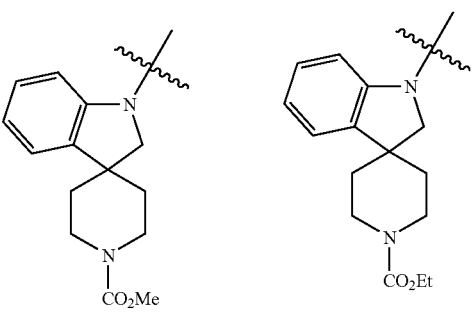
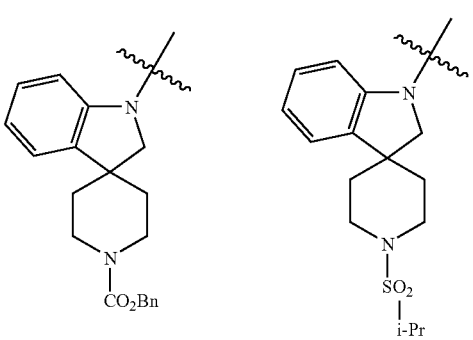
-continued
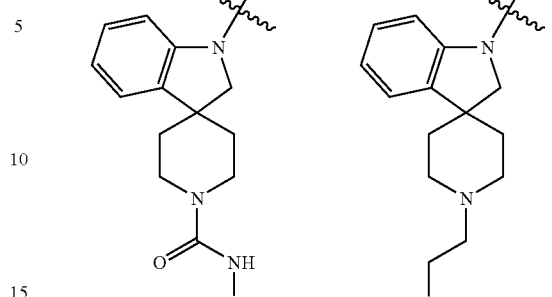
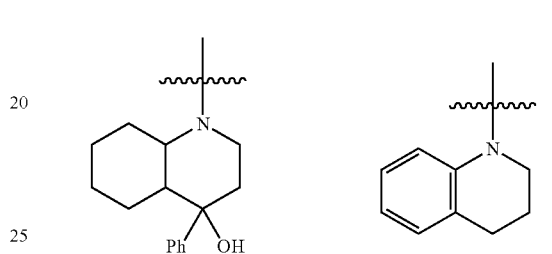
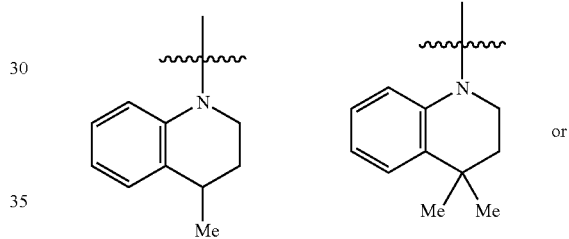
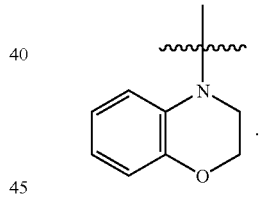
In a sixteenth embodiment, the present invention provides a compound selected from the exemplified examples of the present invention or a stereoisomer or pharmaceutically acceptable salt, solvate, or prodrug form thereof.
In another embodiment, the present invention includes compounds wherein: ring B is
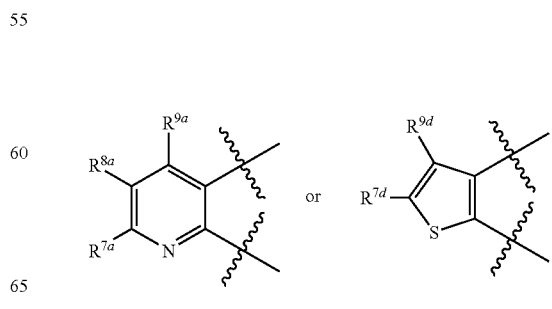

In another embodiment, the present invention includes compounds wherein: ring B is

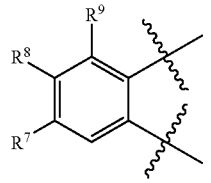

In another embodiment, the present invention includes compounds wherein: ring A is

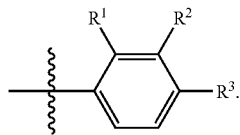

In another embodiment, the present invention provides, inter alia, a compound of Formula (II):

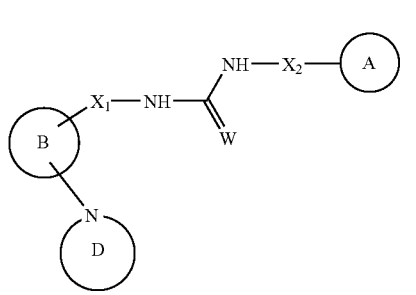

or a stereoisomer or pharmaceutically acceptable salt, solvate, or prodrug thereof, wherein:

ring A is $C_{3-13}$ carbocycle substituted with 0-5 $R^1$, or a 4- to 14-membered heterocycle comprising: carbon atoms and 1-5 ring heteroatoms selected from O, N, $NR^{11}$, and $S(O)_p$, wherein said heterocycle is substituted with 0-5 $R^1$;

ring B is phenyl substituted with 0-4 $R^7$, naphthyl substituted with 0-5 $R^7$, or a 5- to 10-membered heteroaryl comprising: carbon atoms and 1-4 ring heteroatoms selected from N, $NR^{11}$, $S(O)_p$, and O, wherein said heteroaryl is substituted with 0-5 $R^7$;

ring D is a 5- to 10-membered heterocycle comprising: in addition to the N atom shown, carbon atoms and 0-4 ring heteroatoms selected from N, $NR^{11}$, $S(O)_p$, Si, and O, wherein said heterocycle is substituted with 0-5 $R^{6a}$;

W is O or S;

$X_1$ and $X_2$ are, independently at each occurrence, X is $-(CR^{16}R^{17})_s-$, $-(CR^{16}R^{17})_rCR^{16}=CR^{16}(CR^{16}R^{17})_r-$, $-(CR^{16}R^{17})_rC=C(CR^{16}R^{17})_r-$, $-(CR^{16}R^{17})_tO(CR^{16}R^{17})_r-$, $-(CR^{16}R^{17})_tNR^{14}(CR^{16}R^{17})_r-$, $-(CR^{16}R^{17})_tC(O)(CR^{16}R^{17})_r-$, $-(CR^{16}R^{17})_rC(O)O(CR^{16}R^{17})_r-$, $-(CR^{16}R^{17})_rOC(O)(CR^{16}R^{17})_s-$, $-(CR^{16}R^{17})_tC(O)NR^{14}(CR^{16}R^{17})_r-$, $-(CR^{16}R^{17})_tS(CR^{16}R^{17})_r-$, $-(CR^{16}R^{17})_tS(O)(CR^{16}R^{17})_s-$, $-(CR^{16}R^{17})_rS(O)_2(CR^{16}R^{17})_r-$, $-(CR^{16}R^{17})_tSO_2NR^{14}(CR^{16}R_{17})_r-$, or $-(CR^{16}R^{17})_tNR^{14}SO_2(CR^{16}R^{17})_r-$;

$R^1$ is, independently at each occurrence, H, =O, F, Cl, Br, I, $CF_3$, $-CF_2CF_3$, $-OCF_3$, $-OCF_2CF_2H$, $-OCF_2CF_3$, $SiMe_3$, $-(CR^fR^f)_r-OR^c$, $SR^c$, CN, $NO_2$, $-(CR^fR^f)_r-NR^{12}R^{13}$, $-(CR^fR^f)_r-C(O)R^c$, $-(CR^fR^f)_r-CO_2R^c$, $-(CR^fR^f)_r-C(O)NR^{12}R^{13}$, $-C(O)NR^{14}(CR^fR^f)_nN^{12}R^{13}$, $-(CR^fR^f)_r-OC(O)NR^{12}R^{13}$, $-(CR^fR^f)_r-NR^{14}C(O)NR^{12}R^{13}$, $-(CR^fR^f)_r-NR^{14}C(O)R^d$, $-(CR^fR^f)_r-NR^{14}C(O)OR^h$, $-NR^{14}(CR^fR^f)_nC(O)R^d$, $-NR^{14}CO(CR^fR^f)_nOR^c$, $-(CH_2)_r-CR^{13}(=NOR^c)$, $-S(O)_rNR^{12}R^{13}$, $-(CR^fR^f)_r-NR^{14}S(O)_pNR^{12}R^{13}$, $-NR^{14}SO_2CF_3$, $-NR^{14}S(O)_pR^d$, $-S(O)_2CF_3$, $-S(O)R^d$, $-S(O)_2R^d$, $-OP(O)(OEt)_2$, 4,4,5,5-tetramethyl-1,3,2-dioxaborolanyl, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, $-(CR^fR^f)_r-C_{3-13}$ carbocycle substituted with 0-5 $R^b$, or $-(CR^fR^f)_r-5-$ to 12-membered heterocycle comprising: carbon atoms and 1-4 heteroatoms selected from N, $NR^{11}$, O, and $S(O)_p$, wherein said heterocycle is substituted with 0-5 $R^b$;

alternatively, two $R^1$s on two adjacent carbon atoms are combined with the carbon atoms to which they attached, form a 5- to 10-membered carbocycle or heterocycle comprising: carbon atoms and 0-3 additional heteroatoms selected from N, $NR^{11}$, O, and $S(O)_p$, and 0-2 carbonyl groups, wherein said carbocycle or heterocycle is substituted with 0-4 $R^b$;

alternatively, two RIs on the same carbon atom are combined with the carbon atom to which they attached, form a 3- to 10-membered carbocycle or heterocycle comprising: carbon atoms and 0-3 additional heteroatoms selected from N, $NR^{11}$, O, and $S(O)_p$, and 0-2 carbonyl groups, wherein said carbocycle or heterocycle is substituted with 0-4 $R^b$;

$R^{6a}$ is, independently at each occurrence, =O, F, Cl, Br, I, $-(CR^fR^f)_r-OR^c$, $SR^c$, CN, $NO_2$, $CF_3$, $OCF_3$, $-CF_2CF_3$, $-OCF_2CF_2H$, $-OCF_2CF_3$, $-(CR^fR^f)_r-NR^{12}R^{13}$, $-C(O)R^c$, $-(CR^fR^f)_r-C(O)OR^c$, $-(CR^fR^f)_r-C(O)NR^{12}R^{13}$, $-(CR^fR^f)_r-NR^{14}C(O)R_d$, $-S(O)_pNR^{12}R^{13}$, $-S(O)R^d$, $-S(O)_2R^d$, $-Si(Me)_3$, $C_{1-4}$ haloalkyl, $C_{1-4}$ haloalkyloxy-, $C_{1-4}$ alkyloxy-, $C_{1-4}$ alkylthio-, $C_1-C_4$ alkyl-C(O)—, $C_{1-4}$ alkyl-O—C(O)—, $C_{1-4}$ alkyl-C(O)NH—, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, $-(CR^fR^f)_r-C_{3-10}$ carbocycle substituted with 0-3 $R^e$, or $-(CR^fR^f)_r-5-$ to 10-membered heterocycle comprising: carbon atoms and 1-4 heteroatoms selected from N, $NR^{11}$, O, and $S(O)_p$, wherein said heterocycle is substituted with 0-3 $R^e$;

alternatively, when two $R^{6a}$ groups are attached to the same carbon atom or silicon atom, together with the carbon atom or silicon atom to which they are attached, they form a 3- to 7-membered carbocyclic or heterocyclic ring comprising: carbon atoms and 0-3 heteroatoms selected from N, $NR^{11}$, O, Si, and $S(O)_p$, 0-1 carbonyl and 0-3 ring double bonds, wherein said carbocyclic or heterocyclic ring is substituted with 0-3 $R^b$;

alternatively, when two $R^{6a}$ groups are attached to adjacent atoms, together with the atoms to which they are attached they form a 5- to 7-membered carbocyclic or heterocyclic ring comprising: carbon atoms and 0-2 heteroatoms selected from N, $NR^{11}$, O, Si, and $S(O)_p$, 0-1 carbonyl and 0-3 ring double bonds, wherein said carbocyclic or heterocyclic ring is substituted with 0-3 $R^b$;

$R^7$ is, independently at each occurrence, H, =O, F, Cl, Br, I, $OCF_3$, $CF_3$, $OR^c$, $SR^c$, CN, $NO_2$, $-NR^{12}R^{13}$, $-C(O)R^c$, $-C(O)OR^c$, $-C(O)NR^{12}R^{13}$, $-NR^{14}C(O)R^d$, $-S(O)_pNR^{12}R^{13}$, $-S(O)R^d$, $-S(O)_2R^d$, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, $-(CH_2)_r-C_{3-10}$ carbocycle substituted with 0-3 $R^b$, or $-(CH_2)_r$-5- to 10-membered heterocycle comprising: carbon atoms and 1-4 heteroatoms selected from N, $NR^{7b}$, O, and $S(O)_p$, wherein said heterocycle is substituted with 0-3 $R^b$;

alternatively, two $R^7$s on two adjacent carbon atoms form a 5- to 7-membered carbocyclic or heterocyclic ring comprising: carbon atoms and 0-3 ring heteroatoms selected from O, N, $NR^{7b}$, and $S(O)_p$, wherein said carbocyclic or heterocyclic ring is substituted with 0-3 $R^{7c}$;

$R^{7b}$ is, independently at each occurrence, H, $C_{1-4}$ alkyl, $(C_{1-4}$ alkyl)C(O)—, phenyl-C(O)—, benzyl-C(O)—, benzyl-S(O)$_2$—, $(C_{1-4}$ alkyl)NHC(O)—, $(C_{1-4}$ alkyl)$_2$NC(O)—, phenyl-NHC(O)—, benzyl-NHC(O)—, $(C_{1-4}$ alkyl)-S(O)$_2$—, phenyl-S(O)$_2$—, phenyl substituted with 0-3 $R^b$, or benzyl substituted with 0-3 $R^b$;

$R^{7c}$ is, independently at each occurrence, H, =O, F, Cl, Br, I, $OCF_3$, $CF_3$, $OR^c$, $SR^c$, CN, $NO_2$, $-NR^{12}R^{13}$, $-C(O)R^c$, $-C(O)OR^c$, $-C(O)NR^{12}R^{13}$, $-NR^{14}C(O)R^d$, $-S(O)_pNR^{12}R^{13}$, $-S(O)R^d$, $-S(O)_2R^d$, $C_{1-4}$ alkyl, phenyl substituted with 0-3 $R^b$, or benzyl substituted with 0-3 $R^b$;

$R^{11}$ is, independently at each occurrence, H, $C_{1-8}$ alkyl substituted with 0-2 $R^a$, $C_{2-4}$ alkenyl substituted with 0-1 $R^a$, $C_{2-4}$ alkynyl substituted with 0-1 $R^a$, $-C(O)(C_{1-6}$ alkyl), $-C(O)(CH_2)_n(C_{3-6}$ cycloalkyl), $-C(O)(CH_2)_n(C_{6-10}$ aryl), $-C(O)(CH_2)_n$(5- to 10-membered heteroaryl), $-C(O)O(C_{1-8}$ alkyl), $-C(O)O(CH_2)_n(C_{3-6}$ cycloalkyl), $-C(O)O(CH_2)_n(C_{6-10}$ aryl), $-C(O)O(CH_2)_n$(5- to 10-membered heteroaryl), $-C(O)O(CH_2)_{2-4}(C_{1-4}$ alkyl), $-C(O)NH(C_{1-8}$ alkyl), $-C(O)NH(CH_2)_n(C_{3-6}$ cycloalkyl), $-C(O)NH(CH_2)_n(C_{6-10}$ aryl), $-C(O)NH(CH_2)_n$(5- to 10-membered heteroaryl), $-S(O)_2(C_{1-8}$ alkyl), $-S(O)_2(CH_2)_n(C_{3-6}$ cycloalkyl), $-S(O)_2(CH_2)_n(C_{6-10}$ aryl), $-S(O)_2(CH_2)_n$ (5- to 10-membered heteroaryl), $-(CR^fR^f)_r-C_{3-7}$ cycloalkyl, $-(CR^fR^f)_r$-phenyl, or $-(CR^fR^f)_r$-5- to 6-membered heterocycle; wherein said alkyl, cycloalkyl, phenyl, and aryl are substituted with 0-2 $R^b$, and said heteroaryl and heterocycle are substituted with 0-2 $R^b$ and comprise: carbon atoms and 1-4 heteroatoms selected from N, $NR^f$, O, and $S(O)_p$;

$R^{12}$ is, independently at each occurrence, H, $C_{1-6}$ alkyl, $-C(O)(C_{1-6}$ alkyl), $-C(O)(CH_2)_n(C_{6-10}$ aryl), $-C(O)(CH_2)_n$(5- to 10-membered heteroaryl), $-C(O)O(C_{1-4}$ alkyl), $-C(O)OCH_2(C_{6-10}$ aryl), $-(CH_2)_rC(O)OCH_2$(5- to 10-membered heteroaryl), $-(CH_2)_nOC(O)(C_{1-4}$ alkyl), $-(CH_2)_nOC(O)(C_{6-10}$ aryl), $-(CH_2)_nOC(O)$(5- to 10-membered heteroaryl), $-(CH_2)_nC(O)O(C_{1-4}$ alkyl), $-(CH_2)_nC(O)O(C_{6-10}$ aryl), $-(CH_2)_nC(O)O$(5- to 10-membered heteroaryl), $-(CH_2)_nC(O)NH(C_{1-6}$ alkyl), $-(CH_2)_nC(O)NH(C_{6-10}$ aryl), $-(CH_2)_nC(O)NH$(5- to 10-membered heteroaryl), $-(CH_2)_rOC(O)NH(C_{1-6}$ aLkyl), $-(CH_2)_rOC(O)NH(C_{6-10}$ aryl), $-(CH_2)_rOC(O)NH$(5- to 10-membered heteroaryl), $-S(O)_2(C_{1-6}$ alkyl), $-S(O)_2(CH_2)_n(C_{6-10}$ aryl), $-S(O)_2(CH_2)_n$(5- to 10-membered heteroaryl), $-(CH_2)_n-(C_{6-10}$ aryl), or $-(CH_2)_r$-5- to 10-membered heteroaryl; wherein said alkyl, and aryl are substituted with 0-2 $R^g$; and said heteroaryl is substituted with 0-2 $R^g$ and comprises: carbon atoms and 1-4 heteroatoms selected from N, $NR^{11}$, O, and $S(O)_p$;

$R^{13}$ is, independently at each occurrence, H, $C_{1-6}$ alkyl, or $-(CH_2)_n$-phenyl;

alternatively, $R_{12}$ and $R_{13}$, when attached to the same nitrogen, combine to form a 5- to 10-membered heterocyclic ring comprising: carbon atoms and 1-2 additional heteroatoms selected from N, $NR^{11}$, O, and $S(O)_p$;

$R^{14}$ is, independently at each occurrence, H, $C_{1-8}$ alkyl substituted with 0-2 $R^{14a}$, $C_{2-8}$ alkenyl substituted with 0-2 $R^{14a}$, $C_{2-8}$ alkynyl substituted with 0-2 $R^{14a}$, $(CH_2)_r-C_{3-10}$ carbocycle substituted with 0-3 $R^g$, or $-(CH_2)_r$-5- to 10-membered heterocycle comprising: carbon atoms and 1-4 heteroatoms selected from N, $NR^{11}$, O, and $S(O)_p$, wherein said heterocycle is substituted with 0-3 $R^g$;

$R^{14a}$ is, independently at each occurrence, H, $C_{1-4}$ alkyl, $OR^f$, Cl, F, Br, I, =O, $CF_3$, CN, $NO_2$, $-C(O)R^f$, $-C(O)OR^f$, $-C(O)NR^{12}R^{13}$, or $-S(O)_pR^f$;

$R^{16}$ is, independently at each occurrence, H, F, Cl, Br, I, $OCF_3$, $CF_3$, $-(CH_2)_r-OR^c$, $SR^c$, CN, $NO_2$, $-(CH_2)_r-NR^{12}R^{13}$, $-(CH_2)_r-C(O)R^c$, $-(CH_2)_r-CO_2R^c$, $-(CH_2)_r-C(O)NR^{12}R^{13}$, $-(CH_2)_r-OC(O)NR^{12}R^{13}$, $-(CH_2)_r-NR^{14}C(O)R^d$, $-S(O)_pNR^{12}R^{13}$, $-NR^{14}S(O)_pNR^{12}R^{13}$, $-NR^{14}SO_2CF_3$, $-NR^{14}SO_2R^d$, $-S(O)_2CF_3$, $-S(O)R^d$, $-S(O)_2R^d$, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, $-(CH_2)_rC_{3-10}$ carbocycle substitute with 0-5 $R^b$, or $-(CH_2)_r$-5- to 10-membered heterocycle comprising: carbon atoms and 1-4 heteroatoms selected from N, $NR^{11}$, O, and $S(O)_p$, wherein said heterocycle is substituted with 0-5 $R^b$;

$R^{17}$ is, independently at each occurrence, H, OH, $C_{1-6}$ alkyl, or $-(CH_2)_n$-phenyl;

alternatively, $R^{16}$ and $R^{17}$ combine to form a 3- to 7-membered carbocyclic or heterocyclic ring comprising: carbon atoms and 0-2 heteroatoms selected from N, $NR^{11}$, O, and $S(O)_p$, 0-1 carbonyl, and 0-3 double bonds, wherein said carbocyclic or heterocyclic ring is substituted with 0-2 $R^b$;

alternatively, two $R^{16}$ groups on adjacent atoms combine to form a 3- to 7-membered carbocyclic or heterocyclic ring comprising: carbon atoms and 0-2 heteroatoms selected from N, $NR^{11}$, O, and $S(O)_p$, 0-1 carbonyl, and 0-3 double bonds, wherein said carbocyclic or heterocyclic ring is substituted with 0-2 $R^b$;

$R^a$ is, independently at each occurrence, H, =O, F, $OCF_3$, $CF_3$, $OR^c$, $SR^c$, CN, $-NR^{12}R^{13}$, $-C(O)R^c$, $-C(O)OR^c$, $-C(O)NR^{12}R^{13}$, $-NR^{14}C(O)R^d$, $-S(O)_pNR^{12}R^{13}$, $-S(O)R^d$, $-S(O)_2R^d$, $-(CH_2)_r-C_{3-10}$ carbocycle substituted with 0-3 $R^e$, or $-(CH_2)_r$-5- to 10-membered heterocycle comprising: carbon atoms and 1-4 heteroatoms selected from N, $NR^f$, O, and $S(O)_p$, wherein said heterocycle is substituted with 0-3 $R^e$;

$R^b$ is, independently at each occurrence, H, =O, F, Cl, Br, I, $-(CH_2)_r-OR^c$, $SR^c$, CN, $NO_2$, $CF_3$, $OCF_3$, $-(CH_2)_r-NR^{12}R^{13}$, $-C(O)R^c$, $-(CH_2)_r-C(O)OR^c$, $(CH_2)_r-C(O)NR^{12}R^{13}$, $-NR^{14}C(O)R^d$, $-S(O)_pNR^{12}R^{13}$, $-S(O)R^d$, $-S(O)_2R^d$, $C_{1-4}$ haloalkyl, $C_{1-4}$ haloalkyloxy-, $C_{1-4}$ alkyloxy-, $C_{1-4}$ alkylthio-, $C_{1-4}$ alkyl-C(O)—, $C_{1-4}$ alkyl-O—C(O)—, $C_{1-4}$ alkyl-C(O)NH—, $C_{1-8}$ alkyl substituted with 0-2 $R^a$, $C_{2-8}$ alkenyl substituted with 0-2 $R^a$, $C_{2-8}$ aLkynyl substituted with 0-2 $R^a$, $-(CH_2)_r-C_{3-10}$ carbocycle substituted with 0-3 $R^e$, or $-(CH_2)_r$-5- to 10-membered heterocycle comprising: carbon atoms and 1-4 heteroatoms selected from N, NR$^f$, O, and S(O)$_p$, wherein said heterocycle is substituted with 0-3 R$^e$;

R$^c$ is, independently at each occurrence, H, —OP(O)(OEt)$_2$, C$_{1-8}$ alkyl substituted with 0-2 R$^e$, C$_{2-8}$ alkenyl substituted with 0-2 R$^e$, C$_{2-8}$ alkynyl substituted with 0-2 R$^e$, —(CR$^f$R$^f$)$_r$—C$_{3-8}$ cycloalkyl substituted with 0-2 R$^e$, —(CR$^f$R$^f$)$_r$—C$_{6-10}$ aryl substituted with 0-2 R$^e$, or —(CR$^f$R$^f$)$_r$-5- to 10-membered heterocycle comprising: carbon atoms and 1-4 heteroatoms selected from N, NR$^f$, O, and S(O)$_p$, wherein said heterocycle is substituted with 0-2 R$^e$;

R$^d$ is, independently at each occurrence, CF$_3$, OH, C$_{1-4}$ alkoxy, C$_{1-6}$ alkyl, —(CH$_2$)$_r$—C$_{3-10}$ carbocycle substituted with 0-2 R$^e$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-2 R$^e$;

R$^e$ is, independently at each occurrence, H, =O, —(CH$_2$)$_r$—OR$^f$, F, Cl, Br, I, CN, NO$_2$, —(CH$_2$)$_r$—NR$^{12}$R$^{13}$, —C(O)R$^f$, —(CH$_2$)$_r$—C(O)OR$^f$, —NR$^{14}$C(O)R$^f$, —(CH$_2$)$_r$—C(O)NR$^{12}$R$^{13}$, —SO$_2$NR$^{12}$R$^{13}$, —NR$^{14}$SO$_2$NR$^{12}$R$^{13}$, —NR$^{14}$SO$_2$—C$_{1-4}$ alkyl, —NR$^{14}$SO$_2$CF$_3$, —NR$^{14}$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-8}$ alkyl substituted with 0-2 R$^g$, C$_{2-8}$ alkenyl substituted with 0-2 R$^g$, C$_{2-8}$ alkynyl substituted with 0-2 R$^g$, —(CH$_2$)$_r$—C$_{3-8}$ cycloalkyl substituted with 0-2 R$^g$, —(CH$_2$)$_r$—C$_{6-10}$ aryl substituted with 0-2 R$^g$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-2 R$^g$;

R$^f$ is, independently at each occurrence, H, C$_{1-6}$ alkyl, or —(CH$_2$)$_n$-phenyl;

R$^g$ is, independently at each occurrence, H, =O, OR$^f$, F, Cl, Br, I, CN, NO$_2$, —NR$^f$R$^f$, —C(O)R$^f$, —C(O)OR$^f$, —NR$^f$C(O)R$^f$, —C(O)NR$^f$R$^f$, —SO$_p$R$^f$, —NR$^f$SO$_2$NR$^f$R$^f$, —NR$^f$SO$_2$—C$_{1-4}$ alkyl, —NR$^f$SO$_2$CF$_3$, —NR$^f$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl, C$_{2-6}$ alkenyl, or C$_{2-6}$ alkynyl;

R$^h$ is, independently at each occurrence, C$_{1-6}$ alkyl substituted with 0-2 R$^g$, or —(CH$_2$)$_n$-phenyl substituted with 0-2 R$^g$;

n, at each occurrence, is selected from 0, 1, 2, 3, and 4;
p, at each occurrence, is selected from 0, 1, and 2;
r, at each occurrence, is selected from 0, 1, 2, 3, and 4;
s, at each occurrence, is selected from 0, 1, 2, 3, 4, 5, and 6; and
t, at each occurrence, is selected from 1, 2, 3, and 4.

In another embodiment, the present invention provides a pharmaceutical composition comprising a pharmaceutically acceptable carrier and a therapeutically effective amount of at least one of the compounds of the present invention or a pharmaceutically acceptable salt, solvate, or prodrug form thereof.

In another embodiment, the present invention provides a novel process for making a compound of the present invention or a stereoisomer or pharmaceutically acceptable salt, solvate or prodrug form thereof.

In another embodiment, the present invention provides a novel intermediate for making a compound of the present invention or a stereoisomer or pharmaceutically acceptable salt, solvate or prodrug form thereof.

In another embodiment, the present invention provides a pharmaceutical composition further comprising additional therapeutic agent(s) selected from potassium channel openers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phospodiesterase inhibitors, antidiabetic agents, anti-inflammatory agents, antioxidants, angiogenesis modulators, antiosteoporosis agents, hormone replacement therapies, hormone receptor modulators, oral contraceptives, anti-obesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antiflugal agents, cholesterol/lipid lowering agents and lipid profile therapies, and agents that mimic ischemic preconditioning and/or myocardial stunning, or a combination thereof.

In another embodiment, the present invention provides a pharmaceutical composition further comprising additional therapeutic agent(s) selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In another embodiment, the present invention provides a pharmaceutical composition wherein the additional therapeutic agent is an antihypertensive agent selected from ACE inhibitors, AT-1 receptor antagonists, ET receptor antagonists, dual ET/AII receptor antagonists, and vasopepsidase inhibitors, an antiarrythmic agent selected from IKur inhibitors, or an antithrombotic agent selected from anticoagulants selected from thrombin inhibitors, other factor XIa inhibitors, other kallikrein inhibitors, factor VIIa inhibitors and factor Xa inhibitors, and antiplatelet agents selected from GPIIb/IIIa blockers, other P2Y$_1$ antagonists, P2Y$_{12}$ antagonists, thromboxane receptor antagonists, and aspirin, or a combination thereof In a preferred embodiment, the present invention provides pharmaceutical composition, wherein the additional therapeutic agent(s) are an anti-platelet agent or a combination thereof.

In a preferred embodiment, the present invention provides a pharmaceutical composition, wherein the additional therapeutic agent is the anti-platelet agent clopidogrel.

In another embodiment, the present invention provides a method for modulation of platelet reactivity comprising administering to a patient in need of such treatment a therapeutically effective amount of at least one of the compounds of the present invention or a pharmaceutically acceptable salt, solvate, or prodrug form thereof.

In another embodiment, the present invention provides a method for treating thromboembolic disorders comprising: administering to a patient in need of such treatment a therapeutically effective amount of at least one of the compounds of the present invention or a pharmaceutically acceptable salt, solvate, or prodrug form thereof.

In another embodiment, the thromboembolic disorder is selected from the group consisting of arterial cardiovascular thromboembolic disorders, venous cardiovascular thromboembolic disorders, arterial cerebrovascular thromboembolic disorders, venous cerebrovascular thromboembolic disorders, and thromboembolic disorders in the chambers of the heart.

In another embodiment, the thromboembolic disorder is selected from the group consisting of unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

In another embodiment, the present invention provides a novel method of treating a patient in need of thromboembolic disorder treatment, comprising: administering a compound of the present invention or a pharmaceutically acceptable salt, solvate, or prodrug form thereof in an amount effective to treat a thromboembolic disorder.

In another embodiment, the present invention provides a method for treating a thromboembolic disorder, comprising: administering to a patient in need thereof a therapeutically effective amount of a first and additional therapeutic agent(s), wherein the first therapeutic agent is a compound of present invention or a pharmaceutically acceptable salt thereof and the additional therapeutic agent(s) are selected from potassium channel openers, calcium channel blockers, sodium hydrogen exchanger inhibitors, antiarrhythmic agents, anti-atherosclerotic agents, anticoagulants, antithrombotic agents, prothrombolytic agents, fibrinogen antagonists, diuretics, antihypertensive agents, ATPase inhibitors, mineralocorticoid receptor antagonists, phospodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a method for treating a thromboembolic disorder, comprising: administering to a patient in need thereof a therapeutically effective amount of a first and additional therapeutic agent(s), wherein the first therapeutic agent is a compound of present invention or a pharmaceutically acceptable salt thereof and the additional therapeutic agent(s) are selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a cholesterol/lipid lowering agent, or a combination thereof In another embodiment, the present invention provides a method for treating a thromboembolic disorder, wherein the additional therapeutic agent(s) are selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfmpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, a combination thereof.

In another embodiment, the present invention provides a method for treating a thromboembolic disorder, wherein the additional therapeutic agent(s) are selected from an antihypertensive agent selected from ACE inhibitors, AT-1 receptor antagonists, ET receptor antagonists, dual ET/AII receptor antagonists, and vasopepsidase inhibitors, or an antithrombotic agent selected from an antiplatelet agent selected from GPIIb/IIIa blockers, $P2Y_1$ and $P2Y_{12}$ antagonists, thromboxane receptor antagonists, and aspirin, a combination thereof.

In another embodiment, the present invention provides a method for treating a thromboembolic disorder, wherein the additional therapeutic agent(s) are an anti-platelet agent or a combination thereof In another embodiment, the present invention provides a method for treating a thromboembolic disorder, wherein the additional therapeutic agent(s) are the anti-platelet agent(s) clopidogrel and/or aspirin.

In another embodiment, the present invention provides a novel method, comprising: administering a compound of the present invention or a pharmaceutically acceptable salt form thereof in an amount effective to treat a thromboembolic disorder.

In another embodiment, the present invention provides a compound of the present invention for use in therapy.

In another embodiment, the present invention also provides the use of a compound of the present invention for the manufacture of a medicament for the treatment of a thromboembolic disorder.

In another embodiment, the present invention provides a novel article of manufacture, comprising:
(a) a first container;
(b) a pharmaceutical composition located within the first container, wherein the composition, comprises: a first therapeutic agent, comprising: a compound of the present invention or a pharmaceutically acceptable salt form thereof; and,
(c) a package insert stating that the pharmaceutical composition can be used for the treatment of a throbmboembolic disorder.

In another preferred embodiment, the present invention provides a novel article of manufacture, further comprising:
(d) a second container;

wherein components (a) and (b) are located within the second container and component (c) is located within or outside of the second container.

In another embodiment, the present invention provides a novel article of manufacture, comprising:
(a) a first container;
(b) a pharmaceutical composition located within the first container, wherein the composition, comprises: a first therapeutic agent, comprising: a compound of the present invention or a pharmaceutically acceptable salt form thereof; and,
(c) a package insert stating that the pharmaceutical composition can be used in combination with a second therapeutic agent to treat a thromboembolic disorder.

In another preferred embodiment, the present invention provides a novel article of manufacture, further comprising:

(d) a second container;

wherein components (a) and (b) are located within the second container and component (c) is located within or outside of the second container.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. All tautomers of shown or described compounds are also considered to be part of the present invention.

The following are definitions of terms used in this specification. The initial definition provided for a group or term herein applies to that group or term throughout the present specification, individually or as part of another group, unless otherwise indicated.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. When a ring system (e.g., carbocyclic or heterocyclic) is said to be substituted with a carbonyl group or a double bond, it is intended that the carbon atom of the carbonyl group or one carbon atom of the double bond be part of (i.e., within) the ring. Ring double bonds, as used herein, are double bonds that are formed between two adjacent ring atoms (e.g., C=C, C=N, or N=N).

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

When any variable (e.g., $R^{2b}$, $R^{8b}$, etc.) occurs more than one time in any constituent or formula for a compound, its definition at each occurrence is independent of its definition at every other occurrence. Thus, for example, if a group is shown to be substituted with 0-3 $R^{2b}$, then said group may optionally be substituted with up to three $R^{2b}$ groups and $R^{2b}$ at each occurrence is selected independently from the definition of $R^{2b}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms. For example, "$C_1$-$C_{10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

"Alkenyl" or "alkenylene" is intended to include hydrocarbon chains of either a straight or branched configuration having the specified number of carbon atoms and one or more unsaturated carbon-carbon bonds which may occur in any stable point along the chain. For example, "$C_2$-$C_6$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either a straight or branched configuration and one or more carbon-carbon triple bonds which may occur in any stable point along the chain. For example, "$C_2$-$C_6$ akynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like.

"Alkoxy" or "alkyloxy" represents an alkyl group as defined above with the indicated number of carbon atoms attached through an oxygen bridge. For example, "$C_1$-$C_6$ alkoxy" (or alkyloxy), is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" or "thioalkoxy" represents an alkyl group as defined above with the indicated number of carbon atoms attached through a sulphur bridge; for example methyl-S—, ethyl-S—, and the like.

"Halo" or "halogen" as used herein refers to fluoro, chloro, bromo, and iodo; and "counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$-$C_6$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluoroethoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

As used herein, "carbocycle" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Preferred carbocycles, unless otherwise specified, are cyclopropyl, cyclobutyl, cyclopentyl, cyclohexyl, phenyl, naphthyl, and indanyl. When the term "carbocycle" is used, it is intended to include "aryl".

As used herein, the term "bicyclic carbocycle" or "bicyclic carbocyclic group" is intended to mean a stable 9- or 10-membered carbocyclic ring system which contains two fused rings and consists of carbon atoms. Of the two fused rings, one ring is a benzo ring fused to a second ring; and the second ring is a 5 or 6 membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

As used herein, the term "aryl", "$C_6$-$C_{10}$ aryl" or "aromatic residue", is intended to mean an aromatic moiety containing, if specified, the specified number of carbon atoms; for example phenyl or naphthyl. Unless otherwise specified, "aryl", "$C_6$-$C_{10}$ aryl" or "aromatic residue" may be unsubstituted or substituted with 0 to 3 groups selected from H, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle" or "heterocyclic group" is intended to mean a stable 3, 4, 5, 6, or 7-membered monocyclic or bicyclic or 7, 8, 9, 10, 11, 12, 13, or 14-membered bicyclic or tricyclic heterocyclic ring which is saturated, partially unsaturated or fully unsaturated, and which consists of carbon atoms and 1, 2, 3 or 4 heteroatoms independently selected from the group consisting of N, O and S; and including any bicyclic group in which any of the above-defined heterocyclic rings is fused to a benzene ring. The nitrogen and sulfur heteroatoms may optionally be oxidized to —NO—, —SO—, or —$SO_2$—. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen atom in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

As used herein, the term "aromatic heterocyclic group" or "heteroaryl" is intended to mean a stable monocyclic and polycyclic aromatic hydrocarbon that include at least one heteroatom ring member such as sulfur, oxygen, or nitrogen. Preferred heteroaryl groups are stable 5, 6, or 7-membered monocyclic or 7, 8, 9, or 10-membered bicyclic heterocyclic aromatic rings which consists of carbon atoms and 1, 2, 3, or 4 heteroatoms independently selected from the group consisting of N, NH, 0 and S. It is to be noted that total number of S and O atoms in the aromatic heterocycle is not more than 1. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl indazolyl, 1,2,4-thiadiazolyl, isothiazolyl, benzothienyl, purinyl, carbazolyl, benzimidazolyl, 2,3-dihydrobenzofuranyl, 2,3-dihydrobenzothienyl, 2,3-dihydrobenzothienyl-S-oxide, 2,3-dihydrobenzothienyl-S-dioxide, benzoxazolin-2-on-yl, indolinyl, benzodioxolanyl, benzodioxane, and the like. Heteroaryl groups can be substituted or unsubstituted.

Examples of heterocycles include, but are not limited to, 2-pyrrolidonyl, 2H,6H-1,5,2-dithiazinyl, 2H-pyrrolyl, 3H-indolyl, 4-piperidonyl, 4H-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preferred 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5 or 6-membered monocyclic aromatic ring comprising a 5 membered heteroaryl ring, a 6-membered heteroaryl ring or a benzo ring, each fused to a second ring. The second ring is a 5 or 6 membered monocyclic ring which is saturated, partially unsaturated, or unsaturated, and comprises a 5 membered heterocycle, a 6 membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinoline, 2,3-dihydrobenzofuranyl, chromanyl, 1,2,3,4-tetrahydro-quinoxaline, and 1,2,3,4-tetrahydro-quinazoline.

Also included are fused ring and spiro compounds containing, for example, the above carbocycles or heterocycles.

Bridged rings are also included in the definition of carbocycle or heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Greene and Wuts, "Protective Groups in Organic Synthesis" John Wiley & Sons, New York (1991) and "The Peptides: Analysis, Synthesis, Biology, Vol. 3, Academic Press, New York (1981), the disclosure of which is hereby incorporated by reference. Examples of amine protecting groups include, but are not limited to, the following: (Fmoc); (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Compounds of the present invention, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

Radiolabelled compounds of the present invention, i.e., wherein one or more of the atoms described are replaced by a radioactive isotope of that atom (e.g., C replaced by $^{13}$C or by $^{14}$C; and isotopes of hydrogen include tritium and deuterium), are also provided herein. Such compounds have a variety of potential uses, e.g., as standards and reagents in determining the ability of a potential pharmaceutical to bind to target proteins or receptors, or for imaging compounds of this invention bound to biological receptors in vivo or in vitro.

Compounds of the present invention are, subsequent to their preparation, preferably isolated and purified to obtain a composition containing an amount by weight equal to or greater than 99% compound of the present invention ("substantially pure"), which is then used or formulated as described herein. Such "substantially pure" compounds are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, S(O)$_2$H, or S(O)H group.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) *Design of Prodrugs*, edited by H. Bundgaard, (Elsevier, 1985), and *Methods in Enzymology*, Vol. 112, at pp. 309-396, edited by K. Widder, et. al. (Academic Press, 1985);

b) *A Textbook of Drug Design and Development*, edited by Krosgaard-Larsen and H. Bundgaard, Chapter 5, "Design and Application of Prodrugs," by H. Bundgaard, at pp. 113-191 (1991);

c) H. Bundgaard, *Advanced Drug Delivery Reviews*, Vol. 8, p. 1-38 (1992);

d) H. Bundgaard, et al., *Journal of Pharmaceutical Sciences*, Vol. 77, p. 285 (1988); and e) N. Kakeya, et. al., *Chem Phar Bull.*, Vol. 32, p. 692 (1984).

Compounds containing a carboxy group can form physiologically hydrolyzable esters which serve as prodrugs by being hydrolyzed in the body to yield compounds of the present invention per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$ alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

It should further be understood that solvates (e.g., hydrates) of the compounds of the present invention are also with the scope of the present invention. Methods of salvation are generally known in the art.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Therapeutically effective amount"is intended to include an amount of a compound of the present invention that is effective when administered alone or in combination to inhibit P2Y$_1$. "Therapeutically effective amount" is also intended to include an amount of the combination of compounds claimed that is effective to inhibit P2Y$_1$. The combination of compounds is preferably a synergistic combination. Synergy, as described, for example, by Chou and Talalay, *Adv. Enzyme Regul.* 1984, 22:27-55, occurs when the effect (in this case, inhibition of P2Y$_1$) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

The present invention further includes compositions comprising one or more compounds of the present invention and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th ed., 1985, which is incorporated herein by reference in its entirety.

Abbreviations as used herein, are defmed as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "M" for molar, "mmol" for millimole or millimoles, "min" for minute or minutes, "h" for hour or hours, "rt" for room temperature, "atm" for atmosphere, "psi" for pounds per square inch, "conc." for concentrate, "sat" or "sat'd " for saturated, "MW" for molecular weight, "mp" for melting point, "MS" or "Mass Spec" for mass spectrometry, "ESI" for electrospray ionization mass spectroscopy, "HR" for high resolution, "LC-MS" for liquid chromatography mass spectrometry, "HPLC" for high pressure liquid chromatography, "RP HPLC" for reverse phase HPLC, "TLC" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, "tlc" for thin layer chromatography, and "α", "β", "R", "S", "E", and "Z" are stereochemical designations familiar to one skilled in the art.

Me methyl
Et ethyl
MeOH methanol
EtOH ethanol
i-PrOH isopropanol
Ph phenyl
Bn benzyl
t-Bu tertiary butyl
AcOH acetic acid
EtOAc ethyl acetate
2MeS-ADP 2 methylthio adenosine diphosphate
cDNA complimentary DNA
DMEM Dulbecco's modified Eagle media
DMF dimethyl formamide
DMSO dimethyl sulfoxide
DCE 1,2 dichloroethane
DCM dichloromethane
DCC dicyclohexylcarbodiimide
DIC or DIPCDI diisopropylcarbodiimide
DIEA diethylpropyl amine
EDTA ethylenediamninetetraacetic acid
FBS Fetal Bovine Serum
HEPES 4-(2-hydroxyethyl)piperaxine-1-ethanesulfonic acid
D-PBS Dulbecco's Phosphate Buffered Saline
Pd/C palladium on carbon
SCX Strong Cation Exchanger
THF tetrahydrofuran
TFA trifluoroacetic acid
TRIS tris (hydroxymethyl) aminomethane
EDC (or EDC.HCl) or EDCI (or EDCI.HCl) or EDAC 3-ethyl-3'-(dimethylamino)propyl-carbodiimide hydrochloride (or 1-(3-dimethylaminopropyl)-3-ethylcarbodiimide hydrochloride)

Solution ratios express a volume relationship, unless stated otherwise. NMR chemical shifts (δ) are reported in parts per million. Flash chromatography was carried out on silica gel according to Still's method (Still, W. C. et al. *J. Org. Chem.* 1978, 43, 2923).

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C. *Comprehensive Organic Transformations*, VCH: New York, 1989. Preferred methods include, but are not limited to, those described below. All references cited herein are hereby incorporated in their entirety herein by reference.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety herein by reference.

Schemes 1-7 describe synthetic routes of making compounds of the invention. Schemes 1 and 2 describe preparations of compounds of the invention from a key amine intermediate 1 or an isocyanate intermediate 4. Scheme 3 describes a preparation of the key isocyanate intermediate 4 from the corresponding amine 1. Schemes 4, 5 and 6 describe a preparation of the amines from commercially available starting materials. Scheme 6 elaborates further functionalization of ureas.

Scheme 1 describes a one-step preparation of substituted ureas, from the key amine intermediate 1. Substituted isocyanates are commercially available or can readily be prepared from commercially available materials by methods known to one skilled in the art of organic synthesis. Reaction of an isocyanate 2 with the amine 1 typically occurs at temperatures between 20° C. and 80° C. in a variety of solvents such as tetrahydrofuran, dichloroethane or dioxane.

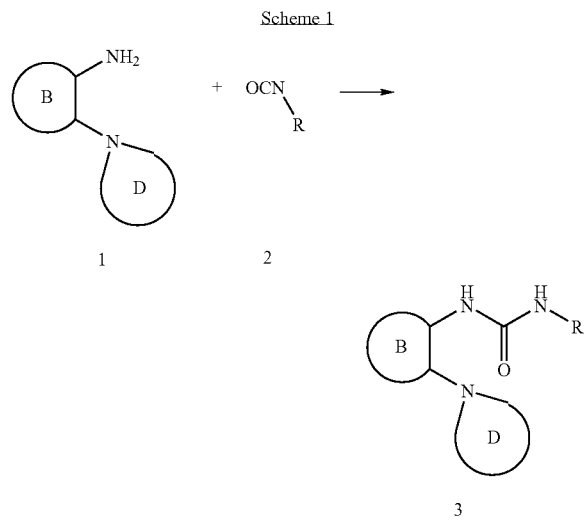

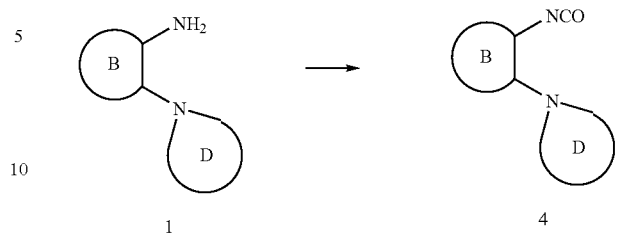

Scheme 2 describes a preparation of substituted ureas from the key isocyanate intermediate 4. Substituted anilines and amino-substituted heteroaromatics are commercially available or can readily be prepared from commercially available materials by methods known to one skilled in the art of organic synthesis. Reaction of the isocyanate 4 with aniline 5 typically occurs at temperatures between 20° C. and 80° C. in a variety of solvents such as tetrahydrofuran, dichloroethane or dioxane.

Scheme 4 outlines one possible preparation of amino derivatives 1, which proceeds by aromatic nucleophilic substitution followed by reduction. Nitro aryl derivatives or nitro heteroaryl derivatives 6, substituted in the ortho position with a halogen (such as chlorine, fluorine or bromine), are commercially available or can readily be prepared by one skilled in the art of organic synthesis. They can be reacted with NH-containing cyclics 7 as nucleophiles to provide the corresponding compounds 8. Typical reaction conditions involve the reaction of a nucleophile and a halonitroaryl/heteroaryl derivative either in an organic solvent such as THF, DMF, toluene, dioxane or n-butanol, or under neat condition, in the presence of a base such as potassium carbonate, cesium carbonate, triethylamine, tert-butoxide, or DIEA, etc. The reaction temperature is usually between room temperature and reflux condition. Reaction conditions can be chosen based on the nucleophilicity of 7 and/or halogen difference. Microwave irradiation and/or heating at higher temperature can also be used to accelerate the rate of reaction. For example, when 7 is tetrahydroquinoline derivative, the $SN_{Ar}$ reaction can be performed with neat 6 and 7 in the presence of 2,4,6-collidine at 250° C. under microwave irradiation.

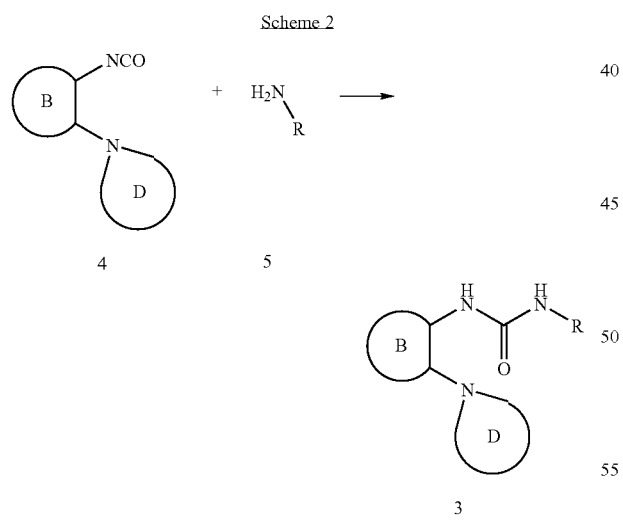

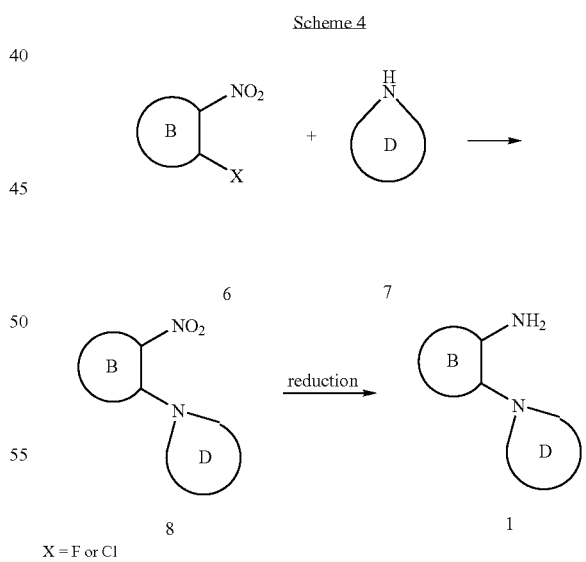

Scheme 3 outlines a preparation of the key isocyanate intermediate 4. Anilines 1, prepared according to Schemes 4 and 5 can be treated with a phosgene equivalent in an organic solvent such as dichloromethane, dichloroethane or toluene, to produce the corresponding isocyanate. Phosgene equivalents include diphosgene, triphosgene, carbonyl diimidazole, trichloromethyl chloroformate and disuccinimidyl carbonate.

Following aromatic nucleophilic substitution, the resulting nitro derivative 8 can be reduced to the corresponding aniline. Typical conditions include hydrogenation in the presence of a metal catalyst such as palladium or platinum. Other conditions include treatment with reducing agents such as $SnCl_2$ or Zinc powder with ammonium chloride.

On the other hand, intermediates 1 can be synthesized via Cu or Pd chemistry (for a review paper, see, *Angew. Chem. Int. Ed.* 42, 5400-5449) between 1,2-substituted aryl/heteroaryl halides and NH-containing cyclics 7 followed by deprotection or functional transformation as exemplified in Scheme 5. Microwave irradiation can also be used to accelerate the rate of reaction in the coupling step when using the Pd or Cu chemistry.

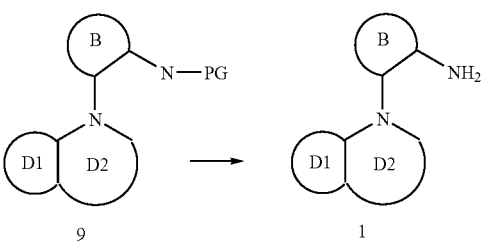

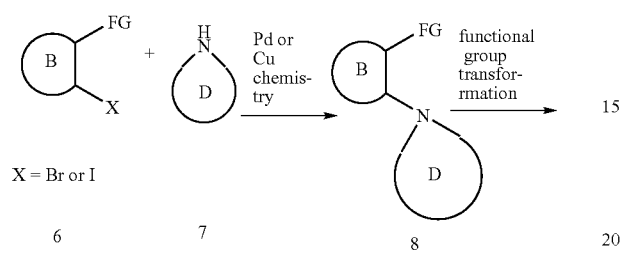

For Example:

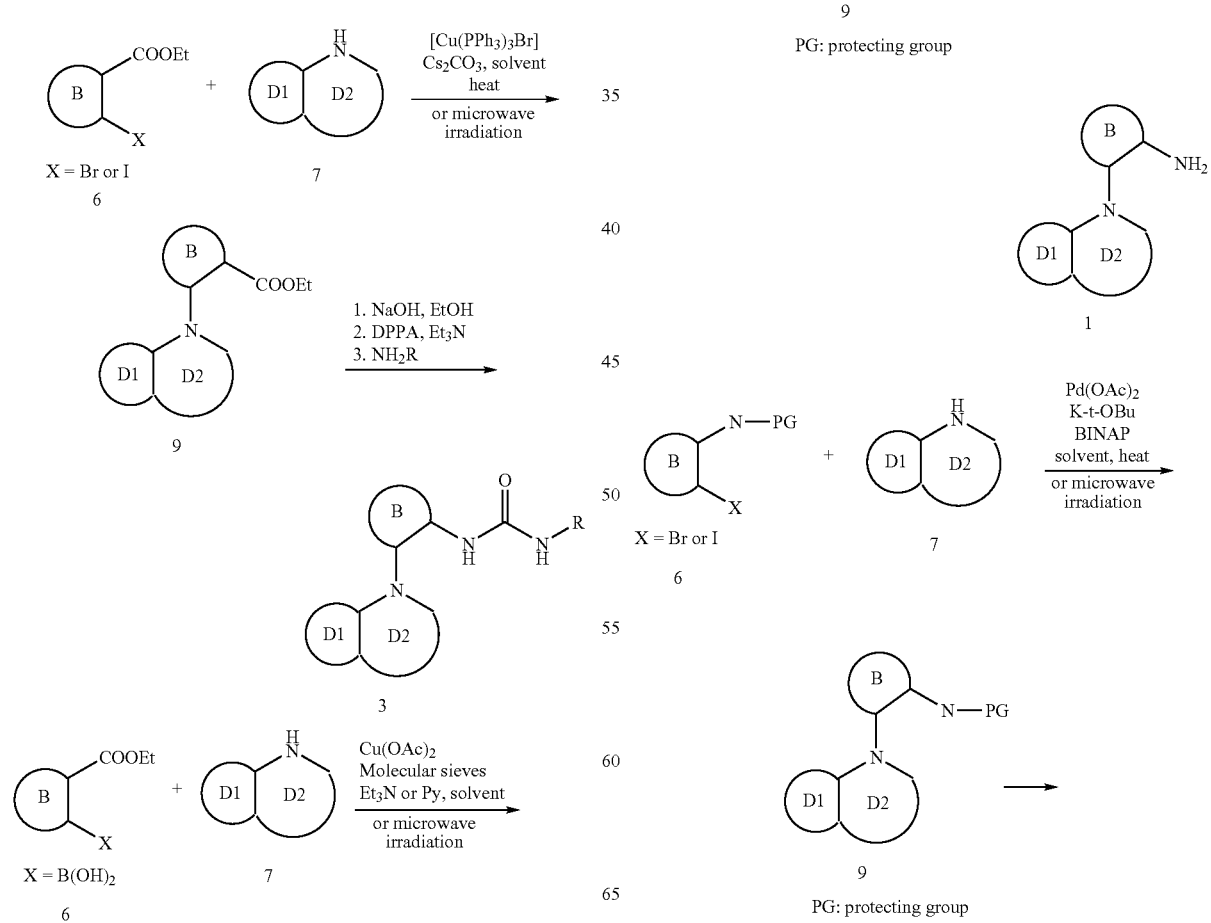

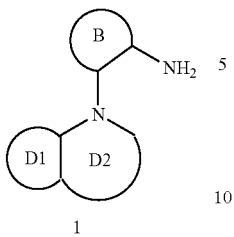

1

Scheme 6 illustrates some of the monocyclic/heterocyclic B halo-aryl, halo-heteroaryl intermediates that can be used to prepare compounds of the present invention. Ring B is optionally substituted. These intermediates are either commercially available or can be prepared using methods known to those skilled in the art of organic synthesis. R' is NO$_2$ or N-PG, PG is protecting group, and X is halogen.

Scheme 6

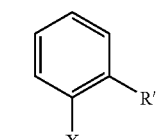 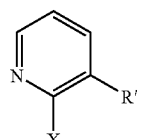
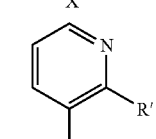 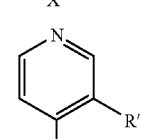
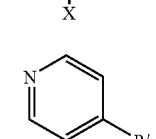 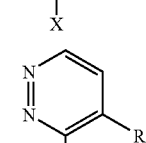
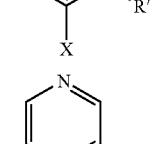 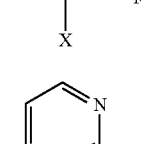
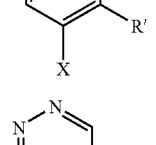 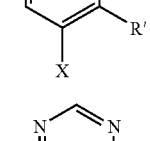
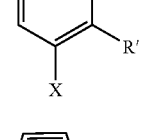 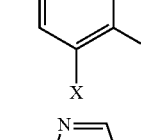
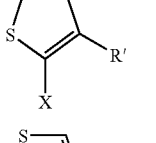 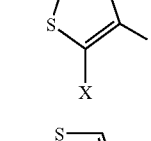
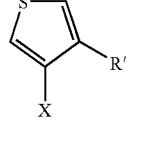 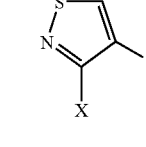

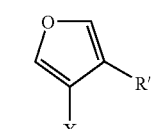 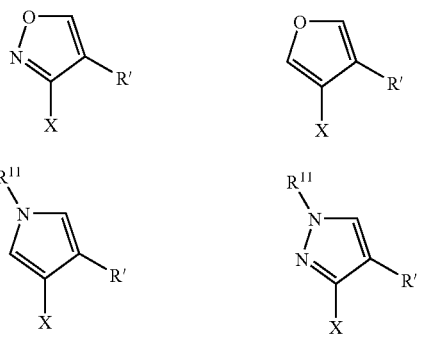
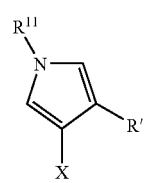 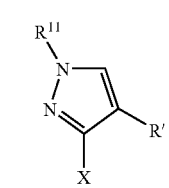
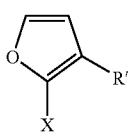 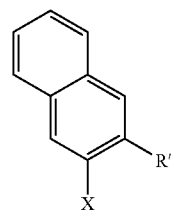
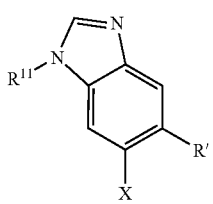 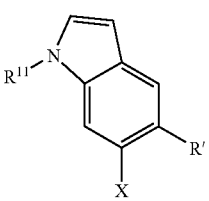
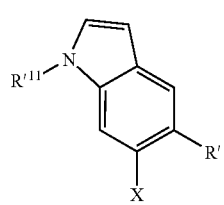 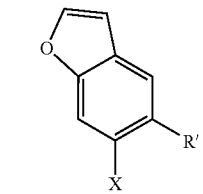
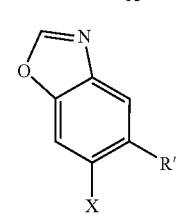 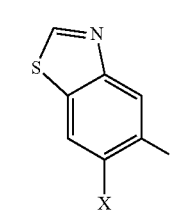
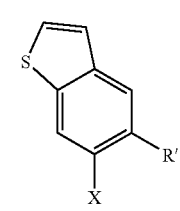 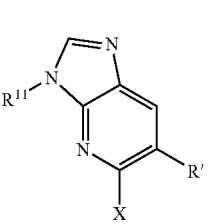

-continued

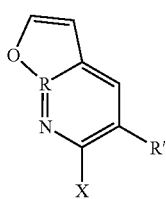
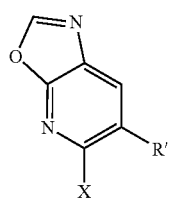
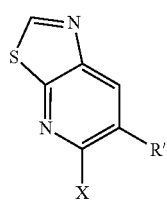
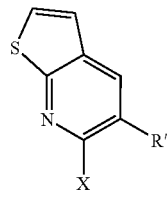

Preparation of substituted pyridine amines such as 11, 12, 13, or 14 is shown in Scheme 7. The pyridine aniline 10 prepared as described in Scheme 4 can be brominated or chlorinated using agents such as N-bromosuccinimide or N-chlorosuccinimide in an organic solvent such as DMF. The resulting aromatic bromide can be converted to the corresponding nitrile by metal catalyzed cyanation. For example, reaction of the bromide 11 (X=Br) with copper (I) cyanide, tris-(dibenzylideneaceteone)-bispalladium, diphenyiphosphine ferrocene and tetrabutylammonium cyanide affords the corresponding nitrile 12. The resulting nitrile can be hydrolyzed to the corresponding carboxylic acid using methods know in the art of organic synthesis such as treatment with aqueous sodium hydroxide. Conversion of the corresponding carboxylic acid to the methyl ester can be accomplished by treatment with trimethylsilyl diazomethane or with hydrochloric acid in methanol. Alternatively, the nitrile 12 can be converted to the corresponding ester 13 and amide 14 by acidic or basic hydrolysis.

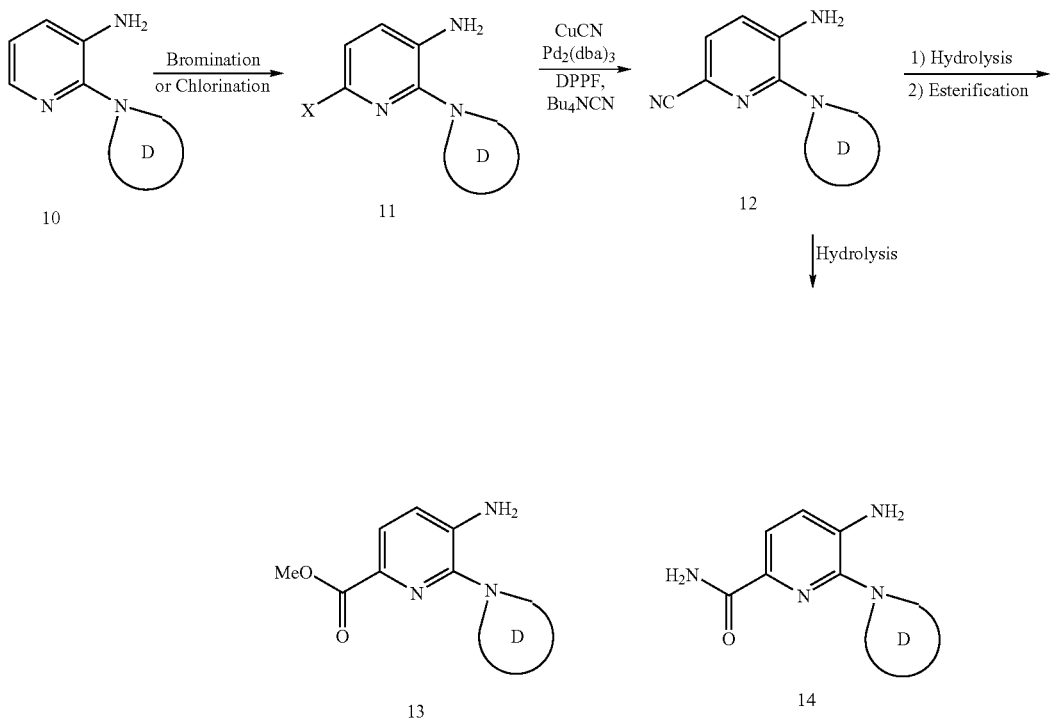

X = Br or Cl

Preparation of substituted pyridine amines such as 16, 18, 19 or 20 is shown in Scheme 8. The nitrochloro pyridine 15 can be prepared as described above for Scheme 4. The resulting aromatic bromide can be converted to the corresponding nitrile by metal catalyzed cyanation. For example, reaction of the bromide 17 (X=Br) with copper (I) cyanide, tris-(dibenzylideneaceteone)-bispalladium, diphenylphosphine ferrocene and tetrabutylammonium cyanide affords the corresponding nitrile 18. The resulting nitrile can be hydrolyzed to the corresponding carboxylic acid using methods know in the art of organic synthesis such as treatment with aqueous sodium hydroxide. Conversion of the corresponding carboxylic acid to the methyl ester 18 can be accomplished by treatment with trimethylsilyl diazomethane or with hydrochloric acid in methanol. Alternatively, the nitrile 18 can be converted to the corresponding amide 20 by acidic or basic hydrolysis.

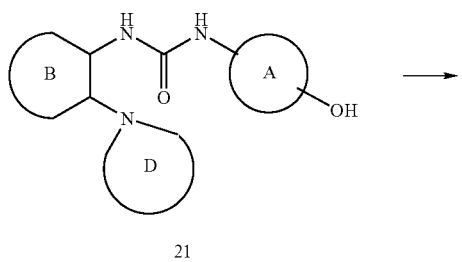

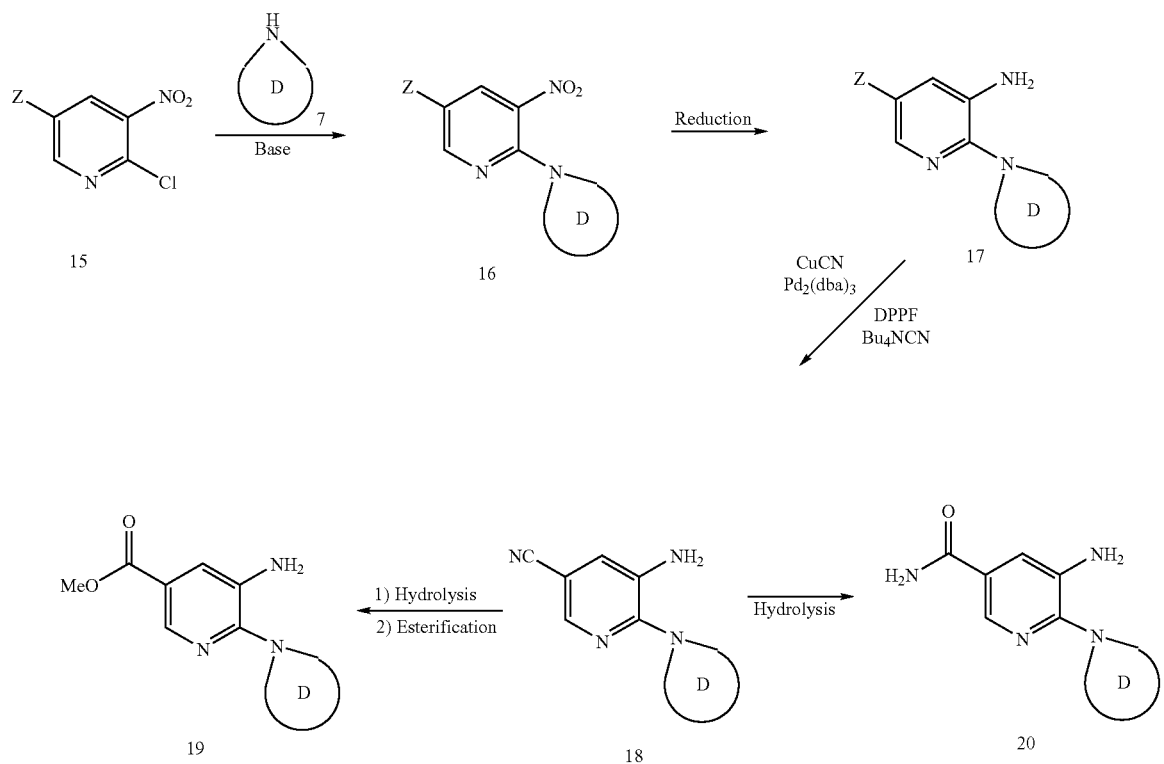

Scheme 9 describes further functionalization of urea 21 to form 22 by alkylation with alcohols via Mitsunobu chemistry or by direct reaction with alkyl halides. Ring B and ring D are optionally substituted. The preferred conditions for the alkylation of such phenols involve treatment with an excess of a primary or secondary alcohol in the presence of an azodicarboxylate equivalent such as diethyl, diisopropyl or di-tert-butyl azodicarboxylate and in the presence of triphenylphosphine or polystyrene bound triphenylphosphine. The reactions can be run in solvents such as tetrahydrofuran, toluene or dichloromethane and from 0° C. to 50° C.

-continued

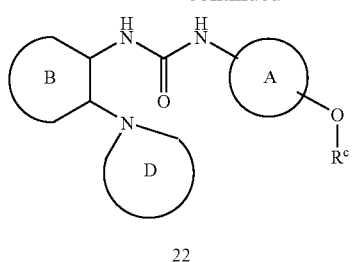

Scheme 10 illustrates numerous NH-containing bicyclic D intermediates that can be used to prepare compounds of the present invention. The phenyl ring in each of the structures listed below is optionally substituted.
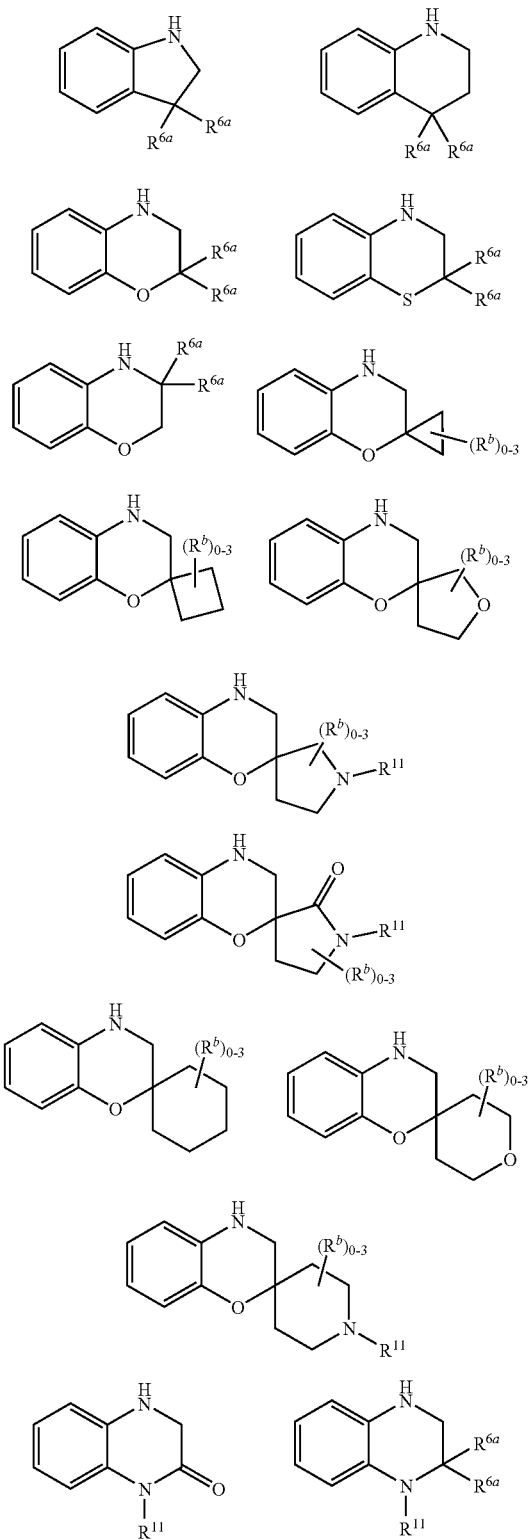
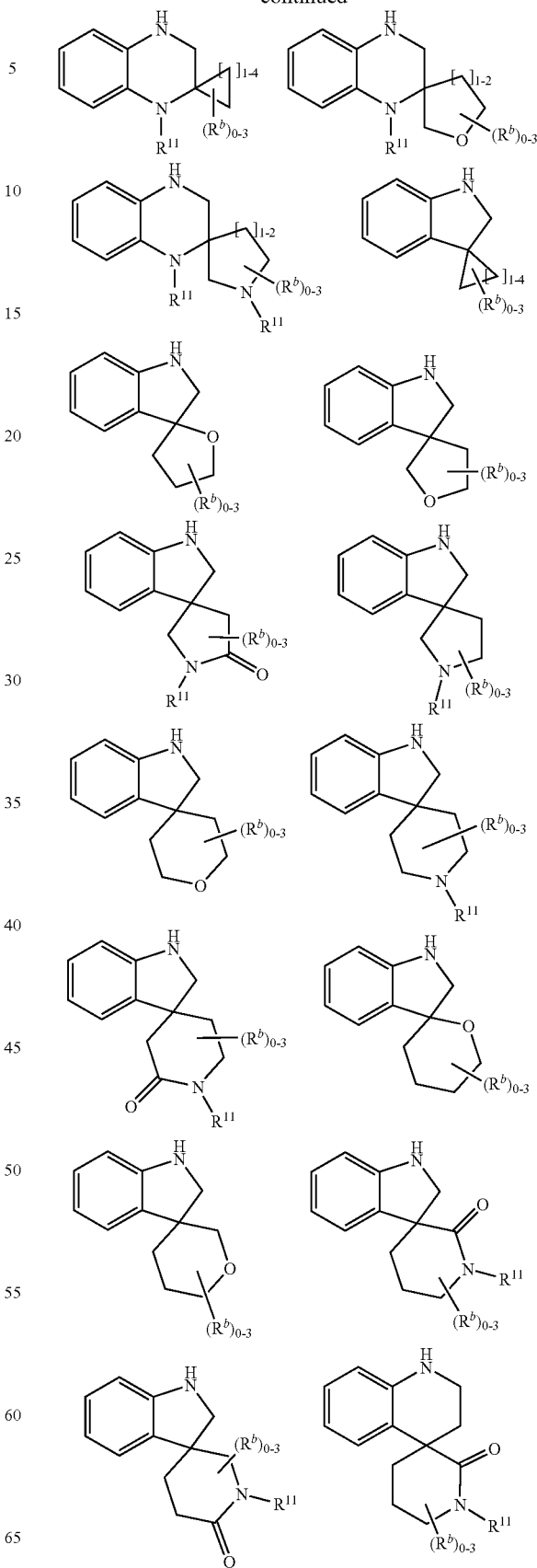

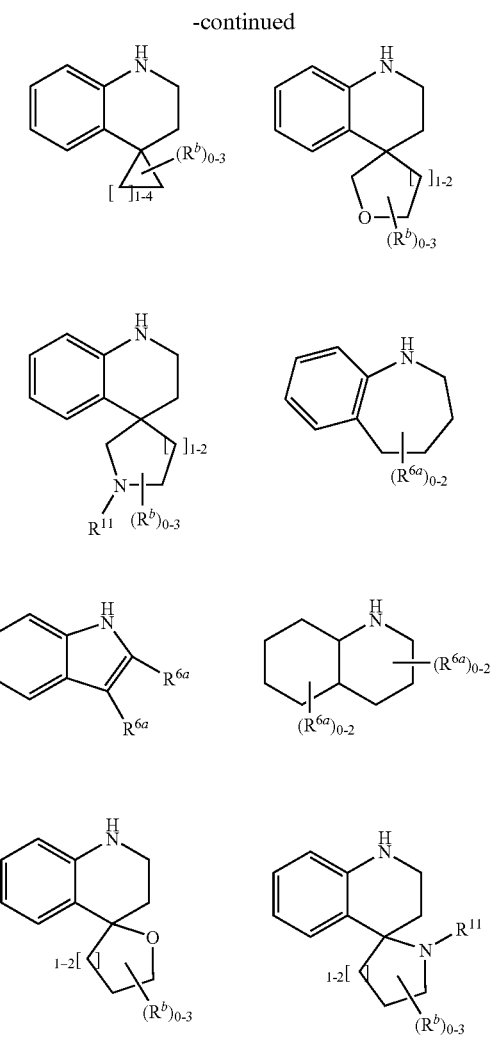
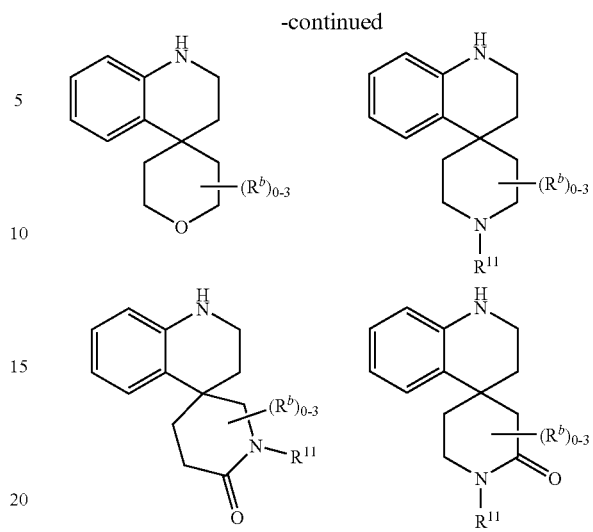

Compounds of the present invention wherein ring D is a NH-containing bicycle can be prepared by using the following methods described in Schemes 11-17 and by using methods known to those skilled in the art of organic synthesis. When D is a substituted indoline derivative, it can be prepared by using the methods shown in Schemes 11-13 and by using methods known to those skilled in the art of organic synthesis. When D is a substituted tetrahydroquinoline derivative, it can be prepared by using the methods shown in Scheme 14 and by using methods known to those skilled in the art of organic synthesis. When D is a substituted 3,4-dihydro-2H-benzo[b][1,4]oxazine derivative or a substituted 3,4-dihydro-2H-benzo[b][1,4]thiazine derivative, it can be prepared by using the methods shown in Scheme 15 and by using methods known to those skilled in the art of organic synthesis. When D is a substituted 1,2,3,4-tetrahydroquinoxaline derivative, it can be prepared by using the methods shown in Scheme 16 and by using methods known to those skilled in the art of organic synthesis. The phenyl ring in each of the structures shown below is optionally substituted.

Scheme 11

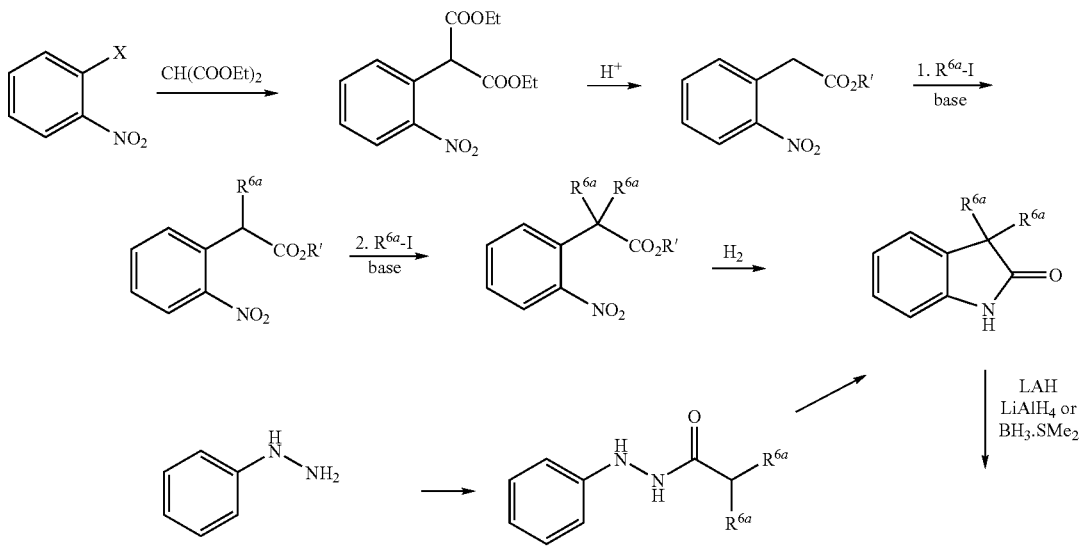

-continued
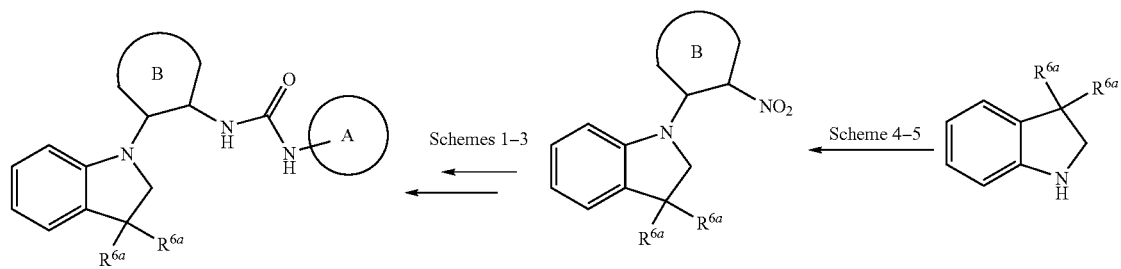
Scheme 12
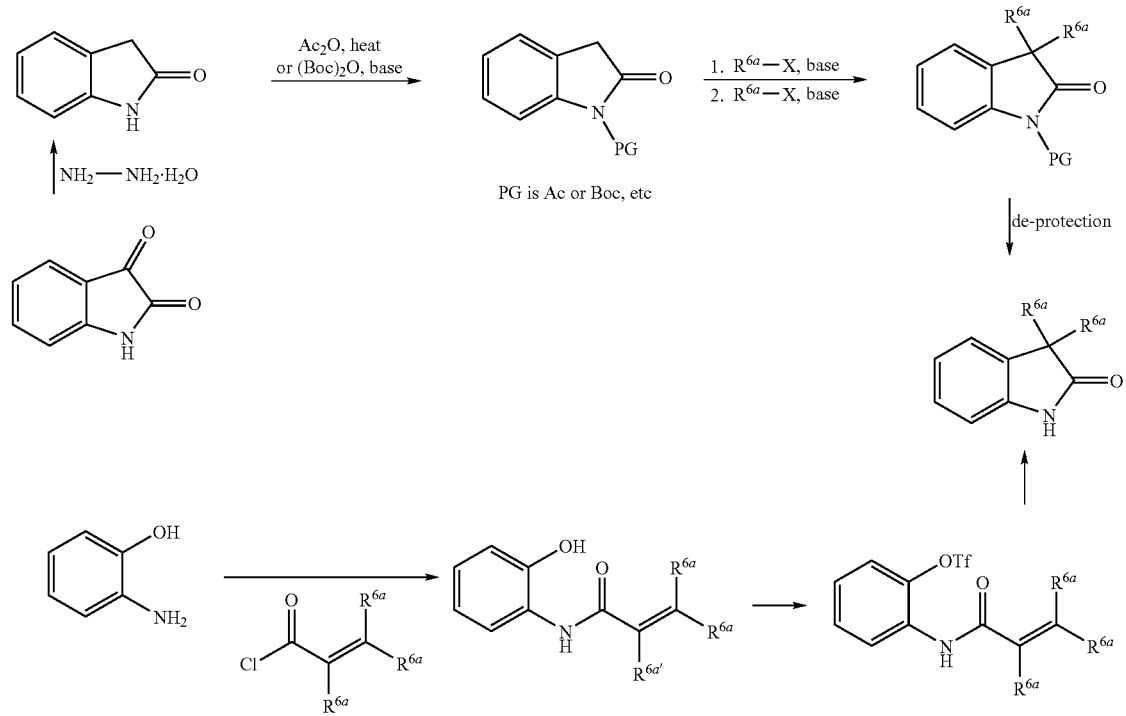
PG is Ac or Boc, etc
Scheme 13
R' = H, Alkyl
reductive amination
R' = H, Alkyl

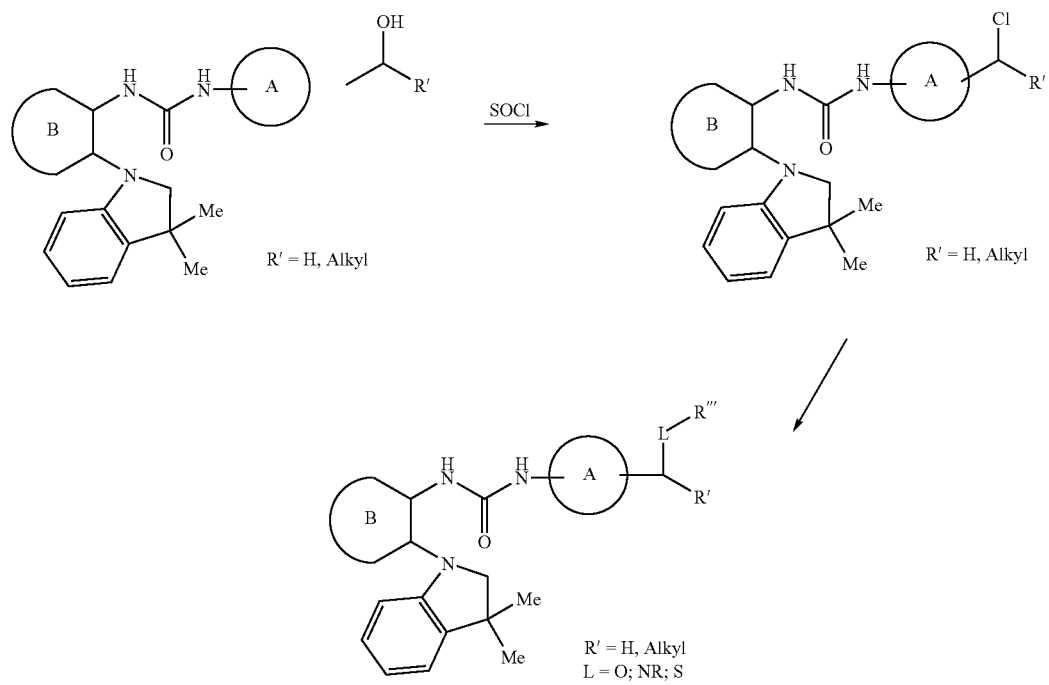
Scheme 14
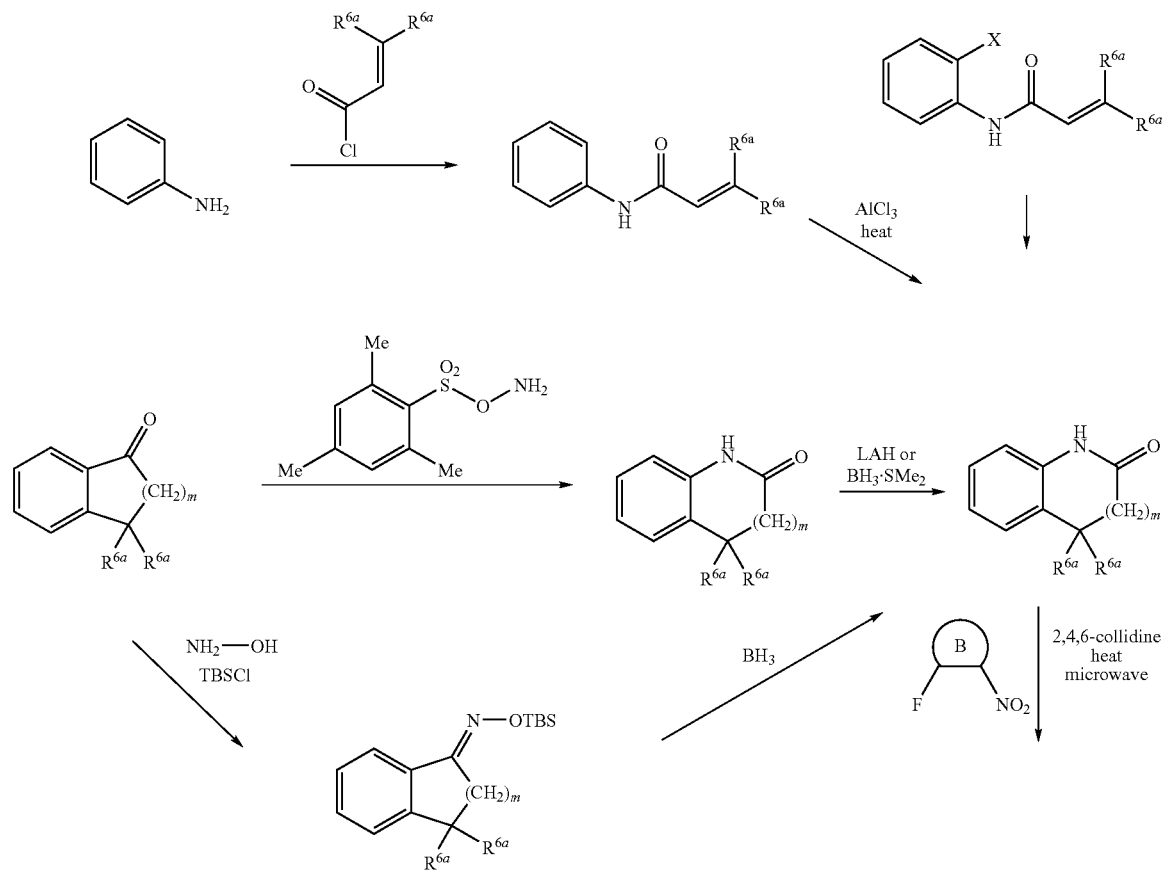

81
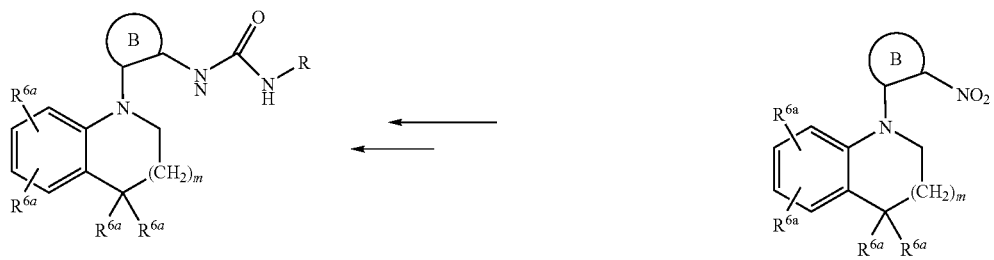
m = 0–3
82
Scheme 15
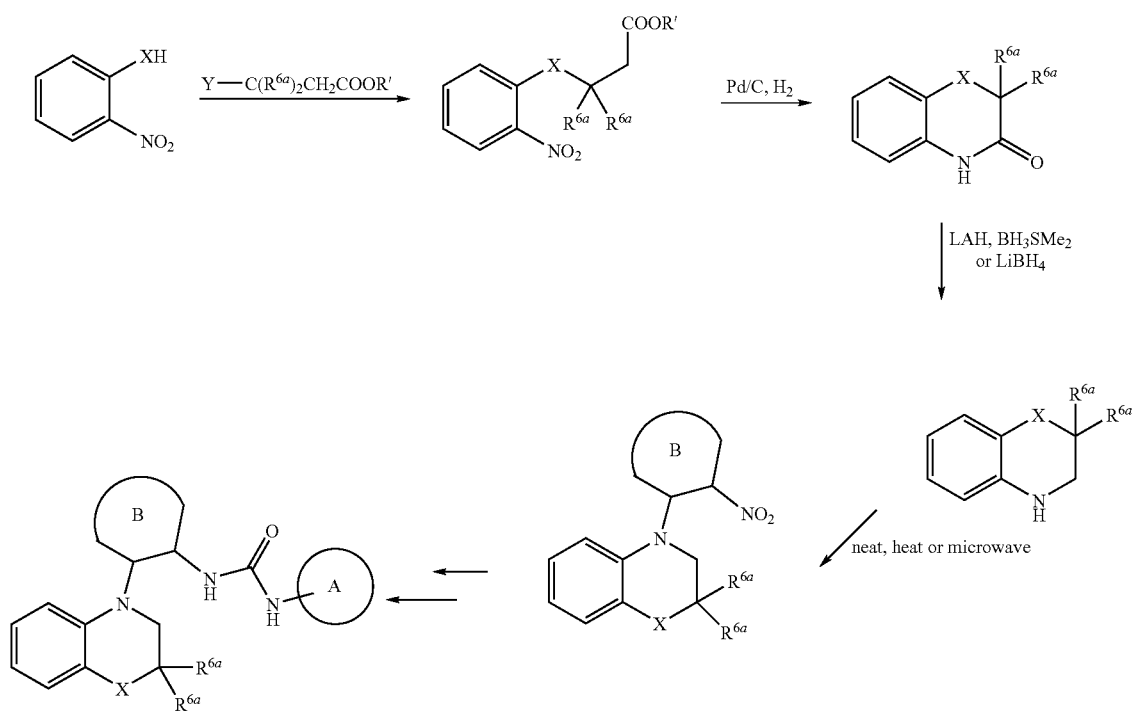
X = O or S
Scheme 16
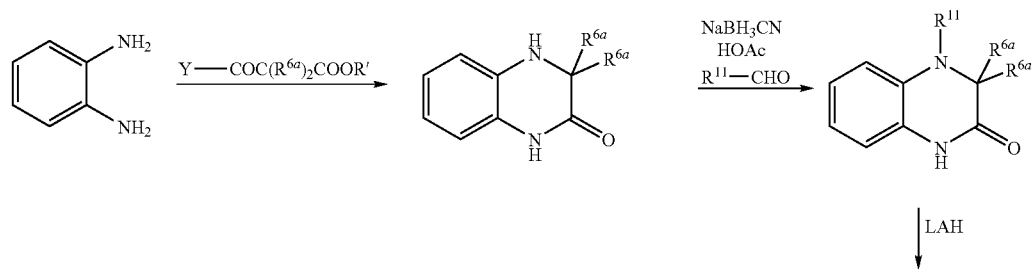

-continued

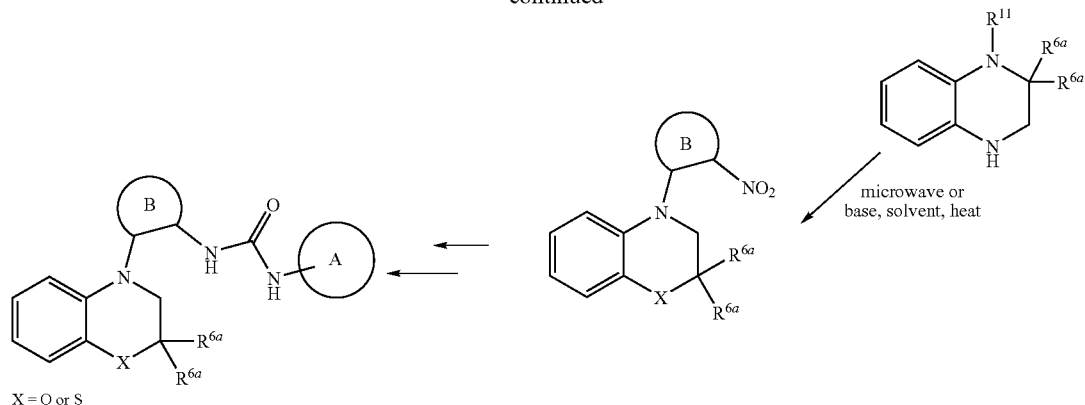

X = O or S

Compounds of the present invention when two $R^{6a}$ groups are attached to the same carbon atom together with the carbon atom to which they are attached, they form a 3-7 membered carbocycle/heterocycle resulting in Spiro NH-containing cyclic D. These spiro systems can be prepared by using methods known to those skilled in the art of organic synthesis and by using methods represented in Schemes 17 and 18.

Scheme 17

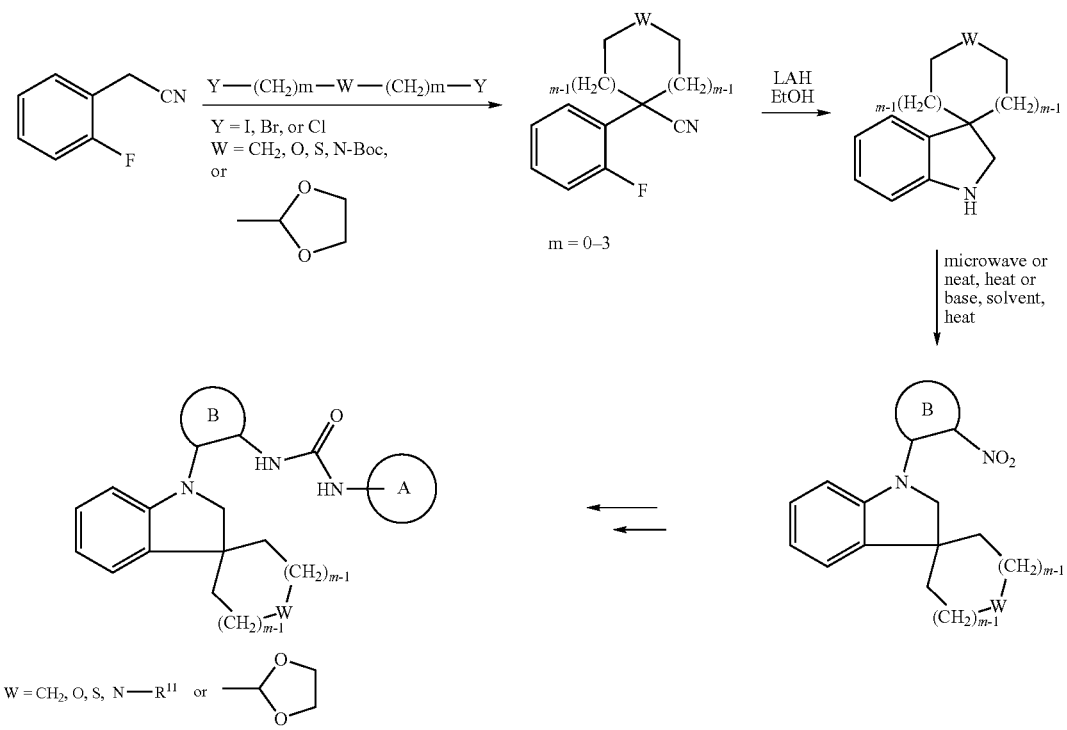

Scheme 18

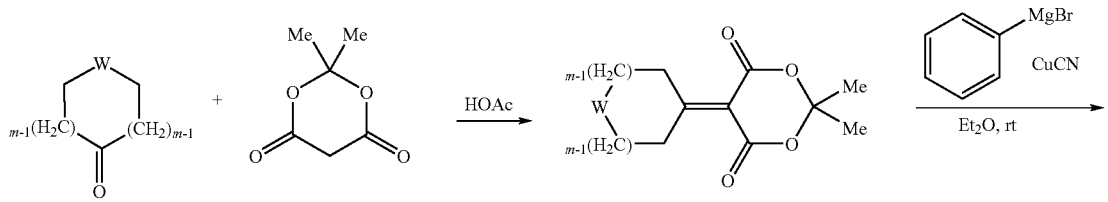

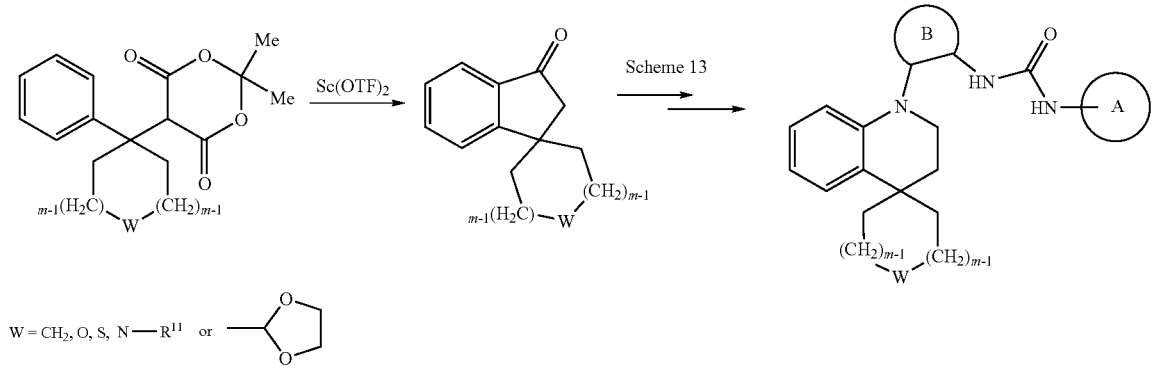

Products were analyzed by reverse phase analytical HPLC carried out on a Shimadzu Analytical HPLC system running DiscoveryVP software using Method A: Phenominex Luna C18 column (4.6×50 mm) eluted at 4 mL/min with a 4 min gradient from 100% A to 100% B (A: 10% methanol, 89.9% water, 0.1% TFA; B: 10% water, 89.9% methanol, 0.1% TFA, UV 220 nm), Method B: Phenominex Luna C18 column (4.6×50 mm) eluted at 4 mL/min with a 4 min gradient from 100% A to 100% B (A: 10% acetonitrile, 89.9% water, 0.1% TFA; B: 10% water, 89.9% acetonitrile, 0.1% TFA, UV 220 nm), or Method C: Zorbax SB C18 column (4.6×75 mm) eluted at 2.5 mL/min with methanol/water with 0.2% $H_3PO_4$ as a gradient of 10% to 90% methanol over 8 min followed by holding at 90% methanol for 3 min (UV 220 nm). Purification of intermediates and final products was carried out via either normal or reverse phase chromatography. Normal phase chromatography was carried out on an ISCO CombiFlash™ System Sq16× using prepacked $SiO_2$ cartridges eluted with gradients of hexanes and ethyl acetate. Reverse phase preparative HPLC was carried out using a Shimadzu Preparative HPLC system running DiscoveryVP software on a Shim-PackVP-ODS column (50L×20 mm) at 20 mL/min, 6 min gradient 100% A to 100% B with the solvent system used for the analytical. LCMS were obtained on a Shirnadzu HPLC system running DiscoveryVP software, coupled with a Waters Model PlatformLC mass spectrometer running MassLynx version 3.5 software using the same column and conditions as utilized for analytical described above.

EXAMPLES

The following Examples have been prepared, isolated and characterized using the methods disclosed herein. The following Examples demonstrate a partial scope of the invention and are not meant to limit the scope of the invention.

General experimental procedures for the preparation of Examples 1-11 are shown below:

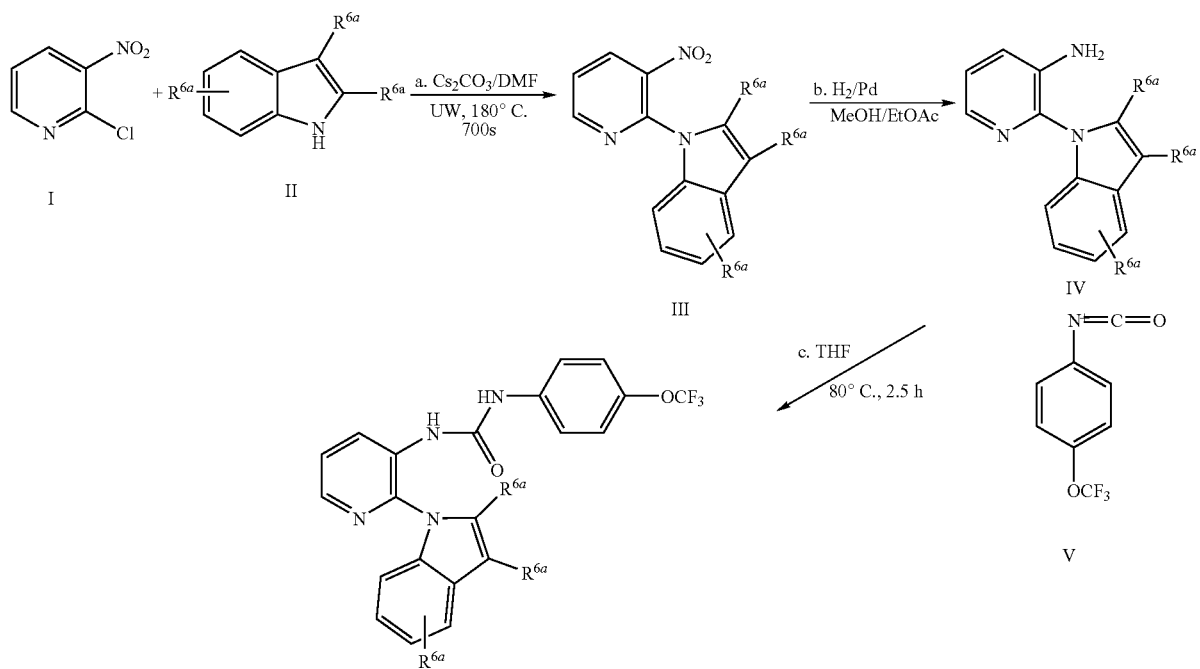

Examples 1–11

A. Preparation of III: 2-chloropyridin I (32 mg, 0.2 mmol) and substituted indole derivatives II (0.2 mmol) were dissolved in dry DMF (0.5 mL), and then Cs₂CO₃ (78 mg, 0.24 mmol) was added. The mixture was heated with stirring at 180° C. at a Personal Chemistry Microwave reactor for 700s. The mixture was diluted with EtOAc (1.5 mL) and filtered through a filter paper to get rid of the Cs₂CO₃ salt. The solvent was dried in speedvac, the crude product was dissolved in MeOH. The insoluble material was removed by filtration and the product in MeOH solution was purified by prep-HPLC using CH₃CN/H₂O/TFA system to give III, which was used in the next step without further characterization.

B. Preparation of IV: the product III from the above reaction was dissolved in a 1:1 mixture of MeOH and EtOAc (2-3 mL), 10 Pd/C (5 mg) was added and hydrogenated under 50 PSI for 2 h. The catalyst was removed by filtration through a bed of Celite®. The solvent was removed in speedvac to yield IV.

C. Preparation of Examples 1-9: To the product IV from the above reaction were added 2.5 eq of 4-(trifluoromethoxy) phenylisocyanate V, and then dry THF was added (amine concentration 0.25 M). The mixture was heated at 80° C. in a capped vial for 2 h. The solvent was removed in speedvac. The product was purified by prep-HPLC using CH₃CN/H₂O/TFA system to yield Examples 1-11.

Preparation of Examples 12-14 is illustrated below:

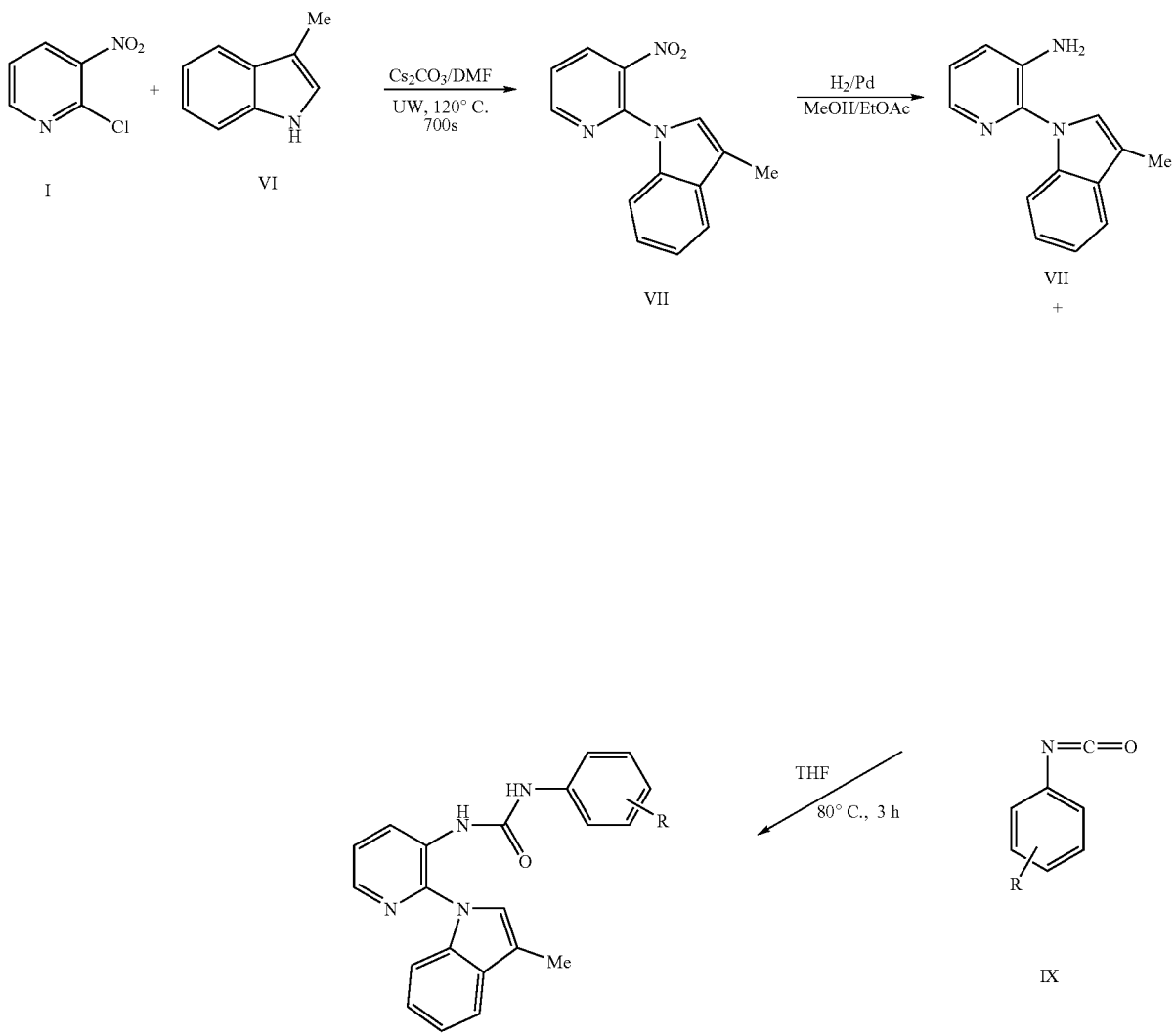

Examples 12–14

Example 12

1-[2-(3-Methyl-indol-1-yl)-pyridin-3-yl]-3-(4-trifluoromethoxy-phenyl)-urea 12a. 3-methyl-1-(3-nitro-pyridin-2-yl)-1H-indole VII: 2-chloro-3-nitro-pyridin I (317 mg, 2 mmol) and 3-methylindole VI (262 mg, 2 mmol) were dissolved in dry DMF (3.5 mL), and then $Cs_2CO_3$ (780 mg, 2.4 mmol) was added. The mixture was heated with stirring at 120° C. at a Personal Chemistry Microwave reactor for 700s. The $Cs_2CO_3$ was filtered off. The mixture was diluted with EtOAc (20 mL) and washed with water, 1×5 mL, and 5% LiCl solution, 3×5 mL. The solution was dried over $Na_2SO_4$, the solvent was removed in vacuo. The crude product was purified by silica column using the ISCO machine system to give 3-Methyl-1-(3-nitro-pyridin-2-yl)-1H-indole.

12b. 2-(3-methyl-indol-1-yl)-pyridin-3-ylamine VIII: The compound VII was reduced to VIII by same procedure used for the preparation of IV.

12c. Example 12: To the product VIII (12 mg, 0.053 mmol) were added phenylisocyanates IX (0.15 mmol) in dry THF (0.6 mL). The mixture was heated at 80° C. in a capped vial for 1-7 h. The solvent was removed in speedvac. The product was purified by prep-HPLC using $CH_3CN/H_2O/TFA$ system to yield product of Example 12. MS ESI 427.05 (M+H).

Examples 13-14 were synthesized using similar procedures as described for Example 12.

Example 15

1-[2-(3-Methyl-2,3-dihydro-indol-1-yl)-pyridin-3-yl]-3-(4-trifluoromethoxy-phenyl)-urea

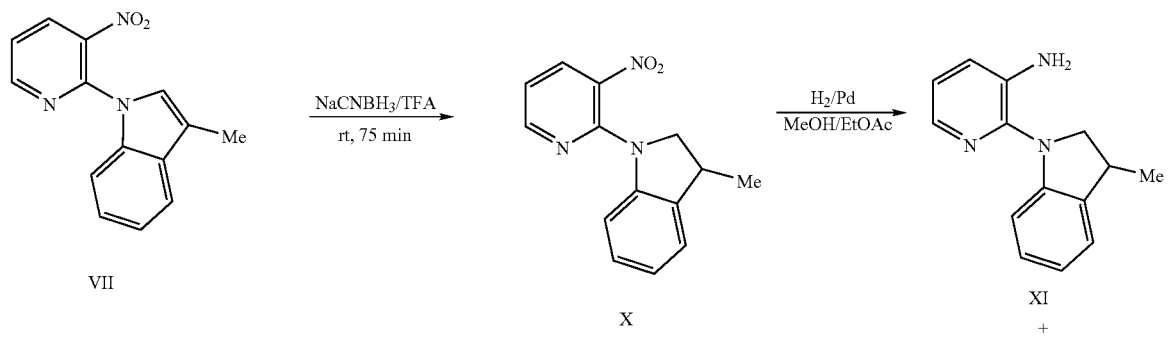

Example 15

15a. Preparation of X: the product VII (172 mg, 0.68 mmol) was dissolved in TFA (3 mL), and then $NaCNBH_3$ (250 mg, 4 mmol) was added in portions. The mixture was stirred at rt for 75 min. The solvent was removed. The compound was dissolved in saturated $NH_4Cl$ solution and extracted with EtOAc, dried over $Na_2SO_4$, and the solvent was removed in vacuo. The product was purified by prep-HPLC using $CH_3CN/H_2O/TFA$ solvent system to yield a brown oil X (52 mg, 30%).

15b. Preparation of XI: Compound X (25 mg, 0.1 mmol) was dissolved in methanol (2 mL), a small spatula of 10% Pd/C was added as catalyst and hydrogenated at 40 PSI for 80 min. The catalyst was removed by filtration through a bed of Celite® and the solvent was removed speedvac to yield a dark brown solid XI (13 mg, 50%).

15c. Example 15: Compound XI (13 mg, 0,05 mmol) was dissolved in dry THF (1 mL), and then 4-(trifluoromethoxy)phenylisocyanate V (15 mg, 0.073 mmol) was added. The mixture was stirred at 80° C. for 1 h. The solvent was removed in vacuo. The product was purified by prep-HPLC using $CH_3CN/H_2O/TFA$ solvent system to yield product of Example 15. MS ESI 429.05 (M+H).

General Procedures for the preparation of Examples 16-19 are shown below:

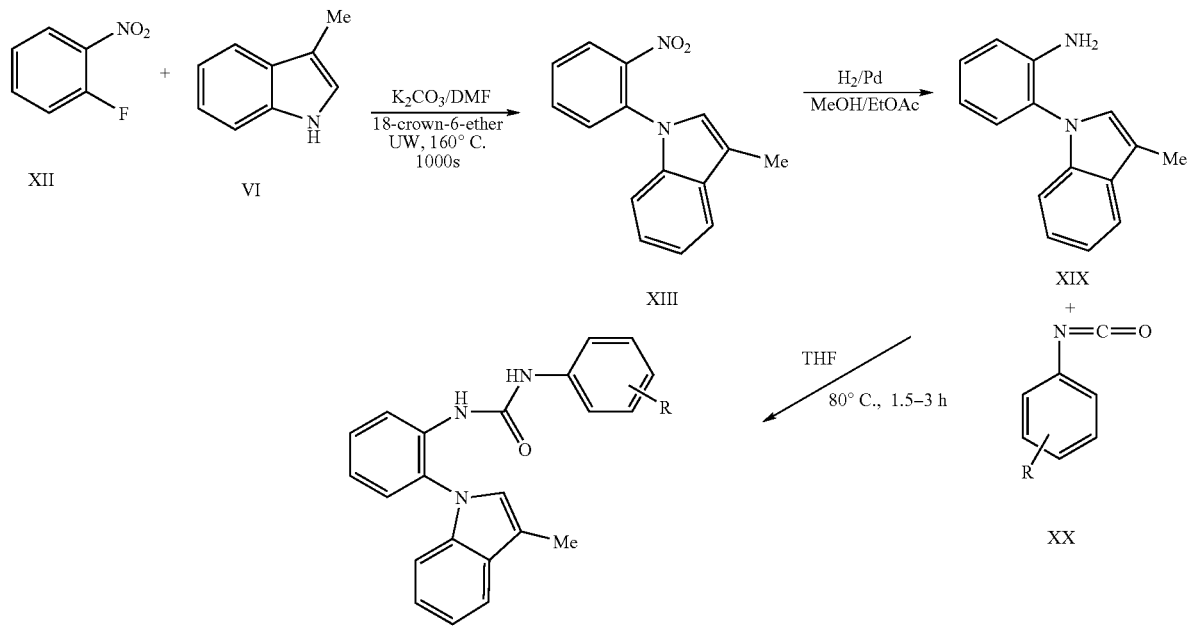

Examples 16-19

A. 2-Fluoronitrobenzene XII (57 mg, 0.4 mmol), 3-methylindone VI (53 mg, 0.4 mmol) and 18-crown-6 ether (106 mg, 0.4 mmol) were dissolved in dry DMF (1.2 mL), and then anhydrous $K_2CO_3$ (65 mg, 0.45 mmol) was added. The mixture heated at 160° C. for 1000s at a Personal Chemistry microwave reactor. The $K_2CO_3$ was removed by filtration, the DMF was removed in vacuo. The mixture was dissolved in EtOAc (4 mL) and washed with $H_2O$, 2×1 ml, and 1N HCl, 1×1 mL, dried over $Na_2SO_4$. The solvent was removed in vacuo to yield a light brown solid XIII, which was used directly in the next reaction.

B. Preparation of XIX: Compound XIII was dissolved in 1:1 MeOH:EtOAc mixture (3 mL), a small spatula of 10% Pd/C was added. The compound was hydrogenated at 40 PSI for 2 h. The catalyst was removed by filtration through a bed of Celite®, the solvent was removed in speedvac to yield a brown oil XIX (90 mg, 100% for 2 steps).

C. Preparation of Examples 16-19: To the product XIX (22.5 mg, 0.1 mmol) were added phenylisocyanates XX (0.15 mmol) in dry THF (0.6 mL). The mixture was heated at 80° C. in a capped vial for 1.5-3 h. The solvent was removed in speedvac. The product was purified by prep-HPLC using $CH_3CN/H_2O/TFA$ system to yield product of Examples 16-19.

Example 20

1-[2-(4,4-Dimethyl-3,4-dihydro-2H-quinolin-1-yl)-phenyl]-3-(4-trifluoromethoxy-phenyl)-urea 20a. 4,4-Dimethyl-3,4-dihydro-1H-quinolin-2-one: Aniline (7.26 g, 45.2 mmol) and 3-methylbut-2-enoyl chloride (53.2 g, 45.2 mmol) were heated in chloroform at reflux for 2 h. After cooling, the mixture was filtered. The filtrate was concentrated to dryness and dried under vacuum. The crude 3-methyl-but-2-enoic acid phenylamide (ca. 10 g) was dissolved in toluene (50 mL). This toluene solution was added to the stirred $AlCl_3$ powder (27 g) portion-wise. After addition, the resulting dark brown solution was heated at 80° C. for 2.5 h. The warm slurry was poured carefully to stirred crashed ice. The resulting mixture was extracted with EtOAc (3×), washed with sat'd $NaHCO_3$, $H_2O$, brine, and dried over $MgSO_4$. The residue was purified by silica gel flash chromatography ($CH_2Cl_2$, then EtOAc) to give 2.2 g of pure 20a and about 4-5 g of less pure portion 20a. LC-MS ESI 176 (M+H).

20b. 4,4-dimethyl-1,2,3,4-tetrahydroquinoline: To a stirred solution of $LiAlH_4$ (1.0 M in THF, 35 mL, 35 mmol), was added a solution of the product from a. (2.17 g, 12.4 mmol) in THF (10 mL) for 5 min at 0° C. under nitrogen. The resulting mixture was warmed gradually to reflux, and heated at reflux for 5.5 h. To the cooled mixture with stirring, was added sat'd $Na_2SO_4$ dropwise till the complete decomposition of $LiAlH_4$. The mixture was filtered, and rinsed with EtOAc. The organic was washed with $H_2O$, brine, dried ($MgSO_4$), and concentrated to dryness. It was purified by flash chromatography (silica gel, 0-20% EtOAc in hexanes) to give pure 20b (1.86 g, yield: 93%). LC-MS ESI 162 (M+H).

20c. 4,4-dimethyl-1-(2-nitro-phenyl)-1,2,3,4-tetrahydroquinoline: 20b (0.762 g, 4.73 mmol), ortho-fluoronitrobenzene (0.88 g, 5.67 mmol, 1.19 eq), and 2,4,6-collidine (0.66 mL, 1.05 eq) were pre-stirred 40s in a conical microwave container. It was then heated with stirring at a Personal Chemistry Microwave reactor with normal absorption at 250° C. for 1 h. The crude mixture was dissolved in $CHCl_3$, and was purified by flash chromatography (hexanes/EtOAc) to give 0.66 g of crude 20c (LC-MS ESI 283 (M+H)).

20d. 2-(4,4-Dimethyl-3,4-dihydro-2H-quinolin-1-yl)-phenylamine: The crude 20c (0.66 g) was stirred in MeOH (20 mL) at r t. Solid $NH_4Cl$ (0.62 g) was added, followed by addition of Zn dust (3.0 g) portionwise. The resulting mixture was stirred at r. t. for 2 h. It was filtered through Celite®, rinsed with $CH_2Cl_2$, and concentrated to dryness. The residue was purified by flash chromatography (hexanes/EtOAc) to give pure amine 20d (0.43 g, 73% for two steps). LC-MS ESI 253 (M+H).

Example 20: 20d (19 mg) and para-trifluoromethyoxyphenyl isocyanate (0.02 mL) were stirred in refluxing THF for 6 h. The cooled solution was concentrated, and purified by flash chromatography (silica gel, hexanes/EtOAc) to give desired product of Example 20. LC-MS ESI 456 (M+H).

Example 21

1-[4-(3-Dimethylamino-2,2-dimethyl-propoxy)-phenyl]-3-[2-(4,4-dimethyl-3,4-dihydro-2H-quinolin-1-yl)-phenyl]-urea 21a. 2,2-Dimethyl-3-(4-nitro-phenoxy)-propyl]-dimethyl-amine: 4-nitrophenol (2.78 g, 20 mmol) and 3-(dimethylamino)-2,2-dimethylpropan-1-ol (3.93 g, mmol, 30 mmol, 1.5 eq) were stirred in dry THF (80 mL) at 0° C. under nitrogen. DIAD (5.9 mL, 30.0 mmol, 1.5 eq) was added, followed by triphenylphosphine (6.81 g, 26.0 mmol, 1.3 eq) at 0° C. The mixture was stirred from 0° C. to rt overnight. The solvent was concentrated. EtOAc was added. The EtOAc layer was separated, washed with 1N HCl (2×). The HCl layers were basified with solid $Na_2CO_3$. The resulting mixture as extracted with EtOAc (3×), washed with brine, dried over ($MgSO_4$), filtered, and concentrated to dryness. The residue as purified by flash column chromatography (30-100% EtOAc in hexanes) to give pure 21a (2.2 g, yield: 43.7%) as white crystalline solids. LC-MS ESI 253 (M+H).

21 b. 4-(3-Dimethylamino-2,2-dimethyl-propoxy)-phenylamine: The product from 21a (1.0 g, 3.97 mmol) was stirred in the presence of 100 mg Ph-C (10%) in MeOH (10 mL) with a hydrogen balloon at rt for 5 h. The mixture was filtered, and rinsed with MeOH. The filtrate was concentrated and vacuum dried to give 21b in quantitative yield (0.88 g). LC-MS ESI 223 (M+H).

21c. The product from 20d (35 mg, 0.14 mmol) was stirred in $CH_2Cl_2$ (2 mL), solid $NaHCO_3$ (35 mg, 0.42 mmol, 3.0 mmol) was added, followed by the addition of a spatula tip of triphosgene at 0° C. under nitrogen. The mixture was stirred from 0° C. to r t for 2 h. It was filtered, and rinsed with $CH_2Cl_2$. The organic solution was concentrated under vacuum, and used directly in the next step.

Example 21. Following similar procedure as described for the preparation of Example 20, Example 21 was prepared. The crude was purified by flash column chromatography ($CH_2Cl_2$:MeOH=9:1) to give pure titled compound. LC-MS ESI 501 (M+H).

Example 22

1-[2-(3,3-Dimethyl-2,3-dihydro-indol-1-yl)-pyridin-3-yl]-3-(4-trifluoromethoxy-phenyl)-urea 22a. 1-Acetyl-1,3-dihydro-indol-2-one: Indoline-2-one (6.65 g, 50 mmol) and acetic anhydride (9 mL) were heated at reflux for 15 h. After cooling, the product was filtered and rinsed with $Et_2O$ to give 1-Acetyl-1,3-dihydro-indol-2-one as solids after vacuum drying (8.2 g, yield: 93.7%).

22b. 3,3-dimethylindolin-2-one: To a stirred solution of 22a (3.2 g, 18.29 mmol) in dry THF (100 mL) was added MeI (2.6 mL, 41.75 mmol, 2.3 eq), followed by the addition of 18-crown-6 (0.51 g, 4.57 mmol, 0.25 eq) at −78° C. under nitrogen. Potassium tert-butoxide (5.12 g, 45.73 mmol, 2.5 eq) was added portionwise. The resulting slurry was stirred at −78° C. for 1 h. The mixture was stirred at −78° C. to rt for 3 h. Cooled in an ice bath, sat'd $NH_4Cl$ was added. It was extracted with EtOAc, washed with $H_2O$, brine, dried over $MgSO_4$, filtered, and concentrated to dryness. The residue was purified by flash chromatography (silica gel, hexanes/EtOAc) to give pure 1-acetyl-3,3-dimethylindolin-2-one (1.3 g) (LC-MS ESI 204(M+H)) and pure 3,3-dimethylindolin-2-one (1.0 g) (LC-MS ESI 162 (M+H)) respectively. 1-Acetyl-3,3-dimethylindolin-2-one (1.3 g) was heated in 6N HCl at reflux for 1 h. After cooling, it was poured into crushed ice. It was extracted with $Et_2O$, washed with sat'd $NaHCO_3$, $H_2O$, brine, dried over $Na_2SO_4$, filtered, and concentrated to dryness to give almost pure 3,3-dimethylindolin-2-one (1.0 g).

22c. 3,3-dimethylindoline: To a solution of 22b (1.0 g, 6.2 mmol) in THF at 0° C. was added LiAlH4 (1M THF solution, 13.6 mL, 2.2 eq) under nitrogen. The resulting slurry was heated at reflux for 4 h. While cooling in an ice bath, sat'd $Na_2SO_4$ was added carefully to quench the extra un-reacted $LiAlH_4$. The solids were filtered out, and were rinsed with EtOAc. The organic was washed with $H_2O$, brine, dried over $MgSO_4$, filtered, and concentrated to dryness to give almost pure 22c (0.82 g, yield: 89%). LC-MS ESI 148 (M+H).

22d. 3,3-dimethyl-1-(3-nitropyridin-2-yl)indoline: The product of 22c (200 mg, 1.35 mmol) and 2-fluoro-3-nitropyridine (0.3 mL) were pre-stirred in a conical microwave container. The mixture was heated at 200° C. under microwave with stirring at high absorption for 10 min. The cooled mixture was dissolved in EtOAc, washed with $H_2O$, brine, dried over $MgSO_4$, filtered, and concentrated to dryness. The residue was purified by flash column chromatography (silica gel, hexanes/EtOAc) to give pure 22d (220 mg, yield: 60.4%). LC-MS ESI 270 (M+H).

22e. 2-(3,3-dimethylindolin-1-yl)pyridin-3-amine: Following similar procedure as described for the preparation of 20d, the titled compound was prepared (180 mg, yield: 92.3%). LC-MS ESI 240 (M+H).

Example 22. Following similar procedure described for the preparation of Example 20, Example 22 was prepared. LC-MS ESI 443 (M+H).

Example 23

N-(2-spiro[cyclohexane-1,3'-[3H]indol]-1'(2'H)-ylphenyl)-N'-[4-(trifluoromethoxy)phenyl]-urea 23a. Spiro[cyclohexane-1,3'-[3H]indol]-2'(1'H)-one: To a solution of oxindole (3 g, 22.5 mmol) in THF (70 mL) was cooled to −78° C. and added LiHMDZ (50 mL, 50 mmol). The reaction temperature was maintained at −74° C. upon the addition. The temperature was brought up to −50° C. for 30 min. Then the temperature was brought down to −78° C. and added 1,5-dibromopentane (3 mL). The reaction mixture was stirred at rt for 3 h, then reflux for 7 h. The solvent was evaporated under reduced pressure and partitioned between ether and sat'd $NH_4Cl$. The ether was evaporated and purified by silica gel chromatography using 5% to 100% EtOAc in hexane as eluting solvents to afford 23a (2.6 g, 57%) as yellowish powder. m/z 202 $[M+H]^+$.

23b. Spiro[cyclohexane-1,3'-[3H]indole], 1',2'-dihydro-: To a solution of 23a (800 mg, 3.98 mmol) in THF (2 mL) was added 1N $LiAlH_4$ in THF (5 mL). The reaction mixture was stirred at room temperature for 4 h. Then it was refluxed for 2 h. The mixture was cooled to room temperature and quenched with $H_2O$ (2 mL), 6N NaOH (2 mL), and $H_2O$ (2 mL). The aqueous layer was extracted with EtOAc (20 mL×3) and the organic layer was washed with brine, dried over $Na_2SO_4$. The solvent was evaporated under reduced pressure to afford 23b (685 mg, 92%) as yellowish powder m/z 188 $[M+H]^+$.

23c. Spiro [cyclohexane-1,3'-[3H]indole], 1',2'-dihydro-1'-(2-nitrophenyl)-: To a neat 23b (300 mg, 1.6 mmol) was added 2-fluoro-nitrobenzene (113 mg, 0.8 mmol). The reaction mixture was stirred 175° C. for 8 h. The reaction mixture was diluted in $CH_2Cl_2$ and the desired product was purified by silica gel chromatography using 0% to 10% EtOAc in hexane as eluting solvent to afford 23c (127 mg, 51%) as reddish foam. m/z 309 $[M+H]^+$.

23d. Benzenamine, 2-spiro[cyclohexane-1,3'-[3H]indol]-1'(2'H)-yl: To a solution of 23c (100 mg, 0.32 mmol) in EtOAc (4 ml) was add $SnCl_2.H_2O$ (165 mg, 0.64 mmol). The reaction mixture was stirred at rt for 16 h. The reaction mixture was quenched by using sat'd $NaHCO_3$ (0.5 mL), followed by $Na_2CO_3$ (5 eq). The reaction mixture was stirred at room temperature for 30 minutes then filtered. The solvent was evaporated under, reduced pressure to afford 23d (70 mg, 80%) as white powder. m/z 279 $[M+H]^+$.

Example 23. To a solution of 23d (60 mg, 0.215 mmol) in $CH_2Cl_2$ (3 mL) was added 4-(trifluoromethoxy)phenyl isocyanate (60 mL, 0.35 mmol). The reaction mixture was stirred at rt for 16 h. The solvent was evaporated under reduced pressure and suspended in hexane. The desired product was filtered and washed with $H_2O$. The filter was re-dissolved in $CH_2Cl_2$ and added 1 eq of TFA. The solvent was evaporated under reduced pressure to afford Example 23 (4 mg, 39%) as white powder. m/z 482 $[M+H]^+$.

Example 24

1-[2-(4-Methyl-3,4-dihydro-2H-quinoxalin-1-yl)-phenyl]-3-(4-trifuoromethoxy-phenyl)-urea 24a. 3,4-dihydroquinoxalin-2(1H)-one: To a solution of o-phenyldiamine (3 g, 27.8 mmol) in DMF (30ml) was added $Et_3N$ (7.8 mL, 55.8 mmol), followed by ethyl 2-bromoacetate (3.4 mL, 30.5 mmol). The reaction mixture was stirred at rt for 16 h, then at 80° C. for 3 h. The DMF was evaporated by distillation. The reaction mixture was partitioned between $H_2O$ and EtOAc. The EtOAc layer was washed with sat. $NaHCO_3$, brine, and dried over $Na_2SO_4$. The solvent was evaporated under reduced pressure. The desired product was precipitated in a mixture of $CH_2Cl_2$ and hexane (1 to 1 ratio). Filtered and the filter was pump to dryness to afford 24a (3.2 g, 80%) as beige powder. LC-MS ESI m/z 149 $[M+H]^+$.

24b. 4-methyl-3,4-dihydroquinoxalin-2(1H)-one: To a solution of 24a (500 mg, 3.378 mmol) in MeOH (3 mL) was added $NaBH_3CN$ (425 mg, 6.76 mmol), paraformaldehyde (102 mg), followed by HOAc (30 μL). The reaction mixture was stirred at rt for 4 h. Another portion of $NaBH_4CN$ (212 mg, 3.37 mmol) and parafornaldehyde (51 mg) were added to the reaction mixture along with conc. HCl (10 μL). The reaction mixture was stirred at 50° C. for 5 h and cooled to rt. The pH was adjusted to 8 and the solvent was evaporated under reduced pressure. The desired product was extracted into EtOAc and washed it with brine, dried over $Na_2SO_4$. The solvent was evaporated under reduced pressure to afford 24b (537 mg, 98%) as beige powder. LC-MS ESI m/z 163 $[M+H]^+$.

24c. 1,2,3,4-tetrahydroquinoxaline: To a solution of 24b (300 mg, 1.85 mmol) in THF (2 mL) was added 1N $LiAlH_4$ (10 mL, 10 mmol). The reaction mixture was stirred at rt for 1 h. The reaction mixture was quenched with $H_2O$ (1 mL) at 0° C., 15% NaOH (1 mL), followed by $H_2O$ (1 mL). The reaction mixture was extracted with EtOAc. The EtOAc was then washed with brine, dried over $Na_2SO_4$. The solvent was evaporated under reduced pressure to afford 24c (260 mg, 95%) as white powder. LC-MS ESI m/z 149 $[M+H]^+$.

24d. 1-Methyl-4-(2-nitro-phenyl)-1,2,3,4-tetrahydro-quinoxaline: To a solution of 1,2,3,4-tetrahydroquinoxaline (60 mg, 0.403 mmol) in DMSO (2 mL) was add potassium tert-butoxide (91 mg, 0.81 mmol), followed by 2-fluoro-nitrobenzene (57 mg, 0.403 mmol). The reaction mixture was stirred at 80° C. for 16 h. The desired product was isolated via silica gel chromatography using 0% to 50% EtOAc in hexane as eluting solvent to afford 24d (49 mg, 45%) as radish foam. LC-MS ESI m/z 270 $[M+H]^+$.

24e. 2-(4-Methyl-3,4-dihydro-2H-quinoxalin-1-yl)-phenylamine: To a solution of 24d (40 mg, 0.148 mmol) in MeOH (5 mL) was add 10% Pd/C (10 mg). The reaction mixture was stirred at room temperature under $H_2$ for 2 h. The catalyst was removed by filtration and the solvent was evaporated under reduced pressure to afford 24e (32 mg, 90%) as white powder. LC-MS ESI m/z 240 $[M+H]^+$.

Example 24 was prepared as Example 1e. The desired product was isolated by Preparative HPLC using ACN—$H_2O$-1% TFA as an eluting system to afford the desired titled compound (7 mg, 76%) as white lyophilate. LC-MS ESI m/z 443 $[M+H]^+$.

Example 25

1-(2-(2,2-Dimethyl-2,3-dihydrobenzo[b][1,4]oxazin-4-yl)phenyl)-3-(4-(trifluoromethoxy)phenyl)urea 25a. 2-bromo-N-(2-hydroxyphenyl)-2-methylpropanamide: To a solution of 2-aminophenol (1 g, 9.17 mmol) in THF (40 mL) was added $Et_3N$ (1.4 mL, 10.1 mmol) at 0° C., followed by 2-bromo-isobutyryl bromide (1.25 mL, 10.1 mmol) dropwise. The reaction was stirred at 0° C. for 30 min and quenched with $H_2O$. The $H_2O$ layer was extracted with EtOAc and the solvent was evaporated under reduced pressure. The desired product was re-dissolved in MeOH and stirred with $K_2CO_3$ (600 mg, 4.6 mmol) for 10 minutes and quench with 1N HCl. The solvent was evaporated under reduced pressure, then partitioned between $H_2O$ and EtOAc. The EtOAc was washed with brine, dried over $Na_2SO_4$. The solvent was evaporated under reduced pressure to afford 25a (I g, 43%) as beige powder. m/z 258 $[M+H]^+$.

25b. 2,2-dimethyl-2H-benzo[b][1,4]oxazin-3(4H)-one: To a solution of 25a (400 mg, 1.55 mmol) in DMF (6 mL) was added $Cs_2CO_3$ (660 mg, 2.02 mmol). The reaction mixture was stirred at 60° C. for 2 h. The solid was removed by filtration and partitioned between EtOAc and $H_2O$. The EtOAc was washed with sat'd $NaHCO_3$, brine, and dried over $Na_2SO_4$. The solvent was evaporated under reduced pressure and was purified by silica gel chromatography using 0% to 40% EtOAc in hexane as eluting solvents to afford 25b (247 mg, 90%) as yellowish powder. m/z 178 $[M+H]^+$.

25c. 2,2-dimethyl-3,4-dihydro-2H-benzo[b][1,4]oxazine: 25c in white powder (100 mg, 94%) was prepared by following the procedure of 23b. m/z 178 $[M+H]^+$.

25d. 2,2-dimethyl4-(2-nitrophenyl)-3,4-dihydro-2H-benzo[b][1,4]oxazine: 25d was prepared by following the procedure of 23c. The reaction mixture was diluted and purified by silica gel chromatography using 0% to 20% EtOAc in hexane as an eluting solvents to afford brownish foam (108 mg, 61%). m/z 285 $[M+H]^+$.

25e. 2,2-dimethyl-3,4-dihydrobenzo[b][1,4]oxazin-4-yl) benzenamine: 25e in white powder (15 mg, 88%) was prepared by following the procedure of 23d. m/z 255 $[M+H]^+$.

Example 25 was prepared by following the procedure of Example 23. The reaction mixture was purified by preparative HPLC using 0% to 100% ACN in $H_2O$ plus 0.1% TFA as mobile phases to afford Example 25 (8 mg, 50%) as white lyophilate. m/z 458 $[M+H]^+$.

Example 26

1-(2-(4-Methyl-3,4-dihydroquinolin-1(2H)-yl)phenyl)-3-(4-(trifluoromethoxy)phenyl)urea 26a. 4-methyl-1,2,3,4-tetrahydroquinoline: To a solution of 4-methylquinoline (1 g, 7.54 mmol) in $Et_2O$ (20 mL) was added $NaBH_4CN$ (0.92 g, 15.08 mmol) followed by the conc. HCl (1.4 mL). The reaction was stirred at room temperature vigorously, then at reflux for 2 h. The reaction mixture was adjusted to pH 9 and was extracted with EtOAc. The EtOAc layer was separated and washed further with $H_2O$, brine, dried over $Na_2SO_4$. The solvent was evaporated under reduced pressure to afford 26a (1.05 g, 95%) as dark orange oil. m/z 148 $[M+H]^+$.

26b. 4-methyl-1-(3-nitropyridin-2-yl)-1,2,3,4-tetrahydroquinoline: To a solution of 3-nitro-2-bromopyridine (200 mg, 0.99 mmol) in toluene (2.5 mL) was added $Pd(OAc)_2$ (10 mg, 0.044 mmol), BINAP (35 mg, 0.038 mmol) followed by 26a (144 mg, 0.89 mmol) and NaOt-Bu (130 mg, 1.35 mmol). The reaction mixture was stirred at 100° C. under for 5 h. The reaction mixture was filtered through a cake of Celite® and washed it with $CH_2Cl_2$. The solvent was evaporated under reduced pressure. The crude product was further purified by silica gel chromatography using 0% to 50% EtOAc in hexane as eluting solvent to afford 26b (36 mg, 15%) as yellowish oil. m/z 269 $[M+H]^+$.

26c. 2,2-dimethyl-3,4-dihydrobenzo[b][1,4]oxazin-4-yl)benzenamine: 26c in white powder (15 mg, 87%) was prepared by following the procedure of 24e. m/z 238 $[M+H]^+$.

Example 26 was prepared by following the procedure of Example 24. The reaction mixture was purified by preparative HPLC using 0% to 100% ACN in $H_2O$ plus 0.1% TFA as mobile phases to afford Example 26 (6 mg, 34%) as white lyophilates. m/z 443.27 $[M+H]^+$.

Using similar procedures as those described for Examples 1-26, the following Examples 27-44 and Example 46-48 were prepared.

Example 49

Spiro[3H-indole-3,4'-piperidine]-1'-carboxylic acid, 1,2-dihydro-1-[2-[[[[4-(trifluoromethoxy)phenyl]amino]carbonyl]amino]phenyl]-, phenylmethyl ester 49a. Spiro[3H-indole-3,4'-piperidine], 1,2-dihydro-: 49a was obtained accroding to literature procedure (Journal of Medicinal Chemistry, 1983, 26, 981-6) from 2-fluorophenylacetonitrile and 2,2'-dichloro-N-methyl-diethylamine hydrochoride. LC-MS, ESI 189 $(M+H)^+$.

49b. Spiro[3H-indole-3,4'-piperidine]-1'-carboxylic acid, 1,2-dihydro-, phenylmethyl ester: To a stirred solution of 49a (0.90 g, 4.78 mmol) in dry THF (25 mL) was added (N-benzyloxycarbonyloxy)-succinimide (1.2 g, 4.8 mmol) in THF (5 mL) over a 2-min period of time at rt under $N_2$. The resulting mixture was stirred at rt for 1 h. EtOAc was added. It was washed with sat'd $NaHCO_3$, $H_2O$, brine, dried over $MgSO_4$, filtered, and concentrated to dryness. The residue was purified by flash chromatography (silica gel, hexanes/EtOAc) to give pure 49b as colorless crystals (0.96 g, yield: 69%). LC-MS ESI 323.15 $(M+H)^+$ ($t_R$=2.62 min, 10%-90% MeOH in $H_2O$ in a 4-min run).

49c. Spiro[3H-indole-3,4'-piperidine]-1'-carboxylic acid, 1,2-dihydro-1-(2-nitrophenyl)-, phenylmethyl ester: 49b (0.25 g) and ortho-fluoronitrobenzene (0.40 mL) was heated with stirring at 200-220° C. for 30 min under microwave irradiation. The resulting mixture was purified via flash chromatography (silica gel, hexanes:EtOAc=1:0 to 1:1) to give 49c (0.24 g, yield: 70%). LC-MS (ESI) 444.

49d. Spiro[3H-indole-3,4'-piperidine]-1'-carboxylic acid, 1-(2-aminophenyl)-1,2-dihydro-, phenylmethyl ester: 49c (0.24 g, 0.54 mmol) was stirred in MeOH (10 mL). $NH_4Cl$ (140 mg, 5 eq.) was added, followed by adding Zn dust (700 mg, 20 eq). The resulting slurry was stirred at rt for 1.5 h. It was filtered through Celite, rinsed with $CH_2Cl_2$, and concentrated to give essentially pure 49d (0.22 g). LC-MS ESI 414.06 $(M+H)^+$ ($t_R$=3.55 min, 10%-90% MeOH in $H_2O$ in a 4 min run).

Example 49 was obtained according to the procedure described for Example 23. The mixture was purified by flash column chromatography (silica gel, hexanes/EtOAc) to give Example 49. LC-MS ESI 617.31 $(M+H)^+$ ($t_R$=4.52 min, 10%-90% MeOH in $H_2O$ in a 4 min run).

Example 50

N-[2-[1'-(1-methylethyl)spiro[3H-indole-3,4'-piperidin]-1(2H)-yl]phenyl]-N'-[4-(trifluoromethoxy)phenyl]-Urea Example 49 (0.20 g, 0.32 mmol) was stirred in MeOH (10 mL). 10% Pd/C (10 mg) was added, followed by adding HOAc (15 µL). The resulting mixture was stirred at rt under $H_2$ for 2 h. The catalyst was removed by filtration and the solvent was evaporated under reduced pressure to afford Example 50 (0.15 g, 96%). LC-MS ESI 483 $(M+H)^+$.

Example 51

Urea, N-[2-[1'-(1-methylethyl)spiro[3H-indole-3,4'-piperidin]-1(2H)-yl]phenyl]-N'-[4-(trifluoromethoxy)phenyl]-

Example 50 (17 mg, 0.032 mmol) was stirred in DMF (1 mL). $Et_3N$ (5 µL) was added, followed by adding isopropyl bromide (5 µL). The resulting mixture was stirred at rt under for 16 h. The reaction mixture was purified by preparative HPLC using 10 to 100% acetonitrile, $H_2O$ and 0.1% TFA as mobile phase to afford Example 51 (6 mg, 36%) as white lyophilate. LC-MS ESI 525 $(M+H)^+$.

Example 52

1-(2-[1'-methylcarbamade-spiro-[1-indoline-3,4'-piperidine]]phenyl)-3-(4-(trifluoromethoxy)phenyl)urea Example 50 (17 mg, 0.032 mmol) was stirred in DMF (1 mL). $Et_3N$ (5 µL) was added, followed by adding methyl chloroformate (10 µl). The resulting mixture was stirred at rt under for 16 h. The reaction mixture was purified by preparative HPLC using 40 to 100% acetonitile, $H_2O$ and 0.1% TFA as mobile phase to afford Example 52 (6 mg, 36%) as white lyophilate. LC-MS ESI 541 $(M+H)^+$.

Example 53

1-(2-[1'-isobutyl-spiro-[1-indoline-3,4'-piperidine]]phenyl)-3-(4-(trifluoromethoxy)phenyl)urea Example 50 (20 mg, 0.040 mmol) was stirred in MeOH (1 mL). NaBH$_4$CN (3 mg, 0.047 mmol) was added, followed by adding isobutyraldehyde (4 µl, 0.08 mmol) and HOAc (5 µL). The resulting mixture was stirred at rt under for 16 h. The reaction mixture was purified by preparative HPLC using 40 to 100% acetonitrile, H$_2$O and 0.1% TFA as mobile phase to afford Example 53 (6 mg, 30%) as white lyophilate. LC-MS ESI 539 (M+H)$^+$.

Examples 54-60 and 67-71 were prepared using similar procedures as described in Examples 51-53. Examples 61-66 were synthesized using similar procedures as described for Example 23.

Example 72

1-(4-acetylphenyl)-3-(2-(3,3-dimethylindolin-1-yl)pyridin-3-yl)urea 82.2 mg (0.344 mmol) of 2-(3,3-dimethylindolin-1-yl)pyridin-3-amine was dissolved in 2 mL of CH$_2$Cl$_2$. To this solution cooled to −20° C. and under argon atmosphere were added 0.1 mL of TEA and 55.4 mg (0.344 mmol) of 1-(4-isothiocyanatophenyl)ethanone portion wise. The stirring continued while the temperature was allowed to increase to ambient. After 1 night stirring at rt, volatiles were evaporated to dryness to yield an oily residue purified by ISCO system flash chromatography (loading with CH$_2$Cl$_2$ eluting with ACOEt/Hexane 0% to 50% over 35 min). [M+H]$^+$=401; $^1$H NMR (400 MHz, CDCl$_3$) δ ppm 1.30 (s, 6H); 2.52 (s, 3H); 3.98 (s, 2H); 6.76 (d, J=7.5 Hz, 1H), 7.04 (m, 1 H), 7.16 (dd, J=7.3 Hz, and J=1.1 Hz, 1H), 7.25 (m, 1 H), 7.40 (d, J=8.8 Hz, 2 H), 7.78 (d, J=8.8 Hz, 2H); 7.9 (d, J=5.7 Hz, 1H); 8.32 (bs, 1H); 8.55 (d, J=7.9 Hz, 1H); 8.76 (bs, 1H). HRMS (ESI) m/z calcd for C$_{24}$H$_{25}$N$_4$O$_2$ [M+H]$^+$401.1979, found 401.1963.

Example 73

1-(2-(3,3-dimethylindolin-1-yl)pyridin-3-yl)-3-(4-(1-hydroxyethyl)phenyl)urea 97 mg (0.242 mmol) of Example 72 were dissolved in 7 mL of isopropanol. To this solution were added 9.2 mg (0.242 mmol) of NaBH$_4$ and the mixture was stirred at rt overnight. Additional 1.8 mg (0.048 mmol) of NaBH$_4$ were added and the reaction mixture stirred for additional 8 h. Volatiles were evaporated, 5 mL of CH$_2$Cl$_2$ added and the solution washed twice with 2 mL of water. The organic phase was dried over MgSO$_4$ filtered and concentrated to yield 84.3 mg of an amorphous solid. [M+H]$^+$=403.15; $^1$H NMR (400 MHz, CDCl$_3$) δ ppm 1.26 (s, 6H); 1.41 (d, J=6.6 Hz, 3H); 3.72 (s, 2H); 4.78 (m, 1H); 6.26 (d, J=7.5 Hz, 1H), 6.31 (s, 1H); 6.84-6.88 (m, 2 H), 6.9-7.06 (m, 2H); 7.10-7.19 (m, 3H); 8.1 (dd, J=1.3 Hz and 4.7 Hz, 1 H), 8.62 (dd, J=1.3 Hz and 8.1 Hz, 1 H); HRMS (ESI) m/z calcd for C$_{24}$H$_{27}$N$_4$O$_2$ [M+H]$^+$403.2134, found 403.2163.

Example 74

1-(4-(1-((3-(trifluoromethyl)benzyl)(methyl)amino)ethyl)phenyl)-3-(2-(3,3-dimethylindolin-1-yl)pyridin-3-yl)urea To 40.2 mg (0.1 mmol) of Example 73 in 1.5 mL of CH$_2$Cl$_2$ was added 177 mg (0.15 mmol) of SOCl$_2$. The solution was stirred for 2 h and concentrated to dryness. 37.9 mg (0.2 mmol) of N-methyl(3-(trifluoromethyl)phenyl)methanamine were added and the mixture stirred for 1 h at rt. Volatiles were evaporated. 3 mL of CH$_2$Cl$_2$ was added and the mixture was washed twice with 1 mL of water. The organic phase was dried over MgSO$_4$ and concentrated to yield an oily residue purified by preparative HPLC Method B (Shimadzu Phenomenex Luna 5u 21.2×100; flow rate 20 ml/min; detection at 220 nM; Gradient elution 0% to 100% B over 20 min; (A=10% MeOH, 90% H$_2$O, 0.1% TFA & B-90% MeOH, 10% H$_2$O, 0.1% TFA)); to yield Example 74. Characterization of the compound is under progress.

Examples 75-79 listed in Table 1 were prepared according to the procedures described in Example 73 or Example 83 and using the appropriated nucleophiles.

Example 80

1,3-bis(2-(3,3-dimethylindolin-1-yl)pyridin-3-yl)urea

Under the reaction conditions described in Example 72, Example 80 was also isolated. [M+H]$^+$=403.15. $^1$H NMR (400 MHz, CDCl$_3$) δ ppM 1.27 (s, 12H); 3.68 (s, 4H); 6.32 (d, J=7.7 Hz, 2H), 6.61 (s, 2H); 6.82 (t, J=7.7 Hz, 2 H), 6.93 (t, J=7.7 Hz, 2H); 7.02-7.16 (m, 4H), 8.11 (d, J=4.4 Hz, 2 H), 8.37 (d, J=8.3 Hz, 2 H); HRMS (ESI) m/z calcd for C$_{31}$H$_{33}$N$_6$O [M+H]$^+$505.2716, found 505.2705.

Example 81

1-(2-(2-tert-butylphenoxy)pyridin-3-yl)-3-(2-(3,3-dimethylindolin-1-yl)pyridin-3-yl)urea 24 mg (0.1 mmol) of 2-(3,3-dimethylindolin-1-yl)pyridin-3-amine (compound of example 22e) were dissolved in 2 mL of CH$_2$Cl$_2$. To this solution under argon and cooled to −20° C. were added 50 µL of TEA and 27 mg (0.1 mmol) of 2-(2-tert-butylphenoxy)-3-isocyanatopyridine. The mixture was stirred at rt for the night. 2 mL of AcOEt were added and the mixture washed with H$_2$O (2×1 mL), dried over MgSO$_4$ and concentrated. The crude oil was purified by preparative HPLC Method B (Shimadzu Phenomenex Luna 5u 21.2×100; flow rate 20 ml/min; detection at 220 nM; Gradient elution 0% to 100% B over 20 min; (A=10% MeOH, 90% H$_2$O, 0.1% TFA & B=90% MeOH, 10% H$_2$O, 0.1% TFA)) to yield pure Example 81. C$_{31}$H$_{33}$N$_5$O$_2$ [M+H]$^+$508.29.

Example 82

1-(2-(2-tert-butylphenoxy)pyridin-3-yl)-3-(2-(3,3-dimethylindolin-1-yl)phenyl)urea Example 82 was prepared:According to the procedure of Example 81. C$_{32}$H$_{34}$N$_4$O$_2$ [M+H]$^+$507.30.

Example 83

1-(2-(3,3-dimethylindolin-1-yl)pyridin-3-yl-phenylethylamino)ethyl)phenyl)urea 20 mg (0.05 mmol) of Example 72 was dissolved in 2 mL of dry toluene. R(+) α-methylbenzylamine (12.1 mg, 0.1 mmol, 2 eq) and TEA (10.1 µL, 0.072 mmol, 1.44 eq) were added. To this mixture was then added 28 µL (0.56 eq) of TiCl$_4$ (IV) in toluene (1M solution). The temperature of the reaction mixture was kept below 60° C. The mixture was stirred at rt overnight. The reaction mixture was cooled to −20° C. 2 mL of AcOEt was added and the mixture was washed with cold 1N NaOH solution (2×1 mL). The organic phase was dried over $MgSO_4$ and concentrated. The crude Schiff base was mixed with 2 mL of MeOH without any purification and reduced in the presence of Raney Ni to yield the desired Example 83. $C_{32}H_{35}N_5O$ [M+H]$^+$506.32.

Tables 1-3 below summarize examples of the prepared compounds in the present invention.

TABLE 1

| Ex # | Chemical Name | D | A | MS (M + 1) |
|---|---|---|---|---|
| 1 | 1-(2-carbazol-9-yl-pyridin-3-yl)-3-(4-trifluoromethoxy-phenyl)urea | carbazol-9-yl | 4-OCF$_3$-Ph | 462.95 |
| 2 | 1-[2-(4-chloro-indol-1-yl)-pyridin-3-yl]3-(4-trifluoromethoxy-phenyl)-urea | 4-chloro-indol-1-yl | 4-OCF$_3$-Ph | 446.93 |
| 3 | 1-(2-indol-1-yl-pyridin-3-yl)-3-(4-trifluoromethoxy-phenyl)urea | indol-1-yl | 4-OCF$_3$-Ph | 413.05 |
| 4 | 1-[2-(4-methyl-indol-1-yl)-pyridin-3-yl]3-(4-trifluoromethoxy-phenyl)-urea | 4-methyl-indol-1-yl | 4-OCF$_3$-Ph | 427 |
| 5 | 1-{3-[3-(4-trifluoromethoxy-phenyl)-ureido]-pyridin-2-yl}-1H-indole-3-carboxylic acid methyl ester | 3-CO$_2$Me-indol-1-yl | 4-OCF$_3$-Ph | 470.93 |

TABLE 1-continued

| Ex # | Chemical Name | D | A | MS (M + 1) |
|---|---|---|---|---|
| 6 | 1-{3-[3-(4-trifluoromethoxy-phenyl)-ureido]-pyridin-2-yl}-1H-indole-4-carboxylic acid methyl ester | 4-carboxymethyl indol-1-yl | 4-OCF$_3$-Ph | 470.93 |
| 7 | 1-[2-(6-fluoro-indol-1-yl)pyridin-3-yl]3-(4-trifluoromethoxy-phenyl)-urea | 6-fluoro-indol-1-yl | 4-OCF$_3$-Ph | 430.97 |
| 8 | 1-[2-(5-methoxy-indol-1-yl)-pyridin-3-yl]-3-(4-trifluoromethoxy-phenyl)-urea | 5-methoxy-indol-1-yl | 4-OCF$_3$-Ph | 442.96 |
| 9 | 1-[2-(4-methoxy-indol-1-yl)-pyridin-3-yl]-3-(4-trifluoromethoxy-phenyl)-urea | 4-methoxy-indol-1-yl | 4-OCF$_3$-Ph | 442.98 |
| 10 | 1-[2-(5-methyl-indol-1-yl)-pyridin-3-yl]-3-(4-trifluoromethoxy-phenyl)-urea | 5-methyl-indol-1-yl | 4-OCF$_3$-Ph | 427.06 |

TABLE 1-continued
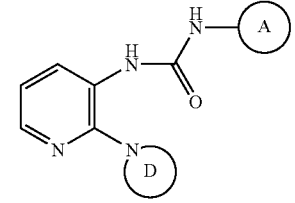
| Ex # | Chemical Name | D | A | MS (M + 1) |
|---|---|---|---|---|
| 11 | 1-[2-(6-methyl-indol-1-yl)-pyridin-3-yl]-3-(4-trifluoromethoxy-phenyl)-urea | 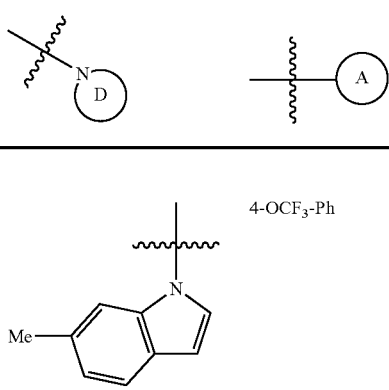 | 4-OCF$_3$-Ph | 427 |
| 12 | 1-[2-(3-methyl-indol-1-yl)-pyridin-3-yl]-3-(4-trifluoromethoxy-phenyl)-urea | 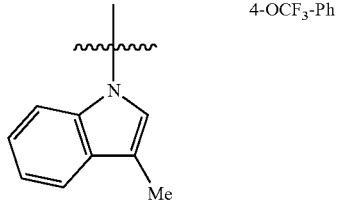 | 4-OCF$_3$-Ph | 427.05 |
| 13 | 1-[2-(3-methyl-indol-1-yl)-pyridin-3-yl]-3-p-tolyl-urea | 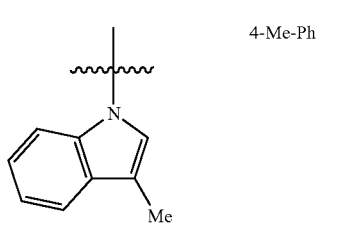 | 4-Me-Ph | 357.1 |
| 14 | 1-[2-(3-methyl-indol-1-yl)-pyridin-3-yl]-3-m-tolyl-urea | 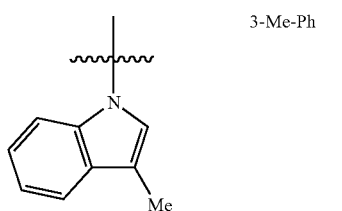 | 3-Me-Ph | 357.1 |
| 15 | 1-[2-(3-methyl-2,3-dihydro-indol-1-yl)-pyridin-3-yl]-3-(4-trifluoromethoxy-phenyl)-urea | 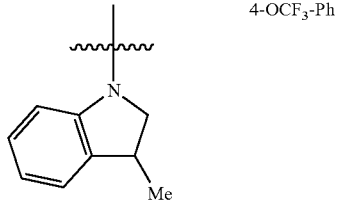 | 4-OCF$_3$-Ph | 429.05 |

TABLE 1-continued

| Ex # | Chemical Name | N-D | A | MS (M+1) |
|---|---|---|---|---|
| 22 | 1-[2-(3,3-dimethyl-2,3-dihydro-indol-1-yl)-pyridin-3-yl]-3-(4-trifluoromethoxy-phenyl)urea | 3,3-dimethyl-2,3-dihydroindol-1-yl | 4-OCF₃-Ph | 443 |
| 26 | 1-(2-(4-methyl-3,4-dihydroquinolin-1(2H)-yl)phenyl)-3-(4-(trifluoromethoxy)phenyl)-urea | 4-methyl-3,4-dihydroquinolin-1(2H)-yl | 4-OCF₃-Ph | 443 |
| 29 | 1-[2-(2-methyl-2,3-dihydro-indol-1-yl)-pyridin-3-yl]-3-(4-trifluoromethoxy-phenyl)-urea | 2-methyl-2,3-dihydroindol-1-yl | 4-OCF₃-Ph | 429.06 |
| 30 | 1-[2-(3,4-dihydro-2H-quinolin-1-yl)-pyridin-3-yl]-3-(4-trifluoromethoxy-phenyl)urea | 3,4-dihydro-2H-quinolin-1-yl | 4-OCF₃-Ph | 429.06 |
| 31 | 1-[2-(4,4-dimethyl-3,4-dihydro-2H-quinolin-1-yl)-pyridin-3-yl]-3-(4-trifluoromethoxy-phenyl)-urea | 4,4-dimethyl-3,4-dihydro-2H-quinolin-1-yl | 4-OCF₃-Ph | 457.28 |
| 43 | 1-[2-(2,3-dihydro-benzo[1,4]oxazin-4-yl)-pyridin-3-yl]-3-(4-trifluoromethoxy-phenyl)-urea | 2,3-dihydro-benzo[1,4]oxazin-4-yl | 4-OCF₃-Ph | 431.03 |

TABLE 1-continued

| Ex # | Chemical Name | N-D | A | MS (M + 1) |
|---|---|---|---|---|
| 47 | 1-[2-(octahydro-quinolin-1-yl)-pyridin-3-yl]-3-(4-trifluoromethoxy-phenyl)-urea | octahydroquinolin-1-yl | 4-OCF₃-Ph | 435 |
| 66 | 1-(2-(3,3-dimethylindolin-1-yl)pyridin-3-yl)-3-p-tolylurea | 3,3-dimethylindolin-1-yl | 4-Me-Ph | 373 |
| 70 | spiro[3H-indole-3,4'-piperidine]-1'-carboxylic acid, 1,2-dihydro-1-[6-[[[[4-(trifluoromethoxy)-pyridin-2-yl]amino]carbonyl]amino]phenyl]-, phenylmethyl ester | spiro[indoline-3,4'-piperidine], N'-CO₂Bn | 4-OCF₃-Ph | 618 |
| 71 | urea, N-[2-[1'-(1-methylethyl)spiro[3H-indole-3,4'-piperidin]-1(2H)-yl]-3-pyridinyl]-N'-[4-(trifluoromethoxy)phenyl]- | spiro[indoline-3,4'-piperidine], N'-i-Pr | 4-OCF₃-Ph | 526 |
| 72 | 1-(4-acetylphenyl)-3-(2-(3,3-dimethylindolin-1-yl)pyridin-3-yl)urea | 3,3-dimethylindolin-1-yl | 4-COMe-Ph | 401 |

TABLE 1-continued

| Ex # | Chemical Name | ⟶N-D | ⟶A | MS (M+1) |
|---|---|---|---|---|
| 73 | 1-(2-(3,3-dimethylindolin-1-yl)pyridin-3-yl)-3-(4-(1-hydroxyethyl)phenyl)urea | 3,3-dimethylindolin-1-yl | 4-CH(O)Me-Ph | 403 |
| 74 | 1-(4(1-((3-(trifluoromethyl)benzyl)(methyl)amino)ethyl)phenyl)-3-(2-(3,3-dimethylindolin-1-yl)pyridin-3-yl)urea | 3,3-dimethylindolin-1-yl | 4-[CH(Me)N(Me)CH2-(3-CF3-Ph)]-Ph | 574 |
| 75 | 1-(3-(1-((4-(trifluoromethyl)benzyl)(methyl)amino)ethyl)phenyl)-3-(2-(3,3-dimethylindolin-1-yl)pyridin-3-yl)urea | 3,3-dimethylindolin-1-yl | 4-[CH(Me)N(Me)CH2-(4-CF3-Ph)]-Ph | 574 |
| 76 | 1-(2-(3,3-dimethylindolin-1-yl)pyridin-3-yl)-3-(3-(1-(methyl(thiophen-2-ylmethyl)amino)ethyl)phenyl)urea | 3,3-dimethylindolin-1-yl | 4-[CH(Me)N(Me)CH2-(thiophen-2-yl)]-Ph | 512 |
| 77 | 1-(3-(1-(4-(trifluoromethyl)benzyloxy)ethyl)phenyl)-3-(2-(3,3-dimethylindolin-1-yl)pyridin-3-yl)urea | 3,3-dimethylindolin-1-yl | 4-[CH(Me)OCH2-(4-CF3-Ph)]-Ph | 561 |

US 7,550,499 B2
TABLE 1-continued
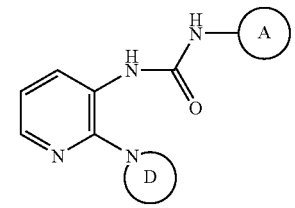
| Ex # | Chemical Name | 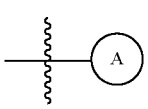 | 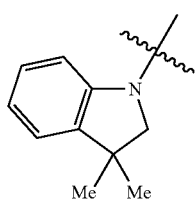 | MS (M + 1) |
|---|---|---|---|---|
| 78 | 1-(2-(3,3-dimethylindolin-1-yl)pyridin-3-yl)-3-(3-(1-isobutoxyethyl)phenyl)urea | 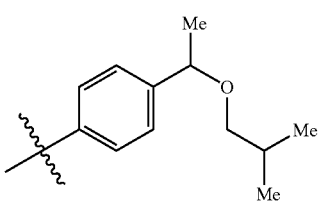 | 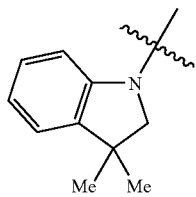 | 459 |
| 79 | 1-(2-(3,3-dimethylindolin-1-((furan-2-yl)pyridin-3-yl)-3-(3-(1-ylmethyl)(methyl)amino)ethyl)phenyl)urea | 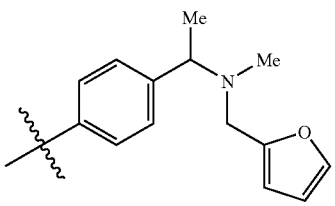 | 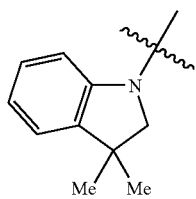 | 496 |
| 80 | 1,3-bis(2-(3,3-dimethylindolin-1-yl)pyridin-3-yl)urea | 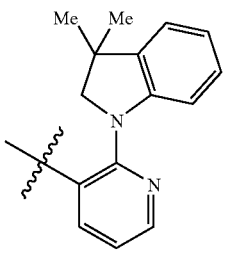 | 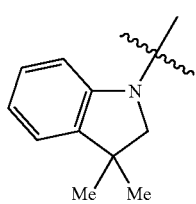 | 403.15 |
| 81 | 1-(2-(2-tert-butylphenoxy)pyridin-3-yl)-3-(2-(3,3-dimethylindolin-1-yl)pyridin-3-yl)urea | 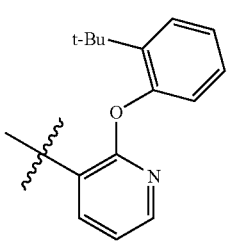 | 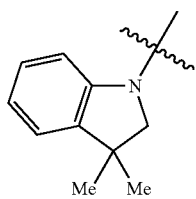 | 508.29 |
| 83 | 1-(2-(3,3-dimethylindolin-1-yl)pyridin-3-yl)-3-(4-(1-((R)-1-phenylethylamino)ethyl)phenyl)urea | 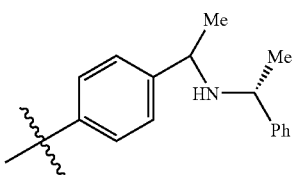 | | 506.32 |

TABLE 2
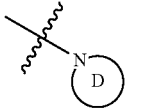
| Ex # | Chemical Name | 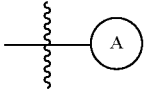 | 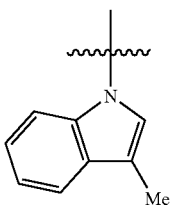 | MS (M + 1) |
|---|---|---|---|---|
| 16 | 1-[2-(3-methyl-indol-1-yl)-phenyl]-3-(4-trifluoromethoxy-phenyl)-urea | 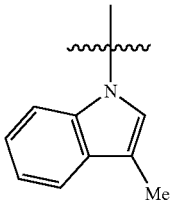 | 4-OCF$_3$-Ph | 426.06 |
| 17 | 1-(4-tert-butyl-phenyl)-3-[2-(3-methyl-indol-1-yl)-phenyl]-urea | 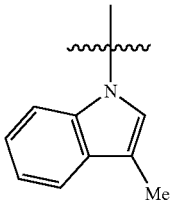 | 4-t-Bu-Ph | 398.11 |
| 18 | 1-[2-(3-methyl-indol-1-yl)-phenyl]-3-p-tolyl-urea | 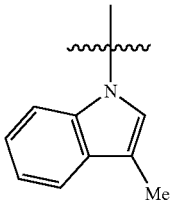 | 4-Me-Ph | 356.08 |
| 19 | 1-[2-(3-methyl-indol-1-yl)-phenyl]-3-m-tolyl-urea | 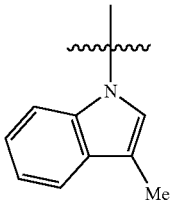 | 3-Me-Ph | 356.08 |
| 20 | 1-[2-(4,4-dimethyl-3,4-dihydro-2H-quinolin-1-yl)-phenyl]-3-(4-trifluoromethoxy-phenyl)-urea | 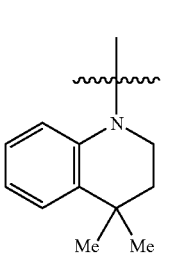 | 4-OCF$_3$-Ph | 456 |

TABLE 2-continued

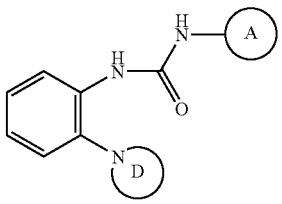

| Ex # Chemical Name | 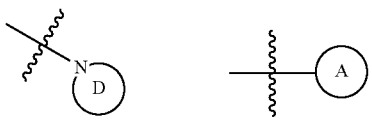 | | MS (M + 1) |
|---|---|---|---|
| 21 1-[4-(3-dimethylamino-2,2-dimethyl-propoxy)-phenyl]-3-[2-(4,4-dimethyl-3,4-dihydro-2H-quinolin-1-yl)-phenyl]-urea | 4,4-dimethyl-3,4-dihydro-2H-quinolin-1-yl | 4-(3-dimethylamino-2,2-dimethyl-propoxy)-phenyl | 501 |
| 23 1-(2-(spiro-cyclochexylindolin-1-yl)phenyl)-3-(4-(trifluoromethoxy)-phenyl)urea | spiro-cyclohexylindolin-1-yl | 4-OCF$_3$-Ph | 482 |
| 24 1-[2-(4-methyl-3,4-dihydro-2H-quinoxalin-1-yl)-phenyl]-3-(4-trifluoromethoxy-phenyl)urea | 4-methyl-3,4-dihydro-2H-quinoxalin-1-yl | 4-OCF$_3$-Ph | 443 |
| 25 1-(2-(2,2-dimethyl-2,3-dihydrobenzo[b][1,4]oxazin-4-yl)phenyl)-3-(4-(trifluoromethoxy)phenyl)-urea | 2,2-dimethyl-2,3-dihydrobenzo[b][1,4]oxazin-4-yl | 4-OCF$_3$-Ph | 458 |
| 27 1-[2-(2-methyl-indol-1-yl)-phenyl]-3-(4-trifluoromethoxy-phenyl)-urea | 2-methyl-indol-1-yl | 4-OCF$_3$-Ph | 426.02 |

TABLE 2-continued

| Ex # | Chemical Name | 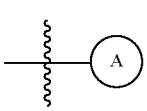 | 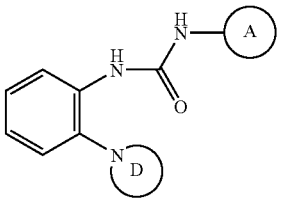 | MS (M + 1) |
|---|---|---|---|---|
| 28 | 1-[2-(3,4-dihydro-2H-quinolin-1-yl)-phenyl]-3-(4-trifluoromethoxy-phenyl)-urea |  | 4-OCF$_3$-Ph | 428.06 |
| 32 | 1-(4-tert-butyl-phenyl)-3-[2-(3,4-dihydro-2H-quinolin-1-yl)-phenyl]-urea |  | 4-t-Bu-Ph | 400.34 |
| 33 | 1-[2-(4-methyl-3,4-dihydro-2H-quinolin-l-yl)-phenyl]-3-(4-trifluoromethoxy-phenyl)-urea |  | 4-OCF$_3$-Ph | 442.27 |
| 34 | 1-(4-tert-butyl-phenyl)-3-[2-(2,3-dihydro-benzo[1,4]oxazin-4-yl)-phenyl]-urea |  | 4-t-Bu-Ph | 402.29 |
| 35 | 1-[2-(2,3-dihydro-benzo[1,4]oxazin-4-yl)-phenyl]-3-(4-trifluoromethoxy-phenyl)-urea |  | 4-OCF$_3$-Ph | 430.28 |
| 36 | 1-(4-tert-butyl-phenyl)-3-[2-(3,3-dimethyl-2,3-dihydro-indol-1-yl)-phenyl]-urea |  | 4-t-Bu-Ph | 415.17 |

TABLE 2-continued

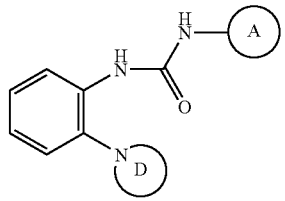

| Ex # Chemical Name | D | A | MS (M + 1) |
|---|---|---|---|
| 37 1-[2-(3,3-dimethyl-2,3-dihydro-indol-1-yl)-phenyl]-3-(4-trifluoromethoxy-phenyl)urea | 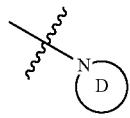 | 4-OCF$_3$-Ph | 442.31 |
| 38 N-(2-spiro[cyclopropane-1,3'-[3H]indol]-1'(2'H)-ylphenyl)-(trifluoromethoxy)phenyl]-urea | 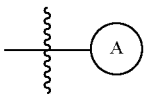 | 4-OCF$_3$-Ph | 440 |
| 39 N-(2-spiro[cyclobutane-1,3'-[3H]indol]-1'(2'H)-ylphenyl)-N'[4-(trifluoromethoxy)phenyl]-urea | 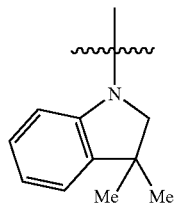 | 4-OCF$_3$-Ph | 454.31 |
| 40 N-(2-spiro[cyclopentane-1,3'-[3H]indol]-1'(2'H)-ylphenyl)-N'[4-(trifluoromethoxy)phenyl]-urea | 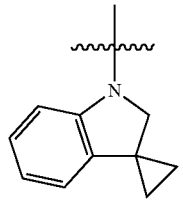 | 4-OCF$_3$-Ph | 468.25 |
| 41 1-[2-(3-ethyl-2,3-dihydro-indol-1-yl)-phenyl]-3-(4-trifluoromethoxy-phenyl)-urea | 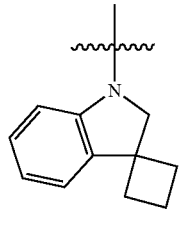 | 4-OCF$_3$-Ph | 440.12 |

TABLE 2-continued

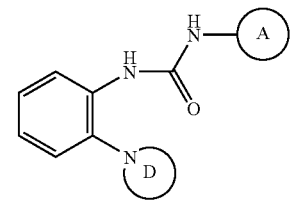

| Ex # | Chemical Name | 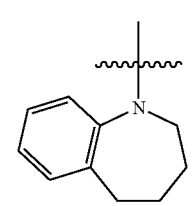 | 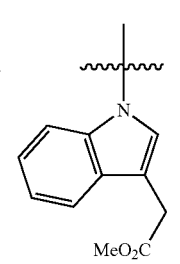 | MS (M + 1) |
|---|---|---|---|---|
| 42 | 1-[2-(2,3,4,5-tetrahydro-benzo[b]azepin-1-yl)-phenyl]-3-(4-trifluoromethoxy-phenyl)-urea | 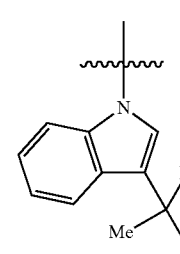 | 4-OCF$_3$-Ph | 442.23 |
| 44 | (1-{2-[3-(4-trifluoromethoxy-phenyl)-ureido]-phenyl}-1H-indol-3-yl)-acetic acid methyl ester | 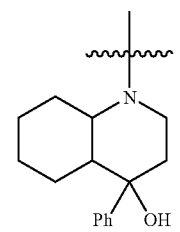 | 4-OCF$_3$-Ph | 484 |
| 46 | 1-{2-[3-(cyano-dimethyl-methyl)-indol-1-yl]-phenyl}-3-(4-trifluoromethoxy-phenyl)urea | | 4-OCF$_3$-Ph | 479 |
| 48 | 1-[2-(4-hydroxy-4-phenyl-octahydro-quinolin-1-yl)-phenyl]-3-(4-trifluoromethoxy-phenyl)-urea | | 4-OCF$_3$-Ph | 526 |
| 49 | spiro[3H-indole-3,4'-piperidine]-1'-carboxylic acid, 1,2-dihydro-1-[2-[[[[4-(trifluoromethoxy)phenyl]amino]carbonyl]amino]phenyl]-, phenylmethyl ester | 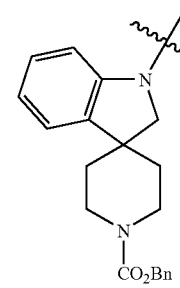 | 4-OCF$_3$-Ph | 617.31 |

TABLE 2-continued

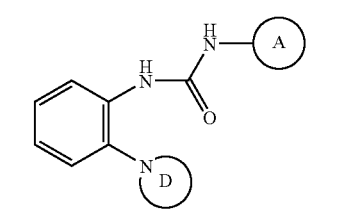

| Ex # Chemical Name | | | MS (M + 1) |
|---|---|---|---|
| 50 urea, N-(2-spiro[3H-indole-3,4'-piperidin]-1(2H)-ylphenyl)-N'-[4-(trifluoromethoxy)phenyl]- | 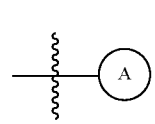 | 4-OCF$_3$-Ph | 483 |
| 51 urea, N-[2-[1'-(1-methylethyl)spiro[3H-indole-3,4'-piperidin]-1(2H)-yl]phenyl]N'-[4-(trifluoromethoxy)phenyl]- | 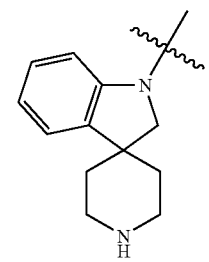 | 4-OCF$_3$-Ph | 525 |
| 52 spiro[3H-indole-3,4'-piperidine]-1'-carboxylic acid, 1,2-dihydro-1-[2-[[[[4-(trifluoromethoxy)phenyl]amino]carbonyl]amino]phenyl]-, methyl ester | 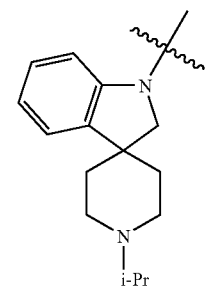 | 4-OCF$_3$-Ph | 541 |
| 53 urea, N-[2-[1'-(2-methylpropyl)spiro[3H-indole-3,4'-piperidin]-1(2H)-yl]phenyl]-N'-[4-(trifluoromethoxy)phenyl]- | 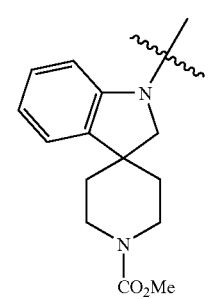 | 4-OCF$_3$-Ph | 539 |

TABLE 2-continued

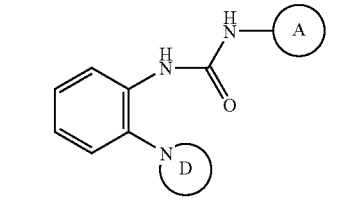

| Ex # Chemical Name | 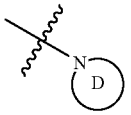 | 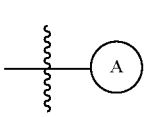 | MS (M + 1) |
|---|---|---|---|
| 54 urea, N-[2-(1'-methylspiro[3H-indole-3,4'-piperidin]-1(2H)-yl)phenyl]-N'-[4-(trifluoromethoxy)phenyl]- | 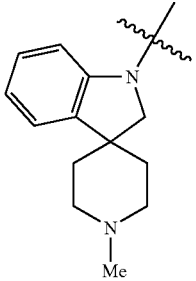 | 4-OCF$_3$-Ph | 497 |
| 55 spiro[3H-indole-3,4'-piperidine]-1'-carboxylic acid, 1,2-dihydro-1-[2-[[[[4-(trifluoromethoxy)phenyl]amino]carbonyl]amino]phenyl]-, ethyl ester | 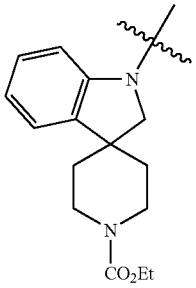 | 4-OCF$_3$-Ph | 555 |
| 56 spiro[3H-indole-3,4'-piperidine], 1'-acetyl-1,2-dihydro-1-[2-[[[4-(trifluoromethoxy)phenyl]amino]carbonyl]amino]phenyl]- | 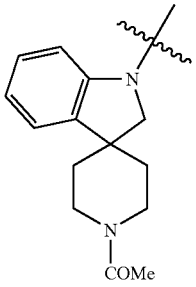 | 4-OCF$_3$-Ph | 525 |
| 57 urea, N-[2-[1'-(phenylmethyl)spiro[3H-indole-3,4'-piperidin]-1(2H)-yl]phenyl]-N'-[4-(trifluoromethoxy)phenyl]- | 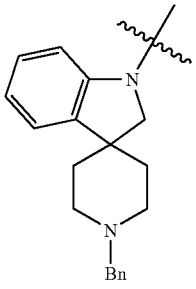 | 4-OCF$_3$-Ph | 573 |

TABLE 2-continued

| Ex # | Chemical Name | D | A | MS (M + 1) |
|---|---|---|---|---|
| 58 | spiro[3H-indole-3,4'-piperidine],1,2-dihydro-1'-(methylsulfonyl)-1-[2-[[[[4-(trifluoromethoxy)phenyl]amino]carbonyl]amino]phenyl]- | indoline-spiro-piperidine with N-SO₂Me | 4-OCF₃-Ph | 561 |
| 59 | urea, N-[2-[1'-(2-hydroxyethyl)spiro[3H-indole-3,4'-piperidin-1(2H)-yl]phenyl]-N'-[4-(trifluoromethoxy)phenyl]- | indoline-spiro-piperidine with N-CH₂CH₂OH | 4-OCF₃-Ph | 527 |
| 60 | urea, N-[2-[1'-(2-methoxyethyl)spiro[3H-indole-3,4'-piperidin-1(2H)-yl]phenyl]-N'-[4-(trifluoromethoxy)phenyl]- | indoline-spiro-piperidine with N-CH₂CH₂OMe | 4-OCF₃-Ph | 541 |
| 61 | spiro[3H-indole-3,4'-piperidine]-1'-acetic acid, 1,2-dihydro-1-[2-[[[[4-(trifluoromethoxy)phenyl]amino]carbonyl]amino]phenyl]- | indoline-spiro-piperidine with N-CH₂CO₂H | 4-OCF₃-Ph | 541 |

TABLE 2-continued
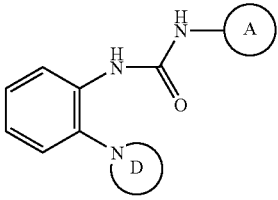
| Ex # | Chemical Name | D | A | MS (M + 1) |
|---|---|---|---|---|
| 67 | spiro[3H-indole-3,4'-piperidine]-1'-carboxamide, 1,2-dihydro-N-(1-methylethyl)-1-[2-[[[[4-(trifluoromethoxy)phenyl]amino]carbonyl]amino]phenyl]- | 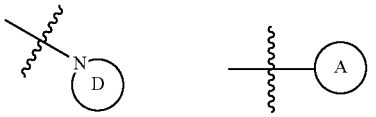 | 4-OCF₃-Ph | 568 |
| 68 | spiro[3H-indole-3,4'-piperidine],1,2-dihydro-1'-[(1-methylethyl)sulfonyl]-1--[2-[[[[4-(trifluoromethoxy)phenyl]amino]carbonyl]amino]phenyl]- | 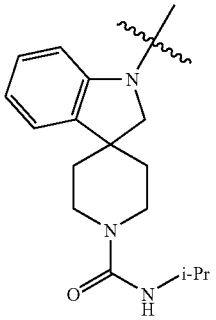 | 4-OCF₃-Ph | 589 |
| 82 | 1-(2-(2-tert-butylphenoxy)pyridin-3-yl)-3-(2-(3,3-dimethylindolin-1-yl)phenyl)urea | 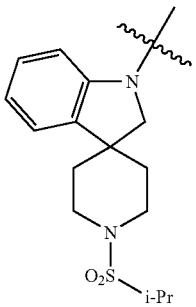 | 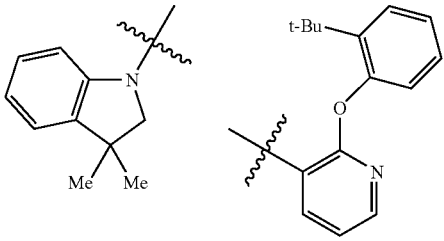 | 507.30 |

TABLE 3

| Ex # | Chemical Name | Structure | MS (M + 1) |
|---|---|---|---|
| 62 | urea, N-(4-cyano-2-spiro[cyclohexane-1,3'-[3H]indol]-1'(2'H)-ylphenyl)-N'-[4-(trifluoromethoxy)phenyl]- | 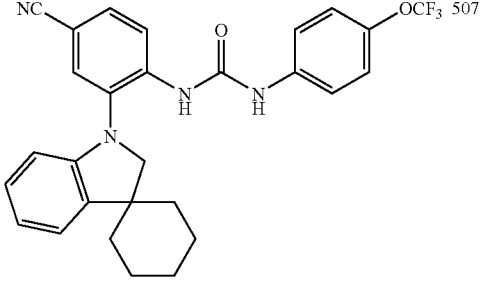 | 507 |
| 63 | urea, N-(5-cyano-2-spiro[cyclohexane-1,3'-[3H]indol]-1'(2'H)-ylphenyl)-N'-[4-(trifluoromethoxy)phenyl]- | 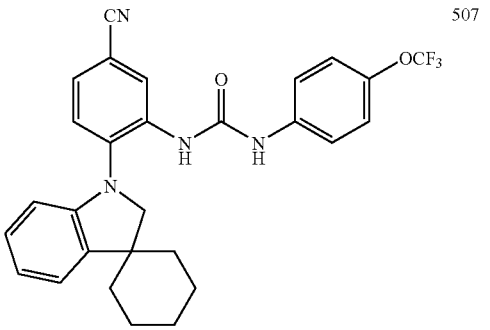 | 507 |
| 64 | urea, N-(4-cyano-2-spiro[cyclohexane-1,3'-[3H]indol]-1'(2'H)-ylphenyl)-N'-[4-(dimethylamino)phenyl]- | 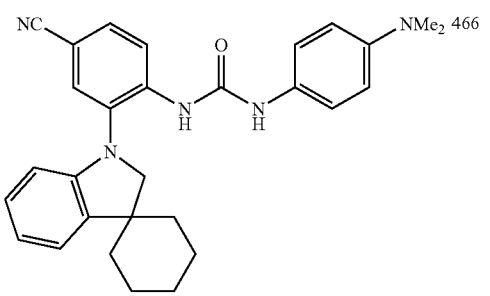 | 466 |
| 65 | 1-(4-(3,3-dimethylindolin-1-yl)pyridin-3-yl)-3-(4-(trifluoromethoxy)phenyl)-urea | 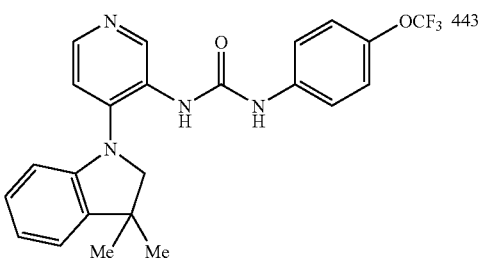 | 443 |
| 69 | urea, N-(2-spiro[cyclohexane-1,3'-[3H]indol]-1'(2'H)-yl-3-thienyl)-N'-[4-(trifluoromethoxy)phenyl]- | 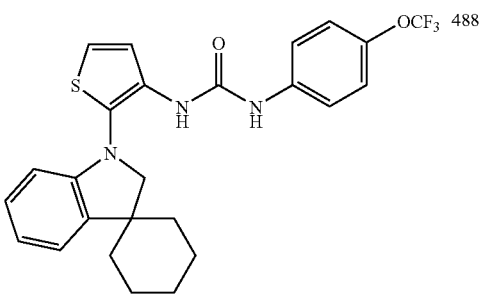 | 488 |

Utility

The compounds of the present invention are anti-platelet agents and thus are useful to maintain the fluidity of blood. Additionally, compounds of the present invention are useful for the treatment or prophylaxis of platelet-associated disorders. As used herein, the term "platelet-associated disorder" refers to any disorder which may be prevented, partially alleviated or cured by the administration of an anti-platelet agent. Thus, the compounds of the present invention are useful in the treatment or prevention of various platelet associated disorders including: Thrombotic or thromboembolic conditions; acute coronary syndromes (such as coronary artery disease, myocardial infarction (MI), unstable angina and non-Q Wave MI); thromboembolic stroke (such as that resulting from atrial fibrillation or from ventricular mural thrombus (low ejection fraction)); venous thrombosis (including deep vein thrombosis); arterial thrombosis; cerebral thrombosis; pulmonary embolism; cerebral embolism; peripheral occlusive arterial disease (e.g., peripheral arterial disease, intermittent claudication, critical leg ischemia, prevention of amputation, prevention of cardiovascular morbidity such as MI, stroke or death); thromboembolic consequences of surgery, interventional cardiology or immobility; thromboembolic consequences of medication (such as oral contraceptives, hormone replacement and heparin); thrombotic consequences of atherosclerotic vascular disease and atherosclerotic plaque rupture leading to tissue ischemia; prevention of atherosclerotic plaque formation; transplant atherosclerosis; thromboembolic complications of pregnancy including fetal loss; thromboembolic consequences of thrombophilia (e.g., Factor V Leiden, and homocystinenimia); prothrombotic consequences and/or complications of cancer; prevention of thrombosis on artificial surfaces (such as stents, blood oxygenators, shunts, vascular access ports, vascular grafts, artificial valves, etc.); coagulopathies (e.g., disseminated intravascular coagulation (DIC)); coagulation syndromes; vascular remodeling atherosclerosis, restenosis and systemic infection; prevention of metastasis and tumor implantation; diabetic complications including retinopathy, nephropathy and neuropathy; inflammation; ischemia (such as that resulting from vascular occlusion, cerebral infarction, stroke and related cerebral vascular diseases); Kasabach-Merritt syndrome; atrial fibrillation; ventricular enlargement (including dilated cardiac myopathy and heart failure); restenosis (e.g., following arterial injury-induced either endogenously or exogenously).

In addition to acting as anti-platelet agents, the compounds of the present invention may also find utility in a variety of other settings including as inhibitors of bone resorption such as encountered in various osteoporotic conditions, as inhibitors of insulin secretion in conditions of hyperinsulinemia, as vasoconstrictive agents such as those used in cases of septic or hypovolemic shock, as inhibitors of smooth muscle relaxation such for the treatment of incontinence or in other cases where inhibition of sympathetic never transmission would be of therapeutic benefit such as nociception or neuronal tissue regeneration. These and many other potential utilities for P2Y$_1$ antagonists have been recently reviewed (Burnstock, G. and Williams, M. *J. Pharm. Exp Ther.* 2000, 295, 862-9) and are suggested therein.

Compounds of the present invention may additionally be useful as diagnostic agents and adjuncts. For example, the present compounds may be useful in maintaining the reactivity of fractionated whole blood containing platelets such as required for analytical and biological testing or transfusions. In addition, the compounds of the present invention may be useful for maintaining blood vessel patency in conjunction with vascular surgery including bypass grafting, arterial reconstruction, atherectomy, vascular graft and stent patency, organ, tissue and cell implantation and transplantation. In addition, the compounds of the present invention may be useful for maintaining blood vessel patency in conjunction with interventional cardiology or vascular surgery including bypass grafting, arterial reconstruction, atherectomy, vascular graft and stent patency, organ, tissue and cell implantation and transplantation.

P2Y$_1$ Assays

A. Binding Assay

A membrane binding assay was used to identify inhibitors of [$^{33}$P] 2MeS-ADP binding to cloned human P2Y$_1$ receptors. The cDNA clone for human P2Y$_1$ was obtained from Incyte Pharmaceuticals and its sequence confirmed by established techniques (for a compendium of techniques used see Ausubel, F. et al. *Current Protocols in Molecular Biology* 1995 John Wiley and Sons, NY, N.Y.). The essential coding sequences were subcloned into pCDNA 3.1 (Invitrogen) to produce a P2Y$_1$ expression construct. This construct was then transfected into the human embryonic kidney cell line HEK-293 and stable transfectants selected in Genetcin® (G418 sulfate; Life Technologies). Several lines were screened for binding activity and one (HEK293 #49) selected for further characterization. Membranes were prepared by growing HEK293 #49 in 150 mm dishes in DMEM/10% FBS in the presence of 1 mg/ml G418 until cells were 80-90% confluent. Plates were then washed with cold (4° C.) D-PBS twice and cells harvested by scraping into 10 mL D-PBS. Cells were pelleted by centrifugation (1,000 g, 10 min, 4° C.) and the resulting pellet resuspended in Lysis Buffer (10 mM Tris (7.4), 5 mM MgCl$_2$ containing Complete® protease inhibitor cocktail (Roche Cat #1873580) as recommended by the manufacturer). The suspension was then homogenized in a Dounce homogenizer (10-15 strokes; B pestle, on ice) and the homogenate spun at 1,000 g, 4° C., 5 min to pellet large debris. The supernatant was centrifuged at 150,000 g, 4° C., for 1 hour and the resulting membrane pellet resuspended in 0.5-1 mL of Buffer B (15 mM HEPES (7.4), 145 mM NaCl, 0.1 mM MgCl$_2$, 5 mM EDTA, 5 mM KCl) and stored at −70° C. until used.

Binding reactions were performed in WGA FlashPlates (PerkinElmer Life Sciences, Cat # SMP105A) in a volume of 200 μL containing ~45 fmol of P2Y$_1$ receptor (5 μg of total protein), 0.5 mM [$^{33}$P] 2MeS-ADP (PerkinElmer; 2,000 Ci/mmol), and various concentrations of the test compound (usually between 50 μM and 10 pM) in Buffer B containing 1% DMSO. Reactions were allowed to proceed to completion at room temperature for 1 hour and then the aqueous solution aspirated. Plates were sealed and the residual [$^{33}$P] bound to the plate determined by scintillation counting. Dose-response curves (IC$_{50}$) were fit by non-linear regression (XLFit, ID Business Solutions Ltd.) and binding constants (K$_i$) calculated using the Cheng-Prusoff relationship (K$_i$=IC$_{50}$/(1+L/K$_d$) in which a K$_d$ for 2MeS-ADP to the P2Y$_1$ receptor was determined to be 1.4 nM.

In general, preferred compounds of the present invention, such as the particular compounds disclosed in the above examples, have been identified to exhibit K$_i$'s of equal to or less than 10 μM in the P2Y$_1$ binding assay, thereby demonstrating these preferred compounds of the present invention as especially effective modulators of P2Y$_1$ activity. More preferred compounds have K$_i$'s of equal to or less than 5 μM, preferably equal to or less than 1 μM, more preferably equal to or less than 0.5 μM.

The compounds of the present invention may be used in combination with each other, or with other anti-platelet agents. Additionally, the present compounds may be used in combination with one or more of various other therapeutic agents, including: anti-arrhythmic agents; anti-hypertensive agents; anti-thrombotic and/or anti-thrombolytic agents; calcium channel blockers (L-type and T-type); cardiac glycosides; diuretics, mineralocorticoid receptor antagonists; phospodiesterase inhibitors; cholesterol/lipid lowering agents and lipid profile therapies; anti-diabetic agents; anti-depressants; anti-inflammatory agents (steroidal and non-steroidal); anti-osteoporosis agents; hormone replacement therapies; oral contraceptives; anti-coagulants; anti-obesity agents; anti-anxiety agents; anti-proliferative agents; anti-tumor agents; anti-ulcer and gastroesophageal reflux disease agents; growth hormone and/or growth hormone secretagogues; thyroid mimetics (including thyroid receptor antagonist); anti-infective agents; anti-viral agents; anti-bacterial agents; and anti-fungal agents.

Examples of suitable anti-arrhythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); K$^+$ channel openers such as I$_{Ach}$ inhibitors, and I$_{Kur}$ inhibitors (e.g., compounds such as those disclosed in U.S. Application Publication US 20030022890).

Examples of suitable anti-hypertensive agents for use in combination with the compounds of the present invention include: alpha adrenergic blockers; beta adrenergic blockers; calcium channel blockers (e.g. diltiazem, verapamil, nifedipine, amlodipine and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., omapatrilat, gemopatrilat and nitrates); and β-blockers (e.g., propanolol, nadolo, or carvedilol).

The term anti-platelet agents (or platelet inhibitory agents), as used herein, denotes agents that inhibit platelet function, for example, by inhibiting the aggregation, adhesion or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicyclic acid or ASA) and piroxicam are preferred. Other suitable platelet inhibitory agents include GPIIb/IIIa blockers (e.g., abciximab, eptifibatide, tirofiban, integrelin), thromboxane-A2-receptor antagonists (e.g., ifetroban), thromboxane-A2-synthetase inhibitors, phosphodiesterase-III (PDE-III) inhibitors (e.g., dipyridamole, cilostazol), and PDE V inhibitors (such as sildenafil), and pharmaceutically acceptable salts or prodrugs thereof.

Other examples of suitable anti-platelet agents for use in combination with the compounds of the present invention, with or without aspirin, include: ADP (adenosine diphosphate) receptor antagonists including P$_2$Y$_{12}$ antagonists and other P$_2$Y$_1$ antagonist. Preferred P$_2$Y$_{12}$ receptor antagonists, but are not limited to, clopidogrel, ticlopidine, Prasugrel, and CS-747, including pharmaceutically acceptable salts or prodrugs thereof. Clopidogrel is an even more preferred agent.

Examples of suitable anti-coagulants (or coagulation inhibitory agents) for use in combination with the compounds of the present invention include warfarin and heparin (either unfractionated heparin such as enoxaparin and dalteparin or any commercially available low molecular weight heparin, for example LOVENOX™), synthetic pentasaccharide, direct acting thrombin inhibitors including hirudin and argatroban, factor VIIa, IXa, Xa, or XIa inhibitors, known in the art.

Examples of suitable anti-thrombotic and/or anti-thrombolytic agents for use in combination with the compounds of the present invention include: tissue plasminogen activator (natural or recombinant), tenecteplase (TNK), and lanoteplase (nPA); factor VIIa inhibitors; factor Xa inhibitors; factor XIa inhibitors; thrombin inhibitors (such as hirudin and argatroban); PAI-1 inhibitors (i.e., inactivators of tissue plasminogen activator inhibitors); alpha2-antiplasmin inhibitors; streptokinase, urokinase and prourokinase; and anisoylated plasminogen streptokinase activator complex.

Examples of suitable calcium channel blockers (L-type or T-type) for use in combination with the compounds of the present invention include diltiazem, verapamil, nifedipine, amlodipine and mybefradil.

Examples of suitable cardiac glycosides for use in combination with the compounds of the present invention include digitalis and ouabain.

Examples of suitable diruetics for use in combination with the compounds of the present invention include: chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone.

Examples of suitable mineralocorticoid receptor antagonists for use in combination with the compounds of the present invention include sprionolactone and eplirinone.

Examples of suitable cholesterol/lipid lowering agents and lipid profile therapies for use in combination with the compounds of the present invention include: HMG-CoA reductase inhibitors (e.g., pravastatin lovastatin, atorvastatin, simvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; choesterol absorption inhibitors; and cholesterol ester transfer protein inhibitors (e.g., CP-529414).

Examples of suitable anti-diabetic agents for use in combination with the compounds of the present invention include: biguanides (e.g. metformin); glucosidase inhibitors (e.g. acarbose); insulins (including insulin secretagogues or insulin sensitizers); meglitinides (e.g. repaglinide); sulfonylureas (e.g., glimepiride, glyburide and glipizide); biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Pat. No. 6,548,529, glucagon-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protien tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., congugated estrogens) and estradiol.

Examples of suitable anti-obesity agents for use in combination with the compounds of the present invention include orlistat and aP2 inhibitors (such as those disclosed in U.S. Pat. No. 6,548,529.

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

The various other therapeutic agents described above may be employed in the same dosage form with the compound of formula I or in different dosage forms, in dosages and regimens as generally known in the art or in the PDR.

The compounds of the present invention may act in a synergistic fashion with one or more of the above agents to prevent reocclusion following a successful thrombolytic therapy and/or reduce the time to reperfusion. The compounds of the present invention may also allow for reduced doses of the thrombolytic agent to be used and therefore minimize potential hemorrhagic side-effects.

The compounds of the present invention are also useful as standard or reference compounds, for example as a quality standard or control, in tests or assays involving the inhibition of platelet ADP receptor. Such compounds may be provided in a commercial kit, for example, for use in pharmaceutical research involving platelet ADP receptor. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving platelet ADP receptor. For example, the presence of $P2Y_1$ in an unknown sample could be determined by addition of the relevant radiolabled compound to the sample and measuring the extend of binding to the $P2Y_1$ receptor.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder (as defined previously). In another embodiment, the package insert states that the pharmaceutical composition can be used in combination (as defined previously) with a second therapeutic agent to treat a thromboembolic disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol.

Suitable pharmaceutical carriers are described in *Remington's Pharmaceutical Sciences,* Mack Publishing Company, a standard reference text in this field.

Where the compounds of this invention are combined with other anticoagulant agents, for example, a daily dosage may be about 0.1 to 100 milligrams of the compound of the present invention and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of the present invention and about 50 to 150 milligrams of the anti-platelet agent, preferably about 0.1 to 1 milligrams of the compound of the present invention and about 1 to 3 milligrams of antiplatelet agents, per kilogram of patient body weight.

Where the compounds of the present invention are administered in combination with thrombolytic agent, typically a daily dosage may be about 0.1 to 1 milligrams of the compound of the present invention, per kilogram of patient body weight and, in the case of the thrombolytic agents, the usual dosage of the thrombolyic agent when administered alone may be reduced by about 70-80% when administered with a compound of the present invention.

Where two or more of the foregoing second therapeutic agents are administered with the compound of the present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

What is claimed is:

1. A compound of Formula (I):

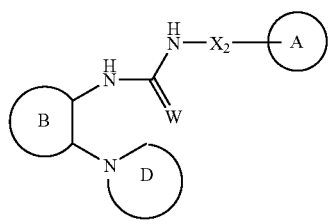

(I)

or a stereoisomer or pharmaceutically acceptable salt thereof, wherein:

ring A is $C_{6-10}$ aryl substituted with 0-5 $R^1$;

ring B is phenyl substituted with 0-4 $R^7$;

ring D is

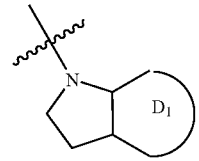

substituted with 0-5 $R^{6a}$;

wherein $D_1$ is a 5- to 7-membered carbocycle or a 5-6-membered heterocycle comprising: carbon atoms and 0-3 ring heteroatoms selected from the group consisting of N, $NR^{11}$, O, and $S(O)_p$, and optionally comprising 0-2 carbonyl groups, and 0-3 double bonds;

W is O or S;

$X_2$ is —$(CR^{16}R^{17})_s$—, or —$(CR^{16}R^{17})_rC(O)(CR^{16}R^{17})_r$—;

R1 is, independently at each occurrence selected from the group consisting of: H, F, Cl, Br, I, $CF_3$, —$CF_2CF_3$, $OCF_3$, —$OCF_2CF_2H$, —$OCF_2CF_3$, $SiMe_3$, —$(CR^fR^f)_r$—$OR^c$, $SR^c$, CN, $NO_2$, —$(CR^fR^f)_r$—$NR^{12}R^{13}$, —$(CR^fR^f)_r$—$C(O)R^c$, —$(CR^fR^f)_r$—$CO_2R^c$, —$(CR^fR^f)_r$—$C(O)NR^{12}R^{13}$, —$S(O)_pNR^{12}R^{13}$, —$NR^{14}SO_2CF_3$, —$NR^{14}S(O)_pR^d$, —$S(O)_2CF_3$, —$S(O)R^d$, —$S(O)_2R^d$, —$OP(O)(OEt)_2$, —$O(CH_2)_2OP(O)(OEt)_2$, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, and —$(CR^fR^f)_r$—$C_{3-13}$ carbocycle substituted with 0-5 $R^b$;

$R^{6a}$ is, independently at each occurrence, selected from the group consisting of: =O, F, Cl, Br, I, —$(CR^iR^i)_r$—$OR^c$, $SR^c$, CN, $NO_2$, $CF_3$, $OCF_3$, —$CF_2CF_3$, —$OCF_2CF_2H$, —$OCF_2CF_3$, —$(CR^fR^f)_r$—$NR^{12}R^{13}$, —$C(O)R^c$, —$(CR^fR^f)_r$—$C(O)OR^c$, —$(CR^fR^f)_r$—$C(O)NR^{12}R^{13}$, —$(CR^fR^f)_r$—$NR^{14}C(O)R^d$, —$S(O)_pNR^{12}R^{13}$, —$S(O)R^d$, —$S(O)_2R^d$, $Si(Me)_3$, $Si(C_{1-4}$ alkyl$)_3$, $C_{1-4}$ haloalkyl, $C_{1-4}$ haloalkyloxy-, $C_{1-4}$ alkyloxy-, $C_{1-4}$ alkylthio-, $C_1$-$C_4$ alkyl-C(O)—, $C_{1-4}$ alkyl-O—C(O)—, $C_{1-4}$ alkyl-C(O)NH—, $C_{1-8}$ alkyl substituted with 0-1 $R^a$, $C_{2-8}$ alkenyl substituted with 0-1 $R^a$, $C_{2-8}$ alkynyl substituted with 0-1 $R^a$, —$(CR^fR^f)_r$—$C_{3-10}$ carbocycle substituted with 0-2 $R^e$;

alternatively, when two $R^{6a}$ groups are attached to the same carbon atom, together with the carbon atom or silicon atom to which they are attached, they form a 3- to 7-membered carbocyclic or heterocyclic ring comprising: carbon atoms and 0-3 heteroatoms selected from the group consisting of N, $NR^{11}$, O, Si, and $S(O)_p$, 0-1 carbonyl and 0-3 ring double bonds, wherein said carbocyclic or heterocyclic ring is substituted with 0-3 $R^b$;

alternatively, when two $R^{6a}$ groups are attached to adjacent atoms, together with the atoms to which they are attached they form a 5- to 7-membered carbocyclic or heterocyclic ring comprising: carbon atoms and 0-2 heteroatoms selected from the group consisting of N, $NR^{11}$, O, Si, and $S(O)_p$, 0-1 carbonyl and 0-3 ring double bonds, wherein said carbocyclic or heterocyclic ring is substituted with 0-3 $R^b$;

$R^7$ is, independently at each occurrence, selected from the group consisting of: H, F, Cl, Br, I, $OCF_3$, $CF_3$, $OR^c$, $SR^c$, CN, $NO_2$, —$NR^{12}R^{13}$, —$C(O)R^c$, —$C(O)OR^c$, —$C(O)NR^{12}R^{13}$, —$NR^{14}C(O)R^d$, —$S(O)_pNR^{12}R^{13}$, —$S(O)R^d$, —$S(O)_2R^d$, $C_{1-8}$ alkyl substituted with 0-2 $R^a$, —$C_{2-8}$ alkenyl substituted with 0-2 $R^a$, $C_{2-8}$ alkynyl substituted with 0-2 R$^a$, and —(CR$^f$R$^f$)$_r$—C$_{3-10}$ carbocycle substituted with 0-3 R$^b$;

R$^{11}$ is, independently at each occurrence, selected from the group consisting of: H, C$_{1-4}$ alkoxy, C$_{1-8}$ alkyl substituted with 0-2 R$^a$, C$_{2-4}$ alkenyl substituted with 0-1 R$^a$, C$_{2-4}$ alkynyl substituted with 0-1 R$^a$, —C(O)(C$_{1-6}$ alkyl), —C(O)(CH$_2$)$_n$(C$_{3-6}$ cycloalkyl), —C(O)(CH$_2$)$_n$(C$_{6-10}$ aryl), —C(O)O(C$_{1-8}$ alkyl), —C(O)O(CH$_2$)$_n$(C$_{3-6}$ cycloalkyl), —C(O)O(CH$_2$)$_n$(C$_{6-10}$ aryl), —C(O)O(CH$_2$)$_{2-4}$-(C$_{1-4}$ alkyl), —C(O)NH(C$_{1-8}$ alkyl), —C(O)NH(CH$_2$)$_n$(C$_{3-6}$ cycloalkyl), —C(O)NH(CH$_2$)$_n$(C$_{6-10}$ aryl), and —(CR$^f$R$^f$)$_r$—C$_{3-10}$ carbocycle; wherein said alkyl, cycloalkyl, aryl, and carbocycle are substituted with 0-2 R$^b$;

R$^{12}$ is, independently at each occurrence, selected from the group consisting of: H, C$_{1-6}$ alkyl, —C(O)(C$_{1-6}$ alkyl), —C(O)(CH$_2$)$_n$(C$_{6-10}$ aryl), —C(O)OCH$_2$(C$_{6-10}$ aryl), —(CH$_2$)$_n$OC(O)(C$_{1-4}$ alkyl), —(CH$_2$)$_n$OC(O)(C$_{6-10}$ alkyl), —(CH$_2$)$_n$C(O)O(C$_{1-4}$ alkyl), —(CH$_2$)$_n$C(O)O(C$_{6-10}$ aryl), —(CH$_2$)$_n$C(O)NH(C$_{1-6}$ alkyl), —(CH$_2$)$_n$C(O)NH(C$_{6-10}$ aryl), and —(CR$^f$R$^f$)$_n$—(C$_{6-10}$ aryl); wherein said alkyl and aryl are substituted with 0-2 R$^g$;

R$^{13}$ is, independently at each occurrence, selected from the group consisting of: H, C$_{1-6}$ alkyl, or —(CH$_2$)$_n$-phenyl;

R$^{14}$ is, independently at each occurrence, selected from the group consisting of: H and C$_{1-6}$ alkyl;

R$^{16}$ is, independently at each occurrence, selected from the group consisting of: H, F, C$_{1-6}$ alkyl substituted with 0-2 R$^a$, C$_{2-6}$ alkenyl substituted with 0-2 R$^a$, C$_{2-6}$ alkynyl substituted with 0-2 R$^a$, and —(CH$_2$)$_r$-phenyl substituted with 0-2 R$^b$;

R$^{17}$ is, independently at each occurrence, H, OH, C$_{1-6}$ alkyl, or —(CH$_2$)$_n$-phenyl;

R$^a$ is, independently at each occurrence, selected from the group consisting of: H, =O, F, OCF$_3$, CF$_3$, OR$^c$, SR$^c$, CN, —NR$^{12}$R$^{13}$, —C(O)R$^c$, C(O)OR$^c$, —C(O)NR$^{12}$R$^{13}$, —NR$^{14}$C(O)R$^d$, —S(O)$_p$NR$^{12}$R$^{13}$, —S(O)R$^d$, —S(O)$_2$R$^d$, and —(CH$_2$)$_r$—C$_{3-10}$ carbocycle substituted with 0-3 R$^e$;

R$^b$ is, independently at each occurrence, selected from the group consisting of: H, =O, F, Cl, Br, I, (CH$_2$)$_r$—OR$^c$, SR$^c$, CN, NO$_2$, CF$_3$, OCF$_3$, —(CH$_2$)$_r$—NR$^{12}$R$^{13}$, —C(O)R$^c$, (CH$_2$)$_r$—C(O)OR$^c$, —(CH$_2$)$_r$—C(O)NR$^{12}$R$^{13}$, —NR$^{14}$C(O)R$^d$, —S(O)$_p$NR$^{12}$R$^{13}$, —S(O)R$^d$, —S(O)$_2$R$^d$, C$_{1-4}$ haloalkyl, C$_{1-4}$ haloalkyloxy-, C$_{1-4}$ alkyloxy-, C$_{1-4}$ alkylthio-, C$_{1-4}$ alkyl-C(O)—, C$_{1-4}$ alkyl-O—C(O)—, C$_{1-4}$ alkyl-C(O)NH—, C$_{1-8}$ alkyl substituted with 0-2 R$^a$, C$_{2-8}$ alkenyl substituted with 0-2 R$^a$, C$_{2-8}$ alkynyl substituted with 0-2 R$^a$, and (CH$_2$)$_r$—C$_{3-10}$ carbocycle substituted with 0-3 R$^e$;

R$^c$ is, independently at each occurrence, selected from the group consisting of: H, —OP(O)(OEt)$_2$, C$_{1-8}$ alkyl substituted with 0-2 R$^e$, C$_{2-8}$ alkenyl substituted with 0-2 R$^e$, C$_{2-8}$ alkynyl substituted with 0-2 R$^e$, —(CR$^f$R$^f$)$_r$—C$_{3-8}$ cycloalkyl substituted with 0-2 R$^e$, and —(CR$^f$R$^f$)$_r$—C$_{6-10}$ aryl substituted with 0-2 R$^e$;

R$^d$ is, independently at each occurrence, selected from the group consisting of: CF$_3$, OH, C$_{1-4}$ alkoxy, C$_{1-6}$ alkyl, and —(CH$_2$)$_r$—C$_{3-10}$ carbocycle substituted with 0-2 R$^e$;

R$^e$ is, independently at each occurrence, selected from the group consisting of: H, =O, —(CH$_2$)$_r$—OR$^f$, F, Cl, Br, I, CN, NO$_2$, —(CH$_2$)$_r$—NR$^{12}$R$^{13}$, —C(O)R$^f$, —(CH$_2$)$_r$—C(O)OR$^f$, —NR$^{14}$C(O)R$^f$, —(CH$_2$)$_r$—C(O)NR$^{12}$R$^{13}$, —SO$_2$NR$^{12}$R$^{13}$, —NR$^{14}$SO$_2$NR$^{12}$R$^{13}$, —NR$^{14}$SO$_2$—C$_{1-4}$ alkyl, —NR$^{14}$SO$_2$CF$_3$, —NR$^{14}$SO$_2$-phenyl, —S(O)$_2$CF$_3$, —S(O)$_p$—OR$^h$, —(CF$_2$)$_r$CF$_3$, Si(Me)$_3$, Si(Me)$_2$(t-Bu), Si(C$_{1-4}$ alkyl)$_3$, C$_{1-8}$ alkyl substituted with 0-2 R$^g$, C$_{2-8}$ alkenyl substituted with 0-2 R$^g$, C$_{2-8}$ alkynyl substituted with 0-2 R$^g$, —(CH$_2$)$_r$—C$_{3-8}$ cycloalkyl substituted with 0-2 R$^g$, —(CH$_2$)$_r$—C$_{6-10}$ aryl substituted with 0-2 R$^g$;

R$^f$ is, independently at each occurrence, selected from the group consisting of: H, C$_{1-6}$ alkyl, or —(CH$_2$)$_n$-phenyl;

R$^g$ is, independently at each occurrence, selected from the group consisting of: H, =O, OR$^f$, F, Cl, Br, I, CN, NO$_2$, —NR$^f$R$^f$, —C(O)R$^f$, —C(O)OR$^f$, —NR$^f$C(O)R$^f$, —C(O)NR$^f$R$^f$, —SO$_2$NR$^f$R$^f$, —NR$^f$SO$_2$NR$^f$R$^f$, —NR$^f$SO$_2$—C$_{1-4}$ alkyl, —NR$^f$SO$_2$CF$_3$, —NR$^f$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl, C$_{2-6}$ alkenyl, and C$_{2-6}$ alkynyl;

R$^h$ is, independently at each occurrence, selected from the group consisting of: C$_{1-6}$ alkyl substituted with 0-2 R$^g$, and —(CH$_2$)$_n$-phenyl substituted with 0-2 R$^g$;

R$^i$ is, independently at each occurrence, selected from the group consisting of: H, C$_{1-6}$ alkyl substituted with 0-2 R$^g$, and —(CH$_2$)$_n$-phenyl substituted with 0-2 R$^g$;

n, at each occurrence, is selected from 0, 1, 2, 3, and 4;

p, at each occurrence, is selected from 0, 1, and 2;

r, at each occurrence, is selected from 0, 1, 2, 3, and 4;

s, at each occurrence, is selected from 0, 1, 2, and 3; and t, at each occurrence, is selected from 1, 2, 3, and 4.

2. A compound according to claim 1, wherein:

ring A is phenyl substituted with 0-4 R$^1$; and ring B is

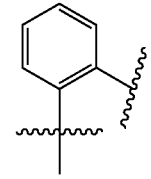

substituted with 0-3 R$^7$.

3. A compound according to claim 1, wherein:

R$^1$ is, independently at each occurrence, selected from the group consisting of: F, Cl, Br, I, CF$_3$, —CF$_2$CF$_3$, OCF$_3$, —OCF$_2$CF$_2$H, —OCF$_2$CF$_3$, SiMe$_3$, —(CR$^f$R$^f$)$_r$—OR$^c$, SR$^c$, CN, NO$_2$, —(CR$^f$R$^f$)$_r$—NR$^{12}$R$^{13}$, —(CR$^f$R$^f$)$_r$—CO$_2$R$^c$, —(CR$^f$R$^f$)$_r$—CO$_2$R$^c$, —(CR$^f$R$^f$)$_r$—C(O)NR$^{12}$R$^{13}$, —OP(O)(OEt)$_2$, C$_{1-8}$ alkyl substituted with 0-2 R$^a$, C$_{2-8}$ alkenyl substituted with 0-2 R$^a$, C$_{2-8}$ alkynyl substituted with 0-2 R$^a$, and —(CR$^f$R$^f$)$_r$—C$_{3-13}$ carbocycle substituted with 0-5 R$^b$.

4. A compound of Formula (Ia):

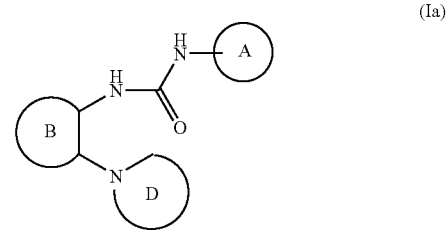

(Ia)

or a stereoisomer or pharmaceutically acceptable salt thereof, wherein:

ring a is

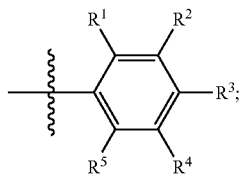

ring B is

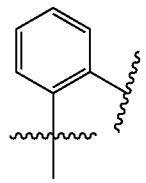

substituted with 0-3 $R^7$;
ring D is

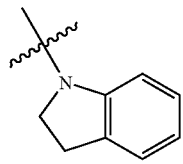

substituted with 0-5 $R^{6a}$;

$R^1$ is selected from the group consisting of: H, F, Cl, Me, $NH_2$, and OH;

$R^2$, $R^3$, $R^4$, and $R^5$, are, independently at each occurrence, each selected from the group consisting of: H, F, Cl, Br, I, $CF_3$, $-CF_2CF_3$, $OCF_3$, $-OCF_2CF_2H$, $-OCF_2CF_3$, $SiMe_3$, $-(CR^fR^f)_r OR^c$, $SR^c$, CN, $NO_2$, $-(CR^fR^f)_r-NR^{12}R^{13}$, $-(CR^fR^f)_u-C(O)R^c$, $-(CR^fR^f)_r-CO_2R^c$, $-(CR^fR^f)_u-C(O)NR^{12}R^{13}$, $-OP(O)(OEt)_2$, $C_{1-8}$ alkyl substituted with 0-2 $R^a$, and $-(CR^fR^f)_u-C_{3-6}$ carbocycle substituted with 0-2 $R^b$;

$R^{6a}$ is, independently at each occurrence, selected from the group consisting of: F, Cl, Br, I, $-(CR^fR^f)_r-OR^c$, $SR^c$, CN, $CF_3$, $OCF_3$, $-CF_2CF_3$, $-OCF_2CF_2H$, $-OCF_2CF_3$, $-NR^{12}R^{13}$, $-C(O)R^c$, $-(CR^fR^f)_r-C(O)OR^c$, $-Si(Me)_3$, $C_{1-4}$ haloalkyl, $C_{1-4}$ haloalkyloxy-, $C_{1-4}$ alkyloxy-, $C_{1-4}$ alkylthio-, $C_{1-4}$ alkyl-C(O)—, $C_{1-4}$ alkyl-O—C(O)—, $C_{1-4}$ alkyl-C(O)NH—, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, and $-(CR_fR^f)_r-C_{3-10}$ carbocycle substituted with 0-2 $R^e$;

alternatively, when two $R^{6a}$ groups are attached to the same carbon atom, together with the carbon atom or silicon atom to which they are attached, they form a 3- to 7-membered membered carbocyclic or heterocyclic ring comprising: carbon atoms and 0-3 heteroatoms selected from the group consisting of N, $NR^{11}$, O, Si, and $S(O)_p$, 0-1 carbonyl and 0-3 ring double bonds, wherein said carbocyclic or heterocyclic ring is substituted with 0-3 $R^b$;

alternatively, when two $R^{6a}$ groups are attached to adjacent atoms, together with the atoms to which they are attached they form a 5- to 7-membered carbocyclic or heterocyclic ring comprising: carbon atoms and 0-2 heteroatoms selected from the group consisting of N, $NR^{11}$, O, Si, and $S(O)_p$, 0-1 carbonyl and 0-3 ring double bonds, wherein said carbocyclic or heterocyclic ring is substituted with 0-3 $R^b$;

R7 is, independently at each occurrence, selected from the group consisting of: H, =O, F, Cl, Br, I, $OCF_3$, $CF_3$, $OR^c$, $SR^c$, CN, $NO_2$, $-NR^{12}R^{13}$, $-C(O)R^c$, $-C(O)OR^c$, $-C(O)NR^{12}R^{13}$, $-NR^{14}C(O)R^d$, $-S(O)_p NR^{12}R^{13}$, $-S(O)R^d$, $-S(O)_2R^d$, $C_{1-6}$ alkyl substituted with 0-2 $R^a$, and $-(CH_2)_u-C_{3-10}$ carbocycle substituted with 0-3 $R^b$;

$R^{11}$ is, independently at each occurrence, selected from the group consisting of: H, $C_{1-8}$ alkyl substituted with 0-2 $R^a$, $-C(O)(CH_2)_n(C_{3-6}$ cycloalkyl), $-C(O)(CH_2)_n$ phenyl, $-C(O)O(C_{1-8}$ alkyl), $-C(O)O(CH_2)_n(C_{3-6}$ cycloalkyl), $-C(O)O(CH_2)_n$phenyl, $-C(O)O(CH_2)_{2-4}$ ($C_{1-4}$ alkyl), $-C(O)NH(C_{1-6}$ alkyl), $-S(O)_2(C_{1-6}$ alkyl), $-S(O)_2(CH_2)_n$phenyl, and $-(CR^fR^f)_r C_{3-7}$ cycloalkyl, and $-(CR^fR^f)_r$-phenyl; wherein said alkyl, cycloalkyl, phenyl, and aryl are substituted with 0-2 $R^b$;

$R^{12}$ is, independently at each occurrence, selected from the group consisting of: H, $C_{1-6}$ alkyl, $-C(O)(C_{1-6}$ alkyl), $-C(O)(CH_2)_n$phenyl, $-C(O)O(C_{1-4}$ alkyl), $-C(O)OCH_2$phenyl, $-(CH_2)_nOC(O)(C_{1-4}$ alkyl), $-(CH_2)_n OC(O)$phenyl, $-(CH_2)_nC(O)O(C_{1-4}$ alkyl), $-(CH_2)_nC(O)O$phenyl, $-(CH_2)_nC(O)NH(C_{1-6}$ alkyl), $-(CH_2)_nC(O)NH$phenyl, and $-(CR^fR^f)_n$phenyl; wherein said alkyl and phenyl are substituted with 0-2 $R^g$;

$R^{13}$ is, independently at each occurrence, selected from the group consisting of: H, $C_{1-6}$ alkyl, and $-(CH_2)_n$-phenyl;

alternatively, $R^{12}$ and $R^{13}$, when attached to the same nitrogen, combine to form a 5- to 10-membered heterocyclic ring comprising: carbon atoms and 1-2 additional heteroatoms selected from the group consisting of N, $NR^{11}$, O, and $S(O)_p$;

$R^{14}$ is, independently at each occurrence, selected from the group consisting of: H and $C_{1-6}$ alkyl;

$R^a$ is, independently at each occurrence, selected from the group consisting of: H, =O, F, $OCF_3$, $CF_3$, $OR^c$, $SR^c$, CN, $-NR^{12}R^{13}$, $-C(O)R^c$, $C(O)OR^c$, $-C(O)NR^{12}R^{13}$, $-NR^{14}C(O)R^d$, $-S(O)_pNR^{12}R^{13}$, $-S(O)R^d$, $-S(O)_2R^d$, and $-(CH_2)_r-C_{3-10}$ carbocycle substituted with 0-3 $R^e$.

$R^b$ is, independently at each occurrence, H, =O, F, Cl, Br, I, $(CH_2)_r-OR^c$, $SR^c$, CN, $NO_2$, $CF_3$, $OCF_3$, $-(CH_2)_r-NR^{12}R^{13}$, $-C(O)R^c$, $(CH_2)_r-C(O)OR^c$, $-(CH_2)_r-C(O)NR^{12}R^{13}$, $-NR^{14}C(O)R^d$, $-S(O)_pNR^{12}R^{13}$, $-S(O)R^d$, $-S(O)_2R^d$, $C_{1-4}$ haloalkyl, $C_{1-4}$ haloalkyloxy-, $C_{1-4}$ alkyloxy-, $C_{1-4}$ alkylthio-, $C_{1-4}$ alkyl-C(O)—, $C_{1-4}$ alkyl-O—C(O)—, $C_{1-4}$ alkyl-C(O)NH—, $C_{1-8}$ alkyl substituted with 0-2 $R^a$, $C_{2-4}$ alkenyl substituted with 0-2 $R^a$, $C_{2-4}$ alkynyl substituted with 0-2 $R^a$, and $(CH_2)_u-C_{3-10}$ carbocycle substituted with 0-3 $R^e$;

$R^c$ is, independently at each occurrence, selected from the group consisting of: H, $-OP(O)(OEt)_2$, $C_{1-8}$ alkyl substituted with 0-2 $R^e$, $C_{2-4}$ alkenyl substituted with 0-2 $R^e$, $C_{2-4}$ alkynyl substituted with 0-2 $R^e$, $-(CH_2)_u-3-8$ cycloalkyl substituted with 0-2 $R^e$; and $-(CH_2)_u-C_{6-10}$ aryl substituted with 0-2 $R^e$;

$R^d$ is, independently at each occurrence, $CF_3$, OH, $C_{1-4}$ alkoxy, $C_{1-6}$ alkyl, and $—(CH_2)_u—C_{3-10}$ carbocycle substituted with 0-2 $R^e$;

$R^e$ is, independently at each occurrence, selected from the group consisting of: H, =O, $—(CH_2)_r—OR^f$, F, Cl, Br, I, CN, $NO_2$, $—(CH_2)_u—NR^{12}R^{13}$, $—C(O)R^f$, $—(CH_2)_r—C(O)OR^f$, $—NR^{14}C(O)R^f$, $—(CH_2)_r—C(O)NR^{12}R^{13}$, $—SO_2NR^{12}R^{13}$, $—NR^{14}SO_2NR^{12}R^{13}$, $—NR^{14}SO_2—C_{1-4}$ alkyl, $—NR^{14}SO_2CF_3$, $—NR^{14}SO_2$-phenyl, $—S(O)_2CF_3$, $—S(O)_p—S(O)_p—C_{1-4}$ alkyl, $—S(O)_p$-phenyl, $(CF_2)_uCF_3$, $C_{1-6}$ alkyl substituted with 0-2 $R^g$, $C_{2-4}$ alkenyl substituted with 0-2 $R^g$, $C_{2-4}$ alkynyl substituted with 0-2 $R^g$, $—(CH_2)_u—C_{3-8}$ cycloalkyl substituted with 0-2 $R^g$, $—(CH_2)_u—C_{6-10}$ aryl substituted with 0-2 $R^g$;

$R^f$ is, independently at each occurrence, H, $C_{1-4}$ alkyl;

$R^g$ is, independently at each occurrence, H, =O, $OR^f$, F, Cl, Br, I, CN, $NO_2$, $—NR^fR^f$, $—C(O)R^f$, $—C(O)OR^f$, $—NR^fC(O)R^f$, $—C(O)NR^fR^f$, $—SO_2NR^fR^f$, $—NR^fSO_2NR^fR^f$, $—NR^fSO_2—C_{1-4}$ alkyl, $—NR^fSO_2CF_3$, $—NR^fSO_2$-phenyl, $—S(O)_2CF_3$, $—S(O)_p—C_{1-4}$ alkyl, $—S(O)_p$-phenyl, $—(CF_2)_rCF_3$, $C_{1-6}$ alkyl, $C_{2-4}$ alkenyl, and $C_{2-4}$ alkynyl;

$R^h$ is, independently at each occurrence, selected from the group consisting of: $C_{1-6}$ alkyl substituted with 0-2 $R^g$, or $—(CH_2)_n$-phenyl substituted with 0-2 $R^g$;

n, at each occurrence, is selected from 0, 1, and 2;

p, at each occurrence, is selected from 0, 1, and 2;

r, at each occurrence, is selected from 0, 1, 2, 3, and 4;

s, at each occurrence, is selected from 0, 1, 2, and 3;

t, at each occurrence, is selected from 1, and 2; and u, at each occurrence, is selected from 0, 1, and 2.

5. A compound of Formula (Ia):

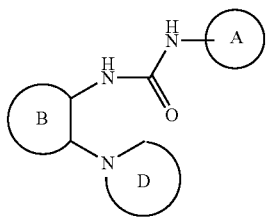

(Ia)

or a stereoisomer or pharmaceutically acceptable salt thereof, wherein:

ring A is

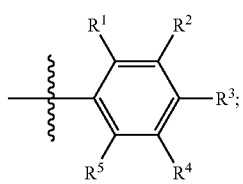

ring B is

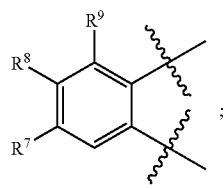

ring D is selected from the group consisting of:

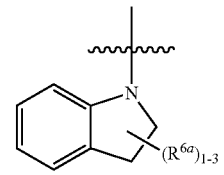

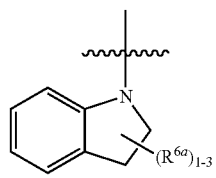
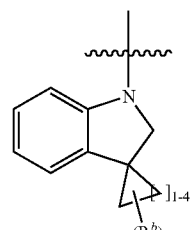

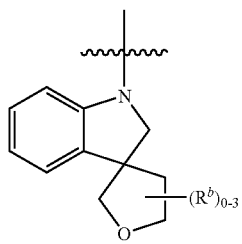
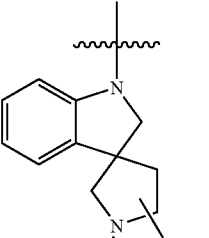

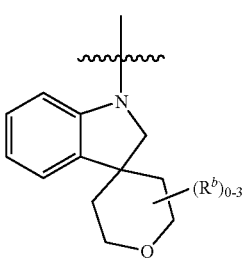
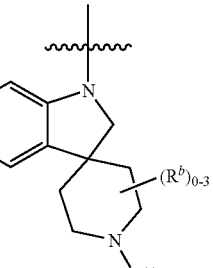

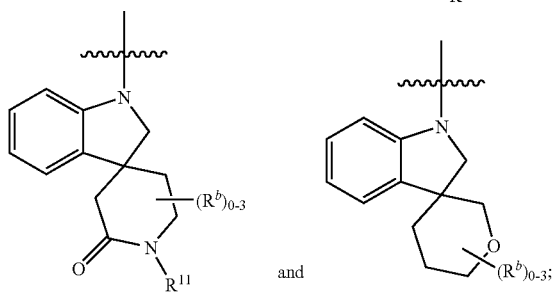

wherein the phenyl ring in each of the structures is substituted with 0-2 $R^{6a}$;

R¹ is selected from the group consisting of: H, F, Cl, Me, NH₂, OH, and phenoxy substituted with 0-2 $R^e$;

R² is selected from the group consisting of: H, F, Cl, Br, $C_{1-6}$ alkyl, C16 alkoxy, —O(CH₂)₈CO₂Me, —O(CH₂)₂C(Me)₂OMe, —O(CH₂)₂OCOMe, NO₂, CF₃, CF₂CF₃, 2-CH₂N(Me)₂-Ph, Ph, cyclohexoxy, 4-Me-cyclohexoxy, cyclohexylmethoxy, benzoxy, and 4-CO₂Me-benzoxy and SiMe₃;

R³ is selected from the group consisting of: H, F, Cl, Br, $C_{1-6}$ alkyl, $C_{1-6}$ alkoxy, —OCH(Me)CH₂O-t-Bu, CF₃, OCF₃, —OCF₂CF₂H, —OCF₂CF₃, SiMe₃, NH₂, NMe₂, —CH₂NMe₂, NEt₂, —NHPh, —N(Me)Ph, —NH(4-OMe-Ph), —NH(2-CF₃-Ph), —NH(2-t-Bu-Ph), —CH(Me)N(Me)(3-CF₃-Bn), —CH(Me)N(Me)(4-CF₃-Bn), —CH(Me)NHCH(Me)Ph, —CH(Me)OH, —CH(Me)O(i-Pr), —CH(Me)O(i-Bu), —CH(Me)O(3-CF₃-Bn), —CH(Me)O(4-CF₃-Bn), —CH(Me)OCH₂C(Me)₂CH₂NMe₂, —CH(Me)OBn, —CH(Me)O(4-i-Pr-Bn), —CH(Me)O(4-OPh-Bn), —CH(Me)O(3,5-diCl-Bn), —CH₂NHBn, —CH₂NH(4-CF₃-Bn), —CH₂N(Me)Bn, —CH(Me)N(Me)(i-Bu), —CH(Me)N(Me)Bn, —CH(Me)N(Me)(4-OMe-Bn), —CH(Me)N(Me)(4-F-Bn), —CH(Me)N(Me)(3-Cl-Bn), —CH(Me)N(Me)(4-Cl-Bn), —CH(Me)N(Me)(3,4-diCl-Bn), —CH(Me)N(Me)CH₂CH₂Ph, —CH(Me)N(Et)Bn, —CH(Me)N(Et)(4-Me-Bn), —CH(Me)N(Et)(2-Cl-Bn), —CH(Me)N(Bn)CH₂CN, —CH(Me)N(Bn)CH₂CH₂OH, —CH(Me)N(Bn)CH₂CO₂Me, —CH(Me)N(Bn)CH₂CONMe₂, —CH(Me)N(Bn)CH₂CON(Me)(Bn), COMe, CO₂Me, CO₂Et, —CH₂CO₂Me, —C(Me)₂CO₂Me, —O(CH₂)₅CO₂Et, —O(CH₂)₈CO₂Me, —O(CH₂)₂C(Me)₂OMe, —O(CH2)₂OCOMe, —OCH₂C(Me)₂CH₂NMe₂, Ph, 2-CH₂OH-Ph, 2-CH₂N(Me)₂-Ph, 3-CH₂N(Me)₂-Ph, 4-CH₂N(Me)₂-Ph, phenoxy, 2-t-Bu-phenoxy, 2-CF₃-phenoxy, Bn, benzoxy, 3-OMe-benzoxy, 4-CO₂Me-benzoxy, 4-OCF₃-benzoxy, 2,4-diF-benzoxy, cyclohexylmethoxy, cyclohexylethoxy, cyclopentoxy, 3-Me-cyclopentoxy, cyclohexoxy, 4-Me-cyclohexoxy, 4-CO₂Et-cyclohexoxy, $C_{3-6}$ cycloalkyl substituted with —CO₂Me, —CH₂OH, —CH₂OMe, and —OP(O)(OEt)₂;

R⁴ is H;

R⁵ is selected from the group consisting of: H, Me, F and Cl;

$R^{6a}$ is, independently at each occurrence, selected from the group consisting of: H, F, Cl, Br, I, CN, —C(Me)₂CN, $C_{1-8}$ alkyl, $C_{2-8}$ alkenyl, OH, SMe, S(i-Pr), —C(Me)₂OMe, —C(Me)₂OEt, —C(Me)₂OPr, —CHMeO(CH₂)₂OMe, —C(Me)₂O(CH₂)₂OMe, —C(Et)₂OMe, —C(Et)₂OEt, COPh, —CHCHCO₂(t-Bu), CF₃, OCF₃, $C_{1-4}$ alkyloxy, CO₂Me, —CH₂CO₂Me, $C_{3-7}$ cycloalkyl, Ph, Bn, and —Si(Me)₃;

alternatively, when two $R_{6a}$ groups are attached to the same carbon atom, together with the carbon atom to which they are attached, they form a 3- to 7-membered carbocyclic or heterocyclic ring comprising: carbon atoms and 0-2 heteroatoms selected from the group consisting of N, NR¹¹, O, and S(O)$_p$, 0-1 carbonyl and 0-3 ring double bonds, wherein said carbocyclic or heterocyclic ring is substituted with 0-2 $R^b$;

alternatively, when two $R_{6a}$ groups are attached to the same carbon atom, together with the carbon atom to which they are attached, they form a 5- to 7-membered carbocyclic or heterocyclic ring comprising: carbon atoms and 0-2 heteroatoms selected from the group consisting of N, NR¹¹, O, and S(O)$_p$, 0-1 carbonyl and 0-3 ring double bonds, wherein said carbocyclic or heterocyclic ring is substituted with 0-2 $R^b$;

R⁷ is selected from the group consisting of: H, Me, Cl, Br, CN, OMe, SMe, and NHMe;

R⁸ is selected from the group consisting of: H, Me, Cl, and CN;

R⁹ is selected from the group consisting of: H, Me, F, Cl, or CN;

R¹¹ is, independently at each occurrence, selected from the group consisting of: $C_{1-6}$ alkyl, —CH₂CH₂OH, —CH₂CH₂OMe, —C(O)($C_{1-6}$ alkyl), —C(O)phenyl, —C(O)benzyl, —C(O)O($C_{1-6}$ alkyl), —C(O)Obenzyl, —CH₂CO₂H, —CH₂CO₂($C_{1-6}$ alkyl), —C(O)NH($C_{1-6}$ alkyl), —C(O)NHbenzyl, —S(O)₂($C_{1-6}$ alkyl), —S(O)₂phenyl, —S(O)₂benzyl, phenyl, and benzyl;

$R^b$ is, independently at each occurrence, selected from the group consisting of H, F, Cl, Br, $C_{1-4}$ alkyl, OH, CO₂H, NH₂, CF₃, OCF₃, $C_{1-4}$ alkyloxy, $C_{3-7}$ cycloalkyl, phenyl, and benzyl;

$R^e$ is, independently at each occurrence, selected from the group consisting of H, F, Cl, $C_{1-4}$ alkyl, OH, CO₂H, NH₂, CF₃, OCF₃, and $C_{1-4}$ alkyloxy; and p, at each occurrence, is selected from 0, 1, and 2.

6. A compound according to claim 5, wherein:

ring A is

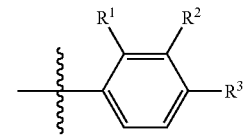

R¹ is H or F;

R² is selected from the group consisting of H, F, Cl, Br, Me, t-Bu, isopentoxy, —O(CH₂)₈CO₂Me, —(CH₂)₂C(Me)₂ OMe, —O(CH₂)₂OCOMe, NO₂, CF₃, 2-CH₂N(Me)₂-Ph, cyclohexoxy, 4-Me-cyclohexoxy, cyclohexylmethoxy, benzoxy, and 4-CO₂Me-benzoxy; and R³ is selected from the group consisting of H, F, Cl, Br, Me, Et, Pr, Bu, t-Bu, OMe, OEt, OPr, O-i-Pr, OBu, O-t-Bu, isopentoxy, neohexoxy, —OCH(Me)CH₂O-t-Bu, CF₃, OCF₃, NH₂, NMe₂, NEt₂, —NHPh, —N(Me)Ph, —NH(4-OMe-Ph), —NH(2-CF₃-Ph), —CH₂NMe₂, —CH(Me)N(Me)(3-CF₃-Bn), —CH(Me)N(Me)(4-CF₃-Bn), —CH(Me)NHCH(Me)Ph, —CH(Me)N(Me)(thien-2-ylmethyl), —CH(Me)OH, —CH(Me)O(i-Pr), —CH(Me)O(i-Bu), —CH(Me)O(3-CF₃-Bn), —CH(Me)O(4-CF3-Bn), COMe, CO₂Et, —CH₂CO₂Me, —C(Me)₂CO₂Me, —O(CH₂)₅CO₂Et, —O(CH₂)₈CO₂Me, —O(CH₂)₂C(Me)₂OMe, —O(CH₂)₂OCOMe, —OCH₂C(Me)₂CH₂NMe₂, Ph, 2-CH₂OH-Ph, 2-CH₂N(Me)₂-Ph, 3-CH₂N(Me)₂-Ph, 4-CH₂N(Me)₂-Ph, phenoxy, Bn, benzoxy, 3-OMe-benzoxy, 4-CO₂Me-benzoxy, 4-OCF₃-benzoxy, 2,4-di-F-benzoxy, cyclohexylmethoxy, cyclohexylethoxy, cyclopentoxy, 3-Me-cyclopentoxy, cyclohexoxy, 4-Me-cyclohexoxy, 4-CO₂Et-cyclohexoxy, 1-CH₂OH-cyclopropyl, 1-CO₂Me-cyclopropyl, 1-CH₂OMe-cyclopropyl, 1-CO₂Me-cyclobutyl, 1-CO₂Me-cyclopentyl, cyclohexyl, 1-CO₂Me-cyclohexyl, and —OP(O)(OEt)₂.

7. A compound of Formula (Ia):

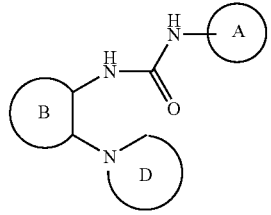

(Ia)

or a stereoisomer or pharmaceutically acceptable salt thereof, wherein:

ring A is

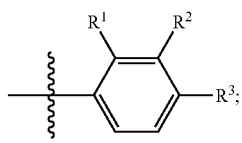

ring B is

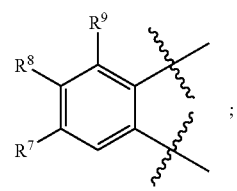

ring D is selected from the group consisting of:

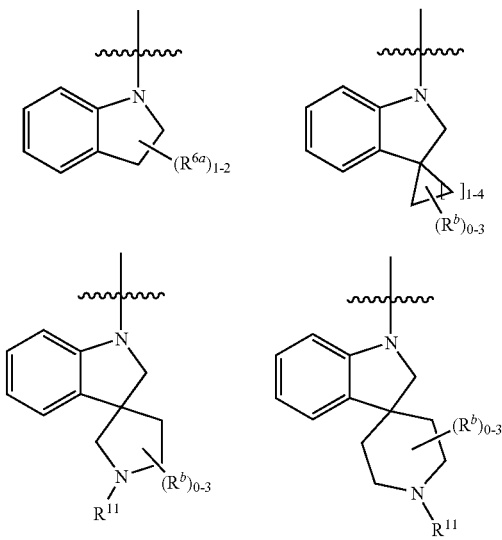

-continued

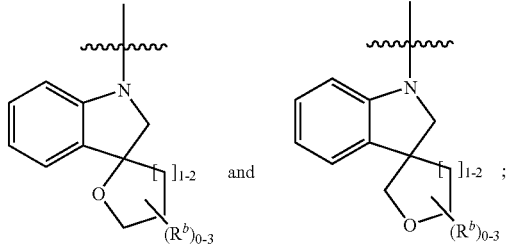

wherein the phenyl ring in each of the structures is substituted with $0\text{-}1R^{6a}$;

$R^1$ is H or F;

$R^2$ is selected from the group consisting of: H, F, Cl, Br, Me, t-Bu, isopentoxy, —O(CH$_2$)$_8$CO$_2$Me, —O(CH$_2$)$_2$C(Me)$_2$OMe, —O(CH$_2$)$_2$OCOMe, NO$_2$, CF$_3$, cyclohexoxy, 4-Me-cyclohexoxy, cyclohexylmethoxy, and 4-CO$_2$Me-benzoxy;

$R^3$ is selected from the group consisting of: H, F, Cl, Br, Me, Et, Pr, Bu, t-Bu, OMe, OEt, OPr, O-i-Pr, OBu, O-t-Bu, isopentoxy, neohexoxy, -OCH(Me)CH$_2$O-t-Bu, CF$_3$, OCF$_3$, NH$_2$, NMe$_2$, NEt$_2$, —NHPh, —N(Me)Ph, —NH(4-OMe-Ph), —NH(2-CF$_3$-Ph), —CH$_2$NMe$_2$, —CH(Me)OH, —CH(Me)O(i-Bu), —CH(Me)O(4-CF$_3$-Bn), -CH(Me)N(Me)(3-CF$_3$-Bn), —CH(Me)N(Me)(4-CF$_3$-Bn), —CH(Me)NHCH(Me)Ph, COMe, CO$_2$Et, —CH$_2$CO$_2$Me, —C(Me)$_2$CO$_2$Me, —O(CH$_2$)$_5$CO$_2$Et, —O(CH$_2$)$_8$CO$_2$Me, —O(CH$_2$)$_2$C(Me)$_2$OMe, —O(CH$_2$)$_2$OCOMe, —OCH$_2$C(Me)$_2$CH$_2$NMe$_2$, 1-CH$_2$OH-cyclopropyl, cyclohexyl, Ph, 2-CH$_2$OH-phenyl, 2-CH$_2$N(Me)$_2$-phenyl, 3-CH$_2$N(Me)$_2$-phenyl, 4-CH$_2$N(Me)$_2$-phenyl, phenoxy, Bn, 3-OMe-benzoxy, 4-CO$_2$Me-benzoxy, 4-OCF$_3$-benzoxy, 2,4-diF-benzoxy, cyclohexylmethoxy, cyclohexylethoxy, cyclopentoxy, 3-Me-cyclopentoxy, cyclohexoxy, 4-Me-cyclohexoxy, 4-CO$_2$Et-cyclohexoxy, 1-CO$_2$Me-cyclopropyl, 1-CH$_2$OMe-cyclopropyl, 1-CO$_2$Me-cyclobutyl, 1-CO$_2$Me-cyclopentyl, 1-CO$_2$Me-cyclohexyl, and —OP(O)(OEt)$_2$;

$R^{6a}$ is, independently at each occurrence, selected from the group consisting of: H, F, Cl, Br, I, CN, —C(Me)$_2$CN, $C_{1-8}$ alkyl, $C_{2-8}$ alkenyl, OH, SMe, S(i-Pr), —C(Me)2OMe, —C(Me)$_2$OEt, —C(Me)$_2$OPr, —CHMeO(CH$_2$)$_2$OMe, —C(Me)2O(CH2)$_2$OMe, —C(Et)$_2$OMe, —C(Et)$_2$OEt, COPh, CO$_2$Me, CO$_2$Bn, —CH$_2$CO$_2$Me, —CH=CHCO$_2$(t-Bu), CF$_3$, OCF$_3$, $C_{1-4}$ alkyloxy, $C_{3-7}$ cycloalkyl, Ph, Bn, and —Si(Me)$_3$;

$R^7$ is selected from the group consisting of: H, Me, Cl, Br, CN, OMe, SMe, and NHMe;

$R^8$ is selected from the group consisting of: H, Me, F, Cl, or CN;

$R^9$ is selected from the group consisting of: H, Me, F, Cl, or CN;

$R^{11}$ is, independently at each occurrence, selected from the group consisting of: Me, i-Pr, i-Bu, t-Bu, Bn, —CH$_2$CH$_2$OH, —CH$_2$CH$_2$OMe, —CO(i-Pr), CO$_2$Me, CO$_2$Et, CO$_2$Bn, —CH$_2$CO$_2$H, —CH$_2$CO$_2$Me, —CONH(i-Pr), and SO$_2$(i-Pr); and $R^b$ is, independently at each occurrence, H, F, Cl, $C_{1-4}$ alkyl, OH, CO$_2$H, NH$_2$, CF$_3$, OCF$_3$, or $C_{1-4}$ alkyloxy.

8. A compound according to claim 7, wherein:

ring A is selected from the group consisting of 3-Me-Ph, 4-Me-Ph, 4-t-Bu-Ph, 4-OCF$_3$-Ph, 4-NMe$_2$-Ph, 4-COMe-Ph, 4-CH(OH)Me-Ph,

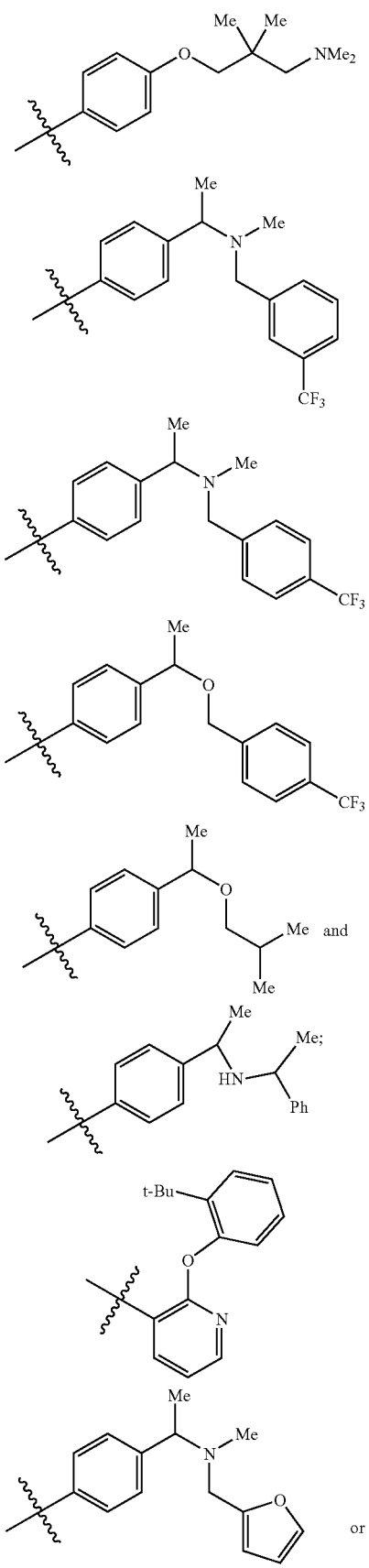
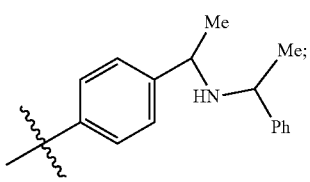
ring B is selected from the group consisting of:
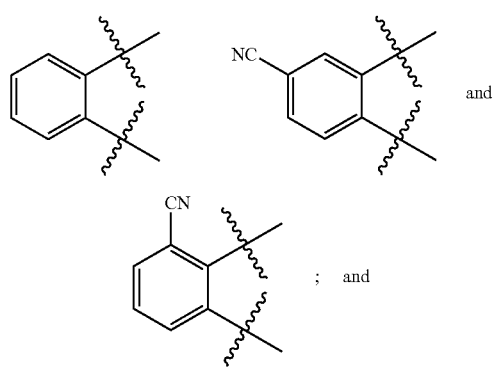
ring D is selected from the group consisting of:
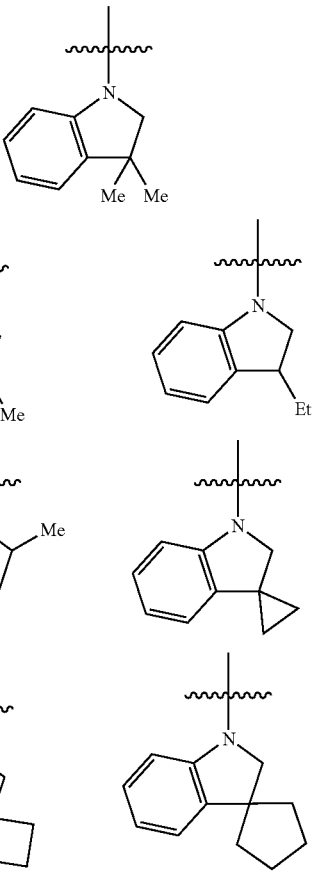

-continued
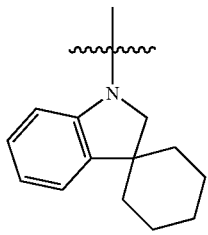
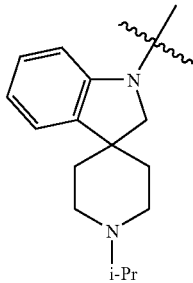 i-Pr
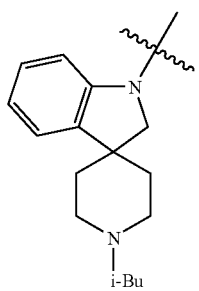 i-Bu
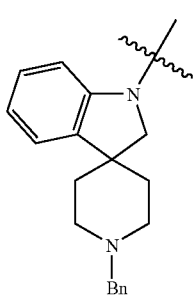 Bn
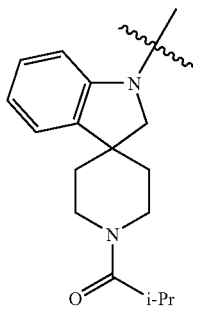 O, i-Pr
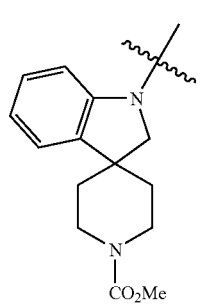 CO₂Me
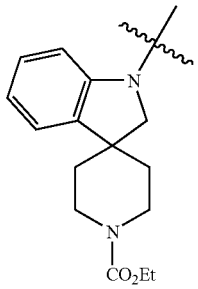 CO₂Et
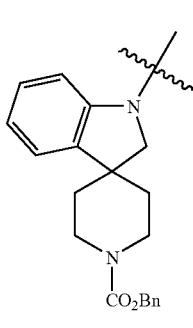 CO₂Bn
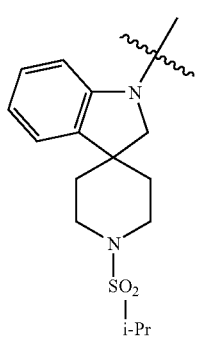 SO₂ i-Pr
-continued
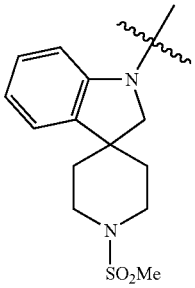 SO₂Me
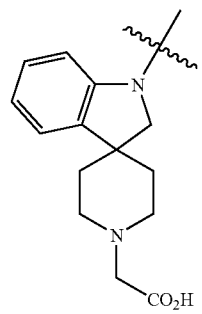 CO₂H
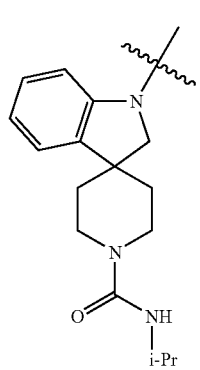 O NH i-Pr
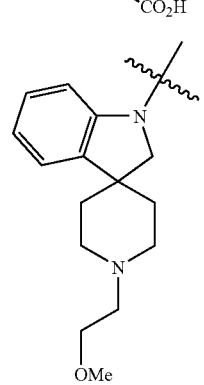 OMe
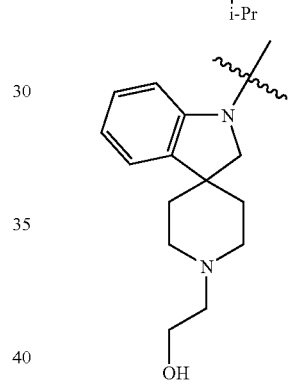 OH
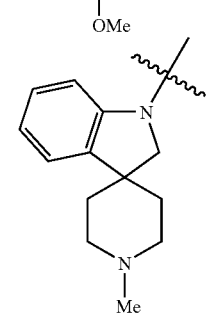 Me
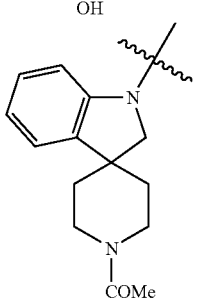 COMe   and   (NH piperidine spiroindoline)
9. A compound according to claim 7, wherein:
ring A is selected from the group consisting of:
4-Me-Ph, 4-t-Bu-Ph, 4-OCF₃-Ph, 4-NMe₂-Ph, 4-COMe-Ph, and
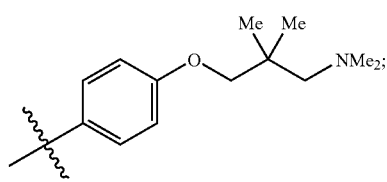

ring B is selected from the group consisting of:
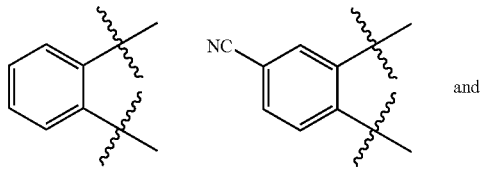
and
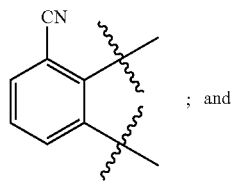
; and
ring D is selected from the group consisting of:
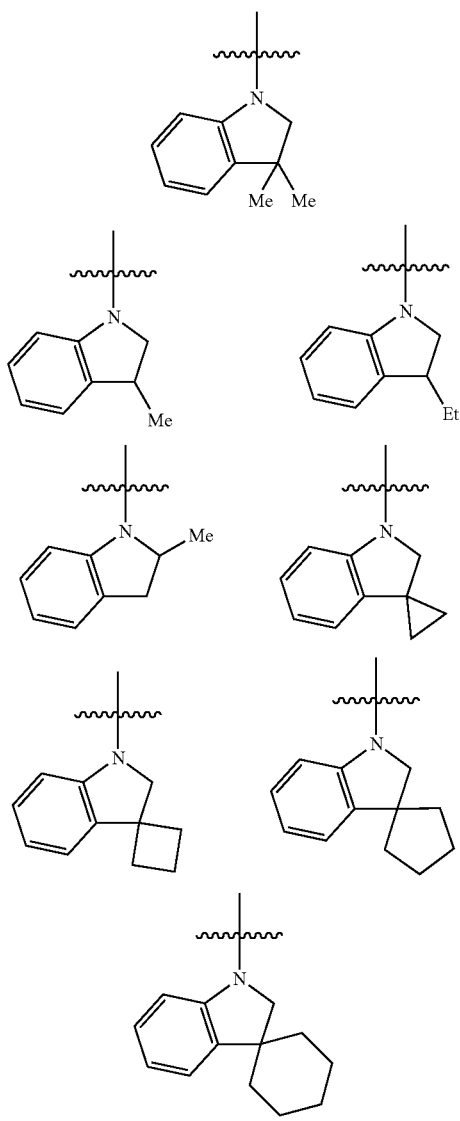
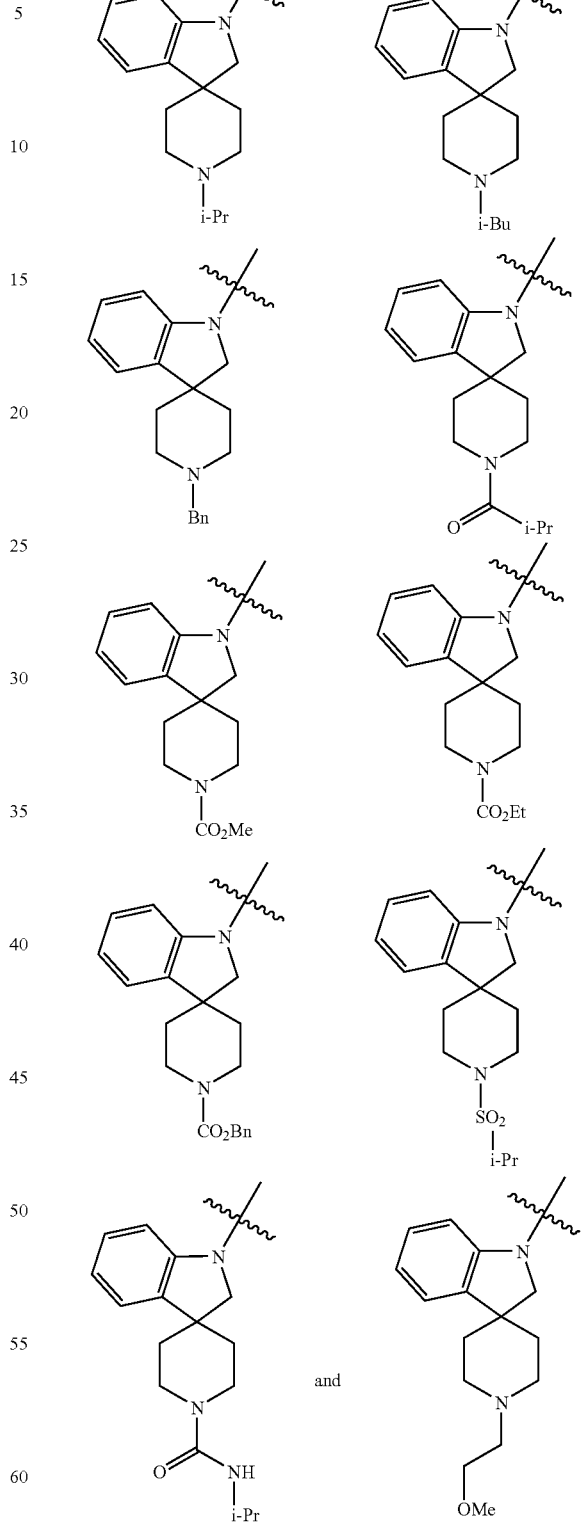
10. A compound according to claim 1, wherein the compound is selected from the group consisting of:
1-(2-(spiro-cyclochexylindolin-1-yl)phenyl)-3-(4-(trifluoromethoxy)-phenyl)urea;

1-(4-tert-butyl-phenyl)-3-[2-(3,3-dimethyl-2,3-dihydro-indol-1-yl)-phenyl]-urea;

1-[2-(3,3-dimethyl-2,3-dihydro-indol-1-yl)-phenyl]-3-(4-trifluoromethoxy-phenyl)urea;

N-(2-spiro [cyclopropane-1,3'-[3H]indol]-1'(2'H)-ylphenyl)-N'[4- (trifluoromethoxy)phenyl]-urea;

N-(2-spiro [cyclobutane-1,3'-[3H]indol]-1'(2'H)-ylphenyl)-N'-[4-(trifluoromethoxy)phenyl]-urea;

N-(2-spiro [cyclopentane-1,3'-[3H]indol]-1'(2'H)-ylphenyl)-N'-[4-(trifluoromethoxy)phenyl]-urea;

1-[2-(3-ethyl-2,3-dihydro-indol-1-yl)-phenyl]-3-(4-trifluoromethoxy-phenyl)-urea;

spiro[3H-indole-3,4'-piperidine]-1'-carboxylic acid, 1,2-dihydro-1-[2-[[[[4-(trifluoromethoxy)phenyl]amino]carbonyl]amino]phenyl]-, phenylmethyl ester;

urea, N-(2-spiro [3H-indole-3,4'-piperidin]-1(2H)-ylphenyl)-N'-[4-(trifluoromethoxy)phenyl]-;

urea, N-[2-[1'-(1-methylethyl)spiro[3H-indole-3,4'-piperidin]-1(2H)-yl]phenyl]-N'-[4-(trifluoromethoxy)phenyl]-;

spiro[3H-indole-3,4'-piperidine]-1'-carboxylic acid, 1,2-dihydro-1-[2-[[[[4-(trifluoromethoxy)phenyl]amino]carbonyl]amino]phenyl]-, methyl ester;

urea, N-[2-[1'-(2-methylpropyl)spiro [3H-indole-3,4'-piperidin]-1(2H)-yl]phenyl]-N'-[4-(trifluoromethoxy)phenyl]-;

urea, N-[2-(1'-methyispiro [3H-indole-3,4'-piperidin]-1(2H)-yl)phenyl]-N'-[4-(trifluoromethoxy)phenyl]-;

spiro[3H-indole-3,4'-piperidine]-1'-carboxylic acid, 1,2-dihydro-1-[2-[[[[4-(trifluoromethoxy)phenyl]amino]carbonyl]amino]phenyl]-, ethyl ester;

spiro[3H-indole-3,4'-piperidine], 1'-acetyl-1,2-dihydro-1-[2-[[[[4-(trifluoromethoxy)phenyl]amino]carbonyl]amino]phenyl]-;

urea, N-[2[1'-(phenylmethyl)spiro [3H-indole-3,4'-piperidin]-1(2H)-yl]phenyl]-N'-[4-(trifluoromethoxy)phenyl]-;

spiro [3H-indole-3,4'-piperidine], 1,2-dihydro-1'-(methylsulfonyl)-1-[2-[[[[4-(trifluoromethoxy)phenyl]amino]carbonyl]amino]phenyl]-;

urea, N-[2-[1'-(2-hydroxyethyl)spiro [3H-indole-3,4'-piperidin]-1(2H)-yl]phenyl]-N'-[4-(trifluoromethoxy)phenyl]-;

urea, N-[2-[1'-(2-methoxyethyl)spiro [3H-indole-3,4'-piperidin]-1(2H)-yl]phenyl]-N'-[4-(trifluoromethoxy)phenyl]-;

spiro[3H-indole-3,4'-piperidine]-1'-acetic acid, 1,2-dihydro-1-[2-[[[[4-(trifluoromethoxy)phenyl]amino]carbonyl]amino]phenyl]-;

spiro [3H-indole-3,4'-piperidine]-1'-carboxamide, 1,2-dihydro-N-(1-methylethyl)-1-[2-[[[[4-(trifluoromethoxy)phenyl]amino]carbonyl]amino]phenyl]-;

spiro [3H-indole-3,4'-piperidine], 1,2-dihydro-1'-[(1-methylethyl)sulfonyl]-1-[2-[[[[4-(trifluoromethoxy)phenyl]amino]carbonyl]amino]phenyl]-;

urea, N-(4-cyano-2-spiro [cyclohexane-1,3 '-[3H]indol]-1' (2'H)-ylphenyl)-N'-[4-(trifluoromethoxy)phenyl]-;

urea, N-(5-cyano-2-spiro [cyclohexane-1,3'-[3H]indol]-1' (2'H)-ylphenyl)-N'-[4-(trifluoromethoxy)phenyl]-; and urea, N-(4-cyano-2-spiro [cyclohexane-1,3'-[3H]indol]-1' (2'H)-ylphenyl)-N'-[4-(dimethylamino)phenyl]-;

or a stereoisomer or pharmaceutically acceptable salt thereof.

11. A pharmaceutical composition, comprising: a pharmaceutically acceptable carrier and a therapeutically effective amount of a compound of claim 1.

12. A pharmaceutical composition, comprising: a pharmaceutically acceptable carrier and a therapeutically effective amount of a compound of claim 2.

13. A pharmaceutical composition, comprising: a pharmaceutically acceptable carrier and a therapeutically effective amount of a compound of claim 3.

14. A pharmaceutical composition, comprising: a pharmaceutically acceptable carrier and a therapeutically effective amount of a compound of claim 4.

15. A pharmaceutical composition, comprising: a pharmaceutically acceptable carrier and a therapeutically effective amount of a compound of claim 5.

16. A pharmaceutical composition, comprising: a pharmaceutically acceptable carrier and a therapeutically effective amount of a compound of claim 6.

17. A pharmaceutical composition, comprising: a pharmaceutically acceptable carrier and a therapeutically effective amount of a compound of claim 7.

18. A pharmaceutical composition, comprising: a pharmaceutically acceptable carrier and a therapeutically effective amount of a compound of claim 8.

19. A pharmaceutical composition, comprising: a pharmaceutically acceptable carrier and a therapeutically effective amount of a compound of claim 9.

20. A pharmaceutical composition, comprising: a pharmaceutically acceptable carrier and a therapeutically effective amount of a compound of claim 10.

\* \* \* \* \*

UNITED STATES PATENT AND TRADEMARK OFFICE
CERTIFICATE OF CORRECTION

PATENT NO. : 7,550,499 B2
APPLICATION NO. : 11/126567
DATED : June 23, 2009
INVENTOR(S) : Huji Turdi et al.

It is certified that error appears in the above-identified patent and that said Letters Patent is hereby corrected as shown below:

Column 144
Line 21, "R1" should read -- $R^1$ --.

Column 145
Line 18-19, "($C_{6-10}$ alkyl)," should read -- ($C_{6-10}$ aryl), --.

Column 146
Line 4, "$R^g$," should read -- $R^g$, and --; and
Line 48-49, "–$CO_2R^c$," should read -- –$C(O)R^c$, --.

Column 147
Line 3, "ring a is" should read -- ring A is --;
Line 57, "–$(CR_fR^f)_r$," should read -- –$(CR^fR^f)_r$ --; and
Line 62, "7-membered membered" should read -- 7-membered --.

Column 148
Line 9, "R7" should read -- $R^7$ --;
Line 22, after "phenyl" delete "and";
Line 50, "–$(CH_2)_r$–$C_{3-10}$" should read -- –$(CH_2)_u$–$C_{3-10}$ --;
Line 51, "0-3 $R^e$." should read -- 0-3 $R^e$; --;
Line 52, after "occurrence" insert -- selected from the group consisting of: --;
Line 59, "$C_{1-8}$" should read -- $C_{1-6}$ --;
Line 65, "–$(CH_2)_u$–$_{3-8}$" should read -- –$(CH_2)_u$–$C_{3-8}$ --; and
Line 66, "$R^e$;" should read -- $R^e$, --.

Column 149
Line 1, after "occurrence" should read -- selected from the group consisting of: --;
Line 11-12, "–$S(O)_p$–$S(O)_p$–$C_{1-4}$ alkyl," should read -- –$S(O)_p$–$C_{1-4}$ alkyl, --;
Line 12, "$CF_2)_uCF_3$," should read -- –$(CF_2)_uCF_3$, --;
Line 18, "H, $C_{1-4}$ alkyl;" should read -- H, or $C_{1-4}$ alkyl; --;
Line 19, after "occurrence" should read -- selected from the group consisting of --;
Line 25, "–$(CF_2)_rCF_3$," should read -- –$(CF_2)_uCF_3$, --;
Line 27-28, after "occurrence" should read -- selected from the group consisting of: --;
Line 35, "1, and 2;" should read -- 1 and 2; --.

UNITED STATES PATENT AND TRADEMARK OFFICE
CERTIFICATE OF CORRECTION

PATENT NO. : 7,550,499 B2
APPLICATION NO. : 11/126567
DATED : June 23, 2009
INVENTOR(S) : Huji Turdi et al.

It is certified that error appears in the above-identified patent and that said Letters Patent is hereby corrected as shown below:

Column 150
Line 20-30, below " 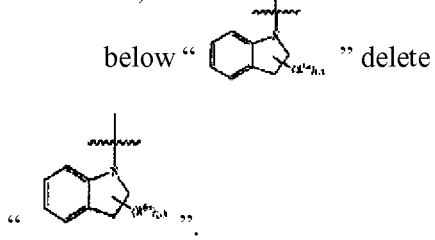 " delete

"  ".

(Second Occurrence)

Column 151
Line 4, "C16" should read -- $C_{1-6}$ --;
Line 32, "–O(CH2)$_2$" should read -- –O(CH$_2$)$_2$ --;
Line 51, "–CHCHCO$_2$ (t-Bu)," should read -- –CH=CHCO$_2$ (t-Bu), --;
Line 54, "R$_{6a}$" should read -- $R^{6a}$ --;
Line 62, "R$_{6a}$" should read -- $R^{6a}$ --;
Line 62-63, delete "to the same carbon atom" should read -- to adjacent atoms, --;
Line 63, before "atom" delete "carbon";
Line 64, "attached," should read -- attached --.

Column 152
Line 35, after "  " insert -- ; --;
Line 54, "CF3" should read -- $CF_3$ --.

Column 154
Line 45-46, "–C(Me)2OMe," should read -- –C(Me)$_2$OMe, --;
Line 47, "–C(Me)20(CH2)$_2$OMe," should read -- –C(Me)$_2$O(CH$_2$)$_2$OMe, --.

UNITED STATES PATENT AND TRADEMARK OFFICE
CERTIFICATE OF CORRECTION

PATENT NO. : 7,550,499 B2  Page 3 of 4
APPLICATION NO. : 11/126567
DATED : June 23, 2009
INVENTOR(S) : Huji Turdi et al.

It is certified that error appears in the above-identified patent and that said Letters Patent is hereby corrected as shown below:

Column 155
Line 50-65, below

" 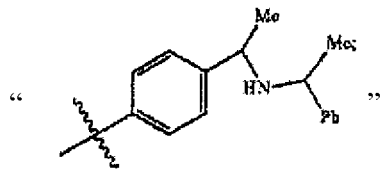 "

delete

" 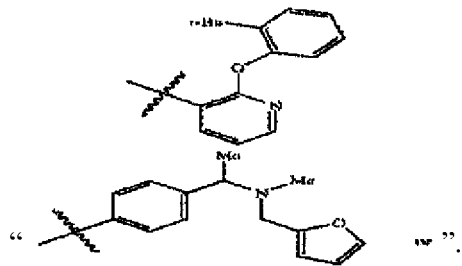 ".

Column 156
Line 1-10, delete " 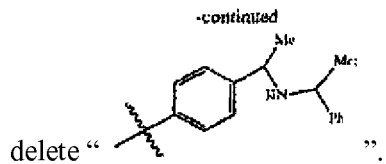 ".

UNITED STATES PATENT AND TRADEMARK OFFICE
CERTIFICATE OF CORRECTION

PATENT NO. : 7,550,499 B2
APPLICATION NO. : 11/126567
DATED : June 23, 2009
INVENTOR(S) : Huji Turdi et al.

It is certified that error appears in the above-identified patent and that said Letters Patent is hereby corrected as shown below:

Column 160
Line 66, "cyclochexylindolin" should read -- cyclohexylindolin --.

Column 161
Line 28, "methyispiro" should read -- methylspiro --.

Signed and Sealed this

Twenty-seventh Day of October, 2009

David J. Kappos
*Director of the United States Patent and Trademark Office*